US009414776B2

(12) United States Patent
Sillay et al.

(10) Patent No.: US 9,414,776 B2
(45) Date of Patent: Aug. 16, 2016

(54) PATIENT PERMISSION-BASED MOBILE HEALTH-LINKED INFORMATION COLLECTION AND EXCHANGE SYSTEMS AND METHODS

(71) Applicants: Karl Arthur Sillay, Nashville, TN (US); John Douglas Birdwell, Oak Ridge, TN (US)

(72) Inventors: Karl Arthur Sillay, Nashville, TN (US); John Douglas Birdwell, Oak Ridge, TN (US)

(73) Assignee: Navigated Technologies, LLC, Madison, WI (US)

( * ) Notice: Subject to any disclaimer, the term of this patent is extended or adjusted under 35 U.S.C. 154(b) by 151 days.

(21) Appl. No.: 13/787,406

(22) Filed: Mar. 6, 2013

(65) Prior Publication Data

US 2014/0257047 A1    Sep. 11, 2014

(51) Int. Cl.
*A61B 5/00* (2006.01)
*G06F 19/00* (2011.01)
(Continued)

(52) U.S. Cl.
CPC .......... *A61B 5/14542* (2013.01); *A61B 5/0022* (2013.01); *A61B 5/02055* (2013.01); *A61B 5/11* (2013.01); *A61B 5/1101* (2013.01); *A61B 5/4082* (2013.01); *A61N 1/36067* (2013.01); *G06F 19/3443* (2013.01); *G06F 19/363* (2013.01); *A61B 5/01* (2013.01);
(Continued)

(58) Field of Classification Search
CPC ...... A61B 5/411; A61B 5/1117; A61B 5/681; A61B 5/0022; A61B 5/7267; A61B 5/0006; A61B 5/0402; A61B 5/726; A61B 2560/0412; A61B 5/02055; A61B 5/14532; A61B 5/021; A61B 5/7214; A61B 5/7257
USPC .................................................. 600/300–301
See application file for complete search history.

(56) References Cited

U.S. PATENT DOCUMENTS 5,313,968 A * 5/1994 Logan .................. A61B 5/1071 600/595
5,573,011 A * 11/1996 Felsing .......................... 600/595
(Continued)

OTHER PUBLICATIONS

Larsen, T. Andreo et al., "Theoretical and Practical Issues in Assessment of Deicits and Therapy in Parkinsonism," pp. 363-373, Lisuride and Other Dopamine Agonists, Caine et al., Raven Press, New York, 1983.
(Continued)

*Primary Examiner* — William Thomson
*Assistant Examiner* — Shirley Jian
(74) *Attorney, Agent, or Firm* — Cameron LLP

(57) ABSTRACT

A suite of components comprising an objective measurement medical data collection device and a cohort database may standardize, simplify, and objectify clinical outcomes tracking, culminating in population health measurements within the restorative neurosciences such as Parkinson disease individuals diagnosed with a disease. A data collection device may comprise one or more of a gyroscope, an accelerometer, a locator, a camera and a magnetometer for collecting, for example, data related to tremors experienced by the individuals diagnosed with disease and receive instruction data responsive to evaluation of the collected data in relation to the cohort database. A related method collects objective measurements during phases of treatment such as preoperative symptomatology, probabilistic atlas linked targeting for neuromodulation, accountancy for gravitational effects of brain shift during surgery, measurements of movement and quality of life during supervised treatment and ongoing community and self-directed treatment and provides feedback to implants, intelligent devices and users thereof.

30 Claims, 125 Drawing Sheets

(51) Int. Cl.
| | |
|---|---|
| A61B 5/145 | (2006.01) |
| A61B 5/11 | (2006.01) |
| A61N 1/36 | (2006.01) |
| A61B 5/0205 | (2006.01) |
| A61B 5/01 | (2006.01) |
| A61B 5/06 | (2006.01) |
| A61N 1/372 | (2006.01) |

(52) U.S. Cl.
CPC .............. *A61B 5/064* (2013.01); *A61B 5/4842* (2013.01); *A61N 1/3605* (2013.01); *A61N 1/37282* (2013.01)

(56) References Cited

U.S. PATENT DOCUMENTS

| | | | |
|---|---|---|---|
| 6,730,049 B2* | 5/2004 | Kalvert | A61F 5/0118 600/545 |
| 6,836,744 B1* | 12/2004 | Asphahani et al. | 702/141 |
| 8,321,004 B2* | 11/2012 | Moon | A61B 5/0006 600/509 |
| 8,364,250 B2* | 1/2013 | Moon | A61B 5/0002 600/513 |
| 8,386,007 B2 | 2/2013 | Williams et al. | |
| 8,475,370 B2* | 7/2013 | McCombie | A61B 5/0002 600/301 |
| 8,527,038 B2* | 9/2013 | Moon | A61B 5/0002 600/513 |
| 2002/0126731 A1 | 9/2002 | Stergiopoulos et al. | |
| 2006/0287614 A1* | 12/2006 | Hogan | A61B 5/1107 600/595 |
| 2007/0027631 A1* | 2/2007 | Cabrera | A61B 5/1107 702/19 |
| 2008/0208914 A1 | 8/2008 | Navani | |
| 2009/0012417 A1 | 1/2009 | Carr | |
| 2009/0118787 A1* | 5/2009 | Moffitt et al. | 607/45 |
| 2010/0030119 A1* | 2/2010 | McNames | A61B 5/4082 600/595 |
| 2010/0268551 A1 | 10/2010 | McNames et al. | |
| 2011/0137138 A1* | 6/2011 | Johansson et al. | 600/301 |
| 2011/0224508 A1* | 9/2011 | Moon | 600/301 |
| 2012/0029369 A1 | 2/2012 | Icove et al. | |
| 2013/0158369 A1* | 6/2013 | Yuen et al. | 600/301 |
| 2014/0257143 A1* | 9/2014 | Friedman | A61B 5/1126 600/595 |

OTHER PUBLICATIONS

Figueiras-Mendez, R., C. Magariños-Ascone, I. Regidor, M. del Alamo-De Pedro, L. Cabañes-Martinez, and M. Gómez-Galán. "Deep brain stimulation: 12 years' experience and 150 patients treated with a follow-up of over a year]." Revista de neurologia 49, No. 10 (2009): 511.

Rusk, H., J. Baran, L. Kumbier, and K. Sillay. "Optimization of tremor assessment using the Apple iPhone 4." In Movement Disorders, vol. 26, pp. S358-S358. Commerce Place, 350 Main St, Malden 02148, MA USA: Wiley-Blackwell, 2011.

Sillay, Karl A., Jason C. Chen, and Erwin B. Montgomery. "Long—Term Measurement of Therapeutic Electrode Impedance in Deep Brain Stimulation." Neuromodulation: Technology at the Neural Interface 13, No. 3 (2010): 195-200.

Stefansic, J., V. Morgan, K. Sillay, M. Gorelik, G. Humbert, and R. Thompson (2003). "Integration of functional MRI into a commercial image-guided surgical system." In Proceedings of the 11th Scientific Meeting and Exhibition of the International Society for Magnetic Resonance in Medicine, Toronto, Ontario, Canada. 1930.

Smith, Joseph R., Karl Sillay, Peter Winkler, Don W. King, and David W. Loring. "Orbitofrontal epilepsy: electroclinical analysis of surgical cases and literature review." Stereotactic and functional neurosurgery 82, No. 1 (2004): 20-25.

Albers, T. W. (2011). Development of an Objective Motor Score for Monitoring the Progression and Severity of Parkinson's Disease. Master of Science in Electrical and Computer Engineering, Portland State University, 92 pages.

Fahn, S. R. L. E., R. L. Elton, and UPDRS Development Committee. "Unified Parkinson's disease rating scale." Recent developments in Parkinson's disease 2 (1987): 153-163.

Mamorita, N., et al. 2009. Development of a system for measurement and analysis of tremor using a three-axis accelerometer. Methods Inf Med. 48: 589-594.

McNames, J., "APDM Wearable Inertial Monitors," APDM Inc., 2012, 5 pages.

Boraud T., Tison F., Gross C. Quantification of motor slowness in Parkinson's disease: Correlations between the tapping test and single joint ballistic movement parameters (1997) Parkinsonism and Related Disorders, 3 (1), Elsevier, pp. 47-50.

Dunnewold, R.J.W., Jacobi, C.E., van Hilten, J.J. 1997. Quantitaive assesment of bradykinesia in patients with Parkinson's Disease. J of Neurosc Mthds, Elsevier, 74: 107-112.

Dunnewold RJW, Hoff JI, Van Pelt CJ, et al. Ambulatory quantitative assessment of body position, bradykinesia and hypokinesia in Parkinson's disease. J Clin Neurophysiol 1998; 15(3): 235-42.

Goetz, Christopher G., Glenn T. Stebbins, David Wolff, William DeLeeuw, Helen Bronte—Stewart, Rodger Elble, Mark Hallett et al. "Testing objective measures of motor impairment in early Parkinson's disease: Feasibility study of an at—home testing device." Movement Disorders 24, No. 4 (2009): 551-556.

Hoehn MM, Yahr M MD. Parkinsonism: onset, progression and mortality. Neurology 1967;17: pp. 427-442 (Ovid reprint 1998).

Hoff, J.I., Wagemans, EA., van Hilten, B.J. 2001. Ambulatory Objective Assessment of Tremor in Parkinson's Disease. Clinical Neuropharm. 24(5): 280-283.

McGirt, Matthew J., et al. "The National Neurosurgery Quality and Outcomes Database (N2QOD): general overview and pilot-year project description." Neurosurgical focus 34.1 (2013): E6.

Sillay, Karl, Dominic Schomberg, Angelica Hinchman, Lauren Kumbier, Chris Ross, Ken Kubota, Ethan Brodsky, and Gurwattan Miranpuri. "Benchmarking the ERG valve tip and MRI Interventions Smart Flow neurocatheter convection-enhanced delivery system's performance in a gel model of the brain: employing infusion protocols proposed for gene therapy for Parkinson's disease." Journal of Neural Engineering 9, No. 2 (2012), IOP Publishing: pp. 1-13.

Okun, Michael S., et al. "Piloting the NPF data-driven quality improvement initiative." Parkinsonism & Related Disorders 16.8 (2010): pp. 517-521.

Papavassilou, E., et al, 2004. Thalamic deep brain stimulation for essential tremor: relation of lead location to outcome. Neurosurg 54: 1120-1130.

Papapetropoulos S, Jagid JR, Sengun C, Singer C, Gallo BV: Objective monitoring of tremor and bradykinesia during DBS surgery for Parkinson disease.Neurology 70:1244-1249, 2008.

Patel, S., K. Lorincz, et al. (2009). "Monitoring motor fluctuations in patients with Parkinson's disease using wearable sensors." IEEE transactions on information technology in biomedicine 13(6): 864-873.

Salarian, A., H. Russmann, et al. (2007). "Quantification of tremor and bradykinesia in Parkinson's disease using a novel ambulatory monitoring system." IEEE transactions on bio-medical engineering 54(2): 313-322.

Taylor Tavares, A., Jefferis, G., Koop, M., Hill, B., Hastie, T., Heit, G., BronteStewart, H., 2005. Quantitative measurements of alternating finger tapping in Parkinson's disease correlate with UPDRS motor disability and reveal the improvement in fine motor control from medication and deep brain stimulation. Mov. Disord., vol. 20, pp. 1286-1298.

Yokoe, M. et al. 2009. Opening Velocity, a novel parameter, for finger tapping test in patients with Parkinson's Disease. Parkinsonism and Related Disorders. 15: 440-444.

Yu, H., and Neimat, J.S., 2008. The treatment of movement disorders by deep brain stimulation. Neurotherap 5(1): 26-36.

Zhang et al., 2009. Long-term results of thalamic deep brain stimulation for essential tremor. J Neurosurg, 112, pp. 1271-1276.

* cited by examiner

PATIENT QUESTIONNAIRE - SYMPTOMS — 500

- When were you diagnosed with PD? — 510
- What was your first symptom? — 520
- When did you begin medical treatment? — 530
- When did you begin taking levodopa? — 540
- When did the disease significantly impact your work / home life? — 550
- When were you first considered for surgical therapy? — 560

FIG. 5

MOBILE DEVICE WITH ACELEROMETER & GYROSCOPE

- The timer was turned on, then Video was started.
- The subject was told to start logging motion.
- Then the subject was asked to do 1 pronation/supination, wait 1 second, then do 10 pronation/supinations then wait one second then do a final promation/supination prior to turning off all devices.

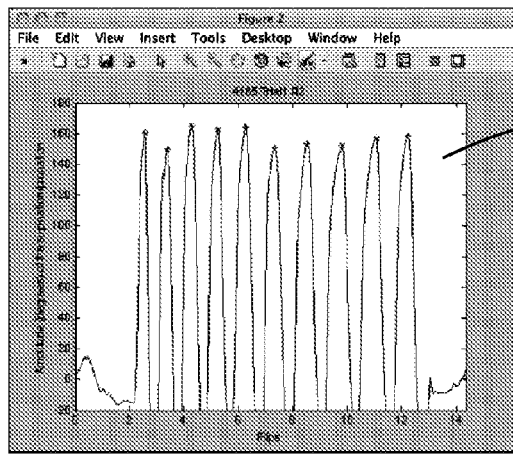
Find the Peaks of the Data
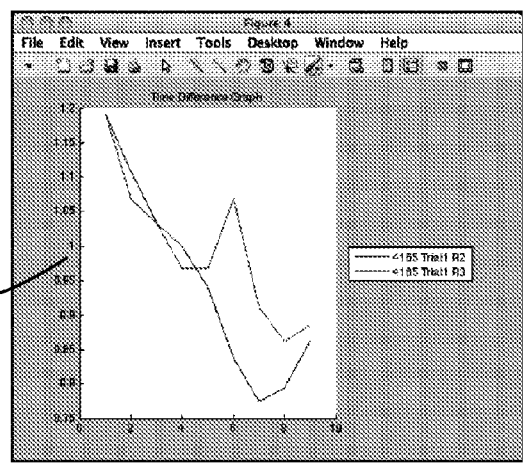
Find the Time Difference Between Peaks
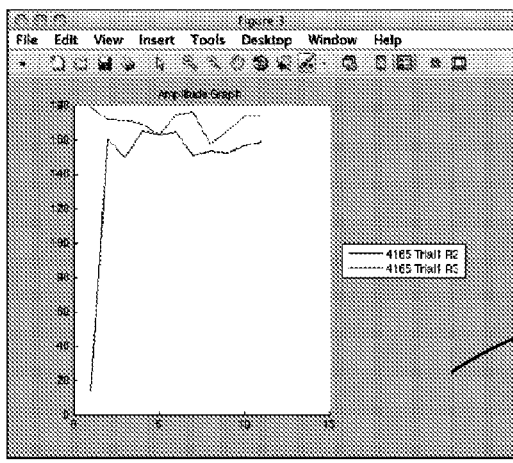
Graph the Peaks over Time
FIG. 13

REPORTING PERMISSIONS MATRIX

| ITEM | GRANULAR | AGGREGATE |
|---|---|---|
| REPORTING TO GOVERNMENT | ( ) YES ( ) NO | ( ) YES ( ) NO |
| REPORTING TO PUBLIC | ( ) YES ( ) NO | ( ) YES ( ) NO |
| REPORTING TO NON-PROFIT | ( ) YES ( ) NO | ( ) YES ( ) NO |
| REPORTING IN FORM OF INVESTIGATOR INITIATED RESEARCH | ( ) YES ( ) NO | ( ) YES ( ) NO |
| REPORTING TO FOR PROFIT ACTIVITIES NON-PAID TO THE DATA OWNER (REPORTING IN FORM OF SPONSORED RESEARCH) | ( ) YES ( ) NO | ( ) YES ( ) NO |
| REPORTING TO FOR PROFIT ACTIVITIES PAID TO THE DATA OWNER | ( ) YES ( ) NO | ( ) YES ( ) NO |

FIG. 17

PD Longitudinal DBS Outcomes Report

| Patient ID<br>Name<br>Age | | | pre-op | | | 6 months | | | 1 year | | |
|---|---|---|---|---|---|---|---|---|---|---|---|
| Target (STN / GPI / Other): Surgery Date: | Exam<br>Examiner: | | | | | | | | | | |
| | | | | | | | | | | | |
| Movement Scores: | MED | DBS | L | R | TTL | L | R | TTL | L | R | TTL |
| SCORED MEASURE:<br><br>UPDRS III | off | off | | | | | | | | | |
| | off | ON | | | ■ | | | | | | |
| | ON | off | | | | | | | | | |
| | ON | ON | | | ■ | | | | | | |
| OBJECTIVE MEASURE:<br><br>Forearm bradykinesia<br>(IOS device) | off | off | | | | | | | | | |
| | off | ON | | | ■ | | | | | | |
| | ON | off | | | | | | | | | |
| | ON | ON | | | ■ | | | | | | |
| Levodopa Equivalents | | | | | | | | | | | |
| Quality of Life Scores: | | | | | TTL | | | TTL | | | TTL |
| PDQ-39 | | | | | | | | | | | |
| NMSQ | | | | | | | | | | | |
| HDRS | | | | | | | | | | | |

FIG. 26

Reports – Gender / Age Breakdown

Back to Reports List
Both Male and Female

| # active implants | # of Men | # of Women | Min Age | Max Age | Mean | # of people in Mean | Std Deviation |
|---|---|---|---|---|---|---|---|
| 0 | 0 | 0 | 99999 | 0 | 0 | 0 | 0 |

Male

| # active implants | # of Men | # of Women | Min Age | Max Age | Mean | # of people in Mean | Std Deviation |
|---|---|---|---|---|---|---|---|
| 0 | 0 | 0 | 99999 | 0 | 0 | 0 | 0 |

Female

| # active implants | # of Men | # of Women | Min Age | Max Age | Mean | # of people in Mean | Std Deviation |
|---|---|---|---|---|---|---|---|
| 0 | 0 | 0 | 99999 | 0 | 0 | 0 | 0 |

All Active Patients

| Patient ID | Name | Age | Gender | Active |
|---|---|---|---|---|

FIG. 27

Consent Report

OK to Contact for Patient Referrals

| Patient ID | Name | Age | Gender | Patient Consent | Notes |
|---|---|---|---|---|---|

OK to Contact for Research

| Patient ID | Name | Age | Gender | Patient Consent | Notes |
|---|---|---|---|---|---|

Consent for Video / Photograph

| Patient ID | Name | Age | Gender | Patient Consent | Notes |
|---|---|---|---|---|---|

FIG. 29

Surgery Report

Back to Reports List

| Patient ID | Name | Surgery Date | Surgery Type | Target | DTI |
|---|---|---|---|---|---|

FIG. 30

Calculated Active X/Y/Z

Back to Reports List
CALCULATED Ax Ay Az
If there are blanks it's because you either don't have the correct Serial Number selected in the patient's "Surgery -> Implant record" or there isn't a "Surgery -> Implant" record to match up with the "Programming Visit" Record.

| Patient ID | Name | Last Visit Date | Loc | Serial # | Target C | 0 | 1 | 2 | 3 | V | PW | Rate | Imp | BV | Cur | O1 | O2 | O3 | O4 | Postop Target X | Postop Target Y |
|---|---|---|---|---|---|---|---|---|---|---|---|---|---|---|---|---|---|---|---|---|---|

| Postop Target Z | Postop Entry X | Postop Entry Y | Postop Entry Z | AX | AY | AZ | CAX | CAY | CAZ | Notes |
|---|---|---|---|---|---|---|---|---|---|---|

FIG. 31

Reports - Left and Right with Distance from Ave Target

Back to Reports List

R GPi

| Patient ID | Name | Surgery ID | Electrode Type | Surgery Date | Hospital | Loc | Target | Type | Target X | Target Y | Target Z | XYZ Distance from Avg R Target |
|---|---|---|---|---|---|---|---|---|---|---|---|---|
| | | | | | | | | R Average | 0 | 0 | Count 0 | 0 |
| | | | | | | | | | | | 0 | 0 |

L GPi

| Patient ID | Name | Surgery ID | Electrode Type | Surgery Date | Hospital | Loc | Target | Type | Target X | Target Y | Target Z | XYZ Distance from Avg L Target |
|---|---|---|---|---|---|---|---|---|---|---|---|---|
| | | | | | | | | L Average | 0 | 0 | Count 0 | 0 |

R & L Averages w/ TTL Average

| | | | | | | | | R Average | 0 | 0 | 0 | 0 |
| | | | | | | | | L Average | 0 | 0 | 0 | 0 |
| | | | | | | | | TTL Average | 0 | 0 | 0 | 0 |

FIG. 32

Active Implant Report

| Patient ID | Name | Visit Date | Loc | Serial # | Target | C | 0 | 1 | 2 | 3 | V | PW | Rate | Imp | BV | Cur |
|---|---|---|---|---|---|---|---|---|---|---|---|---|---|---|---|---|

| O1 | O2 | O3 | O4 | AX | AY | AZ | Postop Target X | Postop Target Y | Postop Target Z |
|---|---|---|---|---|---|---|---|---|---|

| Postop Entry X | Postop Entry Y | Postop Entry Z | Notes |
|---|---|---|---|

FIG. 33

FIG. 34A Outcomes Report 1 (TOP PORTION)

All Active Implants with Impedances

Back to Reports List

Table 'sillay_sandbox.VisitProgrammerData' doesn't exist

| Patient ID | Name | Visit Date | Active | Loc | Serial # | Target | C | 0 | 1 | 2 | 3 | V | PW | Rate | Imp | BV | Cur |
|---|---|---|---|---|---|---|---|---|---|---|---|---|---|---|---|---|---|

| O1 | O2 | O3 | O4 | AX | AY | AZ | Postop Target X | Postop Target Y | Postop Target Z | Postop Entry X | Postop Entry Y | Postop Entry Z | Notes | V | LS | Hz |
|---|---|---|---|---|---|---|---|---|---|---|---|---|---|---|---|---|

| 0&C Imp | 0&C Cur | 1&C Imp | 1&C Cur | 2&C Imp | 2&C Cur | 3&C Imp | 3&C Cur | 0&1 Imp | 0&1 Cur | 0&2 Imp | 0&2 Cur | 0&3 Imp | 0&3 Cur | 1&2 Imp | 1&2 Cur |
|---|---|---|---|---|---|---|---|---|---|---|---|---|---|---|---|

| 1&3 Imp | 1&3 Cur | 2&3 Imp | 2&3 Cur | 4&C Imp | 4&C Cur | 5&C Imp | 5&C Cur | 6&C Imp | 6&C Cur | 7&C Imp | 7&C Cur | 4&5 Imp | 4&5 Cur | 4&6 Imp | 4&6 Cur |
|---|---|---|---|---|---|---|---|---|---|---|---|---|---|---|---|

SURGERY RECORD 1/2

0TEST (AP)

UW # 0123456789

Surgery Record
- Scheduler
- Patients
- Reports
- UPDRS Pool

- Pending
- Candidates
- Completed
- Aborted
- Canceled
- New Patient
- New Surgery
- View Patient Record

General

| Surgery Date | Conference Date | Age at Surgery | Hospital | Diagnosis | Surgery Type | Procedure |
|---|---|---|---|---|---|---|
| 01/01/2007 | 01/01/1999 | 67 | UW | PD | | DBS - STN, Bilateral |

| Surgeon | Resident | Sillay Out of Town | Neurologist | Surgery Category | Status |
|---|---|---|---|---|---|
| Neurosurgeon | NA | | Neurologist | | Completed |

[Save]

Pre-Op

| Weblink # | OR-Time (HH:MM:SS) | Hospital Days | Inpatient Reservation | CPT Description |
|---|---|---|---|---|
| NA | | 39 | NA | NA |

| Admit Date | Discharge Date | Technique | DBS Target | Comments Pre-Op |
|---|---|---|---|---|
| 08/29/2007 | | CRW; Microelectr | STN | NA |

| Protocol | Intra Operative MR | Surgery Side | Arm | Category |
|---|---|---|---|---|
| NA | NO | | MD | Functional |

Mapping

[Save]

Diagnostic Studies

| Diagnostic Studies | Neurologist Available | X-Ray | Angiography | Isotope Scan | Myelography |
|---|---|---|---|---|---|
| YES | YES | YES | NO | NO | NO |
| TCD | EEG | LP | EMG | Duplex Ultrasound | PET |
| NO | NO | NO | NO | NO | NO |
| Preop MRI | Postop MRI | Preop CT | Postop CT | SPECT Scan | WADA scan |
| YES | YES | YES | NO | NO | NO |

FIG. 40

SURGERY RECORD 2/2

FIG. 41

Surgical Record Data Structure 7

Surgery Data - Complications 4900

- Complication Description 4902
- Asymtopmatic Hemorrhage Size 4904
- Non Hemorrhage Stroke 4906
- Intraop Seizures 4908
- Postop Seizure 4910
- Postop Seizure Single 4912
- Postop Seizure Multiple 4914
- Lead Fracture Associated with Cervical Connector 4916
- Lead Fracture Not Associated with Cervical Connector 4918
- Infection IV Only No Hardware Removal 4920
- Infection PO Only 4922
- Infection Requiring Removal 4924
- Device Erosion 4926
- Return to OR for Other HW or Incision Problem 4928
- Return Description 4930
- Suicide Attempt 4932
- Psychiatric Hospital 4934
- Other Complication 4936
- Other Complication Description 4938
- Re-Operation 4940

FIG. 49

Surgical Record Data Structure 8

- Programming Information - Including Active Implants / Contacts and Outcome Measure   5000
  - Date of programming change   5002
  - Stimulator serial numbers   5004
  - Active electrode combinations   5006
  - Active electrode voltages/currents   5008
  - Active elctrode pulse width, duration, waveform   5010
  - Active electrode stimulation frequency   5012
  - Pair-wise and therapeutic electrode impedance   5014
  - Calculated, vectored tissue impedance   5016
  - Battery status, voltage, remaining mAHrs   5018
  - Clinical response at test stimulation settings (including UPDRS III subscores [finger tapping, hand opening, tone, tremor])   5020
  - Clinical side effects (including phospenes, visual changes, tonic contraction, speech changes, and others)   5022
  - Updated Current Active Contact(s)   5024
  - Outcomes (1 month / 3 month/ 6 month / 1Year / 2 Year / 5 Year /10 Year)   5026

FIG. 50

Anatomical Implant Locations

Interoperative Brain Shift

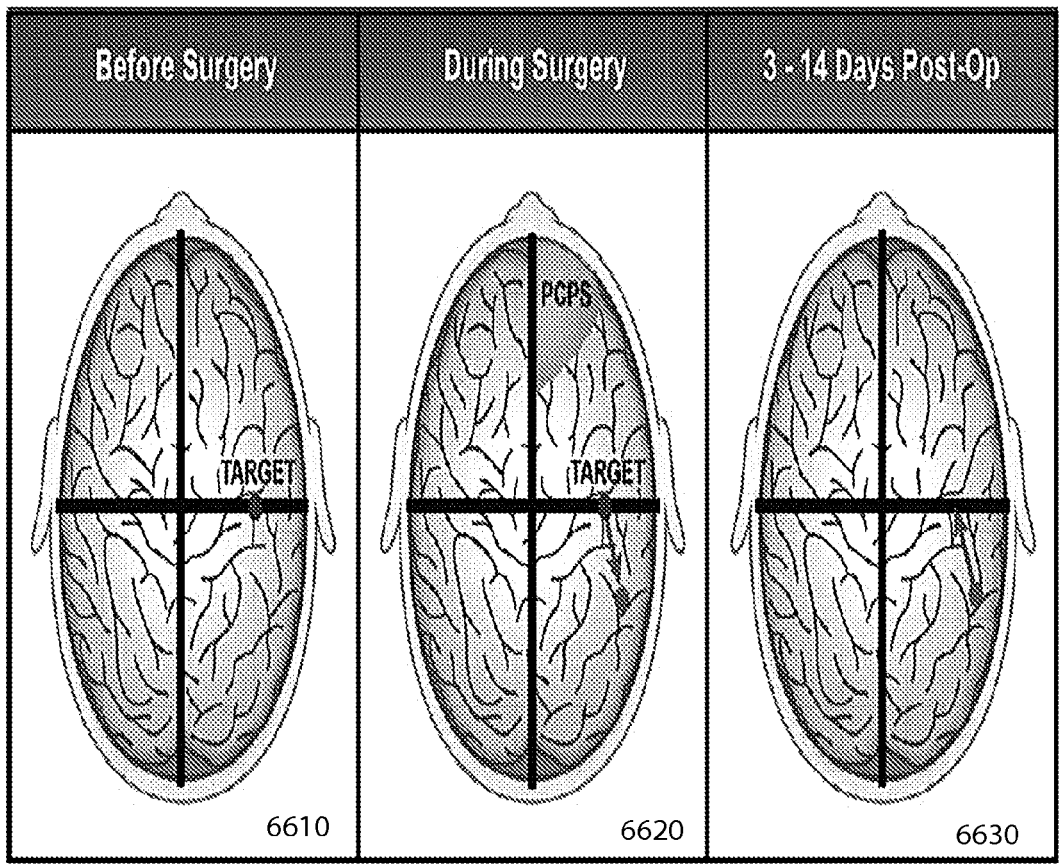

Three stage characterization of brain shift. Brain shift, and thus, electrode displacement, occurs in three distinct stages. Prior to surgery, a target location is determined based on the brain in its original position (no shift has occurred yet). Then, during surgery, as subdural air (PCPS) rushes into the brain, the brain shifts, as does the target location. Intraoperative electrophysiology or imaging is required to adjust the implant trajectory, and the electrode is implanted into a shifted brain. Finally, on average, 3-14 days following surgery, the PCPS resolves, and the brain is allowed to return to its original position and shifts back. However, this means that the target location and electrode will also shift. It is when the brain shifts back to its original position that electrode tip displacement occurs. The figure above depicts a unilateral surgery, with subdural air on the surgery side. Thus, the middle brain shows an unshifted left-brain and a shifted right-brain.

FIG. 66

Electrode Segmentation

Visualization of electrode segmentation of electrode performed from stereotatic CT image following pneumocephalus resolution.

These are UPDRS records from the iPad App that did not match up to any existing Patient MR#

Click a Patient Name to link it to an existing Patient Record

| PDF | Patient | MR# | Exam Date | Examiner |
|-----|---------|-----|-----------|----------|

FIG. 75

OTEST (AP)            UW # 2407863 — 7605

General — 7610

| Last Name | First Name | UW MR# | VA MR# | Epic MR# | Gender |
|---|---|---|---|---|---|
| OTEST | AP | 2407863 | | | Male |

| Birthdate (mm/dd/yyyy) | Current Age | Deceased | Handedness | Smoker | Packs / Day |
|---|---|---|---|---|---|
| 07/12/1942 | 70 | No | | | |

[Save]

History — 7615

| Previously Seen | Most Recent Clinic Visit | Details |
|---|---|---|
| Yes | 03/24/2009 | NA |

| Outside Hospital Care | Referring Physician | Details |
|---|---|---|
| | | NA |

Parkinsons — 7620

| Refractory Date | Date Evaluated | Diagnosis Date (MM/DD/YYY) | Medication Date | Levodopa Date |
|---|---|---|---|---|
| NO | NO | | NA | NA |

Epilepsy — 7625

| Age of Seizure Onset | Seizure Type | Seizure Frequency | Seizure Semiology |
|---|---|---|---|
| NO | NO | NO | NO |

Consent — 7630

| Ok to contact for patient referral? | Details |
|---|---|
| | NA |

| Ok to contact regarding research? | Details |
|---|---|
| | NA |

| Ok to photograph / videotape? | Details |
|---|---|
| | NA |

[Save] — 7635

FIG. 76A

Surgeries — 7640

<u>Add Surgery</u> — 7642

| Surgery ID | Surgery Date | Procedure | Side | Surgery Type | Target | Surgery Category | Status | 1 month | 3 month | 6 month | 1 year | 2 year | 5 year | 10 year |
|---|---|---|---|---|---|---|---|---|---|---|---|---|---|---|
| <u>306</u> | 10/30/2007 | DBS - STN, Bilateral | | | STN | | completed | | | | | | | |
| <u>305</u> | 01/16/2008 | Bilateral IPG | | | | | completed | | | | | | | |

IPG's — 7645

<u>Add IPG</u> — 7647

| ID# | Implant Date | Serial Number | Model | Channels 0-3 | Channels 4-7 | Channels 0-3 Active | Channels 4-7 Active |
|---|---|---|---|---|---|---|---|
| <u>4</u> | 01/16/2008 | N████7 | Soletra | Left | Empty | Yes | No |
| <u>5</u> | 01/16/2008 | N████9 | Soletra | Right | Empty | Yes | No |

Active IPG's — 7650

| ID# | Implant Date | Serial Number | Model | Channels 0-3 | Channels 4-7 | Channels 0-3 Active | Channels 4-7 Active |
|---|---|---|---|---|---|---|---|
| <u>4</u> | 01/16/2008 | N████7 | Soletra | Left | Empty | Yes | No |
| <u>5</u> | 01/16/2008 | N████9 | Soletra | Right | Empty | Yes | No |

FIG. 76B

Anatomic Implants — 7655

| Implant ID | Surgery ID | Serial # | Surgery Date | Hospital Loc | Target | Target X | Target Y | Target Z | Entry X | Entry Y | Entry Z |
|---|---|---|---|---|---|---|---|---|---|---|---|
| 17 | 306 | ▮7 | 2007-10-30 | UW | Left | STN | -10.56 | -5.72 | -6.42 | -28.59 | 29.27 | 56.19 |
| 18 | 306 | ▮9 | 2007-10-30 | UW | Right | STN | 10.79 | -4.13 | -5.97 | 26.62 | 25.77 | 58.23 |

Programming Visits — 7660

7662
Add Visit | View Only Left | View Only Right | View All

| ID# | Active | Visit Date | Loc | Serial # | C | 0 | 1 | 2 | 3 | V | PW | Rate | Imp | BV | Cur | O1 |
|---|---|---|---|---|---|---|---|---|---|---|---|---|---|---|---|---|
| 45 | Yes | 03/24/2009 | Left | N▮7 | 0 | 0 | 1 | -1 | 0 | 3.5 | 90 | 145 | 658 | 3.74 | NA | NA |
| 46 | No | 01/29/2009 | Left | N▮7 | 0 | 0 | 1 | -1 | 1 | 3.5 | 90 | 135 | 643 | 3.75 | NA | NA |
| 19 | No | 11/12/2008 | Left | N▮7 | 0 | 0 | 1 | -1 | 1 | 3.5 | 90 | 135 | 726 | 3.75 | 0 | 0.5 |
| 49 | No | 08/14/2008 | Left | N▮7 | 1 | 0 | 0 | 0 | -1 | 3 | 120 | 130 | 1063 | 3.74 | NA | NA |
| 50 | No | 07/03/2008 | Left | N▮7 | 1 | 0 | 0 | 0 | -1 | 2.5 | 90 | 145 | 1108 | 3.75 | NA | NA |
| 52 | No | 06/10/2008 | Left | N▮7 | 1 | 0 | 0 | 0 | -1 | 2.9 | 90 | 145 | 1078 | 3.75 | NA | NA |
| 55 | No | 01/17/2008 | Left | N▮7 | 1 | 0 | 0 | 0 | -1 | 1.5 | 90 | 130 | 1178 | 3.75 | NA | NA |
| 23 | Yes | 03/24/2009 | Right | N▮9 | 1 | 0 | 0 | 0 | -1 | 1 | 90 | 160 | 1201 | 3.74 | NA | NA |
| 47 | No | 01/29/2009 | Right | N▮9 | 1 | 0 | 0 | 0 | -1 | 1 | 90 | 130 | 1433 | 3.74 | NA | NA |
| 20 | No | 11/12/2008 | Right | N▮9 | 1 | 0 | 0 | -1 | 0 | 2.4 | 90 | 170 | 1373 | 3.72 | NA | 0 |
| 48 | No | 08/14/2008 | Right | N▮9 | 1 | 0 | 0 | -1 | 0 | 2.4 | 90 | 170 | 893 | 3.72 | NA | NA |
| 21 | No | 07/11/2008 | Right | N▮9 | 1 | 0 | -1 | 0 | 0 | 2.5 | 90 | 170 | 816 | 3.72 | NA | 0 |
| 51 | No | 07/03/2008 | Right | N▮9 | 1 | 0 | 0 | -1 | 0 | 2.8 | 90 | 135 | 913 | 3.72 | NA | 0 |
| 22 | No | 06/10/2008 | Right | N▮9 | 1 | 0 | -1 | 0 | 0 | 2.4 | 90 | 160 | 954 | 3.72 | 0 | NA |
| 53 | No | 05/14/2008 | Right | N▮9 | 1 | 0 | -1 | 0 | 0 | 2.1 | 90 | 160 | 982 | 3.72 | NA | NA |
| 54 | No | 01/17/2008 | Right | N▮9 | 1 | 0 | -1 | 0 | 0 | 2.3 | 90 | 130 | 1076 | 3.72 | NA | NA |

UPDRS records — 7665

FIG. 76C

Programming Visit 1

<u>0TEST (AP)</u> — 7810

UW # 0123456789

Programming Visits - Soletra — 7710  IPG Serial Number: NFW117907  Session Date 03/24/2009

Intermediate Data — 7820

| Trial | Voltage | PW | Rate | Case | 0 | 1 | 2 | 3 | 4 | 5 | 6 | 7 | Notes |
|---|---|---|---|---|---|---|---|---|---|---|---|---|---|
|  |  |  |  |  |  |  |  |  |  |  |  |  |  |

[Save & Add Row] [Save Row Data]

Final Data — 7830  Type of Visit [Other]  Session Date [03/24/2009]  Battery Voltage [3.74]

| Ratings Scales Done on Clinical Drive | | |
|---|---|---|
| Dystonia | | |
| BFM |  | |
| GDRS |  | |
| HDRS |  | |
| BECKS |  | |
| Essential Tremor | | |
| TRS |  | |
| Parkinson's | Location | Score |
| Examiner |  | |
| Ham-D |  | |
| UPDRS(Full) off off |  | |
| off on |  | |
| on off |  | |
| on on |  | |

| Electrode 1 | |
|---|---|
| General | |
| Serial Number | NFW117907 / Add IPG |
| Active | Yes |
| Time Stamp (in format hh:mm - hh:mm) |  |
| Lead Location | Left |
|  | |
| Electrodes | C  0 |
|  | 0  0 |
|  | 1  1 |
|  | 2  -1 |
|  | 3  0 |
|  | |

FIG. 78

Programming Visit 2

| | | | Programming | End Results |
|---|---|---|---|---|
| UPDRS(Part3) off off | | | Power State | On |
| off on | | | Amp (V) | 3.5 |
| on off | | | PW | 90 |
| on on | | | Rate | 145 |
| PDQ-39 | | | | |
| NMSQ | | | Therapy Measurements | Values |
| Video | | | Impedance | 658 |
| Video on Server | | | Current | NA |
| Impedance Done | | | Active Contact ACPC coordinates | |
| Impedance Done | | | X | -11.87058563 |
| MVD database | | | Y | -3.176606137 |
| Sillay database | | | Z | -1.922791804 |
| Involved in Research | | | | |

[Save]

Notes

Optional Field 1: NA
Optional Field 2: NA
Optional Field 3: NA
Optional Field 4: NA

Electrode Impedances

| | V | |
|---|---|---|
| | us | |
| | Hz | |

| Pair | Impedance | >2000? | Current | >2000? |
|---|---|---|---|---|
| 0 & c | | 0 | | 0 |
| 1 & c | | 0 | | 0 |
| 2 & c | | 0 | | 0 |
| 3 & c | | 0 | | 0 |
| 0 & 1 | | 0 | | 0 |
| 0 & 2 | | 0 | | 0 |
| 0 & 3 | | 0 | | 0 |
| 1 & 2 | | 0 | | 0 |
| 1 & 3 | | 0 | | 0 |
| 2 & 3 | | 0 | | 0 |

[Save]

FIG. 79

0TEST (AP)

UW # 0123456789

General — 8010

| Surgery Date | Conference Date | Age at Surgery | Hospital | Diagnosis | Surgery Type | Procedure |
|---|---|---|---|---|---|---|
| 01/01/2007 | 01/01/1999 | 67 | UW | PD | | DBS - STN, Bilateral |

| Surgeon | Resident | Sillay Out of Town | Neurologist | Surgery Category | Status |
|---|---|---|---|---|---|
| Neurosurgeon | NA | | Neurologist | | Completed |

Save — 8020

Pre-Op — 8030

| Weblink # | OR-Time (HH:MM:SS) | Hosptial Days | Inpatient Reservation | CPT Description |
|---|---|---|---|---|
| NA | | 39 | NA | NA |

| Admit Date | Discharge Date | Technique | DBS Target | Comments Pre-Op |
|---|---|---|---|---|
| 08/29/2007 | | CRW; Mircoelectr | STN | NA |

| Protocol | Intra Operative MR | Surgery Side | Arm | Category |
|---|---|---|---|---|
| NA | NO | | MD | Functional |

Mapping

Save — 8040

Diagnostic Studies — 8050

| Diagnostic Studies | Neurologist Available | X-Ray | Angiography | Isotope Scan | Myelography |
|---|---|---|---|---|---|
| YES | YES | YES | NO | NO | NO |
| TCD | EEG | LP | EMG | Duplex Ultrasound | PET |
| NO | NO | NO | NO | NO | NO |
| Preop MRI | Postop MRI | Preop CT | Postop CT | SPECT Scan | WADA scan |
| YES | YES | YES | NO | NO | NO |

FIG. 80

| DTI | Psychology Evaluation |
|---|---|
|  | NA |

Save — 8100

Intra-op — 8110

| Pulse Generator Model | Connector Model | Other Connector Model | Pics or Videos | Pathology |
|---|---|---|---|---|
| SOLETRA | 7482-40 | NO | NO | NA |

Notes
NA

Save — 8120

Metrics — 8130

| CRW Frame | AC Location | PC Location | MRI Initial Anatomic Target | MRI Final Anatomic Target | MRI Final Target |
|---|---|---|---|---|---|
| (-12.3,-4,8.4,59. | NA | NA | (-12,-4,-5);(12,- | (-12,-4,-5.02);(1 | (-10.56,-5.72,-6 |
| ACPC Length | T1 3rd Vent Width | Brain Width | Max Brain Width | Brain Length | |
| 26.13 | 5.00 | 126.80 | 129.90 | 171.40 | |

Save — 8140

Target Information — 8150

| Approximate STN Start | Actual STN Start | Approximate STN End | Actual STN End |
|---|---|---|---|
|  |  |  |  |
| STN Motor Top | STN Motor Bottom | Approximate SNR | Actual SNR |
|  |  |  |  |

Save — 8160

Complications — 8170

Were there Complications?

Save — 8180

FIG. 81A

Implants  8190
Add Implant
| Implant ID | Target | Side of Brain | Active |
|---|---|---|---|
| <u>17</u> | STN | Left | Yes |
| <u>18</u> | STN | Right | Yes |
Outcomes  8195
| 1 Month - 2/01/2007 | 3 Month - 4/01/2007 | 6 Month - 7/01/2007 | |
|---|---|---|---|
| ☐ | ☐ | ☐ | |
| 1 Year - 1/01/2008 | 2 Year - 1/01/2009 | 5 Year - 1/01/2012 | 10 Year - 1/01/2017 |
| ☐ | ☐ | ☐ | ☐ |
FIG. 81B

Reports Selection Menu

Consent

Active Implants

Active Implants with Electrode Impedances

All Implants with Electrode Impedances

Anatomic Target XYZ and Entry XYZ

Left and Right Reports with Distance from Ave Target

Calculated Active X, Y, Z

Gender and Age Breakdown

Surgery Type is DBS

Epilepsy

FIG. 84

0TEST (AP) —— 8710

UW #
0123456789

| Target | Side | Electrode Type | IPG —— 8720 | Active |
|---|---|---|---|---|
| STN | Left | m-3387 | | Yes |

[Save] —— 8730

Target Information —— 8740

Approximate STN Start    Actual STN Start    Approximate STN End    Actual STN End STN Motor Top    STN Motor Bottom    Approximate SNR    Actual SNR New Trajectory —— 8750

[submit]

Existing Trajectories —— 8760

| Details ID | Type of Traj | Intra-op Number |
|---|---|---|
| 143 | Intra-op Estimated Implant | 8762 |
| 139 | Intra-op Traj | 1 — 8764 |
| 140 | Post-op Actual Implant | 8766 |
| 138 | Pre-op Traj | 8768 |

FIG. 87

0TEST (AP)

UW # 0123456789

| Target | Side | Active | Intra-op Traj Number | Type of Trajectory |
|--------|------|--------|----------------------|---------------------|
| STN | Left | Yes | | Pre-op Traj |

8802 — Preop (Target)
| (x) | -12 |
| (y) | -4 |
| (z) | -5 |

Preop (Entry) — 8804
| (x) | -29.19 |
| (y) | 30.14 |
| (z) | 53.32 | submit

0TEST (AP)

UW #
0123456789

| Target | Side | Active | Intra-op Traj Number | Type of Trajectory |
|--------|------|--------|----------------------|--------------------|
| STN    | Left | Yes    |                      | Intra-op Estimated Implant |

— 8818

| Preop (Target) | | Preop (Entry) | | Net Intraop Offset | Final Intraop Offset |
|---|---|---|---|---|---|
| (x) | -12 | (x) | -29.19 | (x) | (x) |
| (y) | -4  | (y) | 30.14  | (y) | (y) |
| (z) | -5  | (z) | 53.32  | (z) | (z) |

— 8820

| Target Coordinates CRW / FRAME | | | | Net Offset (ACPC) Method 1 | | Tract Target coordinates (AC-PC) | |
|---|---|---|---|---|---|---|---|
| LAT (x) | | Ring | | Lat (x) (left move (-) / right move (+)) | | LAT (x) | |
| A-P (y) | | Arc | | A-P (y) | | A-P (y) | |
| Vert (z) | | BenGun Hole Offset X | | VERT (z) | | VERT (z) | |
| | | BenGun Hole Offset Y | | Movements Taken | | | |

— 8830

[Save] — 8840

Locations and Notes — 8850

| Track Number | Count | Site Number | Depth | Hz Code | Density Code | Type - Regular | Type - Irregular | Type - Bursting | Type - Transient | Type - Persistant | Type Notes | Probable Target STN | Probable Target GPI | Distance from target | Frequency HZ | Bursting | Pausing | Hz Notes | Activity Descrip |
|---|---|---|---|---|---|---|---|---|---|---|---|---|---|---|---|---|---|---|---|
| | | | | | | | | | | | | | | | | | | | |

Add Row — 8860

FIG. 88C

Surgery Trajectory - Post-op

0TEST (AP)

UW # 0123456789

| Target | Side | Active | Intra-op Traj Number | Type of Trajectory |
|--------|------|--------|----------------------|---------------------|
| STN | Left | Yes | | Post-op Actual Implant |

| Preop (Target) | Preop (Entry) | Postop (Target) | Postop (Entry) |
|----------------|---------------|-----------------|----------------|
| (x) -12 | (x) -29.19 | (x) -10.56 | (x) -28.59 |
| (y) -4 | (y) 30.14 | (y) -5.72 | (y) 29.27 |
| (z) -5 | (z) 53.32 | (z) -6.42 | (z) 56.19 |

| Radial Error | PostPreXYZ Error | PostPreXY Error | PostIntraXYZ Error | PostIntraXY Error | IntraPreXYZ Error | IntraPreXY Error |
|---|---|---|---|---|---|---|
| | | | | | | |

Error Notes

[ Save ]

FIG. 89

IPG Entry Screen

0TEST (AP)

UW #
0123456789

| | | | IPG 9010 | | | |
|---|---|---|---|---|---|---|
| Serial Number | Implant Date | Model | Channels 0-3 | Channels 4-7 | Channels 0-3 Active | Channels 4-7 Active |
| Serial number | 01/01/2008 | Soletra | Left | Empty | Yes | No |

Save — 9020

FIG. 90

EHR Patient Interaction Workflow

Data Exchange Mapping Matrix

| ITEM | GRANULAR | AGGREGATE |
|---|---|---|
| DATA EXCHANGE: ALLOW IDENTIFICATION OF PROTECTED HEALTH INFORMATION | ( ) YES ( ) NO | N/A |
| DATA EXCHANGE: ALLOW EXCHANGE OF DATA WITH OTHER PROVIDERS | ( ) YES ( ) NO | ( ) YES ( ) NO |

FIG. 96

Figures of Individual Users in Various Positions

Mobile Data Acquisition Devices on Feet and Limb

| ELEMENT | RNF CODE | CONFIDENTIAL TO PUBLIC IN AGGREGATE | CONFIDENTIAL TO PUBLIC GRANULAR WITHOUT PERMISSION | CONFIDENTIAL TO PUBLIC GRANULAR PER USER AGREEMENT | CONFIDENTIAL TO PUBLIC WITH EXPLICIT ONE TIME PERMISSION | CONFIDENTIAL TO HEALTH CARE PROVIDER IN AGGREGATE | CONFIDENTIAL TO HEALTH CARE PROVIDER GRANULAR WITHOUT PERMISSION | CONFIDENTIAL TO HEALTH CARE PROVIDER GRANULAR PER USER AGREEMENT | CONFIDENTIAL TO HEALTH CARE PROVIDER EXPLICIT ONE TIME PERMISSION | CONFIDENTIAL TO INDUSTRY IN AGGREGATE | CONFIDENTIAL TO INDUSTRY GRANULAR WITHOUT PERMISSION | CONFIDENTIAL TO INDUSTRY GRANULAR PER USER AGREEMENT | CONFIDENTIAL TO INDUSTRY WITH EXPLICIT ONE TIME PERMISSION | CONFIDENTIAL TO INSURANCE IN AGGREGATE | CONFIDENTIAL TO INSURANCE GRANULAR WITHOUT PERMISSION | CONFIDENTIAL TO INSURANCE GRANULAR PER USER AGREEMENT | CONFIDENTIAL TO INSURANCE WITH EXPLICIT ONE TIME PERMISSION | CONFIDENTIAL TO GOVERNMENT IN AGGREGATE | CONFIDENTIAL TO GOVERNMENT GRANULAR WITHOUT PERMISSION | CONFIDENTIAL TO GOVERNMENT GRANULAR PER USER AGREEMENT | CONFIDENTIAL TO GOVERNMENT WITH EXPLICIT ONE TIME PERMISSION |
|---|---|---|---|---|---|---|---|---|---|---|---|---|---|---|---|---|---|---|---|---|---|
| Last Name | Q-1 | 0 | 0 | 0 | 0 | 0 | 0 | 0 | 0 | 0 | 0 | 0 | 0 | 0 | 0 | 0 | 0 | 0 | 0 | 0 | 0 |
| Zip Code | Q-2 | 1 | 0 | 0 | 1 | 1 | 0 | 1 | 1 | 1 | 0 | 0 | 1 | 1 | 0 | 1 | 1 | 1 | 0 | 1 | 1 |
| Symptom Date | Q-3 | 1 | 0 | 0 | 1 | 1 | 0 | 1 | 1 | 1 | 0 | 0 | 1 | 1 | 0 | 1 | 1 | 1 | 0 | 1 | 1 |
| Meds Date | Q-4 | 1 | 0 | 0 | 1 | 1 | 0 | 1 | 1 | 1 | 0 | 0 | 1 | 1 | 0 | 1 | 1 | 1 | 0 | 1 | 1 |
| Surgery Date | Q-5 | 1 | 0 | 0 | 1 | 1 | 0 | 1 | 1 | 1 | 0 | 0 | 1 | 1 | 0 | 1 | 1 | 1 | 0 | 1 | 1 |
| SM PRE | SM-1 | 1 | 0 | 0 | 1 | 1 | 0 | 1 | 1 | 1 | 0 | 0 | 1 | 1 | 0 | 1 | 1 | 1 | 0 | 1 | 1 |
| OM PRE | OM-1 | 1 | 0 | 0 | 1 | 1 | 0 | 1 | 1 | 1 | 0 | 0 | 1 | 1 | 0 | 1 | 1 | 1 | 0 | 1 | 1 |
| Daily Diary | M-01 | 0 | 0 | 0 | 0 | 0 | 0 | 0 | 1 | 0 | 0 | 0 | 1 | 0 | 0 | 0 | 1 | 0 | 0 | 0 | 0 |
| Ave. Med Use | R-01 | 1 | 0 | 0 | 0 | 0 | 0 | 0 | 1 | 0 | 0 | 0 | 1 | 0 | 0 | 0 | 1 | 0 | 0 | 0 | 1 |

FIG. 108A

| ELEMENT | RNF CODE | M-01: Daily Diary | M-02: Medication Reminder | M-03: Location Based Reminder | M-04: Video Reminder | M-05: Objective Measures Acquisition |
|---|---|---|---|---|---|---|
| Activity | Q-11 | 0 | 0 | 1 | 1 | 1 |
| Medications | Q-12 | 1 | 1 | 1 | 1 | 1 |
| Symptoms | Q-13 | 1 | 0 | 1 | 1 | 1 |
| GPS location | Q-14 | 1 | 0 | 1 | 1 | 1 |
| AVE speed | Q-15 | 1 | 0 | 0 | 1 | 1 |
| SM UPDRS | SM-1 | 1 | 0 | 0 | 1 | 0 |
| OM P/S | OM-1 | 1 | 0 | 1 | 0 | 1 |

FIG. 108B

| ELEMENT | RNF CODE | R-01: Population Density By Zip Code | R-01: Average Medication Use | R-03: Average Objective Measure by Time from Surgery | R-04: Driving vs. Walking vs. Sedentary By Surgery |
|---|---|---|---|---|---|
| Zip Code | Q-02 | 1 | 0 | 0 | 0 |
| Surgery Date | Q-05 | 0 | 0 | 1 | 1 |
| Activity | Q-11 | 0 | 0 | 0 | 1 |
| Medications | Q-12 | 0 | 1 | 0 | 0 |
| Symptoms | Q-13 | 0 | 0 | 0 | 0 |
| GPS location | Q-14 | 0 | 0 | 0 | 0 |
| AVE speed | Q-15 | 0 | 0 | 0 | 0 |
| SM UPDRS | Q-16 | 0 | 0 | 0 | 1 |
| OM P/S | Q-17 | 0 | 0 | 0 | 1 |

FIG. 108C

PATIENT PERMISSION-BASED MOBILE HEALTH-LINKED INFORMATION COLLECTION AND EXCHANGE SYSTEMS AND METHODS

TECHNICAL FIELD

Embodiments of systems and methods for health data collection and sharing relate to the technical field of objective medical health data collection utilizing mobile telecommunications apparatus or an alternative device, a health-linked database hierarchy, social networking for those diagnosed with disease, a permission system for health-based data sharing and linked health data exchange network for access by the diagnosed, medical practitioners, insurance carriers, medical researchers and others having access permission.

BACKGROUND

In today's medical environment, it is common for those diagnosed with chronic disorders, their medical practitioners, insurance carriers, medical researchers and scientists to have a need to provide data to and access a common medical database hierarchy. Subjective testing of those diagnosed is known such as in the diagnosis and measurement of progress of, for example, those inflicted with Parkinson disease (PD). Subjective PD testing may comprise, for example, a timed observation and video camera collection of the individual's moving arms and hands or other extremities in a requested protocol to subjectively assess their susceptibility to tremors, twitches and the like. Medical practitioners contemporaneously collect and record time of day, date, individual with disease data including age, gender, body weight, height, blood pressure, environmental conditions of the test and the like.

Subjective testing suffers from high inter-rater and intra-rater variability depending on the chosen cohort and metric (Larsen et al. 1983, van Hilten et al. 1994). By use of the term cohort in the specification and claims is a group of similarly situated individuals such as a cohort of individuals diagnosed with the same disease, a disease cohort or a cohort of caregivers or others. Subjective measurements further require the burden of observer resources for administration and data capture. Taken together, these factors in combination with a perceived potential for lowering clinical trial burden through lower required sample size and the ability to engage those individuals diagnosed with disease in their home environment have lead to improvements in application specific design offerings for measurements (Mamorita et al. 2009, Great Lakes Neurologic (video and accelerometer), APDM (gyroscope/magnetometer/accelerometer), Mcnames et al. "SYSTEM FOR DATA MANAGEMENT, ANALYSIS, AND COLLABORATION OF MOVEMENT DISORDER DATA." U.S. patent application Ser. No. 12/763,538, filed Apr. 20, 2010), Cambridge Neurologics (a device with an accelerometer), QMAT (Voice, accelerometer, pegboard, and paddles) and techniques (Boraud et al. 1997, Dunnewold et al. 1997 & 1998, Salarian et al. 2007, Yokoe et al. 2009, Albers 2011) and early trials to associate treatment with objective measures (Hoff et al. 2001, Papapetropoulos et al. 2008, Taylor et al. 2009, Rusk et al. 2011), including in the home environment (Goetz et al. 2009).

With Apple Inc.'s (hereinafter, Apple) introduction of wireless telecommunication devices circa 2010-2011, Apple provided hardware within these devices including but not limited to an on-board camera, GPS access, a magnetometer, an accelerometer, time and date data and a gyroscope. In particular, Apple's CMMotionManager is an object gateway to raw gyroscope, magnetometer and accelerometer data, which has been used, for example, by camera users, for example, for attitude data. A poster prepared in 2011 by Dr. Sillay for presentation in Europe shows x, y, and z coordinate data from a gyroscope collected from such an APPLE® telecommunications device that may be collected and graphed to comprise objective hand movement data for use with the known Uniform Parkinson's Disease Rating Scale (UPDRS), discussed further below, to quantify Parkinson's disease symptoms such as tremors with and without brain stimulation via programmed implants, as will be discussed further below. Other devices from other vendors, such as smart phones, smart watches and tablets, for example, using the ANDROID® operating system (available from Google, Inc.), and devices designed for computer games such as the Microsoft XBOX® game console and KINECT® game console can also be used.

Efforts at objective measurement of disease are beginning to take hold with experimental (QMAT) and commercially available devices (Great Lakes Neurological, APDM) and software to make use of commercially available devices (Navigated Technologies/iMovePD motion data logger). While early efforts are underway to include such technologies in clinical trials (UW clinical trial, UCSF clinical trial), randomized clinical trial results benchmarking objective measures are lacking.

On the other hand, such objective data collection, while gatherable, may not be easily entered into known databases. The medical records database hierarchy must be periodically updated to even receive collected data from newly developed subjective/objective data collection. The data entry screens do not permit the entry of such new data or new diagnostic or progress testing, for example, by cameras or other devices. Hurdles to improvements in care of those diagnosed include, but are not limited to the acquisition, processing, and reporting of aggregate health related data from disparate sources. Data sources include multiple medical providers, caregivers, and individuals diagnosed with a disease, and each source typically utilizes a different data store, implying possibly different fields, formats, access methods, and security, privacy and data sharing legal and technical protocols.

Indeed, technical and legal barriers exist for the successful navigation of ideas to fruition, in particular, the migration of data across barriers among the individual with disease, the medical practitioner, the database hierarchy and the surrounding medical and individual with disease community. Referring briefly to FIG. 1 (Prior Art), there is depicted an overlapping hierarchy similar to a Venn diagram on the left whereby the University of Wisconsin 105 is shown distinct from the University of Wisconsin Medical Foundation 110, the University of Wisconsin Hospital and Clinics 115, the medical doctor 120, a given device for data collection or disease control 155 (such as a body implant for drug release or electrode stimulation or a gyroscope motion data collector of an iPhone) which may comprise a memory and transceiver, clinic nurse practitioners 165, a development team 145, biomedical engineering (BME) students 150, clinic nurses 170 and individual with disease care 160 shown. To the right of FIG. 1 is seen an IP designee 125 interfacing with a non-University of Wisconsin (UW) tech transfer entity 130 to a software distribution platform 135 to a further overlapping Venn diagram showing a individual with disease user 140, the device 180 and its software 170 tied back to the UW hospital and clinics 115. Clearly in such a complex medical and individual with disease environment with impediments to data flow, the hierarchy and legal and technical structure tends to most importantly limit individual with disease development and progress if not fail to promote research and development of cures, an individual with disease social network, the need for an insurance carrier to collect individual with disease data and the like.

Parkinson's disease is used in the context of many neurological diseases or other conditions in the present discussion by way of example of many such diseases or conditions ranging from epilepsy, Alzheimer's disease, multiple sclerosis, essential tremor, dystonia, normal-pressure hydrocephalus, spinal and gate disorders to stroke. Parkinson's disease (PD), alone, impacts the quality of life of one percent of the adult population over sixty years of age.

A Parkinson's disease questionnaire (PDQ) is known that is computer-based that a user with disease may navigate and particularly complete to quantify and qualify their symptoms and other data at a given date and time. Referring briefly to FIGS. 5 and 6 (Prior Art), there are shown a symptoms questionnaire (FIG. 5) comprising, for example, diagnosis date 510, first symptom 520, onset of medical treatment and what treatment 530, first use of levodopa or related drug regimen 540, date of significant impact of PD on individuals with diseases' work/home life 550 and first consideration of surgical therapy such as a neuromodulator implant 560. Per FIG. 6, (Prior Art), examples of demographic data collection on the PDQ may include Zip code 610, name of primary care physician 620, neurologist 630, and neurosurgeon 640.

A biometrics information telecommunications software application is known from US Published Patent Application No. 2012/0148115 of Jun. 14, 2012 and is but one example of a plethora of software applications that have been developed for mobile telecommunications devices, in this case, to collect biometrics data such as photographs of individuals, fingerprints, location and other data with respect to a particular time and date, location and particular user such as a first responder.

PD burden is often measured by medical clinicians who subjectively grade the degree, for example, of forearm slowness and pronation/supination movement (a movement similar to screwing in a light bulb) and rated according to a known Uniform Parkinson's Disease Rating Scale (UPDRS) described a quarter century ago (Fahn, et al. 1987). In the clinical setting, the individual diagnosed with disease may be captured on camera as the person goes through the movements in response to the requests of the clinicians. The current method of data inclusion in medical databases for the most part excludes or is not permissive of accepting video data, let alone the subjective data collection such as UPDRS data or the PDQ data completed by the individual with disease. Expanding the use of clinical measures (CM) such as the UPDRS to address population health questions is stymied by rater variability, subjectivity, and provider burden of effort.

An exemplary medical database is one known from US Published Patent Application No. 2008/0208914, published Aug. 28, 2008, in which it is suggested that an individual with disease (IWD) portal may provide IWD access to their medical records. Referring briefly to FIG. 6, FIG. 15 and FIG. 24, the IWD's doctor may also have unrestricted access to her individual with disease's records 1570. But this doctor 2410 may not have access to another doctor's records for a similarly situated individual with disease 2420. Per FIG. 15 and discussion within the published application, the individual data of those diagnosed with disease may be permissively uploaded (with some healthcare data protection) to such entities as the Center for Disease Control (for controlling a possible epidemic), the National Institutes of Health 1520, state level and university level databases for other purposes such as developmental purposes. However, this suggested ideal may not be practical unless the databases are compatible, legally and technically.

Surgical interfaces to medical databases are likewise lacking. These databases may be doctor based, hospital based, maintained at a state level, a regional level or a national or (federal) National Institutes of Health (NIH) or Center for Disease Control (CDC) level 1520. The databases in the hierarchy may not be capable of data sharing, retrieval and query by parties that could use the data for research, progress of individuals with disease, social networking, insurance or other purposes as in FIG. 24.

Neuromodulation is known in restorative neuroscience and functional neurosurgery whereby, by example, a deep brain stimulator may be implanted in the human brain. FIG. 2 is a PRIOR ART data flow diagram for a candidate for neuromodulation (DZ) 250 as an example of a disease being managed with best medical therapy (BMT) 240 or treatment 220 (in this case with deep brain stimulation [DBS] and the comparative effectiveness or efficacy being compared with both subjective measures (SM) 230 and objective measures (OM) 210 in a manual setting of today. Referring briefly to FIG. 3 (Prior Art), there is shown a data flow chart for an individual diagnosed with disease who may benefit from neuromodulation. At step 300, preoperative data is collected at a healthcare provider appointment and entered into a protected health record. At step 310, surgical planning data is collected involving the neurosurgeon and the neurosurgeon's team and maintained at a surgical planning station. At step 320, data from the surgery itself may be collected including photographic or video data and monitored and stored individual with disease data such as blood pressure and brain activity during surgery. At step 330, the individual with disease has their new neuromodulator programmed according to a best projection of how the neuromodulator should perform. At step 340, there is an opportunity for medical and community follow-up of those with disease and feedback as to how the individual diagnosed with disease and subsequently implanted with a neuromodulator is performing with the programmed neuromodulator and whether different programming is appropriate, for example, in combination with L-dopa or another drug regimen or combination of drug therapies as is known in the art.

Yet, data from the surgical room where the implant is performed are not automatically transferred to an electronic health record, which might include a surgical plan, subjective or objective documentation of the procedure, or video record of the surgery itself. In the case of neuromodulation in the restorative neurosciences and functional neurosurgery to implant a deep brain stimulator, the preoperative data held in the electronic medical record are not automatically transferred to the surgical planning station. Data surrounding the implantation of a deep brain stimulator are not transferred from the surgical environment. The current method of data inclusion at many centers is manual entry, photography or scanning of documents, and manual upload of these items into the electronic health record if available. This type of surgery is performed by a neurosurgeon; however, follow-up is performed by a neurologist who in many cases was not present during the pre-op evaluation or in the operating room. When the neurologist meets the individual with disease for the first time in clinic for programming of the deep brain stimulator, in most cases, only limited data are available to the neurologist to assist in the programming of an enormous number of possible combinations of the, for example, quadrapolar implant device having a wide frequency amplitude and pulse width selection available. Further difficulties exist in measuring the outcome of these cohort members of individuals with disease after treatment. No readily available system allows the remote aggregation and integration of mobile medical device-acquired objective measurements along with diary data of these treated individuals with disease in the home environment.

There is limited ability to aggregate and track factors, which may lead to an improvement in surgical technique or individual with disease selection across either the entire or a selected cross-section of the population of individuals with disease treated. There is currently a delay in the meaningful use of the electronic health record for specialty care.

Referring briefly to FIG. 83, the typical current processes include manual data entry 8322, measurements of head position, photography of surgical sites, scanning of documents and manual upload to an electronic health record. Database software may be incapable of performing data analysis such as might be accomplished by known content-based image recognition, data parsing and analysis of the manually input data, database query and retrieval and the like to effectively provide, for example, researchers or clinicians with the data they need to assist a given individual with disease or the population of all individuals with disease sharing the same disease or disorder.

Moreover, surgical follow-up may not be recorded in any database except at a paper level, or it may be recorded by a neurologist unfamiliar or not present at the original surgery or pre-operation individual with disease evaluation. There is limited ability to aggregate and track factors, which may lead to an improvement in surgical technique or individual with disease selection across either the entire or a selected cross-section of the population of individuals diagnosed with a disease treated. There is currently a delay in the meaningful use of the electronic health record (EHR) for specialty care (FIG. 4 showing a delay centered in 2012 between primary and specialty care). Significant hurdles exist to increased adoption of currently known therapies, compliance, and clinical translational research within PD and other restorative neurosciences ailments. Challenges in measuring, aggregating, reporting, and querying the rich dataset surrounding treatments within the restorative neurosciences as well as other areas of research or individual with disease tracking or treatment within neuroscience are subject to improvement with emerging technology.

Current systems designed for use by individuals diagnosed with disease and physicians to handle even a limited subset of the described data are not designed to answer important questions, which may improve healthcare. An example of this is there is no way in aggregate form for individuals diagnosed with a disease to track their outcomes, the battery life of their personal devices (medical, communication or combination), adverse side effects of the therapy or other important factors.

A system is known from US Published Patent Application No.'s 2012/0029369 published Feb. 2, 2012; 2009/0012417 published Jan. 8, 2009 and 2002/0126731 whereby a passive microwave receiver may obtain internal body temperature at various depths by frequency selection (with no active microwave transmission which may be dangerous) from known "black-body" radiation. Moreover, measures of blood flow and pressure may be possible from this apparatus in combination with known automatic apparatus for collection of blood pressure.

Social networks are known such as Facebook and LinkedIn whereby individuals may share information about themselves with others. Friend and business relationships may develop from participation. Disease support groups have sites but these sites are typically anonymous and impersonal and may not permit similarly situated individuals to electronically participate outside of a support group.

In view of the above, there is clearly a need in the art for improved systems and methods for collecting objective data (as well as subjective data collected in a medical environment) of an individual diagnosed with disease at home or at a doctor's office. Given the foregoing, what are needed are systems, methods and computer program products that provide a framework to define a model-based multidimensional medical record that overcomes legal and technical hurdles, may span multiple computer systems, networks, and organizations, and supports new objective data collection as well as provides an input for sharing such multi-media data collection as photographic data and video/movie data as well as provide an opportunity for networking of those diagnosed with disease, disease treatment development, insurance carrier access, medical practitioner access, developer access and the like.

SUMMARY

This summary is provided to introduce a selection of concepts. These concepts are further described below in the Detailed Description. This summary is not intended to identify key features or essential features of the claimed subject matter, nor is this summary intended as an aid in determining the scope of the claimed subject matter. The present invention meets the above-identified needs by providing devices, systems, methods and computer program products that provide a framework for the creation of objective (as well as subjective) medical records, editing, manipulation and shared use of medical records among those diagnosed with disease, doctors, insurance carriers, researchers and the like without technical and legal impediments. Specific example embodiments of apparatus and methods disclosed provide for an instrument or device to assist in the collection of objective data, for example, utilizing an accelerometer, a gyroscope, a camera, a time of day and date clock, a GPS location system, environmental sensors and human biological data collection such as an internal temperature, blood flow rate and the like.

Novel methods and technologies, such as wearable, handheld, or portable devices such as smart phones, tablets, or specialized or customized devices that can sense and record movement and can be programmed to record such movement and utilize communications links to transmit the recorded data to a server for processing and/or storage or communicate with other devices such as implants for brain stimulation or drug release, allow the potential to improve the health of a disease cohort by quantifying results of health care intervention. While a wireless communications link such as WiFi, 3G, or 4G wireless systems provide is preferred, it is also possible to implement the disclosed features using tethered devices, or devices that can be intermittently tethered, or devices having a removable storage or memory component such as a SD memory card, where the removable component can be inserted into or attached to another computer or device, in order to establish a communications link to a server or another device. Such technology empowers the research from the "bench" to the population of at-home individuals, for example, those diagnosed with PD. For example, FIG. 7 is a graph of Sample Objective Measure Data collectable from a device indicating a demonstration of improvement in post operative function solely based upon an objective measure (UPDRS motor score from 0-4) with deep brain stimulator (DBS) on 700 or off 710.

The inventive technologies can be used in a clinical setting with supervision, or at a residence or other facility by the individual diagnosed with disease (unsupervised) or with the assistance of a caregiver, family member, or a trusted person. The possibility is great for advancing this modality rapidly through collaboration with regional, national, and international databases (NPF QII, Okun et al. 2010; neurosurgical N2QOD, McGirt et al. 2013). These databases or computer servers (step 10310, 10315 and 10320 by example; FIG. 103) may provide secure data collection portals that are accessible to and controlled by the individual diagnosed with disease 10355, as well as be available in a clinical or other controlled setting. They may also provide repositories for data collection software and/or device tuning software or data that can be downloaded to and executed or used on an implantable, wearable, hand-held, or portable device step 10370 used by or for the individual diagnosed with disease. The combination of the databases or computer servers and either the implantable, wearable, hand-held, or portable device or a computer such as a laptop or desktop computer, can be used by the individual diagnosed with disease, a caregiver, relative, or assistant, or supervisory personnel to control privacy and sharing settings to enable another person or organization to access objective, subjective or multimedia data, either for the purpose of evaluation or treatment of the individual with disease, or with appropriate controls on the release of information that could undesirably identify the individual with disease for research purposes.

According to the present invention, servers, computers, or computer systems may contain data and implement privacy and sharing policies (FIG. 17) that are controlled by the individual with disease or an individual with disease's representative. Such server-controlled databases provide a mechanism for the transfer of valuable information among the cohort of caregivers and service providers that address the needs of each individual with disease. Systems such as these may provide a broader spectrum of information to teams who perform surgical procedures, including, for example, diary entries, records of the administration of medications, and records from other medical facilities that have been requested by the individual with disease and which the individual with disease has agreed to share with a different provider (FIG. 17). Such systems may also make information from surgical procedures available post-operation, for example to better enable adjustment or tuning of surgical implants or to better coordinate post-operative therapies. The utilization of devices capable of communicating with surgical implants or prostheses capable of receiving communication (client to client) offers the opportunity to both capture data relating to the operation of the implants and to tune or adjust the operation of the implant to better meet individual with disease needs and accommodate the health and recovery profile of the individual with disease. Server systems can be interconnected in a secure manner to enable sharing and aggregation of information across, for example, geographic regions, groups of individuals diagnosed with a disease served by specific medical providers, and members of individual with disease networks or insurer organizations. The aggregation of individual with disease data with appropriate safeguards to ensure the deletion or obfuscation, for example by encryption, of identifying information may provide valuable data for research.

In accordance with the principles of the present invention, permissions from individuals diagnosed with disease may be aggregated to obtain, aggregate, and report healthcare data. These individual with disease-based permissions may be finely tuned to be compatible with existing healthcare information laws such as the Health Insurance Portability and Accountability Act (HIPPA) and the Health Information Technology for Economic and Clinical Health (HITECH) Act. Within the appropriate permissions, all participants within the data exchange can make structured queries. While structures of permission-based data exchange have been previously described, an electronic individual with disease affidavit of permission, according to the present invention, provides a secure ability for individuals diagnosed with a disease also to query within the system hierarchy.

The present invention proposes home monitoring of progress via instructed utilization of mobile and other objective data collection devices in combination with use of the known PDQ (but in electronic, secure form). An individual with disease navigates the questionnaire using a computer or other client device that can communicate with a computer server process such as a web server. Appropriate security to safeguard private or privileged data is essential. This paradigm provides the ability to deliver and gather content using both wireless devices such as a tablet or mobile phone, wired devices such as a computer or (tethered) tablet and specialty devices that may be implanted or coupled to body extremities such as hands and feet.

Subjective measures (SM) used by a clinician as clinician measures (CM) or by others outside the clinical environment (where the measures are frequently described as diary data) may be combined with objective measures (OM) obtained from the individual with disease at home or a medical office. In the case of PD, clinician measured (CM) and scored (CMS) Unified Parkinson's Disease Rating Scale (UPDRS) data may be combined with objective measures (OM) obtained at home or office over time to develop an individual with disease history. The opportunity to develop and validate easy to use, quantitative objective measures (OM) resulting in objective measures scores (OMS) for the longitudinal evaluation of conditions such as for PD is suggested by the present invention. OMS may quantify impact of therapies to the clinic and accelerate translation of new treatments by lowering the administrative burden of disease monitoring. Healthcare OMS are now possible with emerging low-cost, connected, hand-held mobile devices capable of running healthcare Apps (mHealth devices). Such objective measurement devices with communications capability having specialty sensing and detection (examples include the iPhone, iPod touch, Android phones and tablets, wearable appliances such as smart watches or other physically small computerized devices, and similar devices which may be implantable) have extensive and accurate capabilities for recording individual with disease movement and communicating OM. Such emerging technology can enable widespread adoption by a community of OMS (for example, of movement in PD) efficiently and at low cost. By extension of the example, in PD, objective measurements have been related to severity of disease. Tremor and bradykinesia (slowness) in PD, for example, are captured with video (for example, using subjective analysis, UPDRS subscore, and a blinded rater) and with the device (objective analysis).

Preliminary data indicate that forearm angular velocity for the pronation-supination movement (similar to rapidly simulating "screwing in a light bulb" while holding the device (or a special device may be implanted) directly correlates with clinician-provided UPDRS scores, and is highly reproducible even without an experienced clinician's guidance and subjective measure. Increased maximum wrist rotation speed correlates with lower UPDRS scores. In individuals diagnosed with a disease undergoing deep-brain stimulation (DBS) surgery at UW-Health, peak angular velocity increases with stimulator activation and also correlates with the UPDRS. Adding OMS to the study of PD individuals diagnosed with a disease promises to improve research studies by decreasing inter- and intra-rater variability and likely decreasing the number of individuals diagnosed with a disease required for vetting an emerging therapy. Medical and surgical therapies provided at luminary medical centers reduce suffering in the restorative neurosciences and movement disorders, yet objective measures (OM) of the "health" of the disease cohort (such as a cross-section of PD individuals diagnosed with a disease selected by region, age, or ethnicity) as a result of these therapies are lacking.

The current embodiments aim to standardize, simplify, and objectify clinical outcomes tracking, culminating in population health measurements of PD individuals diagnosed with a disease in the home and in the setting of support group-based periodic meetings. The disclosed methods allow an objective test to be performed using devices available within the individual with disease and provider community and allow unprecedented ease of participation for longitudinal testing over time. Adding OM to the study of PD individuals diagnosed with a disease promises to improve research studies by decreasing inter- and intra-rater variability and likely decrease the number of individuals diagnosed with a disease required vetting an emerging therapy.

Objective measures (OM) from devices described herein augment clinician-measured scores (CMS) using either or both clinic-acquired and community-acquired measurements. OM data allow monitored and unmonitored measurements in the home environment by participants/caregivers of those with varied disease burdens. Clinical validation and translational comparative effectiveness research (CER) through a community registry environment facilitate population-based monitoring and optimization of targeted therapy in the community. In the setting of a fluctuating disease process such as PD, a clear understanding of individuals diagnosed with a disease' progression with medical or surgical intervention may require unrealistically high individual with disease participation or individual with disease numbers exceeding those available at a given treatment center using historical outcomes measures.

Meaningful use of consumer devices in the home environment will provide the following: the data flow for standard of care treatment augmenting the following workflow for treatment; an individual with disease reporting to the neurology or neurosurgery clinic, and a relatively inexpensive test (for example, to account for the time value of a rater's time) and taking around 30-60 minutes being performed with paper, or electronic based or manual scoring and being scored according to the training and judgment of the rater. With the embodied disclosure, SM and OM are available and shared across the clinical, home, and community environments according to the wishes of the participant. For example, in addition to the results of the SM from the clinic, OM of movement, distance traveled, average speed, time walking, time sleeping, time with dyskinesias, time with an inability to walk well, participation in exercise activities as marked by GPS location of the facility pr individual user and by activity level are able to be identified, analyzed, exchanged, uploaded, transferred, logged, and "liked" by other members of the community in an ability to influence the end behavior and therefore improvement in coping with or treating disease. PD efficacy trials of OM devices will report the clinician scored Unified Parkinson's Disease Rating Scale (UPDRS) and be matched by the individual user performing their own test and obtaining a personal UPDRS score at home.

Further features and advantages of the present invention, as well as the structure and operation of various aspects of the present invention, are described in detail below with reference to the accompanying drawings.

BRIEF DESCRIPTION OF THE DRAWINGS

The features and advantages of the present invention will become more apparent from the detailed description set forth below when taken in conjunction with the drawings in which like reference numbers indicate identical or functionally similar elements.

FIG. 5 is a PRIOR ART drawing of a typical Parkinson's Disease Questionnaire (PDQ) wherein FIG. 5 requests symptom data.

FIG. 13 is the second of the two figures depicting methods for preparing objectively measured data from the forearm bradykinesia test for further analysis.

FIG. 14A and FIG. 14B are figures demonstrating the clinical trial design of a currently active investigation and analysis trial of the objective measure of forearm bradykinesia wherein FIG. 14B is a continuation of an objective measures scores (OMS) assessments flowchart of FIG. 14A. The depictions of FIGS. 14A and 14B show the control and treatment groups and, as this is a neuromodulation trial, the examination of the treatment group on and off therapeutic neurostimulation.

FIG. 17 identifies a reporting permissions matrix for use by participants within a registry to allow selectivity of data reporting to government, public nonprofit, investigator initiated research, and commercial partners.

FIG. 26 depicts an Individual with disease Outcomes Report in response to an input query and generation of a disease cohort database from EHR. In this case, the report depicts results for deep brain stimulation designed to be viewed by the clinician and rapidly demonstrate individual with disease progress.

FIG. 27 depicts a Demographic Report detailing the treatment cohort demographic in response to a query from a requesting client device. In this example, a gender and age report, the report allows for rapid viewing of age and gender based relationship to the number of procedures or treatments performed, in this case, surgical implants with automated identification of outliers within the automatically generated cohort.

FIG. 29 depicts a sample Consent Report detailing the status of consents for 1) individual with disease to individual with disease collaboration, 2) videotaping and photography, and 3) inclusion within research paradigms and data exchange.

FIG. 30 depicts a representative Surgery Report detailing surgical procedures by: identification code, name, surgery date, type of surgery, surgical target, and presence of specific associated tests such as diffusion tensor imaging on MRI scanning.

FIG. 31 depicts a representative Calculated Active X/Y/Z report depicting the automatically calculated location of active therapy as derived from the last visit for programming, location of the implant to neurostimulator's target of nerve stimulation programming parameters such as activated contacts, voltage/current, pulse width, rate, impedance measurements, device voltage, current measurements, outcomes measurements (objective and subjective) as well as the targeted entry points for director direction vector calculation as well as the active stimulation location based upon computational methods of determining the center of active stimulation and other notes and or linkages to other types of implant data such as infusion data.

FIG. 32 represents an automated error checking of electrode implant location. This report provides a listing and graphical representation of implant or therapy delivered by location and provides automated target averaging with automated detection of outliers.

FIG. 33 depicts Active Implants within the 3D framework of certain brain internal landmarks. This report lists numerically displays separately graphically the location and stimulation parameters of an active implant. In the case of protein, gene therapy or other therapy relevant metrics are substituted.

FIG. 34A and FIG. 34B depict the top and bottom portions, respectively, of a representative outcomes report for the display of relevant outcomes measures with and without the combination of medication and neurostimulation according to an evaluation protocol.

FIG. 35 is representative population listing report for significant metrics regarding active implants. This report may be generated from a cohort database listing of impedance and device statistics for automated battery life and impedance change detection to determine the health of population of neurostimulators.

Figure 36:
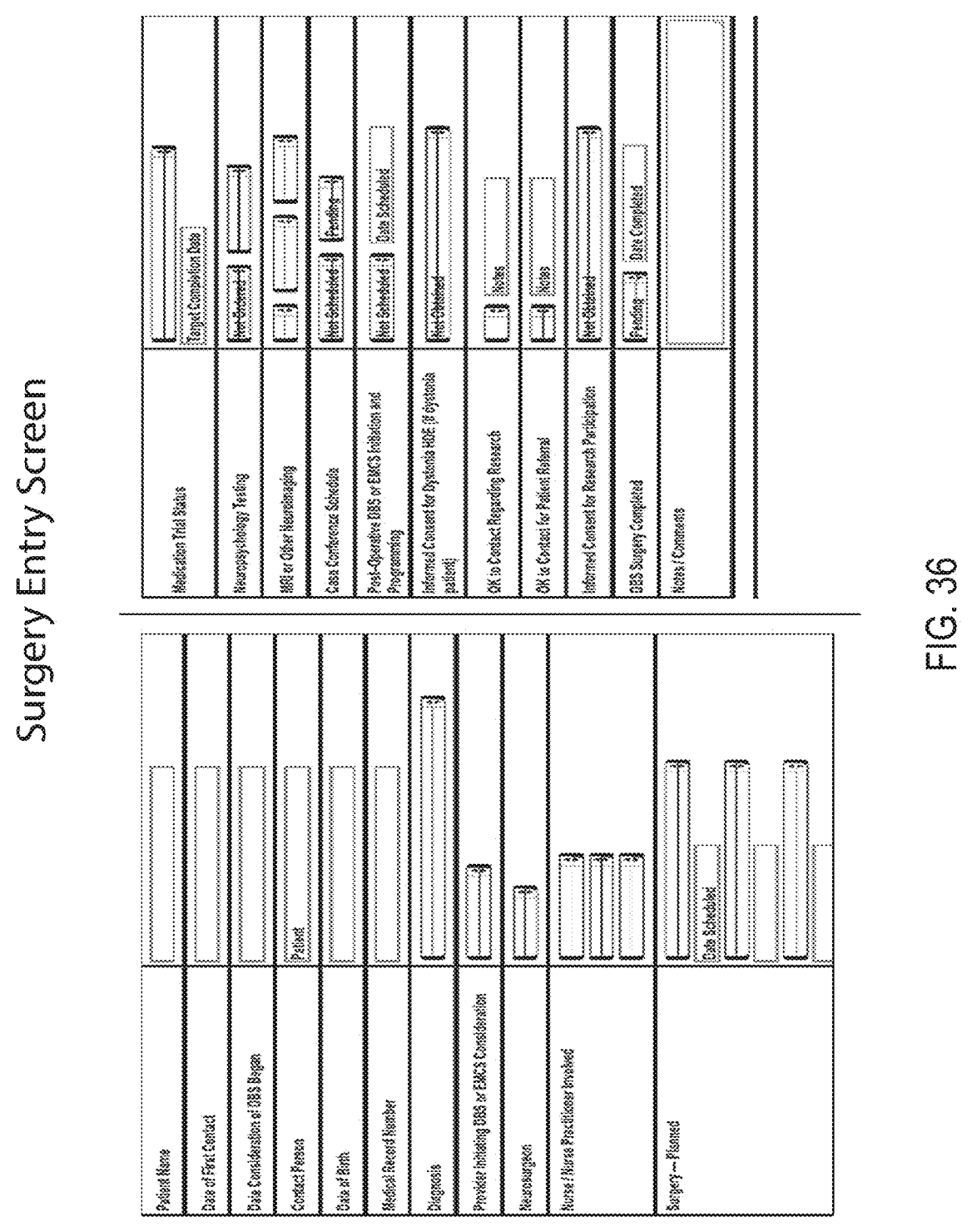

FIG. 36 depicts a conference report form example. Collaborators from neurosurgery, neurology, physical therapy, and other collaborators interact in a collaborative setting to automatically share information pertinent to workflow.

FIG. 39A-D displays a representative screen capture of a surgery schedule report for pending surgeries, wherein FIG. 39A shows a scheduler query screen; FIG. 39B represents a patients query screen; FIG. 39C represents a Reports tab screen and FIG. 39D represents a UPDRS Pool tab screen.

FIG. 40 is the first of two depictions of an example surgery record prepared for scheduling, including diagnostic studies, intraoperative metrics, targeting information, complications, implant or therapy given and outcomes measures. This figure contains the scheduling and a portion of a diagnostic section.

FIG. 41 is the second of two depictions of an example surgery record prepared for scheduling, including diagnostic studies, intraoperative metrics, targeting information, complications, implant or therapy given and outcomes measures. This figure contains the remainder of the diagnostic section, the intraoperative, metrics, target information, complications, implants and outcomes sections.

FIG. 49 depicts Surgery Record Data Structure 7—Data—Complications—outlining complications envisioned within the data structure.

FIG. 50 depicts Surgery Record Data Structure 8—Programming Information—Including Active Implants/Contacts and Outcome Measures outlining information regarding the neurostimulator device programming and relevant outcomes measures.

FIG. 60A, FIG. 60B and FIG. 60C to the putamen according to an aspect of the present invention.

FIG. 66 depicts the effects upon the resolution of intracranial brain shift on implanted brain devices (Sillay et al. 2012) according to an aspect of the present invention.

FIG. 75 depicts an "in box" for rating scales or data with known identifiers, however uncertainty regarding a data item identity according to an aspect of the present invention.

FIGS. 76A, 76B, 76C, and 76D depict a representative patient data input and report summary screen for the restorative neurosciences wherein the IPG serial numbers have been intentionally redacted but may be displayed according to an aspect of the present invention.

FIG. 78 is the first of two screen captures from a representative database for the restorative neurosciences specifically for the logging of outcomes measures and device programming for neurostimulation according to an aspect of the present invention.

FIG. 79 is the second of two screen captures from a representative database for the restorative neurosciences specifically for the logging of outcomes measures and device programming for neurostimulation.

FIG. 80 is the first of three screen captures from a representative database for the restorative neurosciences specifically for the logging of events and data surrounding the implantation of a neurostimulator or similar device.

FIG. 81A, with FIG. 80 representing the first screen, is the second of three screen captures from a representative database for the restorative neurosciences specifically for the logging of events and data of a surgical treatment summary surrounding the implantation of a neurostimulator or similar device.

FIG. 81B is the third of three screen captures from a representative database for the restorative neurosciences specifically for the logging of events and data of a surgical treatment summary surrounding the implantation of a neurostimulator or similar device according to an aspect of the present invention.

FIG. 84 is a representative listing of representative reports within a representative database for the restorative neurosciences.

FIG. 87 is a representative figure allowing the association of neurostimulation devices to neurostimulator pulse generators and displaying summary target information about the location of the neurostimulator device given trajectory information from the surgery and from images taken after the completion of the surgery for localization purposes.

Figure 88B:
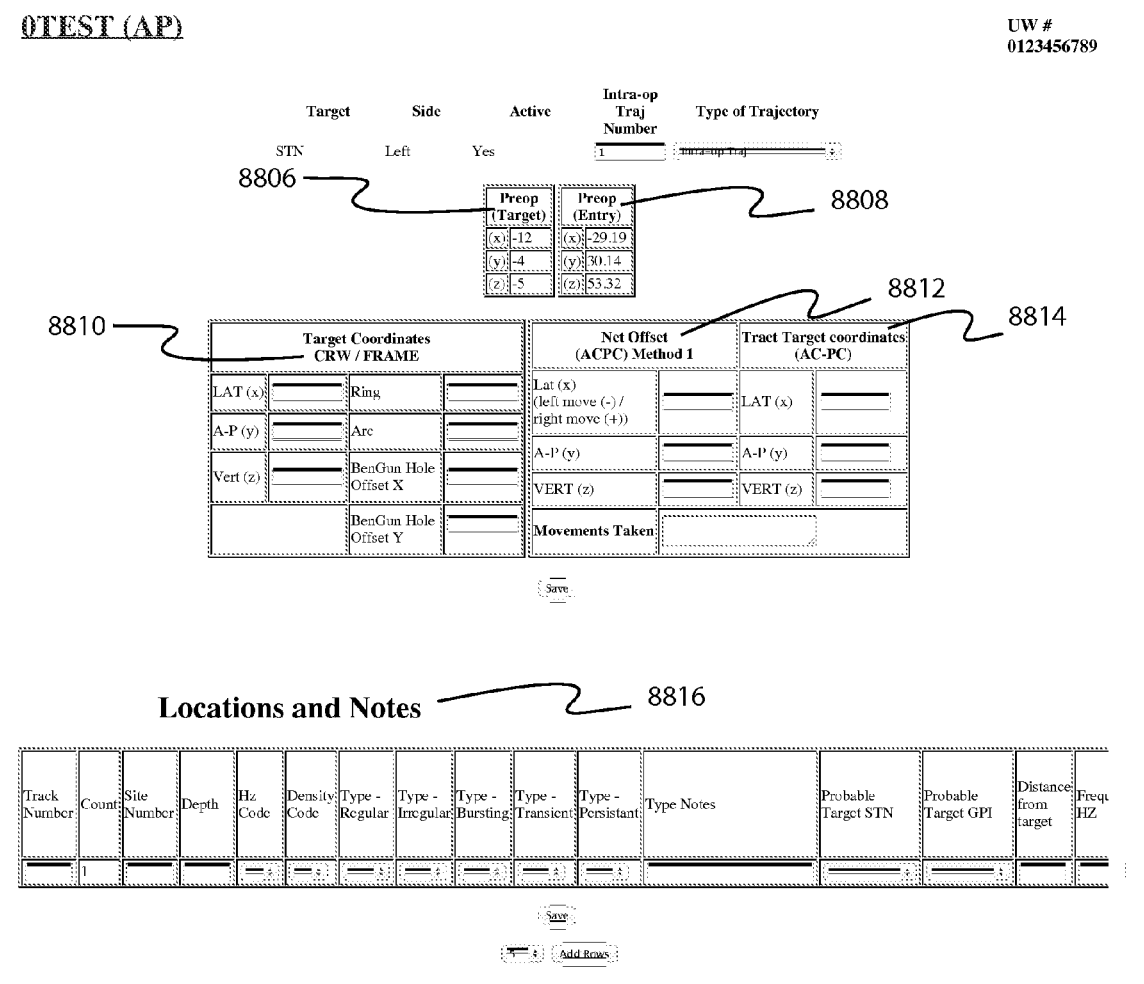

FIGS. 88A, 88B, and 88C are screen captures from a representative database for the capturing of perioperative trajectories and associated metrics for identifier UW (University of Wisconsin) 0123456789.

FIG. 89 is a representative screen capture depicting the post implantation location, errors, and notes associated with the procedure.

FIG. 90 is a representative screen capture depicting the addition of a new neurostimulator pulse generator device and associated linkages to brain implants.

FIG. 96 is an example data exchange mapping matrix for users to allow de-identified reporting to be identified or identified data to be exchanged with healthcare providers.

FIGS. 108A, B, and C depict an exemplary RNF database and RNF codes providing the ability of field, report, task, and other similar aggregate protocols and events to be queried and initiated via a central codebook or lookup table.

Copyrights are claimed for all figures of the Brief Description of the Drawings which are not labeled Prior Art as of the date of filing of the present application and their date of publication as a published US application (if not earlier published).

DETAILED DESCRIPTION

Figure 1:
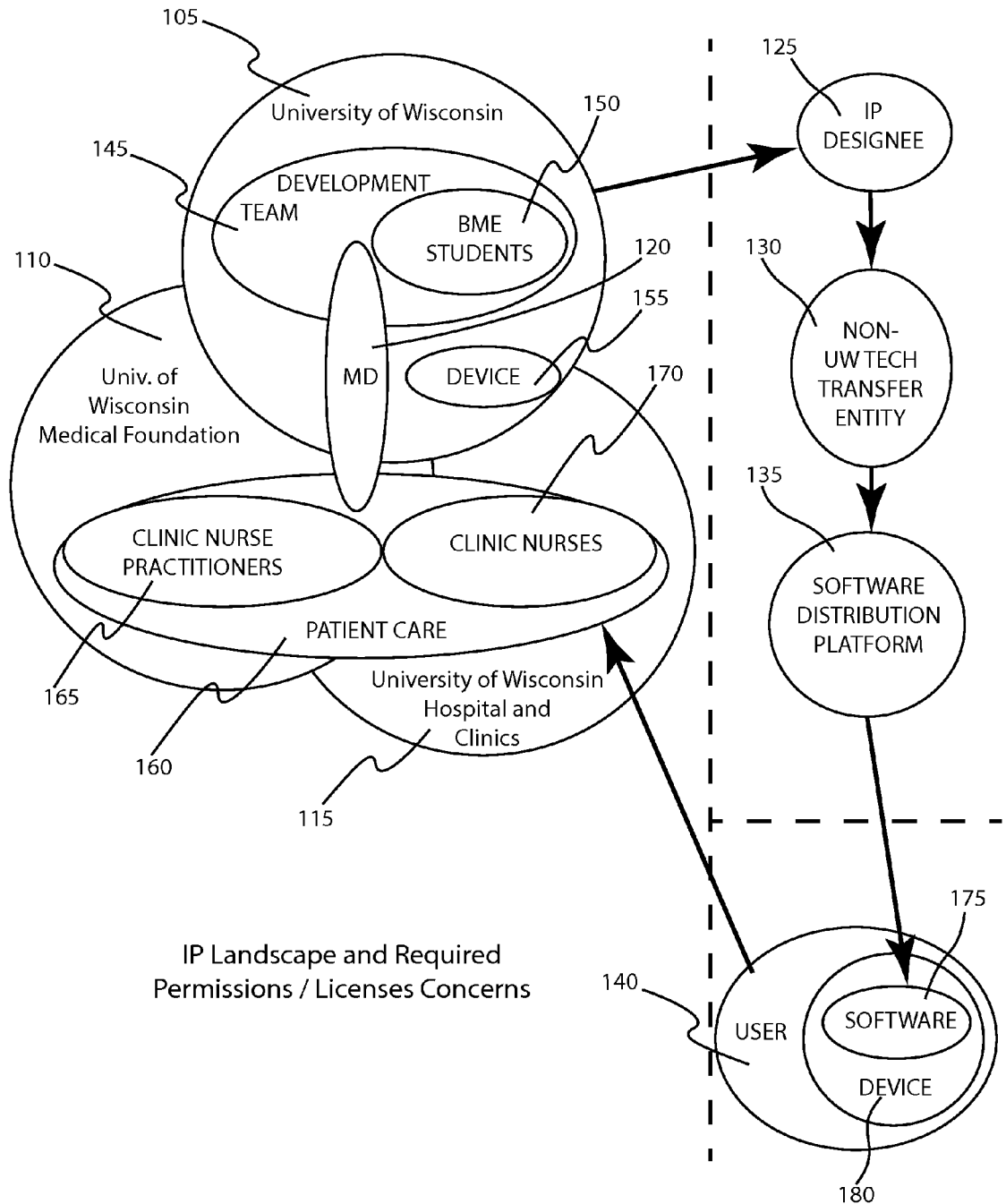
FIG. 1 is a PRIOR ART diagram of a typical complex hierarchical technical and legal permission system, in particular, involving the University of Wisconsin, associated organizations, the individual with disease, the doctor and others.
Figure 2:
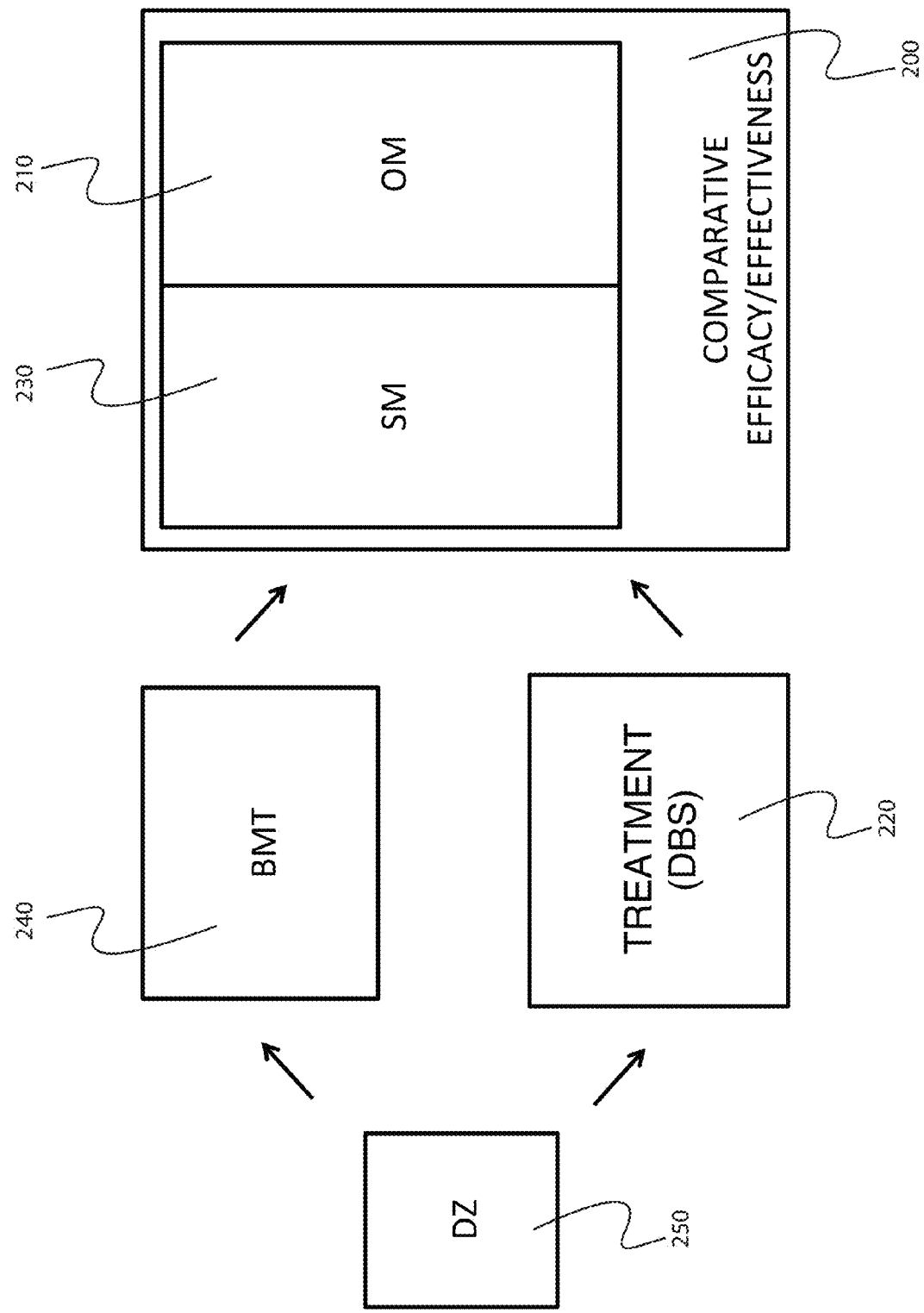
FIG. 2 is a PRIOR ART data flow diagram for a candidate for neuromodulation (DZ) as an example of a disease being managed with best medical therapy (BMT) or treatment (in this case with deep brain stimulation [DBS] and the comparative effectiveness or efficacy being compared with both subjective measures (SM) and objective measures (OM).
Figure 52:
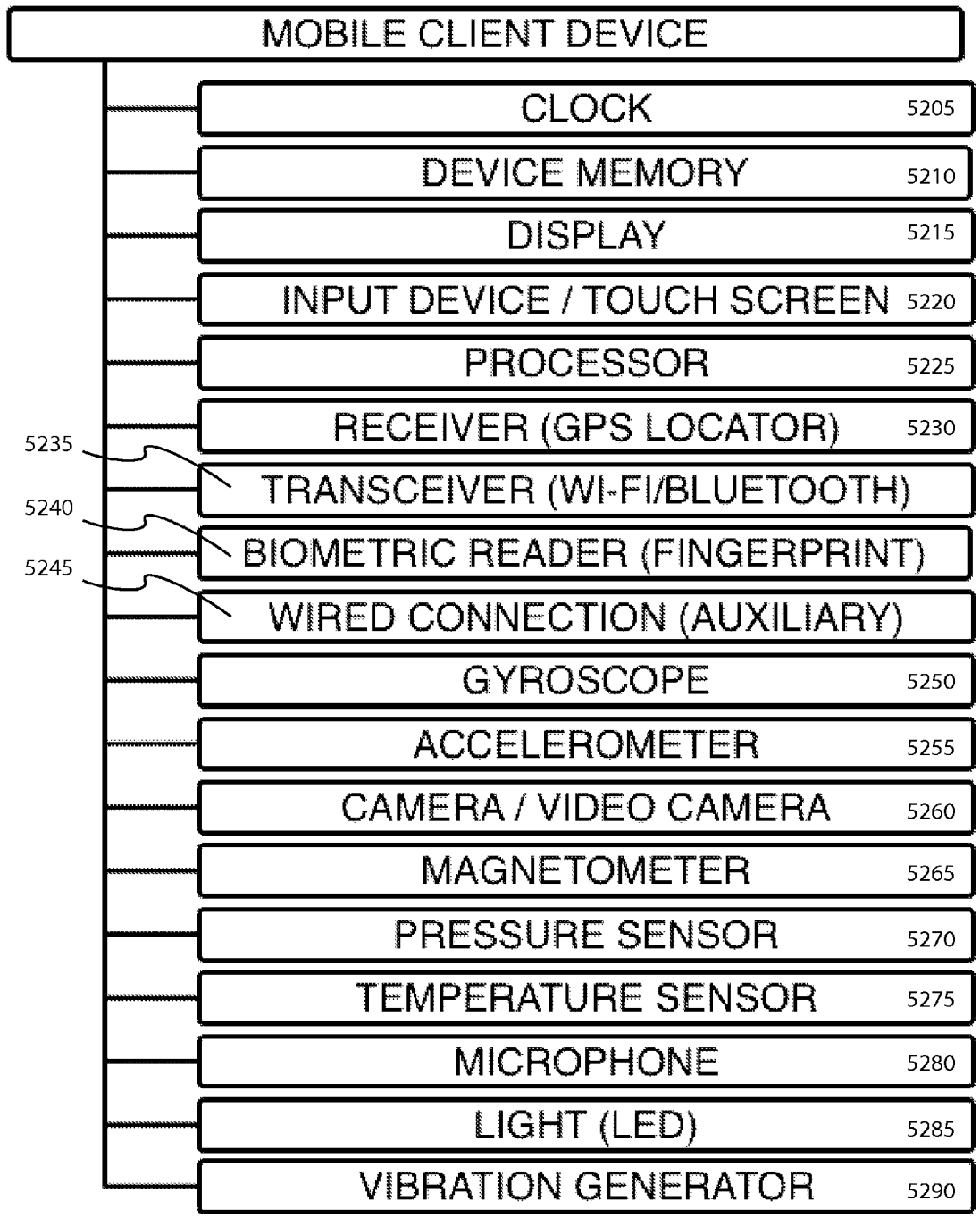
FIG. 52 depicts an onboard device envisioned within a mobile communications medical device according to an aspect of the present invention.
Figure 102:
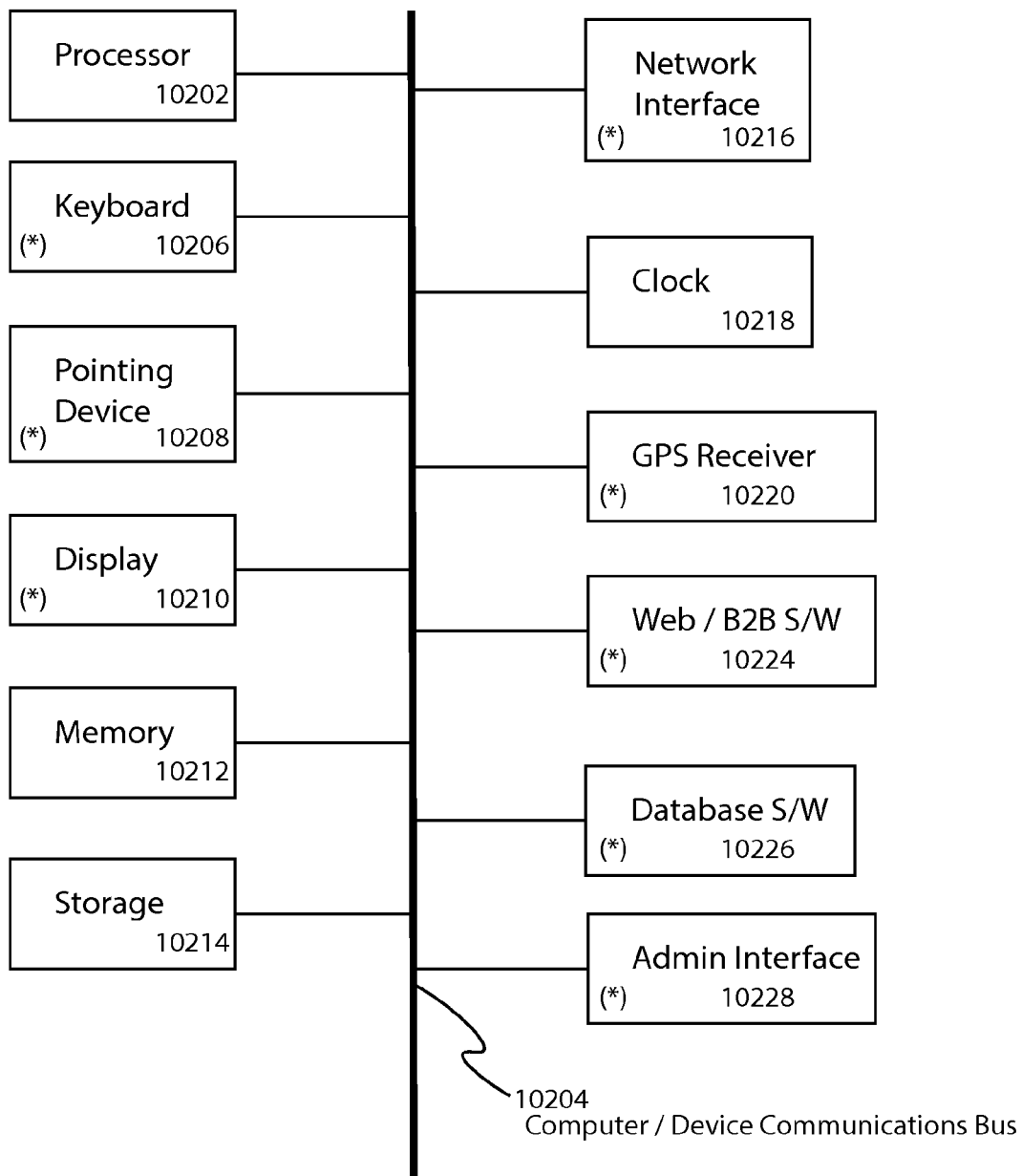
FIG. 102 depicts a Computer Server Platform according to an aspect of the present invention.
Figure 103:
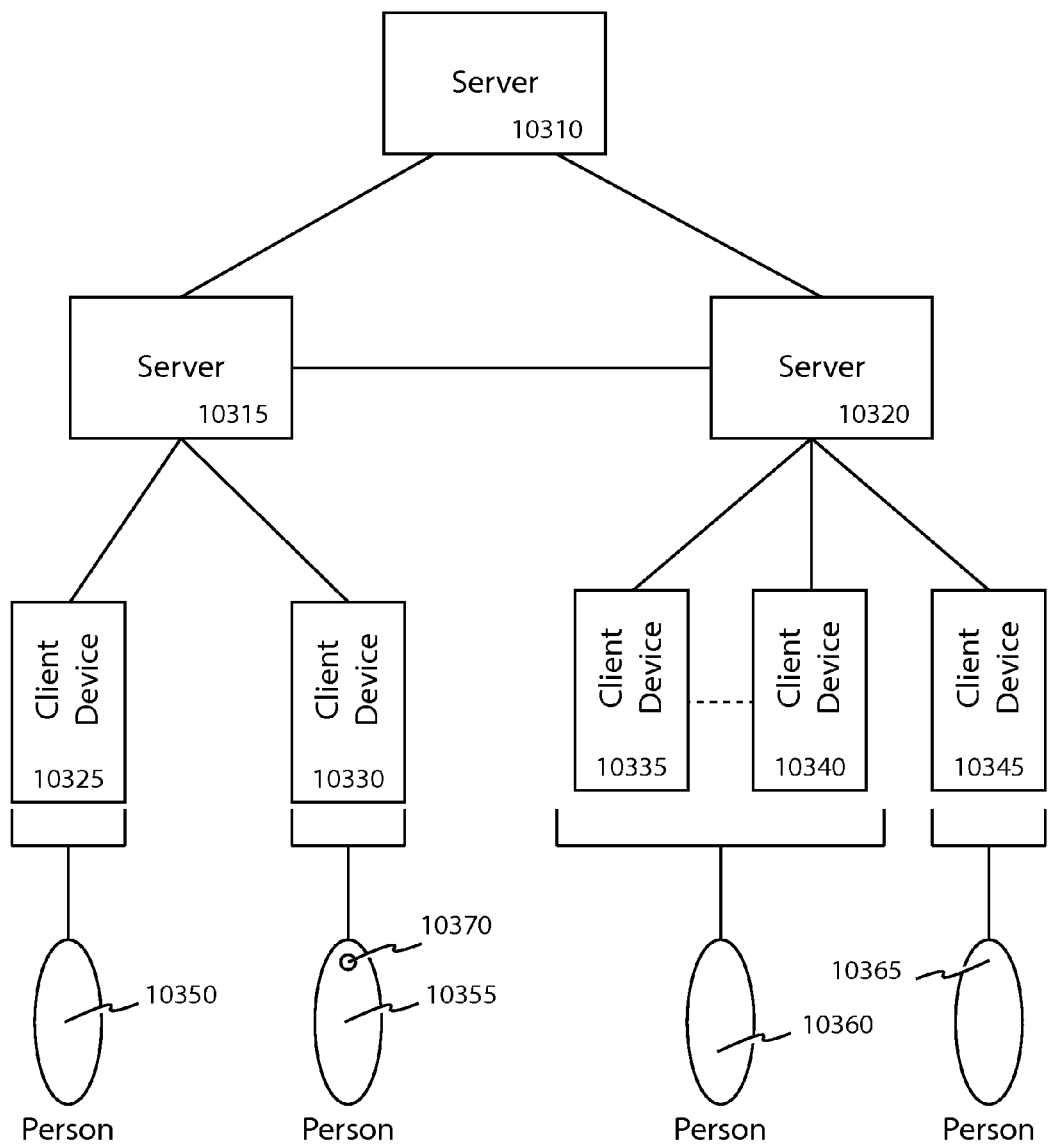
FIG. 103 depicts A Patient Based Mobile Health Linked Information Exchange Supporting Client/Mobile and Implantable Devices according to an aspect of the present invention.
Figure 104:
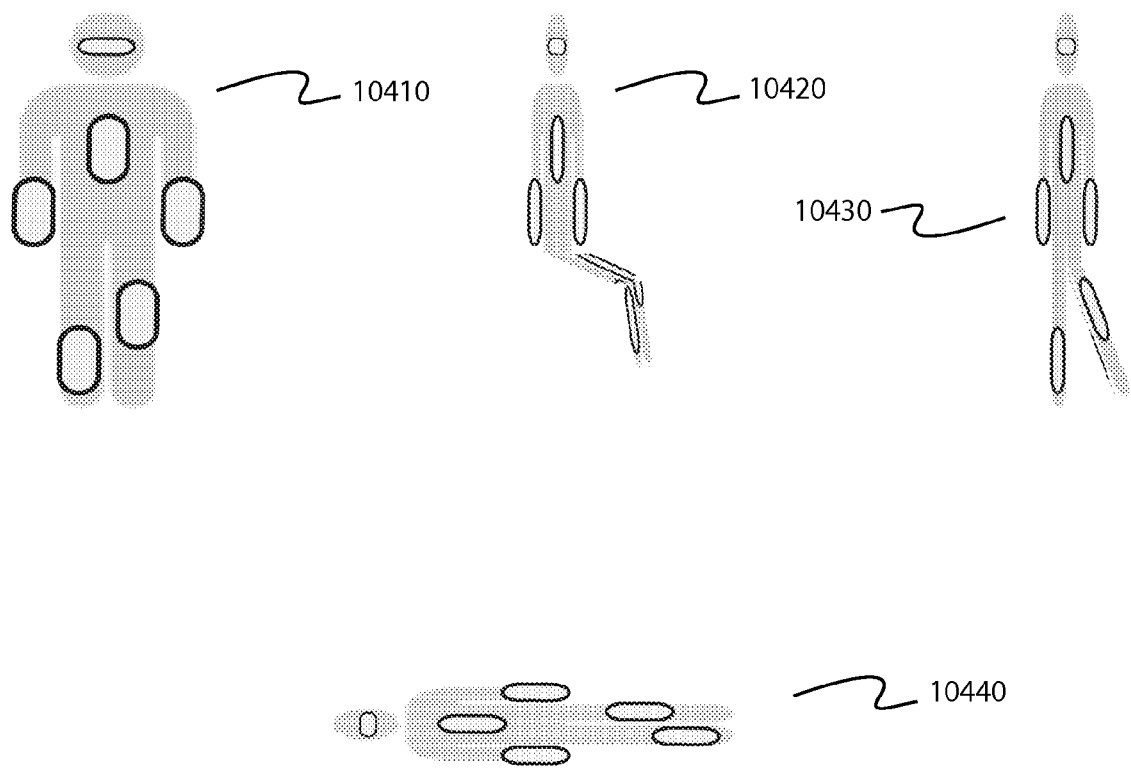
FIG. 104 is a figure of a Sitting versus Standing Patient showing locations where a mobile communications device for transmitting OM and SM data or receiving control data may be located according to an aspect of the present invention.
Figure 105A:
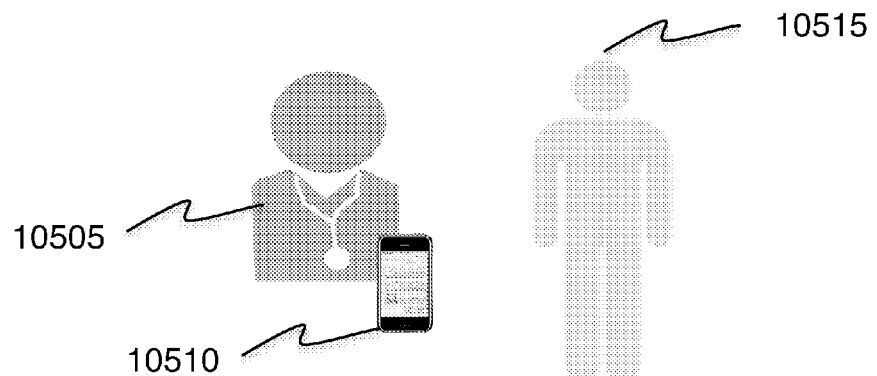
FIG. 105A is a drawing of wearable computers including a neck worn device and a larger view of a typical computer/transceiver device and FIG. 105B depicts other locations on a body of a user for the device and onboard capabilities of a wireless mobile health communications device and an exemplary device according to an aspect of the present invention.

Aspects of the present invention will now be described with reference to FIGS. 1-109 wherein the first digits of a reference numeral are intended to indicate the figure number wherein the depicted element first appears. An aspect of the present invention is to enable the individual with disease or their caregiver or assistant to record objectively measured OM data, in addition to subjectively measured (SM) data such as a diary of medications taken or other observations, and to control the selective and secure dissemination and sharing of the data to other parties such as clinical or hospital facilities, pharmacies, insurance providers, support or peer groups, and researchers. The invention utilizes personal devices such as smart phones (FIG. 8) or other wearable computers (FIG. 105), which may contain data acquisition components such as gyroscopes, accelerometers, a universal time clock, a GPS receiver coupled to the clock, and wireless network transceivers (FIG. 52, FIG. 102), to acquire/transmit data using these data acquisition components or other components such as a touch screen 1020, physical or virtual buttons, a keyboard, a temperature sensor, or an antenna (all collectively referred to herein as "input components") and provide control data to an individual user or an associated wireless device. Once the data are acquired, or intermittently as the data are acquired, the data can be transferred to a server computer using wired or wireless networks or other communications media such as a SD memory card and control data returned developing a special cohort database permissively from EHR records in disbursed databases with permissive data sharing.

Figure 53A:
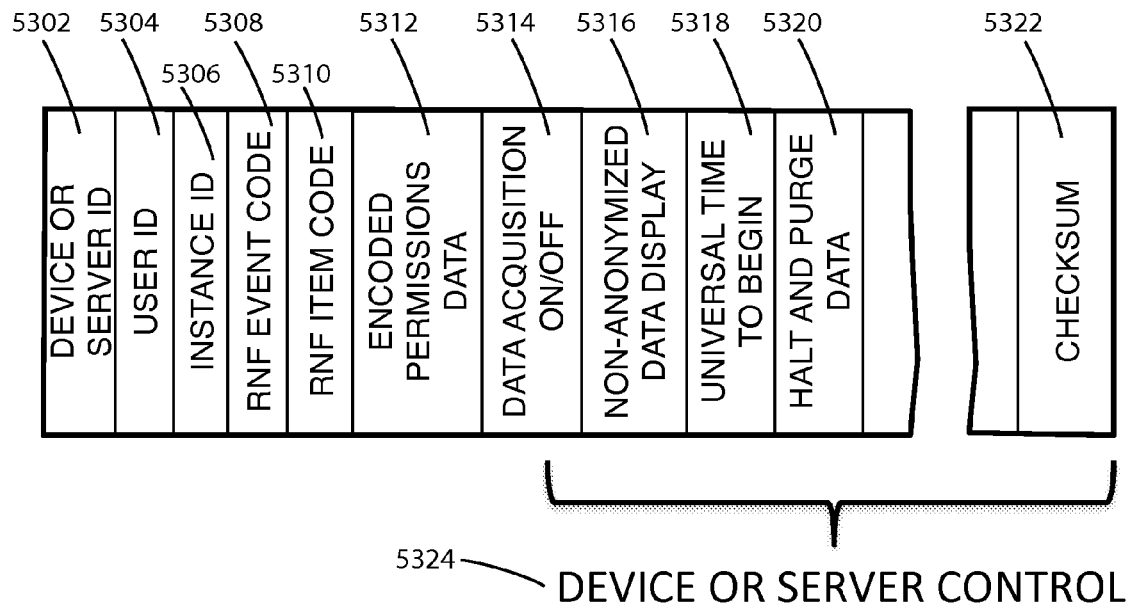
FIG. 53A is a diagram depicting identification data, exemplary control data of a device or server and a checksum according to an aspect of the present invention.
Figure 53B:
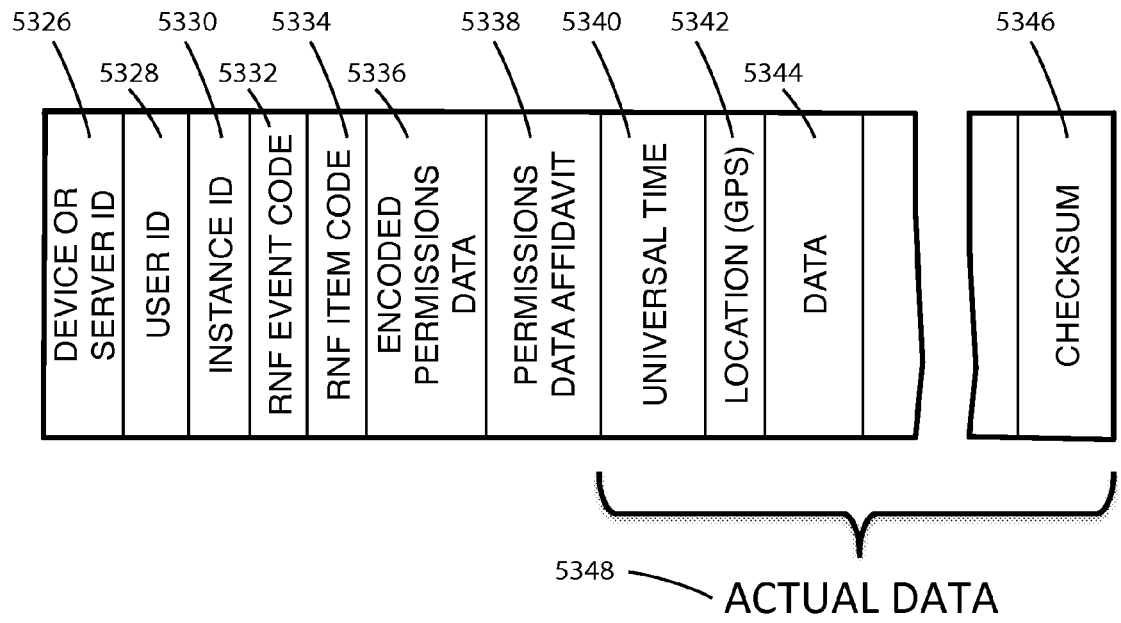
FIG. 53B is a diagram depicting data acquisition or transfer from a device or server according to an aspect of the present invention comprising identification data, actual data and a checksum.

Some input components, such as an antenna, may facilitate communications with devices attached to or embedded within an individual with disease in order to either collect data from the device or to adjust parameters of the device to effect improvements in the individual with disease's comfort, well-being, health, or prognosis. For example, an embedded device can be a deep brain stimulator or an implanted device to monitor neural activities, levels or concentrations of oxygen or other dissolved gases, nutrients, neurotransmitters or neurotransmitter by-products, proteins, and therapeutic agents, temperature, or pressure within a selected region of the brain or a muscle. As a second example, an attached device can be a handheld device or device attached with straps using Velcro or elastic to a limb 1140, the device containing at least one of an accelerometer and a gyroscope 820, which may be mechanical or optical and may be implemented using microelectronic mechanical systems (MEMS), where the device executes a program stored in its memory to measure, for example, rectilinear, angular, or both rectilinear and angular acceleration, velocity, or position in one or more degrees of freedom as a function of time. When the individual with disease performs a defined movement or sequence of movements, such as movements of a hand or walking, the attached device and executing program locally or remotely controlled (FIG. 053A) can capture OM data that can be used to monitor the progress or treatment of disease in the individual with disease, and with a communications interface such as a wireless interface 5235 to a WiFi, 3G, or 4G network, a tether 5245, which may be intermittently attached, or a removable memory or storage device can transmit the OM data (FIG. 53B) to a server computer with associated permissions.

Figure 107:
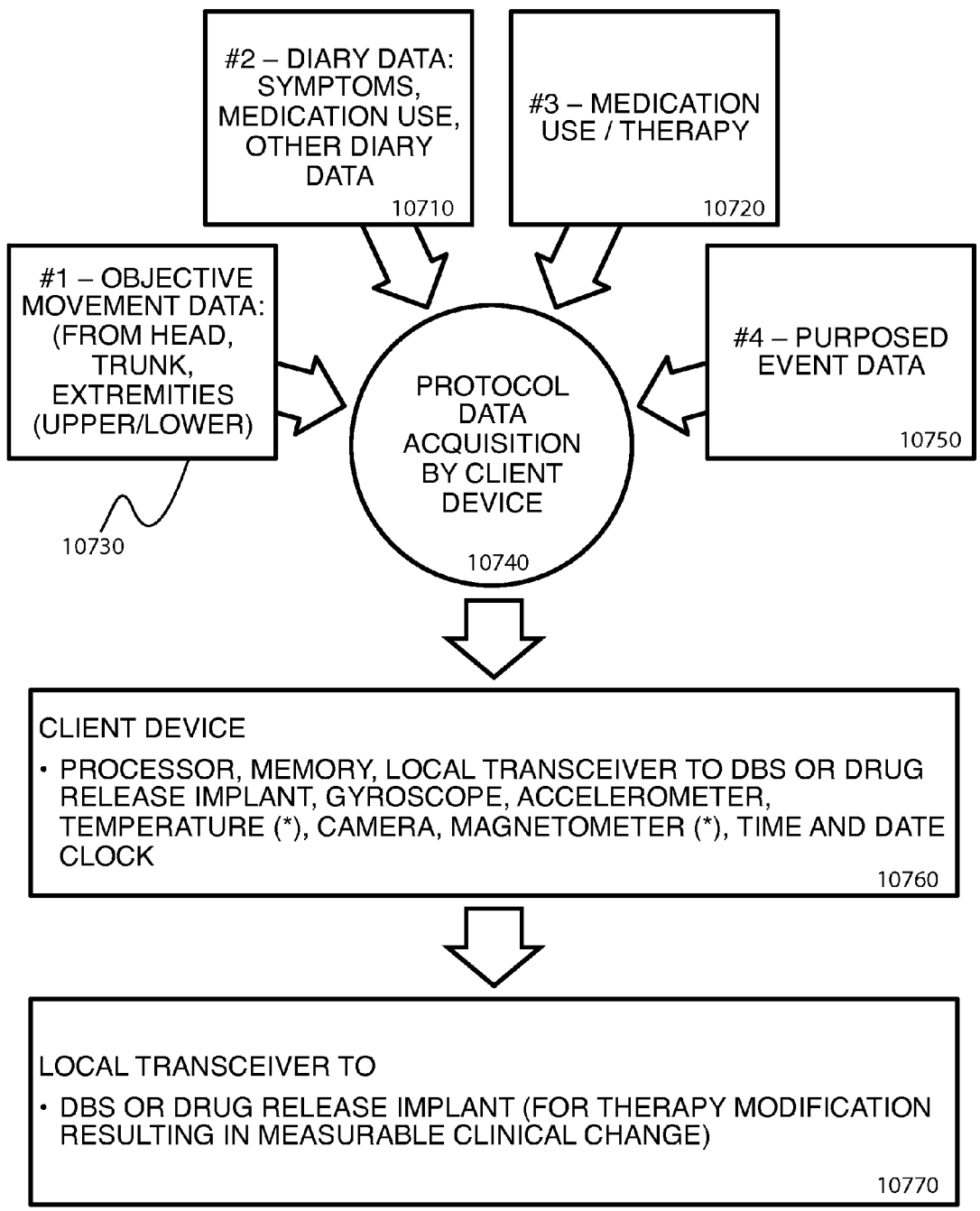
FIG. 107 depicts a method of initiating events on the client device via transmissions from a server in response to received OM and SM data according to an aspect of the present invention.

It is desirable that OM data be collected on a regular or periodic basis (FIG. 107), either by the individual with disease or with the assistance of a caregiver, or in a clinical setting, and that the collected OM data be analyzed (FIG. 92) to determine long-term trends in the efficacy 2330 of treatment 2310 or disease progress 2320 or to compare the OM data acquired from one 2240 or a group of individuals diagnosed with a disease to another group of individuals 2230 diagnosed with a disease using statistical analysis. The stored program 175 in the device 180, 10330 or a system generated request (FIG. 53A) causes the device to provide a reminder to the individual with disease, a caregiver, or a clinician, using for example a light generated by a LED or a display 1020 or an audible or vibration alarm to perform a specified protocol based upon internal software or in accordance with protocols in an external server-linked database such as the RNF database (FIG. 108A) in order to reliably collect a sequence of OM or SM data sets (FIG. 107), where each OM data set can be transmitted to a server computer. It is advantageous to have a mechanism for time keeping in the device, or accessible by the device via a wireless or wired communication medium, in order to accurately associate with collected data a time stamp of when the data are collected. It is further possible to associate additional data such as geographic location data (if a OPS receiver is included in or accessible from the device 5250), as well as data such as from temperature and humidity measurements.

An individual with disease or a caregiver or assistant may use the device, or a different device such as a desktop or laptop computer, tablet, or smart phone, to access a server computer in order to control access to stored information about or derived from the individual with disease. The individual with disease may, for example, instruct the server computer 10315 to provide controlled access to all or a portion of this data by a third party such as a clinic, hospital, doctor, or physical therapist via a user agreement or a one time explicit permission (FIG. 108A). The individual with disease may also instruct a server computer, not necessarily the same server computer, to deliver records stored about the individual with disease and related to the individual with disease's care to the individual with disease, or to a server computer for storage at that server on the individual with disease's behalf where a cohort database for similarly situated individuals may be generated from EHR records. Security may be carefully controlled through both authentication of the individual with disease or individual with disease's representative to each server computer and encryption of data during transmission between devices (whether server computers, devices under the control or used by the individual with disease, or devices used by other individuals such as personnel at a hospital or a clinic, in order to ensure that access or use of the data is not consistent with the individual with disease's directives. All individuals, organizations, or computers or other devices may be properly authenticated to establish their identity before access to the individual with disease's data is permissively allowed as will be further explained herein.

Many authentication, encryption, and secure data exchange methods exist and are well known in the fields of computer science, computer engineering, and computer security (or cyber security). For example, public and private key pairs can be generated and used to identify individuals, organizations, or devices prior to exchange of sensitive data. These public/private key pairs can be used to encrypt and exchange session keys for the exchange of sensitive data in an encrypted form. A server computer can execute a program to generate a public/private key pair and optionally a session key to provide to a user or another device or computer. If the program is designed and executed in such a way that the public/private key pair is maintained only in the memory of the server computer prior to transmission to the recipient, and if the memory location or locations where the key data are stored is erased following use, then there is a very small window of time during which an unauthorized program might intercept the key data and transmit it or use it in an unauthorized manner, significantly diminishing the risk that the individual with disease's directives for security, privacy, and information sharing might be violated.

Such a public/private key pair may be utilized to maintain sensitive data that are stored on the server in an encrypted form, where the key data that are necessary to decrypt the information are stored only by the owner of the data, which is normally the individual with disease who is associated with that data. By not storing key data within a server computer and storing sensitive non-key data such as OM data on a server computer only in encrypted form, such that the individual with disease or individual with disease's representative provides the key data only when needed to the server computer and the server computer decrypts sensitive information only upon demand and does not store the decrypted data in a persistent form (such as in a file or database), the risk of compromise of the security of the data is substantially transferred to the individual with disease or owner of the data. The method outlined herein for the security of sensitive information is but one method of many that are known in the field of computer security; other methods may be utilized. For example, a public key infrastructure (PKI) system can be utilized using signed certificates, firewall rules such as those provided by the iptables or ipchains interface and the kernel firewall in a Linux operating system, or similar capabilities in a UNIX or Windows operating systems, and methods such as those enabled by Security Enhanced Linux (SELinux) can be utilized to control access to computer or device resources, and secure data exchange mechanisms such as secure shell (ssh), secure copy (scp), secure authentication mechanisms such as SSL and TLS, and secure XML and HTTPS protocols can be utilized. In addition, many encryption algorithms are well known in the field, as are multiple algorithms for the generation and exchange of key information, and can be used in place of portions of the approach described herein.

The invention contemplates a network of server computers, individuals diagnosed with a disease, caregivers and care facilities, and devices that can each communicate with other selected computers, individuals, facilities, and devices within the network. A web of trust can be established by the participants in the network to allow the selective exchange of or access to stored data associated with individuals diagnosed with a disease, care facilities, or insurance providers. In the medical field, the individual with disease plays, or can play, a central role as a broker of data because the individual with disease typically has access to all data about himself or herself. Once the individual with disease acquires data, by request, from, for example, a hospital or other service provider, the individual with disease typically has the right to do what he or she wishes with the data, including causing it to be stored in a server computer, modified by algorithms or other process, or creating new data or analyses from the data. Exceptions to this do occur, for example, if the data (as opposed to the form or vehicle used to collect the data) are copyrighted, in which case a individual with disease's rights to the use of the data may be curtailed by the terms of use of a license agreement. In general, however, the individual with disease can control who and what organizations can access and use the data, and how the data can be used. This offers a mechanism to ameliorate a severe problem in current medical practice, which is the inability of caregivers to access data generated at or held in another location when the data offers the potential for improved individual with disease treatment outcomes so as to generate a cohort database tuned to the needs of the individual user who may be any one in a community (for example, per FIG. 15). The digitization of data, and of medical records in particular, provides the opportunity for the individual with disease to play a much more active role in his or her treatment by controlling access to data about the individual with disease and providing access for his or her benefit to the appropriate caregivers and facilities. The use of public/private key pairs offers a mechanism for authentication of access rights and data transfers which allows the data to remain encrypted and inaccessible to other parties.

A medical information delivery system as disclosed herein is composed of at least a server, computer, or computer system (a server) that stores data about more than one individual with disease, where the data may be OM, SM, or a combination of data types. This system has, at any given time, a state, which is determined by the totality of the stored individual with disease-related data, and implements a method to select a subset of the data for further processing (cohort data) based upon one or more criteria such as the age, gender, ethnicity, geographic location, disease status, treatment or treatments applied, service provider(s), services rendered, participation in a program, duration and type(s) of data stored, devices or protocols used to gather data, and time(s) or time interval(s) for diagnosis, treatment, or participation in a program, for each individual with disease for which data are stored. This method to select may be implemented, for example, using a commercial off-the-shelf (COTS) database product such as Oracle or MySQL or software developed for this purpose that may utilize either a database or files to store information for the server's use. MUMPS is a programming language that originated in the 1970's and was developed for applications within the medical community. MUMPS incorporates features of databases within the language using global variables that persist in a database. It is still heavily utilized in medical applications 1560; however, there has been significant divergence between the development of mainstream business-to-business (B2B) applications development environments and the MUMPS environment. As a result, it is more likely that the medical information delivery system disclosed herein will be designed to interface to other systems implemented using MUMPS than that it will be implemented using MUMPS. Multiple computer systems or processors may be utilized to implement the server; for example, a processor may be used to execute a stored program and implement the method to select, and a second processor may be used to manage the storage of data. These processors may execute within a single physical computer, or within multiple computers that can communicate via a computer network, as is well known in the art. Parallel programming paradigms such as those using the Message Passing Interface (MPI) software library and Hadoop may be used to coordinate the computing activities across multiple processors and multiple physical computers.

The disclosed medical information system can differentiate stored data into multiple groups of data, each group having different privacy or security attributes used to control the distribution or dissemination of data associated with that group, and can implement a method to anonymize any selected subset of data associated with a group, including all data associated with a group, in a manner that precludes the identification of an individual with disease from knowledge of the anonymized data. This anonymization can be performed by, for example, suppressing or removing fields of information within data records that have been flagged as providing personally identifiable information; anonymization can also be performed by encryption of these fields using either a symmetric key encryption algorithm or one key of a public/private key pair, or by application of a secure cryptographic hash such as the MD5 hash algorithm to the data and using the computed hash value in place of personally identifiable information from one or more fields of a data record in subsequent operations. When fields of information are suppressed or removed, it is no longer possible to recover the suppressed information, unless the remaining fields can be used to uniquely identify the data record in the stored data. When encryption is used, an entity can recover the suppressed information if the symmetric encryption key or the other half of the public/private key pair is known by that entity. When a secure cryptographic hash is used, and if the hash values have been uniquely associated with the data record, knowledge of this association allows access to the data record personally identifiable information by an entity that has access to the original stored data. These methods of anonymization or protection of sensitive information are well known in the fields of computer science, computer engineering, and computer security. Anonymization may be performed on demand, or on an as-needed basis in response to a request for information, or it may be performed as data are received for storage by the system. The second method is preferred, where one or more symmetric or public/private encryption key(s) are utilized to control the anonymization process. In this case, additional encryption keys may be utilized to either distribute anonymized data to an entity that requests it by re-encrypting the data or distribute encryption key information in an encrypted form.

The disclosed medical information system also implements at least one method of processing anonymized data produced by anonymization of a selected subset of a group of data. The method of processing creates aggregate data or information that is representative of one or more characteristics of the selected subset of data, where the aggregate data or information may be in a computer-readable form such as a data structure stored within a computer's memory or storage device, or it may be in a human-readable form such as a graph, chart, or table displayed on a display device or printed on paper. For example, the aggregate data may be a timeline showing the anticipated or average progression of a disease such as PD together with visual indicators, icons, or a histogram or other graphic showing the distribution of individuals diagnosed with a disease associated with the selected subset of data with respect to the status or progression of the disease. A table or tabular listing or a chart may be utilized in place of a timeline. Optionally, additional information may be generated by the method of processing such as a listing of service providers utilized by individuals diagnosed with a disease at a selected point or portion along the timeline, or a listing of options considered by individuals diagnosed with a disease within a selected portion of the timeline. The timeline may be presented to an entity in a manner that allows the entity to query the medical information system for additional information, such as the distribution of outcomes, such as the mean or median time to progression to the next stage of a disease, in response to the possible selection of a treatment option or of an activity by a individual with disease at a selected point along the timeline. The timeline may include, in addition to information based upon anonymized data, sensitive, private, or personally identifiable information to which the entity has rights that include the right to view or use such data. This allows, for example, the comparison of a individual with disease's disease progress against information derived from anonymized data related to a cohort or selected group, subset, or population of other individuals diagnosed with a disease.

The disclosed medical information system also implements at least one method of processing use of an external table of tables (by example the Restorative Neurosciences Foundation (RNF) codebook (RNF-C). This disclosed reference repository of tables and standards can be used for database queries and to build a tuned cohort database for an individual user as well as for use in social media to locate similarly situated and local individuals to an individual diagnosed with a disease (FIGS. 108A, 108B and 108C).

The timeline may be implemented and presented to an entity such as a individual with disease as a software application that can be executed on a computer such as a desktop, laptop, or tablet or on a portable or handheld device such as a tablet, smart phone, or game device, in which case it is preferable, but not required, that the computer or device that executes the software has communications components such as a network interface or a wireless (WiFi, 3G, or 4G) interface that enables communications between this computer or device and the medical information system. In this manner, the timeline can be presented in an interactive manner to a person, who can utilize the timeline to query the medical information system for information related to the person's disease or disease status and compare the person's own situation with the selected group or cohort. If communication between this computer or device and the medical information system is either intermittent or not feasible (except for the initial delivery of the timeline software application and anonymized data), then the user's queries can be answered by the software application using the delivered anonymized data, but it is preferable that the answers be provided using current data, either by intermittently delivering new anonymized data to the computer or device or by performing the necessary computations within the medical information system and delivering the answers to the computer of device, so that the answers to the user's queries are consistent with data recently stored in the medical information system.

The medical information system may consist of many servers, computer, or computer systems that store data related to individuals diagnosed with a disease, anonymize data, aggregate anonymized data, and implement at least one method of processing to generate and deliver information based upon the anonymized and aggregated data to entities, which may be other servers or computers, or humans, in either machine-readable or human-readable form. Each server, computer, or computer system may perform one or more of these functions, and there is no requirement that more than one function must be performed by a single server, computer, or computer system. One or more servers may also provide an interface that can be used by a client data acquisition and/or interface device to deliver individual with disease-related data to a server, effecting the storage of the individual with disease-related data within the medical information system. Such servers may also provide, as a function of their interface(s), methods whereby a individual with disease or authorized individual with disease's representative can direct the exchange of individual with disease-related data, including data that contain sensitive, private, or personally-identifiable information, between servers, computers, or computer systems using communications methods that optionally implement authentication and/or non-repudiation strategies, thereby implementing a data exchange among individuals diagnosed with a disease, providers, and other entities. This method enables individuals diagnosed with a disease to "own" their data and effect the exchange of data relevant to the management of the treatment and progression of their disease between their medical service providers. A client data acquisition and/or interface device may optionally be mobile and/or be able to communicate wirelessly with another device. This provide the opportunity to collect objective measurement (OM) data related to a individual with disease's disease status and communicate that OM data to a server, computer, or computer system.

Mobile Data Acquisition/Display:

An example is the use of an on-board gyroscope or accelerometer of a mobile device (FIG. 8) with sensors and connectivity (FIG. 52, FIG. 91) such as a mobile phone or tablet manufactured by Apple Inc., Blackberry Ltd. (Research In Motion), or Google Inc., or a wearable device such as a watch or ankle bracelet or glasses running the ANDROID® or other operating system platform to sense angular or rectilinear acceleration or interpret motion from processed visual data (video of movement), according to a protocol, for calculating degree of Parkinson's symptoms (e. g., pronation protocol). As an example, APDM Inc., a corporation based in Portland, Oreg., provides wearable inertial monitoring devices similar in size and shape to a watch that have an accelerometer, a gyroscope, and a magnetometer, and that also provide wireless communications to other such devices (McNames et al. 2010, 2012).

Figure 105B:
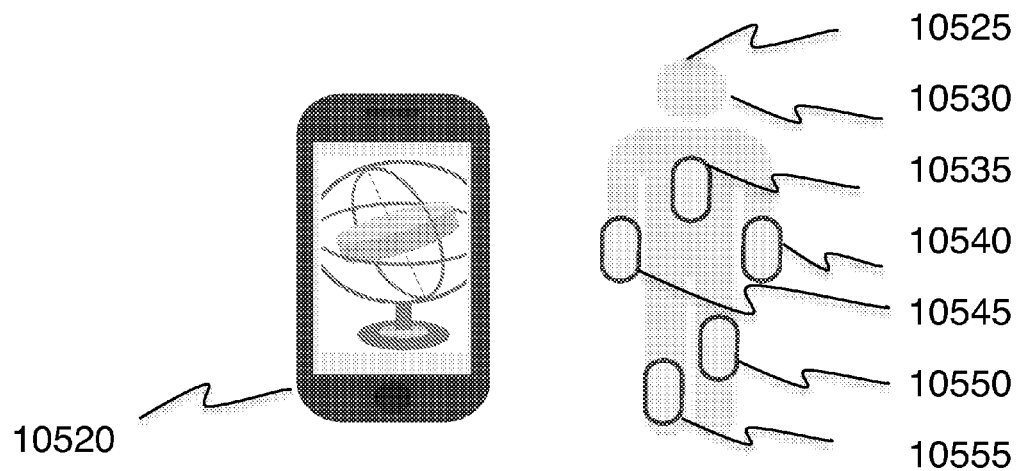

A mobile data acquisition device can be secured to an individual's limb, such as strapped to a wrist or ankle or hand or foot, or held by a hand, in order to sense motion, or attached to the neck or head to sense orientation or motion, preferably including an acceleration or velocity around at least one axis of motion, but other configurations sensing rectilinear acceleration or velocity along another axis or direction of motion or any other combination are possible (FIG. 105B). The device may include one or more sensors, such as a gravitational sensor 5255 to determine the direction of gravity (or an up-and-down axis) or a GPS receiver 5230 or other receiver to determine a coordinate frame of reference with respect to the Earth's surface (consisting of at least a horizontal plane or a vertical axis) in order to determine orientation, velocity, and/or acceleration in one or more axes or degrees of freedom with respect to that coordinate frame of reference. Such sensed orientation or motion (acceleration and/or velocity along one or more degrees of freedom or axis) can be sampled using a program stored in the mobile or wearable device, either on a periodic basis or intermittently, and may be temporarily stored within the memory of the device 5210 and optionally processed 5225 using the stored program 175 to obtain objective measurement data 210, and uploaded to a computer server 910 using a communication link, which may be wireless or wired and may only be connected intermittently to the mobile or wearable device. A second example is a wireless or wired access device, which may be mobile or wearable but may also be a less mobile device such as a desktop computer, a workstation, or a dedicated or specially designed device used in a clinic or home health care setting for this purpose, with an algorithm for encoding data input or received from a neurostimulator or embedded measurement device. Such a device can also be utilized to modify the operation of the neurostimulator or embedded measurement device according to directions input or received from a medical provider, where the directions may be communicated or transmitted to the device either using a wired or wireless communication link, which may be intermittent or continuously available. The modification of the operation of or obtaining input or received data from the neurostimulator or embedded measurement device is preferably performed or directed by the execution of a stored program in the memory of the wireless or wired access device, but may be performed by a computer or other processor such as a programmable hardware device (such as an application-specific integrated circuit) within the neurostimulator or embedded measurement device, or performed through coordination of the operation of the two devices by the programming of each device. The disclosed GPS functionality also serves to obtain universal time to coordinate multiple devices and longitudinal analysis.

Figure 9:
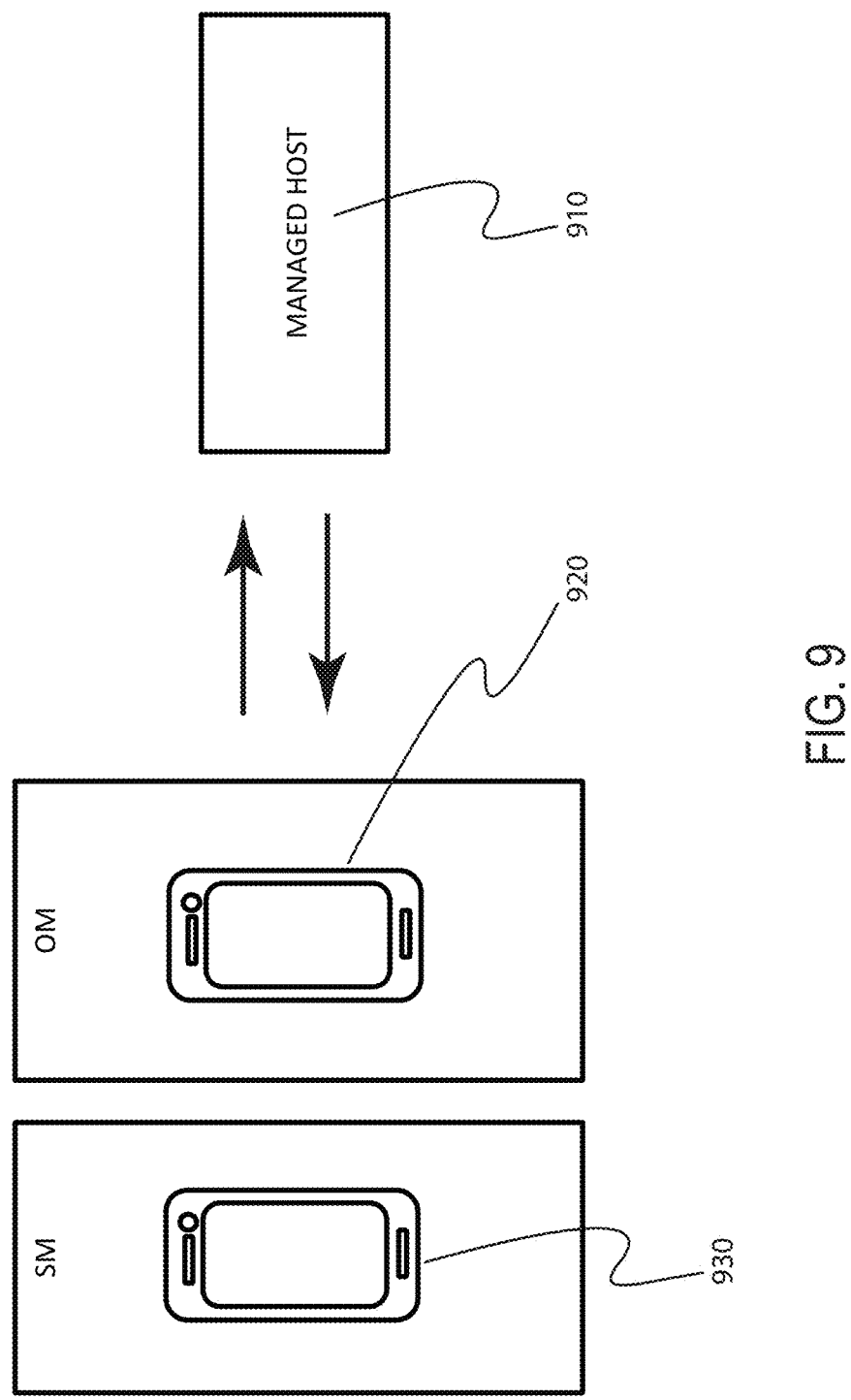
FIG. 9 depicts wireless transfer of user entered and objectively measured data to a managed host or web environment.
Figure 10:
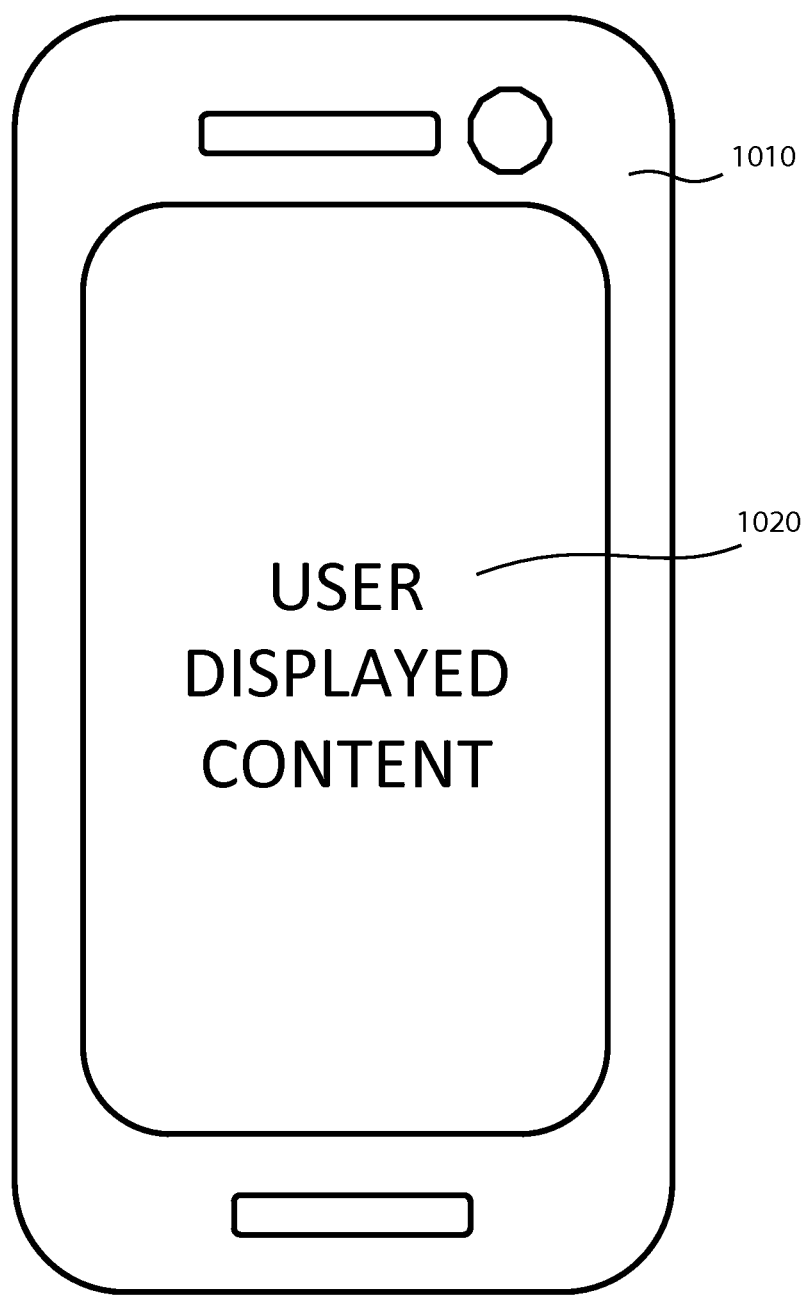
FIG. 10 depicts a wirelessly linked mobile health device displaying User Displayed Content via wireless delivery.

FIG. 9 depicts wireless transfer of user entered and objectively measured data to a managed host or web environment wherein client devices 920, 930 provide OM, SM to a server 910 and the server returns, for example, data of a cohort database, progress data, queried data or control data. A secure computer server platform (Server) can provide storage of received data in a file or database, and can use protocols such as HTTP and HTTPS to communicate with one or more mobile devices, wearable devices, or wireless or wired access devices 920, 930. FIG. 10 depicts a wirelessly linked mobile health device displaying User Displayed Content via wireless delivery: alarm data, implant control data, medication protocol data, drug delivery implant data among other feedback data from server 910 developing a cohort database and automatically calculating such feedback data for storage, display or control. The Server 910 can implement a data retrieval system using, for example, web based protocols such as HTTP and HTTPS (FIG. 9) to implement a web based display system or a statistical analysis system of devices 920, 930. The Server 910 will have at least a processor such as an Intel or AMD processor that executes x86 instructions or an Oracle processor that executes SPARC instructions, a computer bus that enables the processor to communicate with other components of the Server, where such communication may include communications across a network or communications channel such as a parallel or serial communication channel used to communicate with disk drives (using for example a SATA or SCSI channel, or a virtualized communication channel such as iSCSI across a communication network) or a keyboard (using for example a PS/2 or USB communication channel) or display (using for example a VGA, DVI, or HDMI communication channel), memory to store a program that directs the execution of the Server and stores data received from or transmitted to another device, a network interface or other communications interface that enables communication with another device such as one or more mobile devices, wearable devices, or wireless or wired access devices or other Servers or computers used either for the same or similar purposes as disclosed herein or used for different purposes such as within a clinic or hospital setting for individual with disease records or to support medical procedures or treatments, or by an insurance company or government agency for financial and/or medical treatment records, or by an association formed for the benefit of either individuals diagnosed with a disease, medical or clinical practitioners or staff, or by one or more researchers, enabling the exchange of information between the Server and other servers or computers to support collaborative activities, a storage device such as a hard disk drive (HDD), a solid state disk drive, or a memory card such as a SD card, or a network-accessible storage device (NAS) or other storage device that is used for long-term or persistent storage of the program and data, and an interface to allow administration of the Server by another computer or a human operator, the interface being either at least a keyboard and display device, and optionally a pointing device such as a mouse or a touch pad, or a virtual interface such as a Lights Out Manager or an implementation of the VNC or other remote desktop protocol that emulates at least a keyboard and display device using another device such as a second computer that can communicate with the Server using a network. If the server uses a database to store data rather than files stored within its filesystem, database software such as MySQL or Oracle may be used and included in the Server. Communication protocols such as HTTP, HTTPS, or other protocols using XML, can be implemented using web server and/or business-to-business communications software such as Apache, Tomcat, J2EE, or Java Beans. The combination of the Server and the one or more mobile devices, wearable devices, or wireless or wired access devices enable monitored or unmonitored measurements in either the home or a clinical environment.

Activities performed in the home environment by the individual with disease or individuals diagnosed with a disease' caregivers using one or more mobile devices, wearable devices, or wireless or wired access devices support or perform the collection of information from or about the individual with disease that relate to the documentation of the status or progress of the disease for which the individual with disease is being treated and/or the individual with disease's response to such treatment. These activities can utilize consumer devices such as smart phones, tablets, laptops, desktop computers, wearable computer devices such as watches, and one or more components of game devices, some of which may contain sensors that can measure position or location (such as GPS receivers or WiFi communications devices) or acceleration and velocity (such as gyroscopes and accelerometers) or receive data from an implanted medical device or device attached to the individual with disease (such as neural activity, heart rate, blood pressure, body temperature, respiration, and motion or tremor). Such activities may be monitored or unmonitored, or may be performed autonomously and preferably on a regular or periodic basis by a device under the control of a stored program, or as directed by data received or communicated from a Server or other computer using a wireless or wired communication channel. Activities can include tests performed in a home environment by a individual with disease or a individual with disease's caregiver(s) and may use a protocol such as, by example, a protocol described herein for the collection of motion data using a wearable or handheld device, where the device is attached to a hand, wrist, ankle, foot, torso, limb, or the neck or head. The test activity can result in the acquisition of objective measurement (OM) data using, for example, an accelerometer or gyroscope or GPS receiver, where the raw measurement data may optionally be processed using an algorithm in order to obtain OM data.

Device for interrogating individual with disease on-board medical devices: Examples of leading neurostimulators systems FDA approved for implantation include Deep Brain Stimulators (DBS) [an example is the Medtronic Activa series], Peripheral Nerve Stimulators [an example is the Cyberonics Vagal Nerve Stimulators (VNS)]. Others [Boston Scientific, NeuroPace, etc.] are nearing FDA approval. Each of these systems has the potential of communicating with a data exchange. Such devices may be in the position to report metrics of health such as temperature, position, movement, or other useful metrics. A cohort database may be generated of information from these devices using sensors (magnetometers, or other sensors) to scan for emitted signals and correlate with a subset of known programming parameters, which correlate for several similarly situated permission granting individuals with disease. In the event device manufacturers wish to partner with the exchange, they could provide access through their individual with disease device interrogation systems to provide a complete dataset about the delivered neuromodulation or other signals (EEG in the case of the NeuroPace RNS device).

Figure 106:
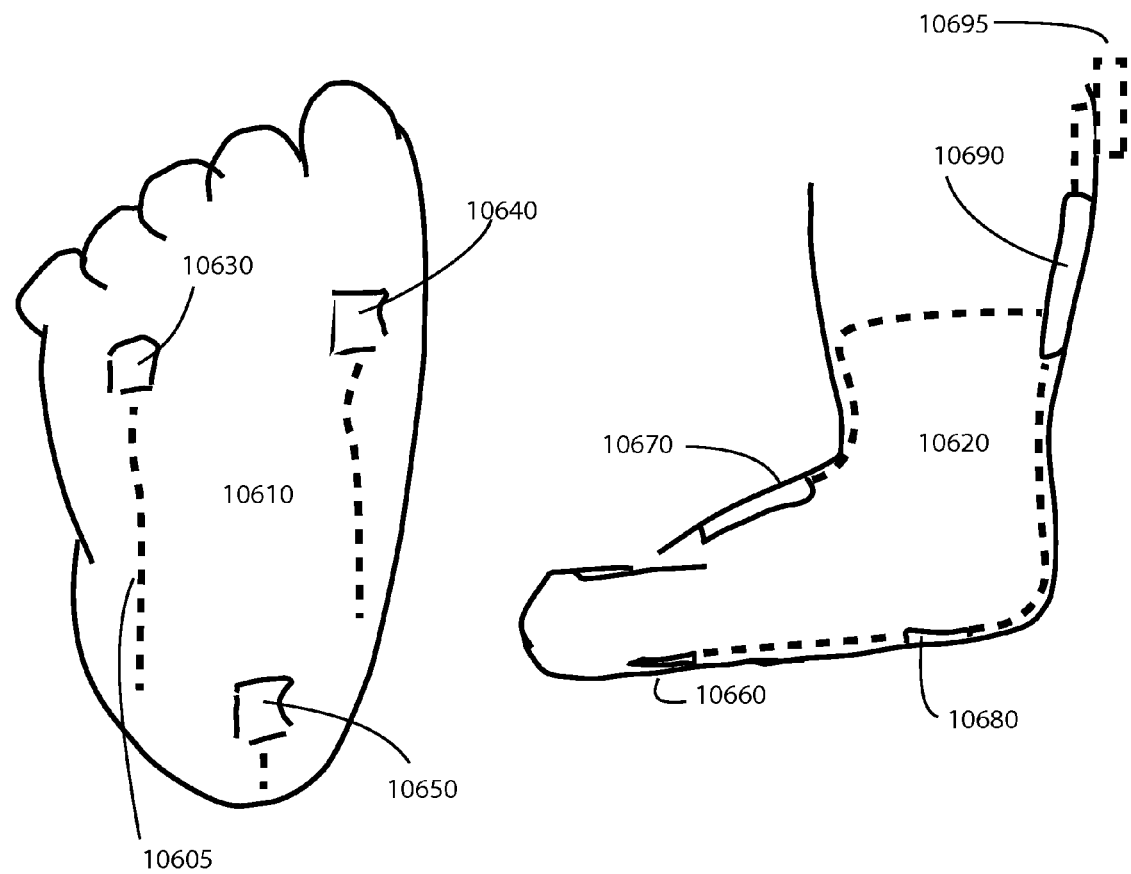
FIG. 106 depicts a method of sensing and transmitting triangulation foot pressure via pressure transducers at locations at the bottom of a foot and movement via a sock/glove for, for example, gait correction and sensing movement according to an aspect of the present invention.

Device for holding multiple sensors on the foot: One or many sensors (of an intelligent client device equipped with a transceiver) may be located on the lower extremities (FIG. 105B, 106) in a position to be able to measure metrics of 1) gait 10430 and the relative difference between measurements from each leg to determine the presence or absence of an asymmetric gait, for example, or an antalgic gait, for example, or determine time of walking, acceleration, turns, or other metric 2) pressure or relative use of the anterior, posterior, medial, or lateral aspects of the foot. Such devices are secured via connections to external physical features of the foot covering device such as: 1) embedded within a sock or foot worn device within a shoe, or 2) attached to the shoe sufficiently to capture the movement of the foot, or 3) to other external device with or without a strap attached externally to the leg, 4) or in the form of an implantable sensor with transmission to the external environment powered via primary cell battery, rechargeable battery, or deriving power via regenerative, ambulation based methods or via a rectified circuit method deriving power from external sources such as power from cellular or other transmissions.

Device for holding multiple sensors on the hand/wrist. One or many sensors (of an intelligent client device equipped with a transceiver) may be located on the upper extremities in the position to be able to measure metrics of 1) arm swing and position and the relative difference between measurements from each arm to determine the presence or absence of an asymmetric arm swing, for example, or determine time or velocity of arm swing, acceleration, turns, or other metric 2)

pressure or relative use of the hand. Such devices are secured via connections to external physical features of the hand covering device such as: 1) embedded within a glove or hand/arm worn device within a clothing item such as a jacket, or 2) attached to the arm/glove sufficiently to capture the movement of the arm, or 3) to other external device (such as a glove) with or without a strap attached externally to the arm, 4) or in the form of an implantable sensor with transmission to the external environment powered via primary cell battery, rechargeable battery, or deriving power via regenerative, ambulation based methods or via a rectified circuit method deriving power from external sources such as power from cellular or other transmissions.

Device for holding multiple sensors on the torso or head. One or many sensors (of an intelligent client device equipped with a transceiver) may be located on the torso or human body head in the position to be able to measure metrics of 1) torso/head movement (including capturing head movement gestures), postural sway/head movement, for example, or determine time or velocity of arm swing, acceleration, turns, or other metric 2) pressure or relative use of the torso/head. Such devices are secured via connections to external physical features of the torso/head covering device such as: 1) embedded within a shirt or jacket or sweater/hat, head mounted device or glasses like device mounted or worn by on the head, or 2) attached to the torso or head/jacket or hat sufficiently to capture the movement of the torso or head, or 3) to other external device (such as a strap or backpack or headband) with or without a strap attached externally to the head, 4) or in the form of an implantable sensor with transmission to the external environment powered via primary cell battery, rechargeable battery, or deriving power via regenerative, ambulation based methods or via a rectified circuit method deriving power from external sources such as power from cellular or other transmissions.

Client data acquisition/display device for use by a individual with disease: An intelligent device with sensors may be used to acquire diary or objectively measured data such as GPS position, relative movement, motion data (accelerometer, gyroscope), monitors speed of typing or other finger inputs, and may be able to record speech (via a microphone) and facial expressions of the user. Additionally, the device may be used in an emergency to reach out for further help and assistance.

Client data acquisition/display device for use by a healthcare professional: Such an intelligent device may be used to display checklists and forms, progress reports, alarms and updated drug regimen or implant control data such as the unified Parkinson's disease rating scale for use in a clinical setting and provide a display of the disease state of the index individual with disease.

Client data acquisition/display device for use by a researcher: Such an intelligent device may be used to acquire non-health care data for the specific purpose of research acquired in a meaningful way for aggregation and dissemination to others based upon permissions and queries presented to develop a specific cohort database. Data for use by a researcher may be obtained by processing or aggregating data from individuals diagnosed with a disease using a Server, or, in order to adequately safeguard the privacy of individuals diagnosed with a disease, by a second Server that obtains data from one or more Servers that have stored individual with disease OM, CM, and/or SM data that, such obtained data having been anonymized by, for example, removing, encrypting, or hashing (using, for example a cryptographically secure hash such as MD5) information that can be used to identify a individual with disease. The processing or aggregating to form a specific cohort database may be performed by, for example, providing one or more graphs, reports or maps of individual with disease data for a group of individuals diagnosed with a disease such as a subset of individuals diagnosed with a disease selected by geographic region, by age, gender, ethnicity, or occupation, or by the stage of a individual with disease's disease or the type or types of procedures that have been performed or devices that have been implanted within the individuals diagnosed with a disease. Such a map, graph, or report may be made accessible to researchers, to a group such as individuals or organizations within a government, a company, or an association, or to administrators or medical professionals associated with clinical or hospital facilities using a Server that implements a web site on which this information is published, either without access controls, or disseminated privately to individuals or groups using a secure web interface and authentication by token, biometric such as a fingerprint or iris scan, or user identifier and password. It may be preferable to utilize multiple Servers to process and or aggregate individual with disease data in the chain from the Server that initially stored data received from a device used by the individual with disease a individual with disease's caregiver, or a clinician or other medical professional to perform the steps of anonymization, analysis, which may included statistical modeling and analysis, aggregation, generation of specific cohort database, preparation of maps, graphs, or reports, and presentation or dissemination of the prepared data to the public or for research purposes.

Figure 11:
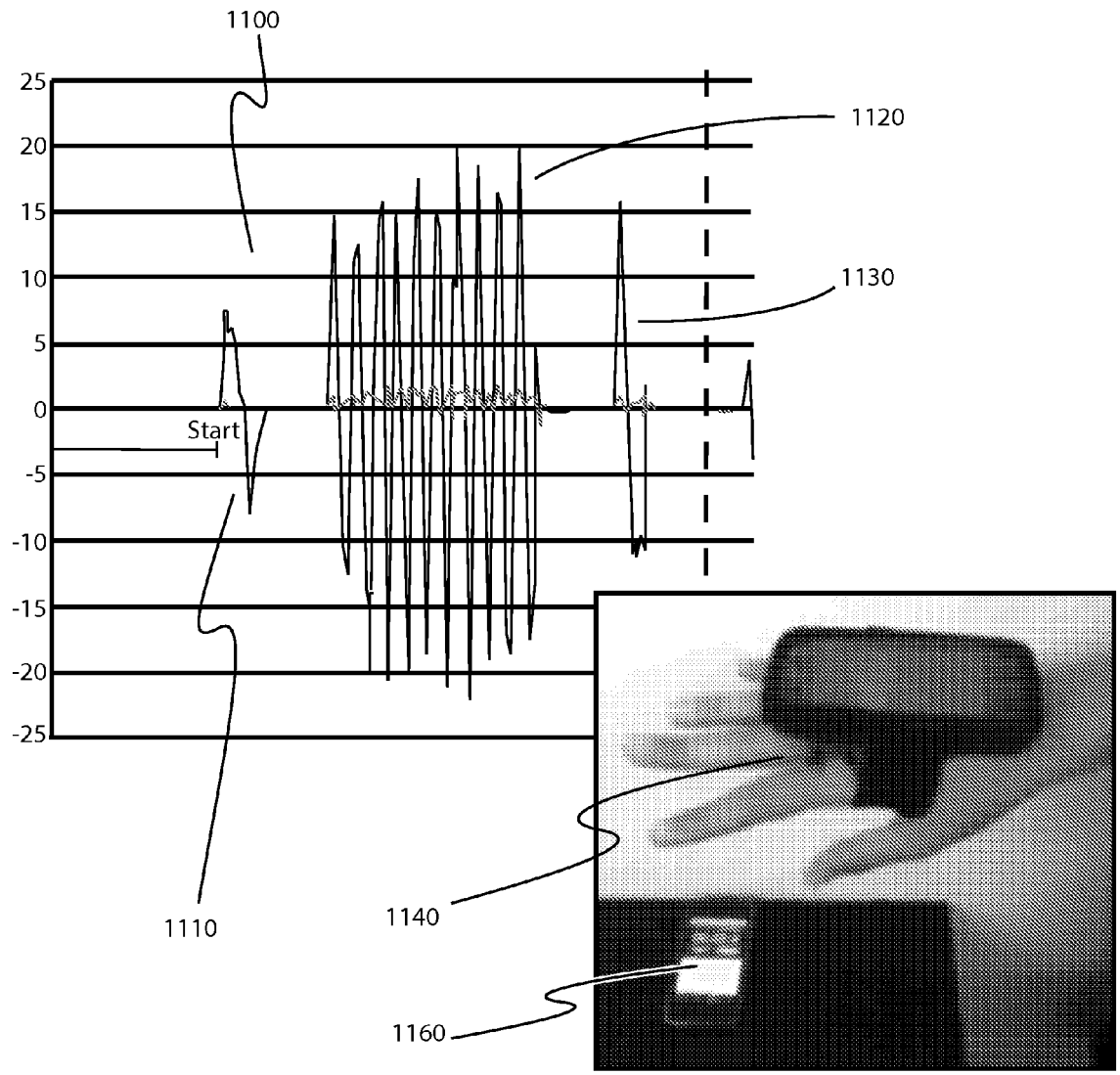
FIG. 11 specifies a novel data acquisition method for obtaining clinically meaningful maximum effort data in measuring forearm bradykinesia. Both the protocol and sample data are shown.

Objective Measures Via Mobile Medical Devices:

FIG. 11 specifies a novel data acquisition method for obtaining clinically meaningful maximum effort data in measuring forearm bradykinesia among other OM. Worn device 1140 may communicate with another device 1160. Graphs 1100 may be generated where a smaller signal inside larger signal 1130 may quantify a tremor after start 1110. Both the protocol and sample data are shown. Method of assessing physical movements bradykinesia with a mobile phone, tablet, device manufactured or customized for this application or market, or visual recognition of such movements (such as with a Microsoft Kinect™ device), or devices manufactured especially for this market. For example, a company could produce a $50 device that connected to WiFi, contained a gyroscope and an accelerometer, implemented the method disclosed herein, and interacted with a server or other device by connecting through a packet-switched network such as the Internet. This embodiment involves objective and clinician measures within mobile device applications: Examples include a method of performing a forearm pronation/supination test for bradykinesia including optimization for computer algorithm testing, objective measurement (OMS) of forearm bradykinesia (pronation/supination) as a surrogate for the clinician measured (CMS) Unified Parkinson's disease Rating Scale (UPDRS) subscores, and measurements performed in varied medication and neuromodulation states (ON MEDS/ON STIM, ON MEDS OFF STIM, OFF MEDS ON STIM, OFF MEDS OFF STIM). A representative physical test is as follows (Sillay mobile medical bradykinesia test: Step 1—(optional but recommended for the clinical setting) Position video camera 20 feet from subject sitting in an armless chair against an appropriate background; Step 2—Subject applies devices to both upper extremities (or to one upper extremity followed by the other upper extremity in sequence for which steps 3-7 are repeated with the second extremity via a device—anchoring system; Step 3—Subject holds arms toward the axis of videotaping with palms facing down; Step 4—Subject performs one external rotation maneuver as rapidly as possible with both instrumented forearms; Step 5—Subject pauses for one second; Step 6—Subject performs external then internal rotation with maximum speed for 10 repetitions: Step 7—Subject pauses for one second; Step 8—Test is complete.

Figure 7:
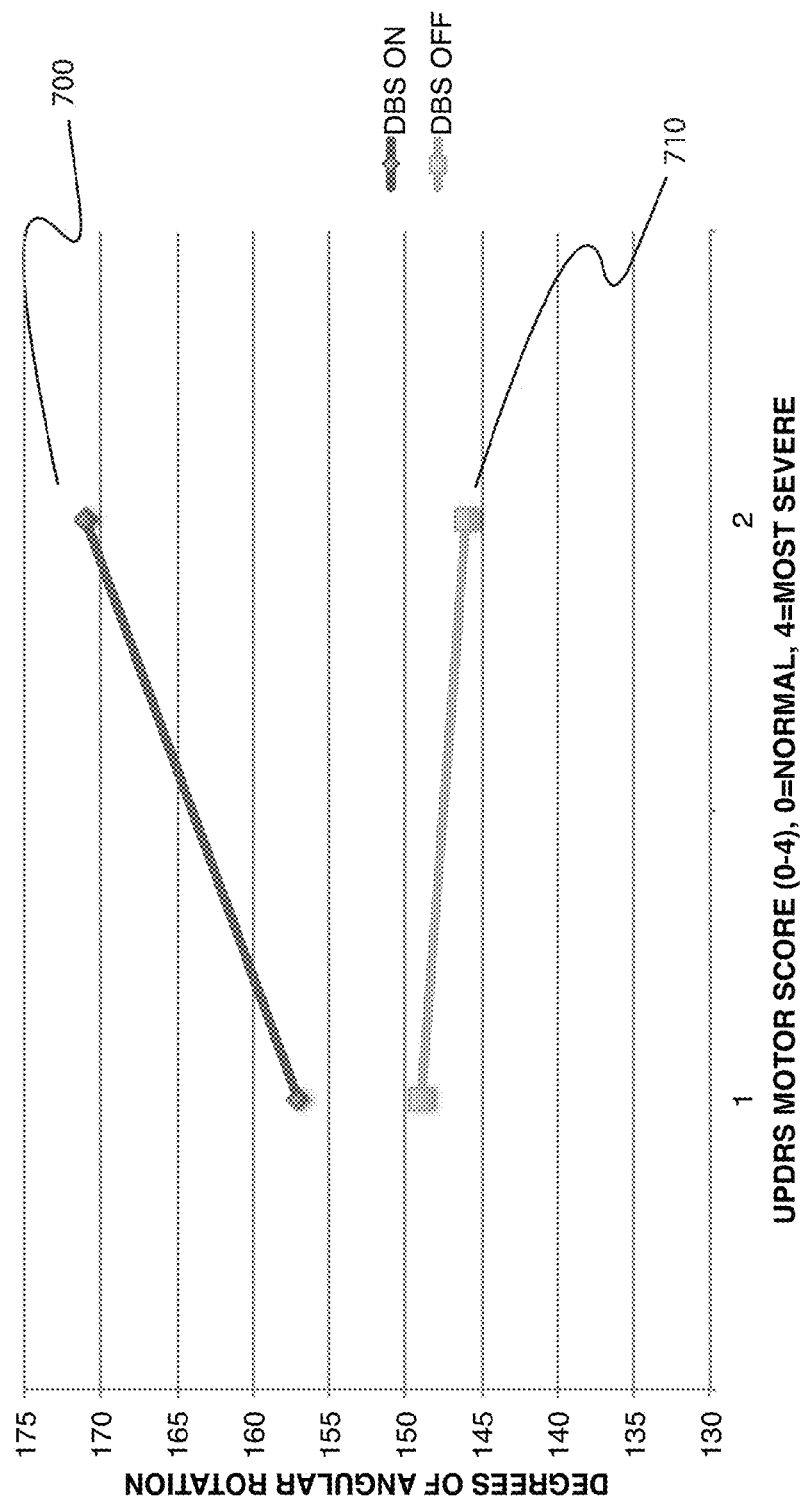
FIG. 7 is a graph of Sample Objective Measure Data indicating a demonstration of improvement in post operative function solely based upon an objective measure.
Figure 12:
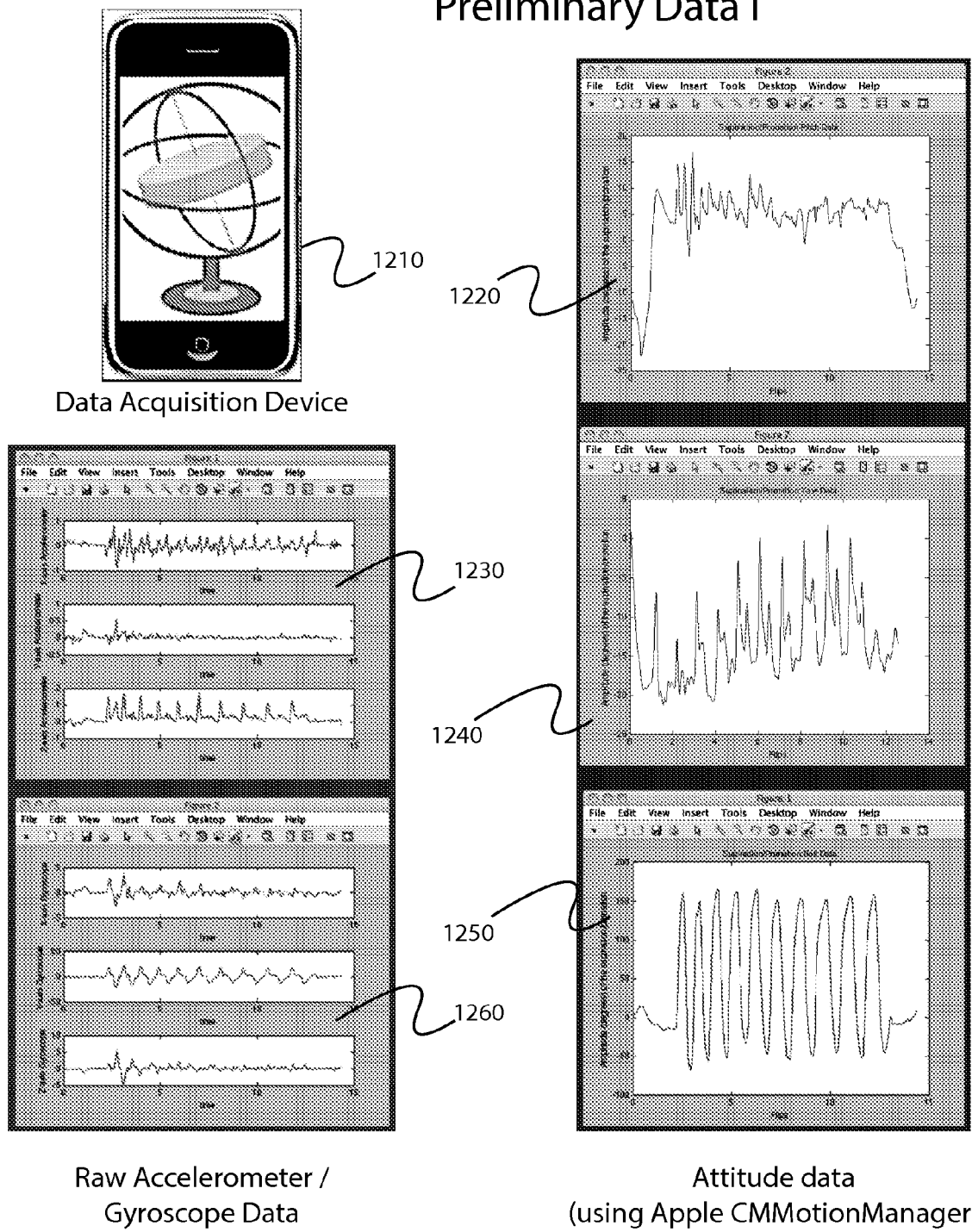
FIG. 12 is a first of two figures depicting methods for preparing objectively measured data from the forearm bradykinesia test for further analysis.

During the data processing and analysis, the following steps are performed: Step 1—Determine maximum rate of angular acceleration, degrees traveled per oscillation, peak angular velocity, hesitations, fatiguing, and amplitude of angular velocity. Step 2—Determine objective rating score, Step 3—Apply reference algorithm to calculate the equivalent UPDRS (Fahn et al. 1987), or reference score (0-4, within 50% in a single individual with disease and within 10% within a population) [Note here: the reference information could be downloaded from a server or other device with which the data acquisition device communicates, and difference references could be used, for example, a reference derived from data collected from a cross-section of a measured population. This concept is possibly in addition to using a standardized (for example, national) reference score. (Increased maximum wrist rotation speed correlates with lower UPDRS scores (FIG. 7) as calculated (FIG. 12), (FIG. 13)), between those with neurostimulators activated 1460 and those with neurostimulators deactivated 1470 (FIGS. 14A and 14B), peak angular velocity increases with stimulator activation and also correlates with the UPDRS (FIG. 7); Step 4—Correlate to historic data: on/off medication and on/off stimulation status in a wide cohort [again, different cross-sections of individuals diagnosed with a disease could be selected for the correlation or comparison study, especially for research purposes] of individuals diagnosed with a disease varying disease burden (Hohen and Yahr stage (II-V)).

A feedback path or an alarm path to the individual with disease, for example, is provided to trigger to begin a Sillay test at home, to take a prescribed medication at a particular level by comparison of medication taken by the individual with disease with cohort data or to provide real time control of DBS or neurostimulation and/or a drug regimen.

Method of Securing Multiple Sensors on the Foot—(Triangulation foot pressure and movement sock/glove). Pressure sensors within a shoe or sock with or without a device worn on the shoe (for example, secured to the shoelaces) in combination with or without an accelerometer/gyroscope system on the foot measure movements during gait in order to identify metrics for speed and cadence as well as for measuring gait and differential pressure. Differential pressure of one extremity versus the contralateral extremity is used to correlate with symptomatology. An example of this is for individuals diagnosed with a disease who state they are having gait problems; times of the day are recorded and their reported symptoms can be benchmarked against the objective measures.

It is desirable to align the mobile device in a manner that is consistent between tests and that accurately captures the motion (acceleration and/or velocity data) along the direction of maximum motion of the limb (whether rotation or translation) in order to minimize the effects such variations can have on the captured data and any derived OM quantities. Alternatively, and preferably, it is desirable to process the acquired data in a manner that minimizes or removes these effects. The following approach discloses by example one method that achieves this goal. Other methods and variations may be employed. For example, the square root of the sum of squares of all components of a 3-dimensional vector acceleration or velocity measurement may be used, or the component having the maximum magnitude, over the data collection time interval, may be used. However, the sum of squares method incorporates the effects in the measurements caused by the motions of joints or limbs other than the one of primary interest, and the maximum magnitude method assumes more precise alignment that is necessary using the preferred method. During the data processing and analysis, the following steps are performed: Step 1—Determine maximum rate of angular acceleration, degrees traveled per oscillation, peak angular velocity, hesitations, fatiguing, and amplitude of angular velocity. Step 2—Determine objective rating score, Step 3—Apply reference algorithm to calculate the equivalent UPDRS, or reference score (0-4, within 50% in a single individual with disease and within 10% within a population). The reference information could be downloaded from a server or other device with which the data acquisition device communicates, and difference references could be used, for example, a reference derived from data collected from a cross-section of a measured population. Alternatively, a standardized, for example, national reference score could be used. (Increased maximum wrist rotation speed correlates with lower UPDRS scores, peak angular velocity increases with stimulator activation and also correlates with the UPDRS; Step 4—Correlate to historic data: on/off medication and on/off stimulation status in a wide cohort [again, different cross-sections of individuals diagnosed with a disease could be selected for the correlation or comparison study, especially for research purposes] of individuals diagnosed with a disease varying disease burden (H and Y stage (II-V)).

Again, it is desirable to align the mobile device in a manner that is consistent between tests and that accurately captures the motion (acceleration and/or velocity data) along the direction of maximum motion of the limb (whether rotation or translation) in order to minimize the effects such variations can have on the captured data and any derived OM quantities. Alternatively, and preferably, it is desirable to process the acquired data in a manner that minimizes or removes these effects. The following approach discloses a first preferred method that achieves this goal; other methods may be utilized. A second preferred method is the alignment of the device with the axis of rotation or translation of a joint or limb so that it is sufficient to sense the motion of a single axis of rotation or translation. The first preferred method requires acquisition of data (whether acceleration, velocity, or both, and whether rotation, translation, or both) for three axes or coordinates in 3-dimensional space (for example, in x, y, and z translational coordinates for translational data, in theta_x, theta_y, and theta_z rotational coordinates around x, y, and z axes for rotational data, or in all six directions when both angular and translational data are captured). The three (or six) coordinates do not have to be orthogonal, but they must constitute a basis for 3-dimensional (or 6-D) space. These coordinates form a coordinate system that is typically determined by the physical characteristics of the measurement device, and their relationship to a coordinate system defined by an individual's joint, limb, head, or torso is typically determined by the manner in which the device is attached to or connected with the individual and any alignment procedure that has been utilized.

This method assumes acquisition of data at a sequence of times within a desired time interval over which data are to be acquired, where the sequence of times may or may not be equally spaced. A goal is to estimate the variation present in the data, for example, the difference between the maximum and minimum angular accelerations around an axis that is not necessarily aligned with one of the axes or coordinates used by a sensor. Other goals can be applied, including the estimation of at least one spectral component in the measured signals to produce an OM, estimation of one or more parameters to provide an OM of repeatability of motion, and estimation of the time or frequency signature of motion either coincident with a primary axis of motion or perpendicular to a primary axis of motion. An example of the last case is to estimate or provide an OM related to tremor. Regardless of how well one may attempt to align a mobile or wearable device with the axis of, for example rotation of a individual with disease's wrist, it is difficult or impossible to align the device with perfect accuracy or to achieve the exact same alignment each time the device is aligned. Any misalignment can introduce errors into the measurements and adversely impact the quality of the acquired OM data. If data are captured along three (or six) independent degrees of freedom, then the effects of misalignment errors can be greatly reduced, if not eliminated, by processing the acquired data using the first preferred method disclosed herein, enabling the accurate capture of OM data, for example of the maximum acceleration achieved by the individual with disease when rotating his or her wrist (FIG. 11). Alternatively, if the device is carefully aligned so that a single sensor accurately measures the motion along a coordinate defined by a joint or limb, or by the head, then the measurement data provide by that single sensor can be utilized to compute an OM (the second preferred method). The first preferred method extends to the analysis of captured data that involves simultaneous motion along multiple (3 or 6) degrees of freedom using either velocity or acceleration data, or both. In effect, alignment is achieved with a coordinate system that is orthogonal and is selected so that the first, or a distinguished, coordinate captures the greatest motion (velocity, acceleration, or both) and subsequent coordinates are orthogonal to previously selected coordinates and capture the greatest motion in the remaining data. Because the relative positions of an individual's joints and limbs change with movement, it may be desirable to utilize an additional optional method to re-determine the chosen coordinate system on a regular, periodic, or occasional basis, or to utilize a mounting or positioning system that contains additional sensors to provide information that can be utilized to re-determine or update or estimate the chosen coordinate system. For example, a flexible harness or strap can be utilized that incorporates sensors to detect and measure the flexure or extension of a joint such as a wrist, an ankle, a knee, a hip, or an elbow. The method can be performed using a variety of computational algorithms, including eigenvector and eigenvalue analysis and matrix factorizations such as QR decomposition and SVD (singular value decomposition). SVD is generally recognized as the most accurate and preferred algorithm and will be used to illustrate the method herein, but another method may be used because SVD requires more computation than some alternatives. For example, a computational algorithm can be utilized to estimate the first principal component or eigenvector associated with the largest real eigenvalue of a matrix as an alternative. The method is related to the methods of principal component analysis and partial least squares methods and algorithms used for data analysis, and SVD can also be used to solve problems of those types. The method is described by example using by way of illustration a synthetic data set.

Once raw measurement data have been collected using accelerometers or gyroscopes, or an equivalent type of sensor, the data can be organized or thought of as a matrix (referred to herein as D for "data" matrix) having n rows and m columns, where n is 3, 6, 9, or 12 (corresponding to three degrees of freedom each in some combination of rotational or angular velocity, rotational or angular acceleration, translational velocity, and translational acceleration measurement data), and where m is the number of measurements. Each row corresponds to and contains measurement data collected with respect to one axis, coordinate, or degree of freedom, and each column corresponds to and contains measurement data collected as one measurement time or as a part of one measurement. The functions of rows and columns can be exchanged, and in this case the resulting method is fully equivalent to the method described herein; the exchange being the same as using the transpose of the matrix of data measurement. Furthermore, there is no requirement that the data actually be stored or represented within a computer's or device's memory as a matrix, such as within contiguous elements of memory; it is only required that the elements of the data be indexed by both a coordinate identifier and a time. The i-th row of the matrix D will be represented in this text as $D(i,:)$ and will correspond to all measurement data in the matrix D associated with the i-th axis, coordinate, or degree of freedom, and the j-th column of the matrix D will be represented as $D(:,j)$ and will correspond to all measurement data in the matrix D acquired at the j-th measurement time. There is no requirement that the measurement times be ordered in ascending or descending order, although any implementation may do so for convenience.

The objective of the method is to determine a direction of maximum variation in the data as described by the measurement data, and to use this direction to estimate one or more properties of the measured data such as the maximum variation, which may for example be the maximum and minimum angular or translational acceleration or velocity of a individual with disease's joint, limb, hand, foot, or head. Subsequent directions of maximum variation in the residual of the data (after the components of maximum variation are removed by subtraction from the data) may be computed in either a recursive or iterative manner, and additional properties of the measured data may be estimated using these directions, such as maximum and minimum angular or translational accelerations or velocities of a second joint or lateral motion of a foot, head, or leg. If multiple types of measurements are available (acceleration, velocity, angular, and translational), these measurements may be analyzed using this method either in combination or in parts (individually or with two or more types taken together). For the purpose of example, a single type of data, which may be any one of these types, is assumed and is therefore 3-dimensional.

The method used to determine the direction of maximum variation may utilize either all of the columns (data from all measurement times) in the matrix D, or any subset of the columns. When the quantity of data is large it is preferable to sample the data by selecting a subset of the columns to use in the determination of the direction of maximum variation in order to reduce the computational burden. There is, however, a trade-off between accuracy (which increases as the number of samples utilized increases) and the impact of measurement noise (which decreases as the number of samples utilized increases) and sample size on the quality of the estimate of the direction of maximum variation. For the purpose of the example, a synthetic data set is created using a sampled sinusoidal waveform having a period of one second and including ten periods, where 20 samples per second are used. This results in a 3-dimensional waveform of 201 samples. An amplitude of 10, corresponding to a maximum variation of 20 units, is chosen, and the data are shown, along the direction of maximum variation, showing variation between −10.0 and +10.0 units. A rotation matrix is randomly generated and applied to these data values, assuming the initial direction of maximum variation is in the third dimension, resulting in synthetic measurement data with respect to three coordinate axes, are shown. To demonstrate that the results of the disclosed method's application are not dependent upon the choice of rotation matrix, a second rotation matrix is randomly generated and applied, and the resulting synthetic measurement data are shown. If the data from the measurement axis that displays the greatest variation are used to compute the range of variation, or motion, the first synthetic data set produces an estimated range of variation of approximately 13.7, while the second synthetic data set produces an estimated range of variation of approximately 13.3 Both estimates are significantly below the actual range of variation of 20, due to the lack of alignment between the (randomly generated) measurement coordinate system and the coordinate or axes of actual variation. This illustrates the problem that the method addresses and solves: A method is desired that yields an estimated range of variation, as an example of a property that can be estimated from the measurement data, of approximately 20 rather than the significantly lower values of 13.3 and 13.7.

As an optional step, relatively smaller subsets of the columns of the two matrices D containing the synthetic measurement data are randomly selected and used to estimate the range of variation represented by each set of measurement data. Let this subset of columns of D be represented by the matrix D_s. This optional step reduces the amount of computation that is required but increases the error in the estimate. For the first synthetic data set, 22 rows are selected, and 23 rows are selected for the second data set. The singular value decomposition (SVD) is used to decompose the matrices D, as is well-known in the field of linear algebra, into the products of three matrices $USV^T=D\_s$, where U and V are orthogonal n×n and m×m matrices, respectively, and S is a diagonal n×m matrix with non-negative elements that appear in decreasing order along the diagonal. Using this decomposition, the first column of U, U(:,1), is the direction of maximum variation, as estimated using the randomly selected columns in D_s from D. The maximum variation present in the measurements (columns of the matrix D) can be reconstructed, or estimated, by multiplying the columns of D on the left by the transpose of U(:,1). When this is performed using the two example cases presented herein, the maximum and minimum values of the reconstructed signal are +10 and −10, for a total variation of 20, within the precision of the computer used to perform the computation. When the reconstructed signals are graphed, the reconstructions lie on top of the actual (synthesized) signals of maximum variation, and the errors between the original and reconstructed maximum variation signals are shown in the FIG's. The magnitudes of these errors, for these two simulated cases, are in all cases less than $2\times10^{-15}$, or roughly the limit of precision of the computer used to perform these computations. This example demonstrates the effectiveness of the disclosed method in the reconstruction of the signal and signal properties such as amplitude associated with motion in a degree of freedom such as rotation of a joint such as the wrist. The method can be applied to accurately estimate other properties of motions (rotations or translations) along one or more coordinate axes in a straightforward manner using one or more columns of the matrix U obtained using the SVD and the corresponding singular values, which are the diagonal elements of the matrix S. For example, the reconstructed data, along one or more axes of motion, can be used to determine spectral estimates or estimate spectral components of the data or to determine one or more measures of the repeatability of motion. Other algorithms can be used in place of the SVD such as algorithms based upon eigenvector and eigenvalue analysis or an algorithm to estimate or determine only one or more selected directions of maximum variation. The use of the sampled columns of the matrix of measurement data D, D_s, is optional, as the same method can be applied to the measurement date matrix D.

The method utilized to determine the direction of maximum variation using SVD or another method can be implemented by a computational algorithm encoded in a stored program within the device used to acquire the data, or all or a portion of the measurement data matrix D can be transmitted to a second device from the data acquisition device, which can perform all or a portion of the computational steps and either return the results to the data acquisition device, store the results if the second device is a Server, or forward the results to a third device or Server. For example, the SVD algorithm can be implemented by a stored program in a Server, which receives the data in the matrix D_s from the data acquisition device and utilizes these data to determine the direction of maximum variation. The Server can then communicate this direction of maximum variation to the data acquisition device, where a stored program can be executed to apply the direction of maximum variation to the measurement data in the matrix D to compute one or more OM from the measurement data. The data acquisition device can subsequently transmit the one or more OM to a Server or other computer, which may be the same Server used to compute the direction of maximum variation or a different Server or computer. This scenario is provided as an example; other variations are possible. For example, a Server or computer other than the data acquisition device can execute a stored program to calculate an OM using an estimate of the spectrum of the data, where the estimate can be computed either on the data acquisition device, on the Server or computer, or on an additional Server or computer. In these cases, each pair of devices (each one of a data acquisition device, a Server, and a computer) must have components that enable the communications between those two devices, such as a connection to a wired network, a memory card such as a SD card or Compact Flash card that can be removed and inserted in a memory card interface attached to each device of the pair, a wireless network interface using, for example, a WiFi, 3G, or 4G network, or a serial communication interface. The devices of each pair need not have the same type of components to enable their communications, but the components must be sufficient to enable the necessary exchange of data.

OBJECTIVE MEASURES BY INDIVIDUAL WITH DISEASE WEB PORTAL (and mobile device): According to user consent, certain metrics will be recorded during the use of the web portal and mobile devices including decision-making speed when presented with a question. In this example, the time to respond to a selection will be aggregated by the position of the individual with disease on the TIMELINE and by other factors and correlated to known neurostimulator or other device states. Typing speed will be monitored and correlated to known factors including medication, sleep, and neurostimulator state. Time of use will be logged to calculate objectively certain wake and sleep and other activity states. Certain metrics will be obtained on the front end of the site such as average typing speed and mouse click for all visitors to the portal. Options may be made available to record samples of video or speech or to have certain movements monitored via video stream or via kinect or similar method of tracking movement. Order of progression through a decision tree such as the site map will be aggregated and correlated.

On Screen Display:

A display 1020 (FIG. 10) may be used to present a series of user interface screens whereby a person such as a trained nurse, a helper or caregiver, the individual being measured or monitored, or someone at home enters data such as individual with disease name, date, time, address, doctor(s), clinic(s), or other medical or assistive facilities that have provided treatment(s), contact information of a caregiver, a helper, a friend, or one or more family members, one or more diagnostic procedures or diagnoses that have been applied to the individual with disease, records related to the individual with disease's conditions that the patent has acquired and for which the individual with disease has the right to enter into an electronic or computer system, and other similar or related information. The display is connected to a client device or a device in a clinic, where the device (Client Interface Device) has at least a processor such as an Intel or AMD processor that executes x86 instructions or an ARM processor that executes ARM instructions, a computer bus that enables the processor to communicate with other components of the Client Interface Device, where such communication may include communications across a network or communications channel such as a parallel or serial communication channel used to communicate with disk drives (using for example a SATA or SCSI channel, or a virtualized communication channel such as a software implementation of the SMB, CIFS, or NFS storage access protocols across a communication network), an interface having a keyboard (using for example a PS/2 or USB communication channel or a virtual keyboard using a touch screen display) and optionally having a pointing device such as a mouse or a cursor on a display that can be manipulated by a wheel, a button, or another type of device allowing user input as is well-known in the field of computer engineering, a display which may be a touch screen display and may use for example a VGA, DVI, or HDMI communication channel, memory to store a program that directs the execution of the Client Interface Device and stores data received from or transmitted to another device, a network interface or other communications interface that enables communication with another device such as a Server or other computer, one or more mobile devices, wearable devices, or wireless or wired access devices used either for the same or similar purposes as disclosed herein or used for different purposes such as within a clinic or hospital setting for individual with disease records or to support medical procedures or treatments, or by an insurance company or government agency for financial and/or medical treatment records, or by an association formed for the benefit of either individuals diagnosed with a disease, medical or clinical practitioners or staff, or by one or more researchers, enabling the exchange of information between the Client Interface Device and one or more Servers or computers to support the exchange of data or other information related to a individual with disease, and a storage device such as a hard disk drive (HDD), a solid state disk drive, or a memory card such as a SD card, or a network-accessible storage device (NAS) or other storage device that is used for long-term or persistent storage of the program and data. The Client Interface Device may be a tablet computer, a laptop computer, a notebook computer, a desktop computer, a smart phone, a computer game console, a smart phone, or a special-purpose or customized device containing a processor and the other listed components that have been developed for a medical application.

The Client Interface Device plays a central role that allows a individual with disease or a representative of a individual with disease to securely interact with one or more Servers or other computer systems to access, acquire, and distribute or disseminate information related to the individual with disease, the individual with disease's disease, and treatments the individual with disease has undergone or will undergo. US law and HIPAA regulations provide for both the regulation and protection of medical records and individual privacy and the control of information about a individual with disease or related to a individual with disease by the individual with disease. The individual with disease or an authorized representative of the individual with disease always has the right to obtain medical, insurance, or financial records containing data about that individual with disease and in most cases can use the information in those records in any manner he or she wishes. The disclosed methods enable individuals diagnosed with a disease to take an active role by controlling the exchange of information related to their care and address significant current problems where information that can beneficially influence the outcome of individual with disease treatments such as surgical procedures and therapy is not accessible to the providers or care or services that need it.

The individual with disease has the right and the authority to effect exchanges of information among the individual with disease's caregivers and providers, as a individual with disease can now do by obtaining physical records from one provider and delivering those records, or copies thereof, to another provider. The disclosed technologies enable construction of systems composed of Client Interface Devices, Servers, and other computers or computer systems that can communicate using communication channels such as computer networks, mobile telephone/cellular data networks, WiFi networks, metropolitan networks, serial communication links and links enabled by wireless and wireline telecommunications service providers (for example, fax machines and serial communications protocols using modems), where such systems provide methods for individual with disease-directed exchange of individual with disease-related and health care information between or among providers of services to the individual with disease. These systems for permission based data advocacy on behalf of the participants allow health linked information exchange and are capable of interacting with existing electronic medical record systems, cellular, wireless, and wired telecommunication and other communication networks to support the exchange of health data from existing electronic medical record systems and paper-based and off-line record systems and to facilitate the exchange of data between hospitals, clinics, public entities, private foundations, insurers, vendors, sponsors, and other interested parties through a individual with disease avadavat system linking home measurements, recording, diary, and community and support group-based periodic meeting acquired information. The exchanged information or data can include both subjective measures such as diary data and diagnoses or measures by clinicians grading the degree of, for example, forearm slowness in PD, and objective measures of treatment and individual with disease response or status such as during phases of treatment such as preoperative symptomatology, probabilistic atlas linked targeting for neuromodulation, accountancy for gravitational effects of brain shift during surgery, measurements of movement and quality of life during the perioperative and postoperative phases of treatment and ongoing community and self-directed treatment. The existence of the disclosed systems enables aggregation across populations or selected subpopulations of individuals diagnosed with a disease by disease, geographic area, ethnicity, age, gender, occupation, treatment(s), or other categories and comparison of objective or subjective measure data associated with one individual with disease with aggregated data of similar types for the selected population or subpopulations. Such comparisons can be performed by the individual with disease, the individual with disease's authorized representative, or, with appropriate authorization by the individual with disease, medical or clinical personnel who provide services to the individual with disease.

The Client Interface Devices can be mobile and can utilize mobile networks such as 3G, 4G, WiFi, and metropolitan wireless systems such as WiMAX to communicate with one or more Servers or other computers or computer systems, and can thus be available for use by the individual with disease or an authorized representative of the individual with disease within clinics or other medical facilities, enabling the individual with disease or representative to provide and control access to data related to the individual with disease whenever and wherever the need arises. Security protocols such as the use of authentication and encryption methods that are well-known in the art are preferably used to ensure privacy, protection of sensitive data, appropriate levels of authorization to data, and non-repudiation of access to, modification of, or change of access rights to any protected sensitive data. For example, certificates associated with Client Interface Devices, Servers, other computer systems, and the individuals (individuals diagnosed with a disease, representatives, and care givers such as clinical or medical staff) ensure appropriate access control and proper identification of individuals and entities that access the data in this manner. Logs maintained by Client Interface Devices, Servers, and other computers or computer systems and logging facilities implemented by stored programs within these devices, servers, and computers or computer systems ensure the proper maintenance of audit trails to support detection of data or data rights misuse and verification that appropriate access rights were granted prior to data access.

A Client Interface Device that includes sensor components such as a gyroscope, an accelerometer, or a GPS can utilize a stored program to acquire measurement data such as the motion of a joint, limb, head or torso, or the orientation of a head, in order to determine objective measures related to a individual with disease's condition or disease status. The Client Interface Device is preferably mobile, handheld, or wearable, and preferably contains one or more components such as a transceiver, software-defined radio, or wireless or cellular communication interface to enable the Client Interface Device to communicate with a Server as or soon after measurement data are acquired, but this is not required. For example, the Client Interface Device can be a smart phone such as an Apple iPhone® mobile digital device running the Apple Inc. (hereinafter, Apple) iOS operating system or a tablet such as the Apple iPad® mobile digital device, also running the Apple iOS operating system, or a smart phone or tablet running the ANDROID® operating system platform available from Google Inc., such as ANDROID operating system equipped smart phones or tablets manufactured by Samsung. (ANDROID is a registered trademark of Google Inc.) (iPhone and iPad are registered trademarks of Apple Inc.) The Client Interface Device can contain a removable memory card such as a USB memory device, a SD memory card, or a Compact Flash memory card on which acquired measurement data can be stored by the Client Interface Device under the direction of a stored software program residing either within the memory of the Client Interface Device or on the removable memory card or other memory or storage device, and the measurement data can be transferred to a Server or another computer or computer system by the physical removal of the memory card from the Client Interface Device and insertion of the memory card into an appropriate interface component such as a memory card reader connected to the Server or other computer/computer system. Alternatively, an interface cable such as a USB cable or a directly connected interface such as a USB interface can be used to connect the Client Interface Device to the Server or other computer/computer system to effect the transfer of the measurement data. The Client Interface Device may also have a camera, which can acquire either still or motion (video) image data, or both, and one or more stored programs that can be selectively executed by a user to acquire still or motion image data to be used or evaluated, either by a person or using a computer algorithm, and from which objective or subjective measurement data can be derived. A stored program in the memory of the Client Interface Device can be utilized to record symptom data or objective measurement data using the disclosed user interface components such as a display, which may be a touch screen display, a keyboard such as a virtual keyboard displayed on a touch screen display, or a graphical user interface containing fields and selection buttons or check boxes that a user can manipulate using, for example a touch screen display or a pointing device such as a mouse, a virtual input device such as, for example, displayed touch-sensitive icons corresponding to directional pointers that cause a cursor to move on the display, or a track ball, which may be associated with a button or other component to enable the selection or checking of an item or may be depressed to selects or check an item. The Client Interface Device's communications or networking component(s) can, under the direction of a stored program executed by the processor, upload data to a medical records system implemented, by example, on a Server or other computer or computer system adapted to receive the data into an individual with disease's file via a communications interface.

Connectivity:

The Client Interface Device enables individuals diagnosed with a disease, or other groups having similar interests related to management of disease such as clinical staff members, physicians, physical therapists, researchers, government employees, contractors' employees, or employees within the insurance or financial sectors, to utilize social networking technologies and social networking sites on the Internet such as Facebook, Google+, and LinkedIn to share information related to individual with disease management. While social networking and social networking sites share problems and issues related to computer security and privacy, the Client Interface Device, and Servers or other computers and computer systems with which the Client Interface Devices communicate, can overcome many of these problems by using a pointer system that provides links to information related to individuals diagnosed with a disease and disease management or treatment that resides on protected infrastructure such as Servers, or other computers and computer systems that provide additional privacy and security safeguards.

The pointer system can be as simple as a uniform resource locator (URL), which may indicate the use of a web protocol such as HTTP or HTTPS but may also utilize other protocols such as Extensible Markup Language (XML) or Subversion (SVN) for version-controlled information and secure communications or data transfer protocols such as secure shell (SSH) and secure copy (SCP). The URL can contain an encrypted key or identifier field that can be understood (decrypted) only by a device containing the private key of an intended recipient or group of recipients. For example, the encrypted key or identifier may be understood and correctly interpreted by a Server or another Client Interface Device having the correct recipient's private key. Decryption of the key then provides access to addition information, which may include information that allows other recipients to access protected information. The pointer system could use other methods of pointing to protected information content instead of or in addition to a URL; for example, a one-dimensional or two-dimensional bar code can be used, or an image can be used that contains encrypted data that can be utilized in much the same manner as an encrypted key field. In this manner, an individual or an organization can post information relating to disease status, disease management or services related to disease management on social networking sites that are accessible and readable only by individuals, Servers, Client Interface Devices, or organizations having access to an appropriate private key. Other methods of secure information exchange can be used, such as a shared symmetric encryption key that is provided, usually in the payload of a message protected by encryption using a public/private key pair, to a group or population of individuals or organizations.

A key feature of this method is that knowledge of the URL, bar code, image, or other device or object obtained from a social network or social networking site on the Internet confers no information about the underlying identity or identities of individuals or organizations, or of the protected stored information, when such individuals or organizations participate in the services that implement and practice the disclosed method. In each instance before the information to which the URL or other device or object references can be accessed or used, in the preferred embodiment a user is directed to a permission affidavit specifying the terms and conditions under which the information can be accessed or used, and to which the accessing entity must agree. Such agreement can be indicated by a digital signature that can not be repudiated and as associated with a private encryption key assigned to the entity.

Figure 14A:
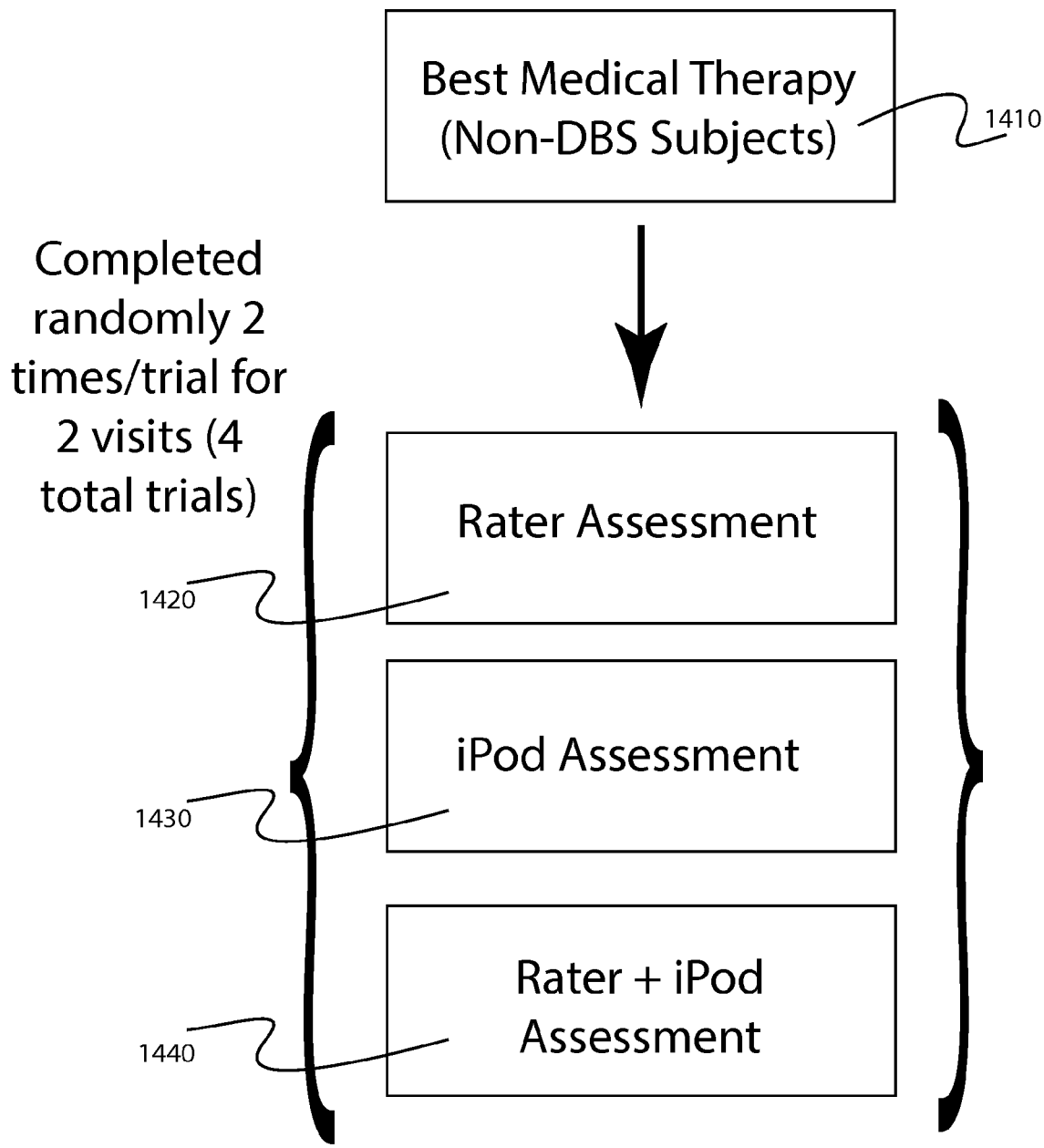
Figure 14B:
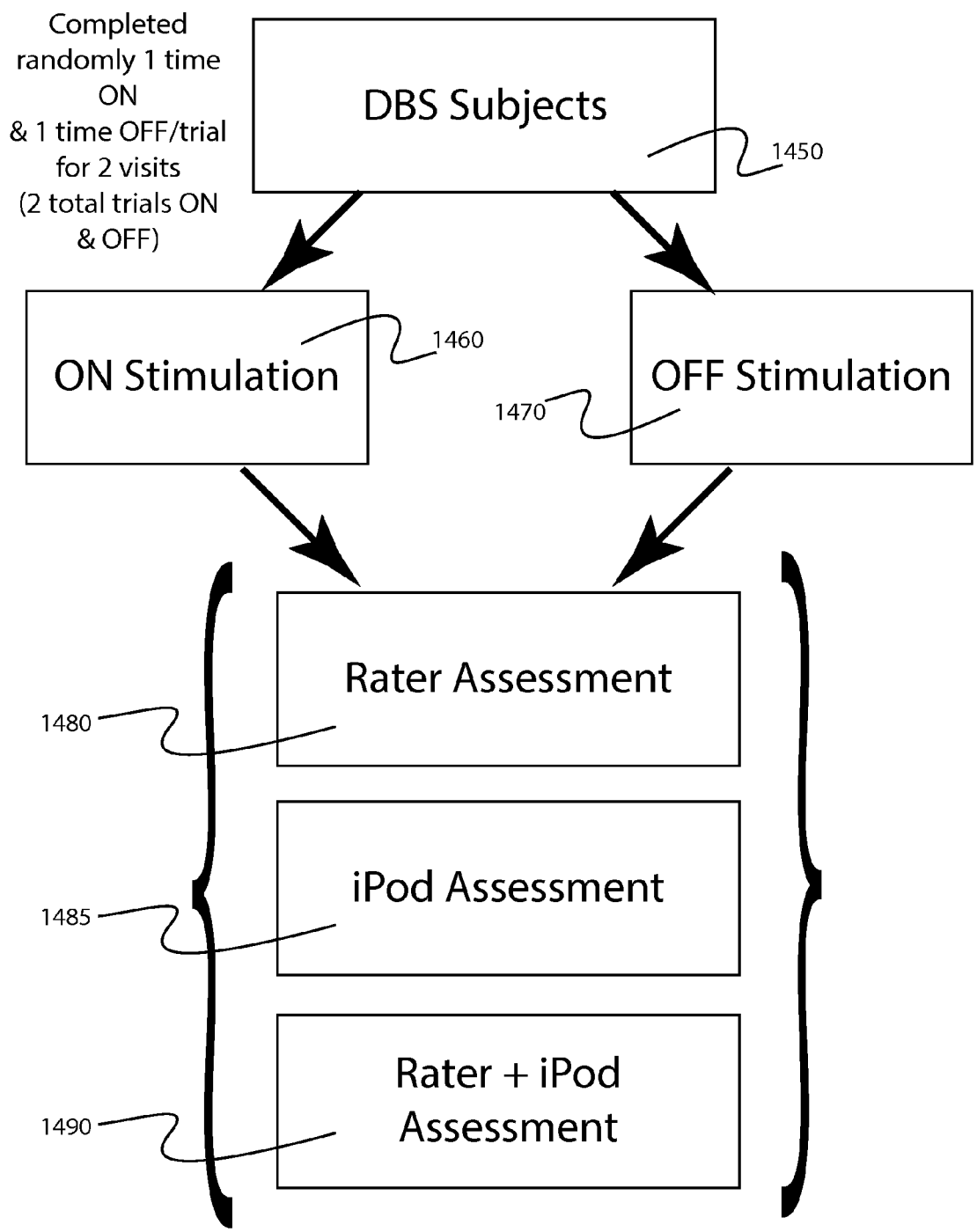
Figure 15:
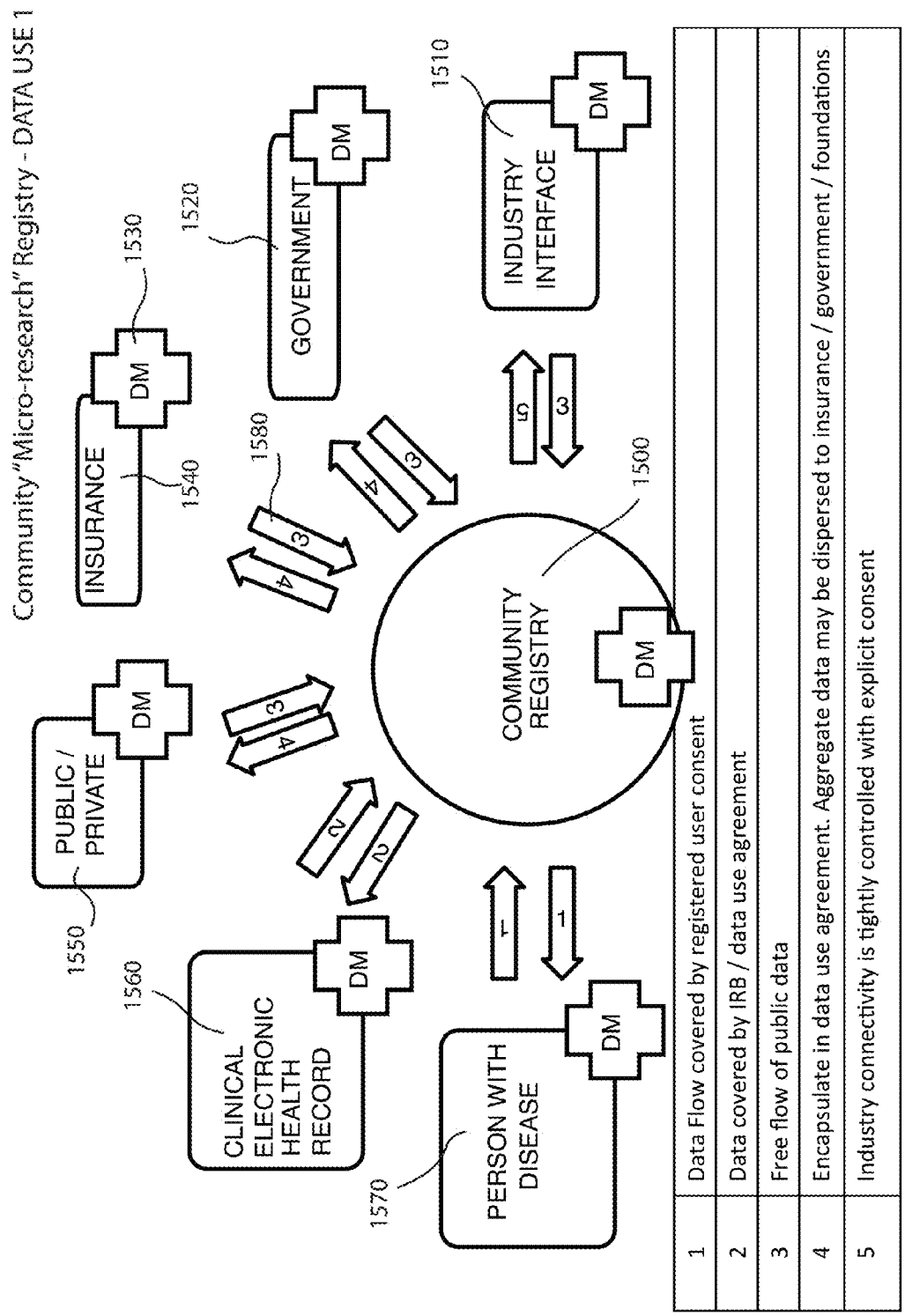
FIG. 15 depicts the organization of data exchange of a community micro-research registry figure with a description of data and permissions algorithms for data exchange partners.
Figure 16:
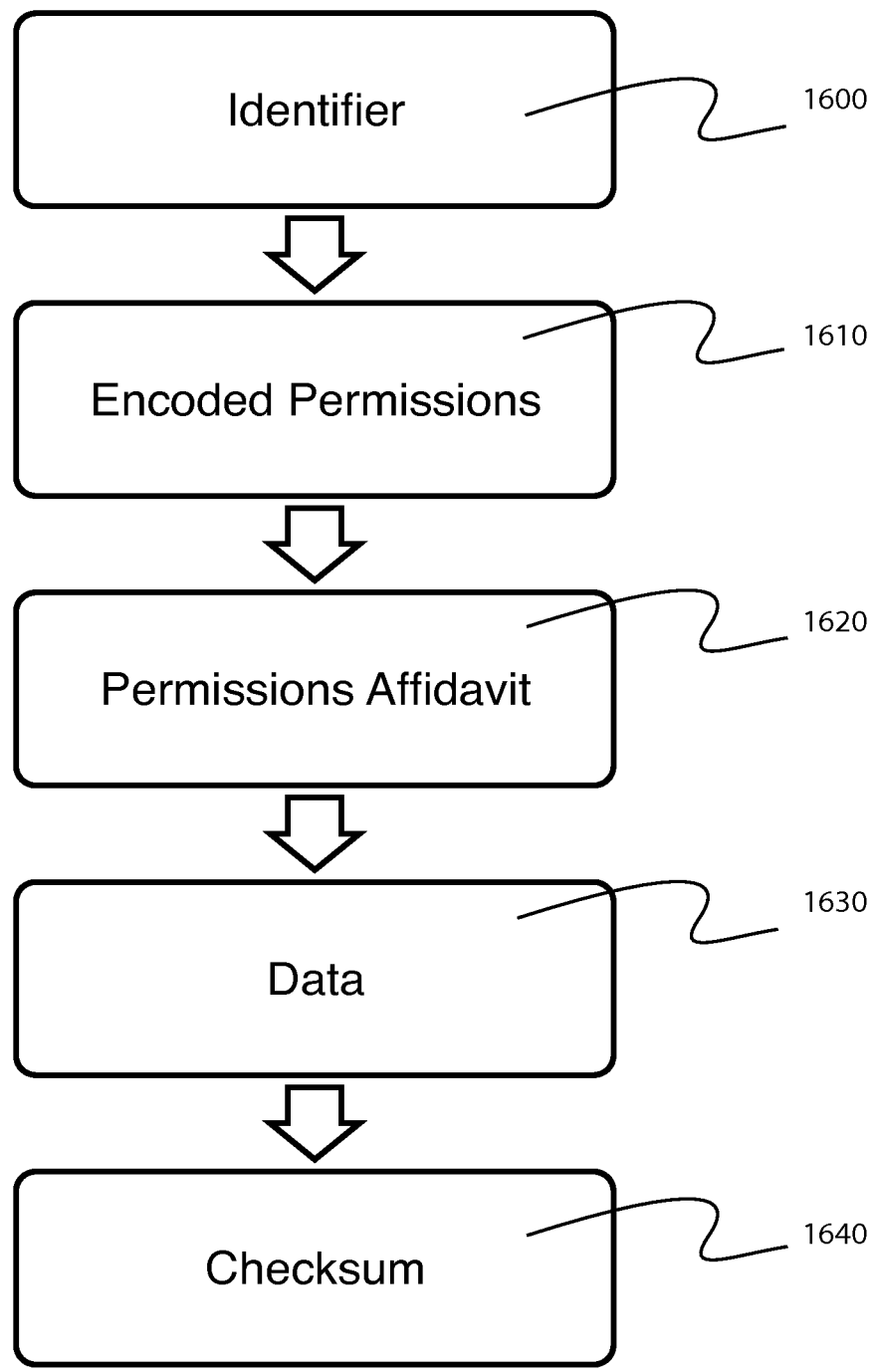
FIG. 16 provides details of a DATA TRANSMISSION PROTOCOL for transmitting an encoded permissions affidavit along with data and with an identifier and a checksum.

Data Exchange:

FIG. 16 provides details of a DATA TRANSMISSION PROTOCOL for transmitting an encoded permissions affidavit along with data and with an identifier and a checksum. This embodiment describes a process for enabling cross-institutional rapid exchange of information to the furtherance of rapid assembly of research questions (FIG. 14A and FIG. 14B). Preferably, a individual with disease information exchange affidavit is used, which may be a written document signed by the owner(s) or other individual(s) having rights to exchange or access the data, and which optionally may be implemented using a private key. Exchanged data will be associated with a unique individual with disease exchange affidavit (FIG. 15). A unique data structure element is to be encoded in the data structure used by all exchange partners. This facilitates the addition of future modules within the exchange structure. There are shown person with disease having a client device 1570, a clinical EHR 1560, a public or private entity such as a hospital database 1550, an insurance entity 1540, the government represented, for example, by the National Institutes of Health and the Center for Disease Control 1520 and an industry interface 1510 representing, for example, device manufacturers and programmers, all communicating to form a community registry 1500 for sharing data on a permissive basis whereby the common EHR may generate specific cohort databases for specific purposes responsive to the querying entity. Consents are shown as 1, 2, 3, 4 and 5 identified. (Industry interface 1510 is, for example, tightly controlled with explicit consent).

Method of enabling public private data exchange.

Method of organizing data for exchange, query, and hosted collaborative research. Information that can be exchanged includes tables of reports, tables of fields, and previous searches or "bundles". A permission form for the data exchange is contained within the "bundle". The data field structures can contain objects such as, by example, an identifier, a number of elements, an element declaration, and a type (such as a question, report, calculation, or request for data). Exchange and use of data are defined via a private license for outcomes measures by individuals diagnosed with a disease within the data affidavit. Data available for exchange, query, or hosted collaborative research can be stored in a Server or computer or computer system in either memory or persistent storage such as a hard disk drive, a network attached storage device, or a solid-state drive. A data-mapping matrix or database is utilized to associate data with the appropriate party for exchange and can reside on the same Server or computer or computer system as is used to store the data made available, or on a separate Server, computer, or computer system.

Method of Interface for Upgrade or Downgrade of Information from Protected Health and Reporting A method of verifying permissions of aggregate reports is disclosed in the form of a reporting permissions matrix (FIG. 17), database, or similar method of organizing data with permissions for reporting. Participants can be presented with a permissions matrix using a graphical user interface implemented by a Client Interface Device or other computer or device with a radio or check box. Preferably, the left side of the graphical user interface displays example data, and the right side shows one or more possible uses; the roles of the left and right sides can be reversed in an equivalent implementation.

Multiple user verifications are necessary if items are to be upgraded to the release of granular data for "profit".

Method of tracking release or data exchange for the possible reimbursement of participants A Server or other computer or device that stores data for exchange, query, and hosted collaborative research can preferably implement a method for a user to obtain permission to use a particular rating scale and then grant a limited power of attorney for the use of the rating scale for a defined purpose of associating exchanged fields with permissions of user and participant.

Figure 18:
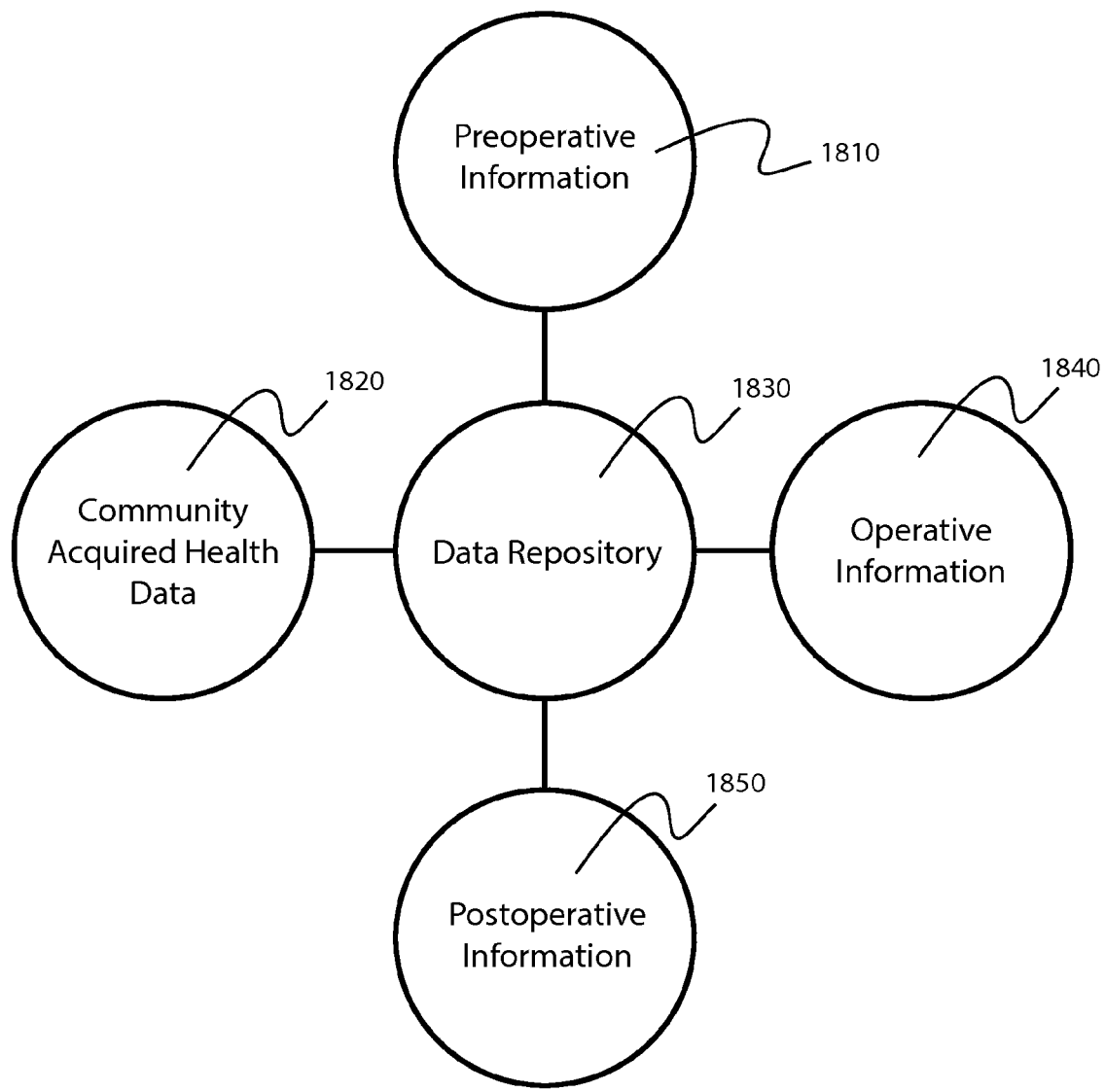
FIG. 18 demonstrates connectivity to a data repository in the simplest case of a single site integration of external community acquired health data.
Figure 19:
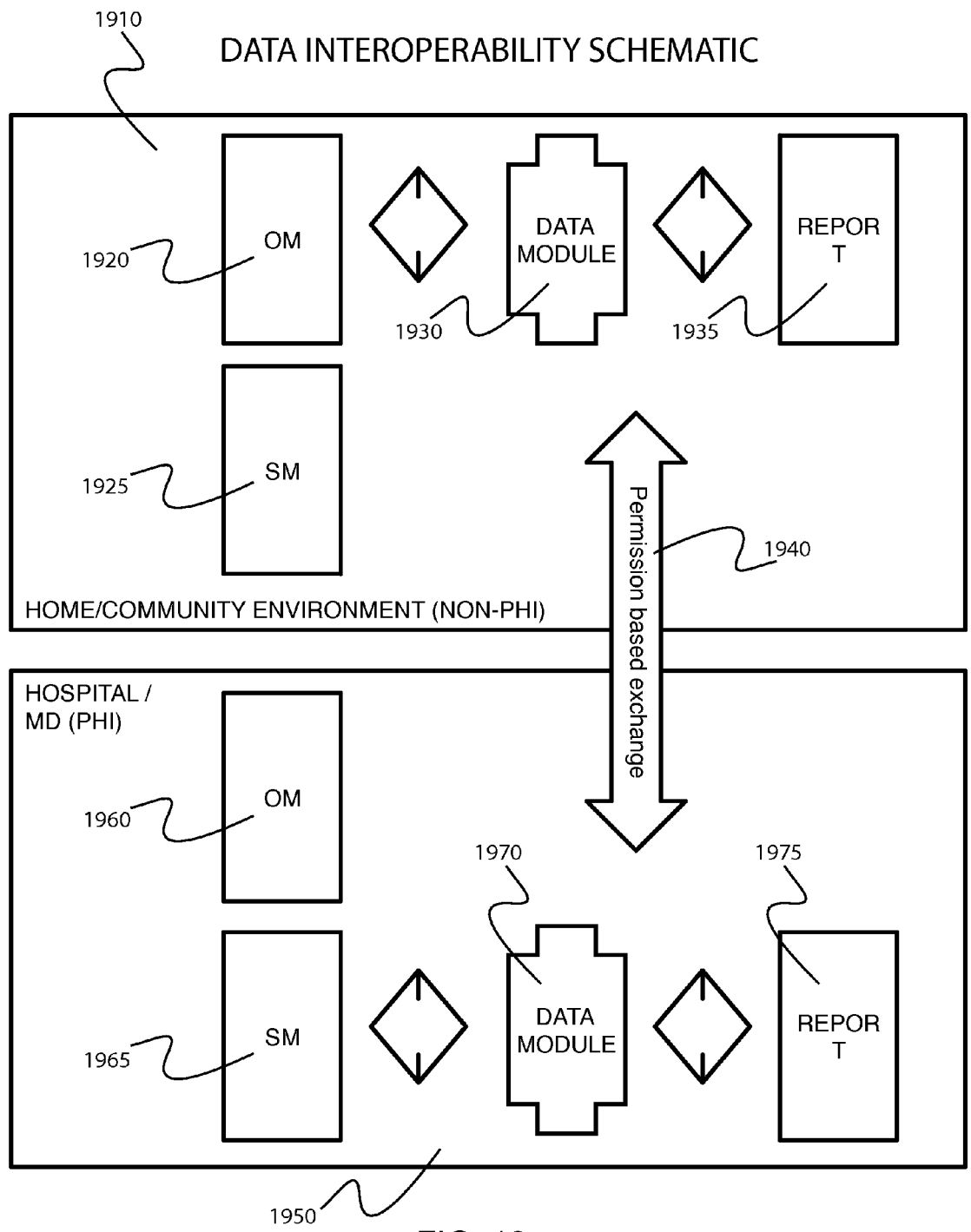
FIG. 19 depicts data interoperability in the simplest case of exchange between a single hospital electronic medical record containing protected health information and a community/home environment containing subjective and objective measures, both with reporting.
Figure 20:
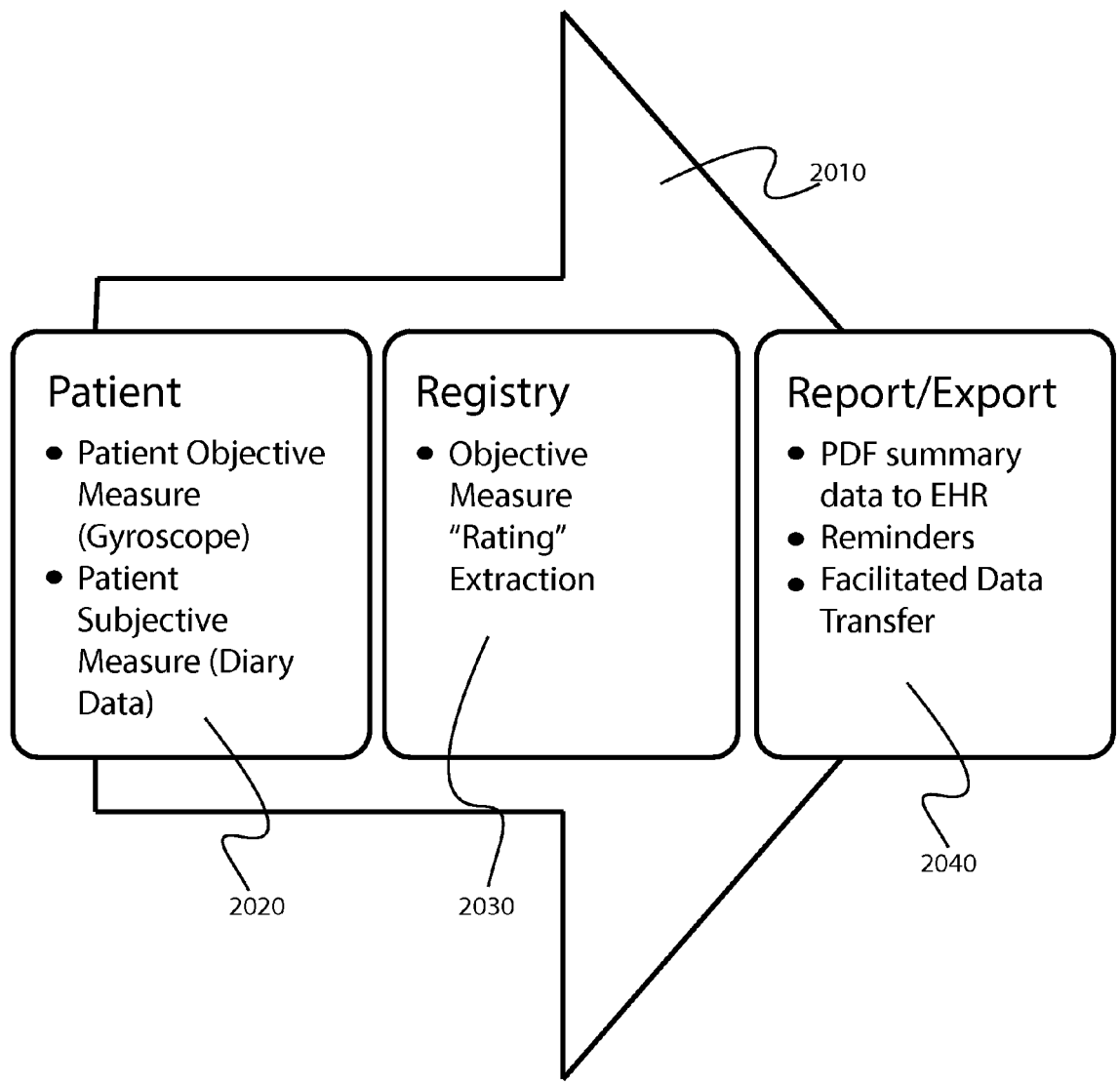
FIG. 20 depicts an EHR individual with disease interaction workflow beginning with the entry of an individual with disease subjective and objective data to extracting the ratings and analytics from the registry to reporting and exporting summary reports.

Analytics and Learning Database:

In the reduced case of a single site, the data exchange with objective measures is represented as (FIG. 18). Even in the case of data exchange within a single medical center, the exchange and or blending and or combined reporting of protected and non-protected health care data may be accomplished (FIG. 19). A method of developing a learning cohort database is disclosed as follows. Standard queries, reports, and searches are contained in a master data table for reporting. In a second table, aggregate "learning" matrices are populated. Population queries create averages for recent searches and provide the basis for new tools to be utilized. Users may create their own search and may also choose from recent searches or reports. Only responses found to be statically significant are added to the calculation list. Community partners and others providing feedback may tailor the interface for registrants as well as provide a non-computerized modality for interacting with the registry through the setting of community outreach events and conjoint volunteers. Objectively measured and diary data are imported and processed for 1) report generation, and 2) internal use as part of the base of data for which abstractions occur from the cohort (FIG. 20).

Data Visualization

Figure 21:
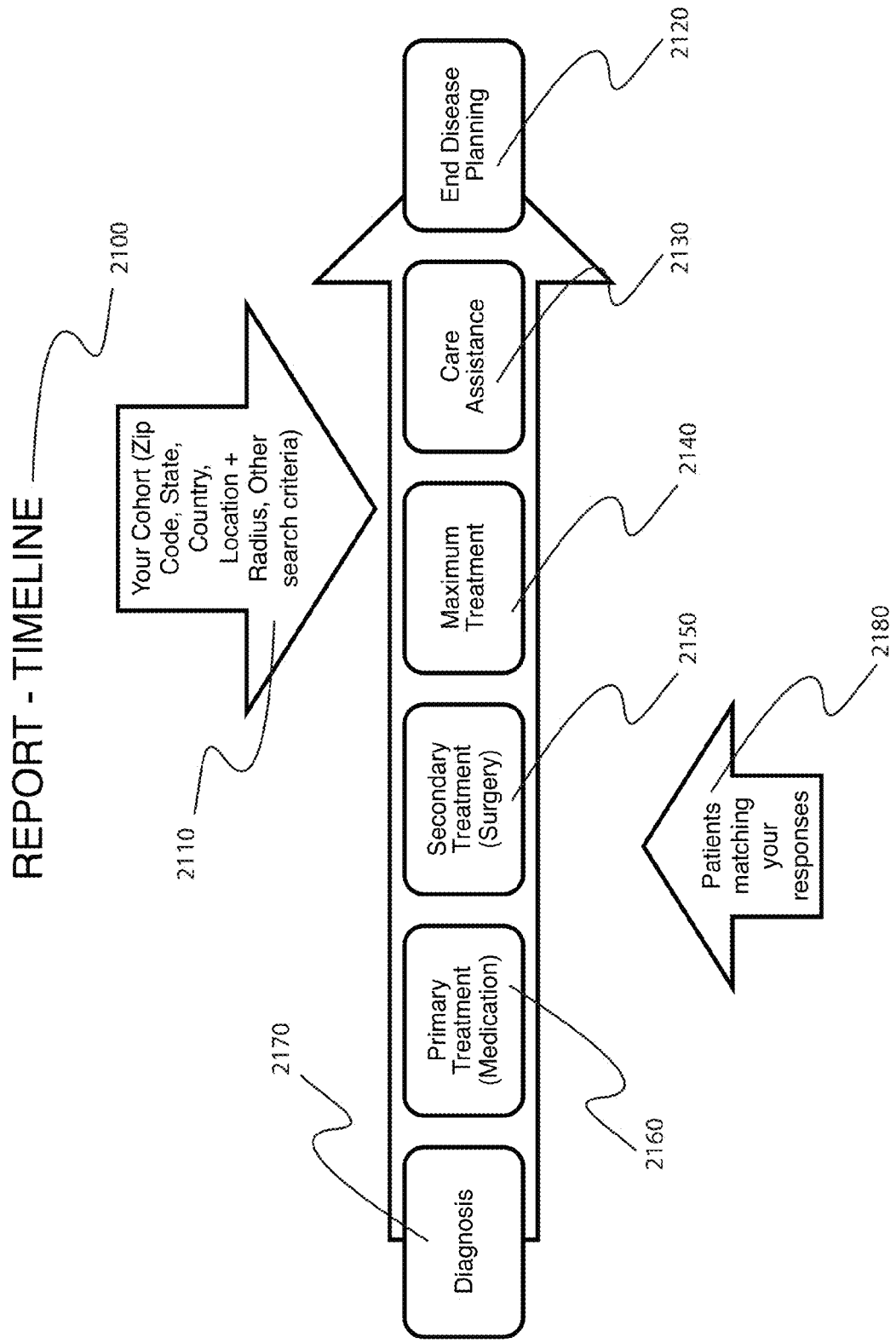
FIG. 21 depicts a Timeline Report detailing metrics and milestones on the timeline from the time of diagnosis to medical and surgical interventions to end of disease planning.

TIMELINE INDIVIDUAL WITH DISEASE TO COHORT ASSESSMENT REPORT: A timeline visualization (FIG. 21) is presented and serves as a reference of where the participant is in the disease process. Answers to several questions are correlated with others in the cohort or a selected population to give a relative position of the subject on the timeline. The timeline can begin with the first symptom, progress to the first treatment, include when the first treatment becomes ineffective and a second treatment is added and then include when medication treatments have failed and then when surgical treatments have failed, and then when a individual with disease passes several milestones of loss of ability to participate in activities of daily living and then progresses to end of life care and wishes. Based upon aggregate answers to the quality of life questions of other participants, a range of improvement in symptoms of the "index individual with disease" is predicted for the individual with disease. Examples of aggregate answers include: (for example, for PD: 1) diagnosis of PD, 2) onset of levodopa use, 3) medication refractory status, 4) date of first consideration of surgery as a next step in treatment, 5) surgery, 6) falls, 7) meaningful work/leisure activity engagement, 8) independent living).

Figure 22:
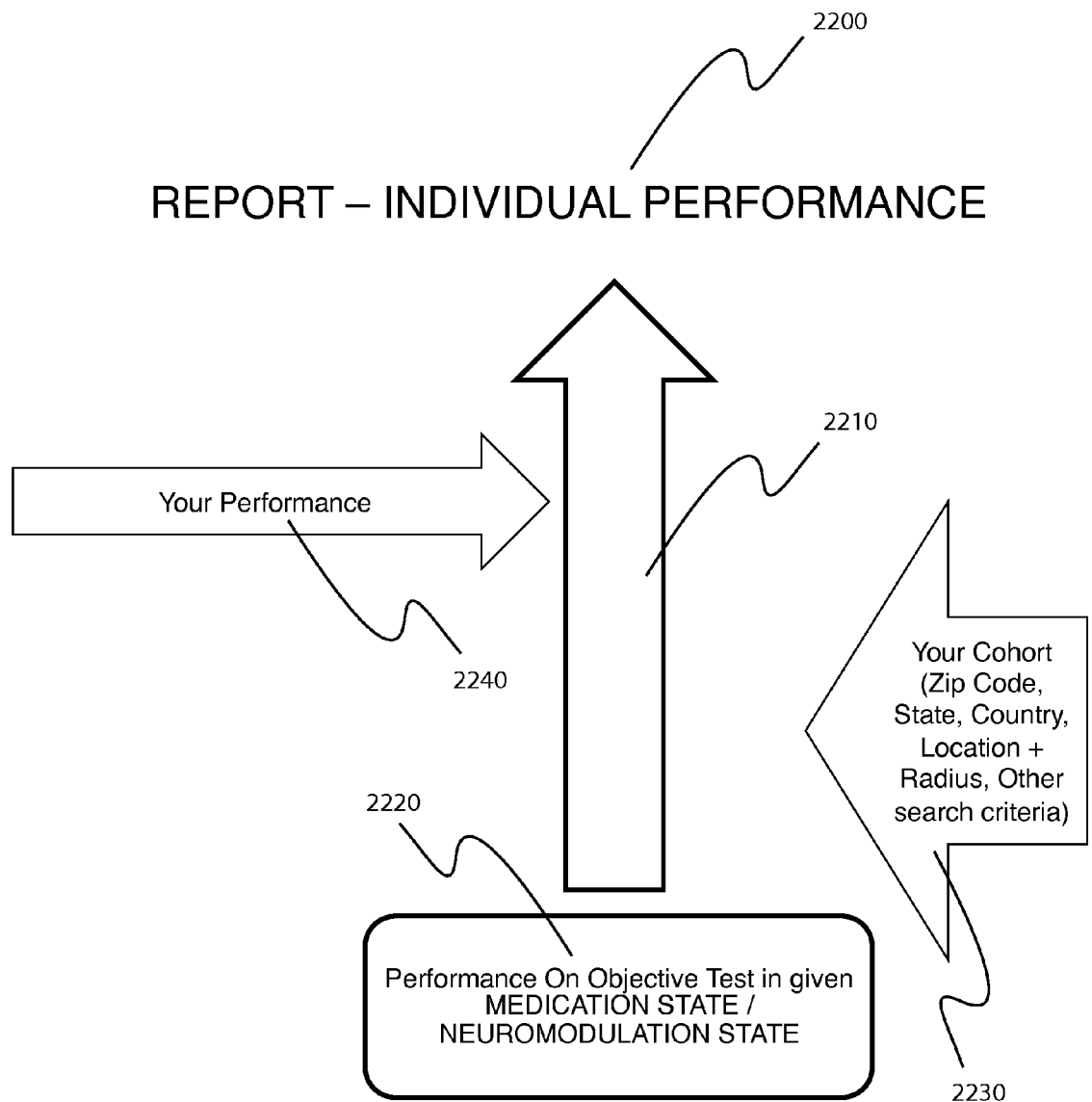
FIG. 22 depicts an Individual Performance Report detailing a method of providing an individual performance report in relation to a cohort an automated fashion.
Figure 23:
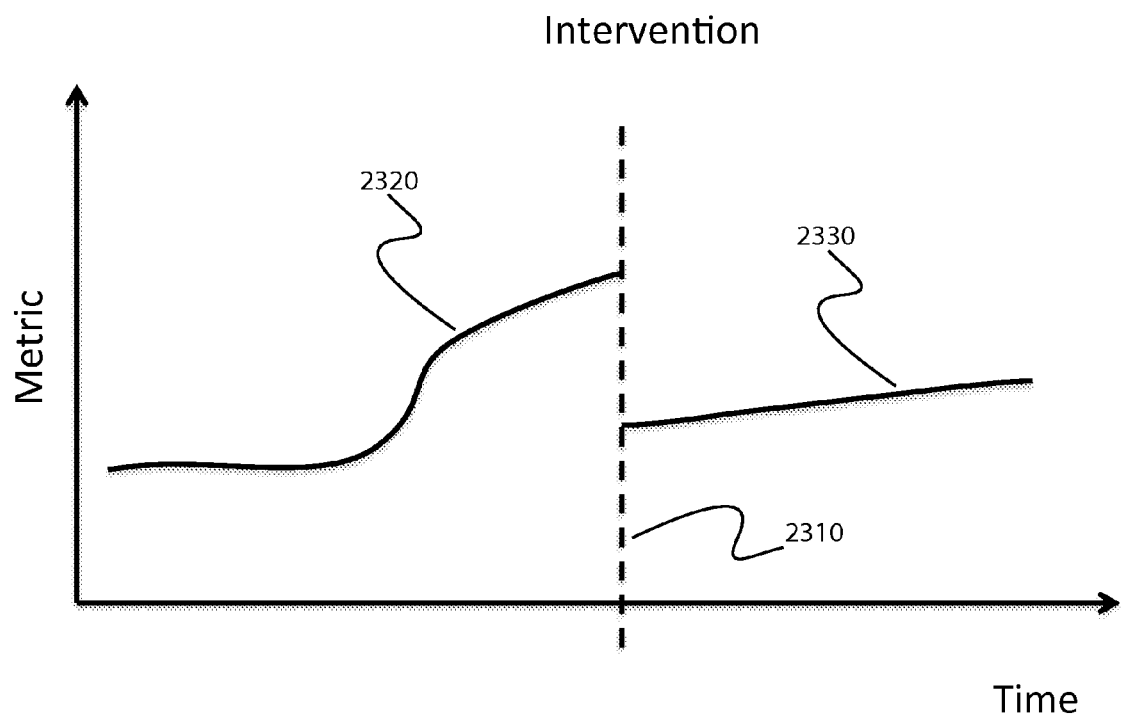
FIG. 23 depicts a Change with Intervention Report of a metric or metrics over time facilitating the visualization of disease burden before and after an intervention in order to measure results the intervention or depict them visually.

TEST PERFORMANCE: An aim of this embodiment is to enable youthful and progressed participants to visualize their disease state progress within the cohort in relative performance of a test (FIG. 22), for example, a simple motor test, objectively obtained with respect to medication intake and surgical treatment. Aggregate results are plotted in time with respect to significant interventions such as neuromodulation (FIG. 23).

Figure 24:
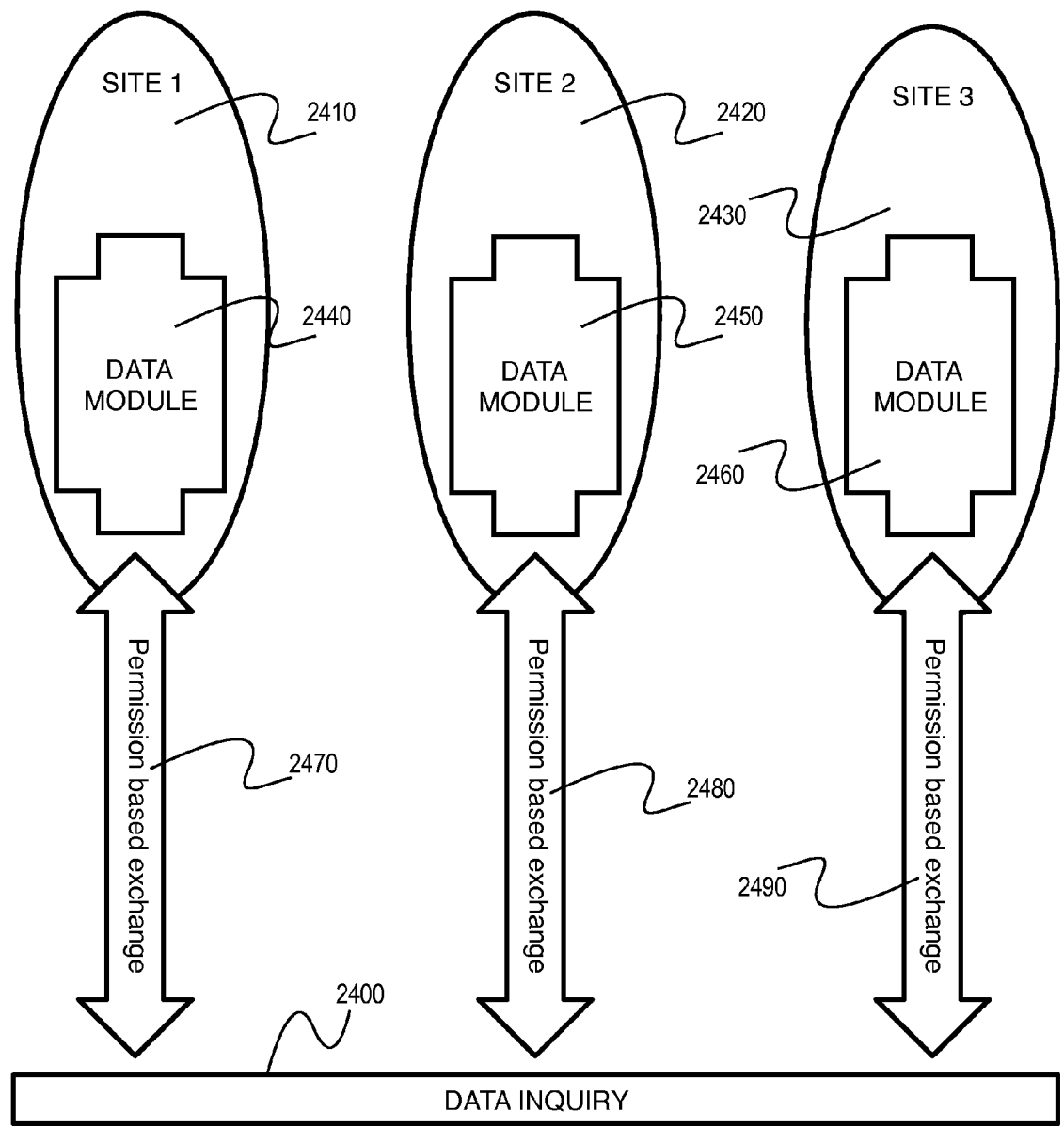
FIG. 24 depicts a method of aggregating data according to use permissions in response to a registry data inquiry made to the various sites or repositories facilitated by the exchange module and permission-based exchange paradigm.
Figure 25:
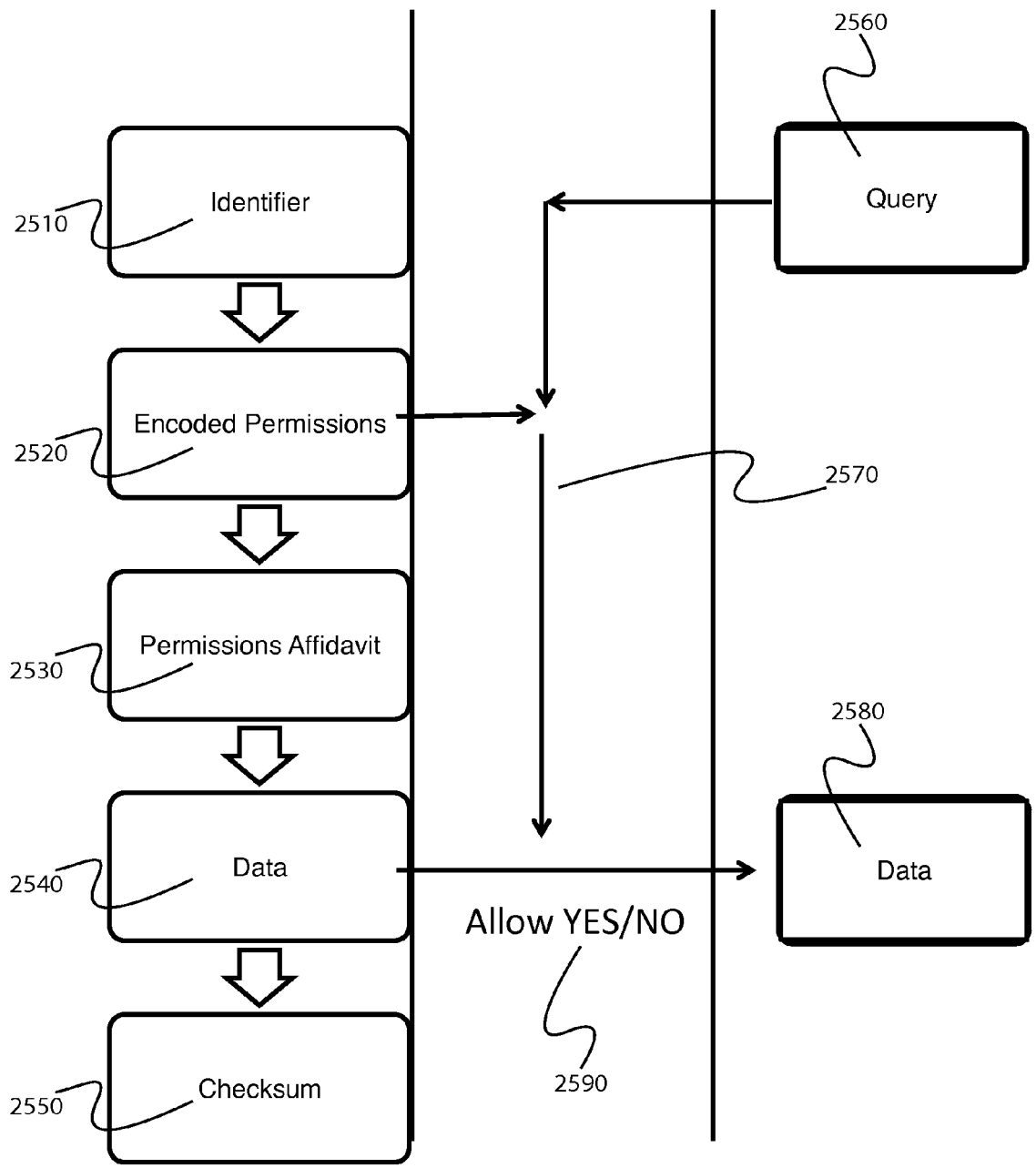
FIG. 25 depicts a Permission Based Exchange paradigm detailing specifics including the interaction between the query and the encoded permissions as well as the data and the allowance of exported data to be aggregated.

COMPARE: A method of examining data clustering around Native American or other cultural/genetic/social factors is provided. Queries are enabled across multiple sites for maximum analysis power of the numerator and denominator for a given metric (FIG. 24). Data aggregation is facilitated based upon a permission based exchange (FIG. 25) and the intended use/user of the data. A unique identifier 2510 identifies an entity providing encoded permissions 2520, a permissions affidavit 2530, data 2540 and a checksum for the data transmission for a permission based exchange via allow or not 2590 so that a query by another 2560 may be responded to with data 2580 responsive to permission 2590. Statistical measures of predictive quality, such as sample variance or standard deviation, can optionally be computed using the data from a cohort or selected population, and can optionally be visualized using a graphical user interface. Access to the examination of data clustering can be enabled using a Client Interface Device or other computer or device having a user interface.

A Server, computer, or computer system can implement a database of providers and provide information on providers accessible to or appropriate for a individual with disease or authorized representative of a individual with disease given a zip code, an address, or information about the individual with disease, such as gender, age, ethnicity, membership in an association or other group, or disease status or progression. The database can be collected from providers or can be derived from an aggregation of data collected from users who access the Server, computer, or computer system.

ENCOUNTER REPORT: An encounter report can be generated by a Server or Client Interface Device that is a downloadable or printable progress report germane to a given physician's visit. Expected outcomes can be included. For example, a representative method includes a summary with the reporting and or graphical display of metrics to provide a clear understanding of individuals diagnosed with a disease progression with medical or surgical intervention in the setting of a fluctuating disease process. Such a report may contain, for example items such as: 1) Medication data, TIMELINE data, TEST PERFORMANCE data, as well as diary data. Another example of an encounter report would contain aggregate data relevant to the cohort of those with similar encounters or based upon the reported data within the system could provide the known cohort reference data for the provider where the individual with disease is undergoing the visit. By example, individuals diagnosed with a disease often ask the provider how individuals diagnosed with a disease treated by them or with a similar treatment modality perform on certain outcomes measures or with reference to certain benchmarks. By example here the individual with disease could arrive at such an encounter for a surgical procedure with a report of symptoms before and after treatment by the 1) provider, 2) institution, 3) other cohort and could ask the question of how their treatment would compare to the known outcomes of the cohort or could ask why their case or treatment was similar to or dissimilar to the cohort group. Should there be a mismatch or objection of the provider to the denominator chosen or the cohort chosen to represent the analysis, feedback could be provided to update the algorithm. By example, should the individual with disease attend a visit with cohort data showing a 5% infection rate for a surgical implant and ask if this rate applied to their case, the provider could state that they expected a 2% infection rate due to the choice of a lower volume implanted stimulator device and cite literature linking the overall volume of an implanted device to the infection rate. The individual with disease could, by example, return from the visit with comments that the provider informed them at the visit that the provided cohort data was 1) valid, however 2) for a different cohort, and 3) could generate a new cohort analysis by model of implant and location of implant to associate with the provider's practice over the past, by example 24 months. Therefore the algorithm would "learn" by knowing the practice pattern of implant and risks. The volume of implant data is available from the device manufacturer. To the extent that enrollees grant the retrieval of specific model and serial number information from the manufacturer or medical repository record of implants, the determination of device volume in this example would occur with little effort on behalf of the individual with disease. There are many other examples of report learning. For example, the fields requested within a report can be displayed by example on with use statistics. For example, under this system, individuals diagnosed with a disease would be shown the most "popular" or most often selected report based upon the TIMELINE algorithm and learning to suggest which treatments may be needed in the disease process. By example, in the case of the surgical implant, such a individual with disease is more likely to have failed medical management and would be placed in a different location based upon the TIMELINE process. In the case of a newly diagnosed individual with disease, the report may contain, by example, information such as the percentage of individuals diagnosed with a disease with a given treatment paradigm who are started on a particular medication as initial treatment. One could alert individuals diagnosed with a disease and insurers if there appeared to be a trend for care to be directed based upon insurance status or other factors and that questions could be asked. By example, individuals diagnosed with a disease with insurance status (A) may be started on a dopamine agonist or other more expensive treatment whereas a self-pay or uninsured individual with disease may be started on levodopa or other medication. This example would not be to determine which is more appropriate medically, as physicians make such informed decisions with their individuals diagnosed with a disease with a balance of coverage and resulting expense to the individual with disease. In this example, however a individual with disease with a certain insurance status with a statistically known likelihood of resulting in a certain therapy could be informed of possibilities for lower cost medication offers from the insurance provider or pharmaceutical provider or from foundation or private financing to assist in bridging the gap of treatment cost. By example, there may be a trial medication offer by a pharmaceutical company for xxx years of treatment at a reduced price. Such an offering may not be widely known within the treatment community at large or within the provider community. Should a report show that individuals diagnosed with a disease on the TIMELINE or given a certain set of criteria are asking for their information to be sent to company yyy or foundation zzz or state government or federal government program 123 in order to facilitate altering the treatment from one pathway to another, they may ask about this with their provider or inquire directly with the company to their benefit. Such a report could, by example, state that 35% of individuals diagnosed with a disease matching your profile are taking advantage of a free medication trial by company yyy. This offering and the suitability of the treatment for the individual with disease could then be discussed with the care provider during the visit. One can envision many similar variations of individual with disease information empowerment within the setting of a brief report provided prior to a physician encounter.

INDIVIDUAL WITH DISEASE TO INDIVIDUAL WITH DISEASE DISCUSSION REFERRAL REPORT: Potential referrals can be displayed on a Client Interface Device, computer, or other device having a user interface in response to a request by a individual with disease or an authorized representative of a individual with disease. Referrals can be based upon the disease burden of the individual with disease and upon responses from the cohort. This method facilitates participant referral for further clinical care or non-clinical activities modified by responses from the cohort.

PROVIDER VISIT SUMMARY: This summary includes medication changes, recommended activity goals, neurostimulation changes with visualization of new areas of stimulation and advice of data to log. The home logging can be enabled if the individual with disease or authorized representative chooses to, and the desired metrics will then be acquired according to the listing on the individual with disease visit summary using the user interface capabilities of the Client Interface Device, computer or other device to which the individual with disease or representative has access. The collected data are protected as confidential data owned by the individual with disease and may be stored within the Client Interface Device, computer or other device used by the individual with disease or individual with disease's representative, or may be stored on a Server with which the Client Interface Device, computer or other device can communicate. Any exchange of data across public or shared communications channels or networks is protected from unauthorized access or use by encryption using one or more encryption key(s) and method(s) known to the Client Interface Device, computer or other device and Server.

Participant Portals:

Individual with Disease Home Data Entry/Use Portal:

Method of Entry points for participants include the home environment as well as in the setting of community regional support meetings. Technology such as the Client Interface Device, a computer or computer system, or a device such as a tablet computer or smart phone (FIG. 8) empowers disease society representatives (APDA) with linked tools while traveling to attend regional support meetings. A method enabling participants to visualize their progress within the cohort based upon participant delivered content is provided. A method is provided for organizing individual with disease data for the treatment of Parkinson's disease in an efficient manner. The method enables participants to visualize their progress within the cohort in relative performance of a simple motor test objectively obtained with respect to medication intake and surgical treatment.

Reports available for the individual with disease portal include an INDIVIDUAL WITH DISEASE ENCOUNTER REPORT, INDIVIDUAL WITH DISEASE TO INDIVIDUAL WITH DISEASE DISCUSSION REFERRAL REPORT, and INDIVIDUAL WITH DISEASE TO COHORT ASSESSMENT REPORT.

Figure 3:
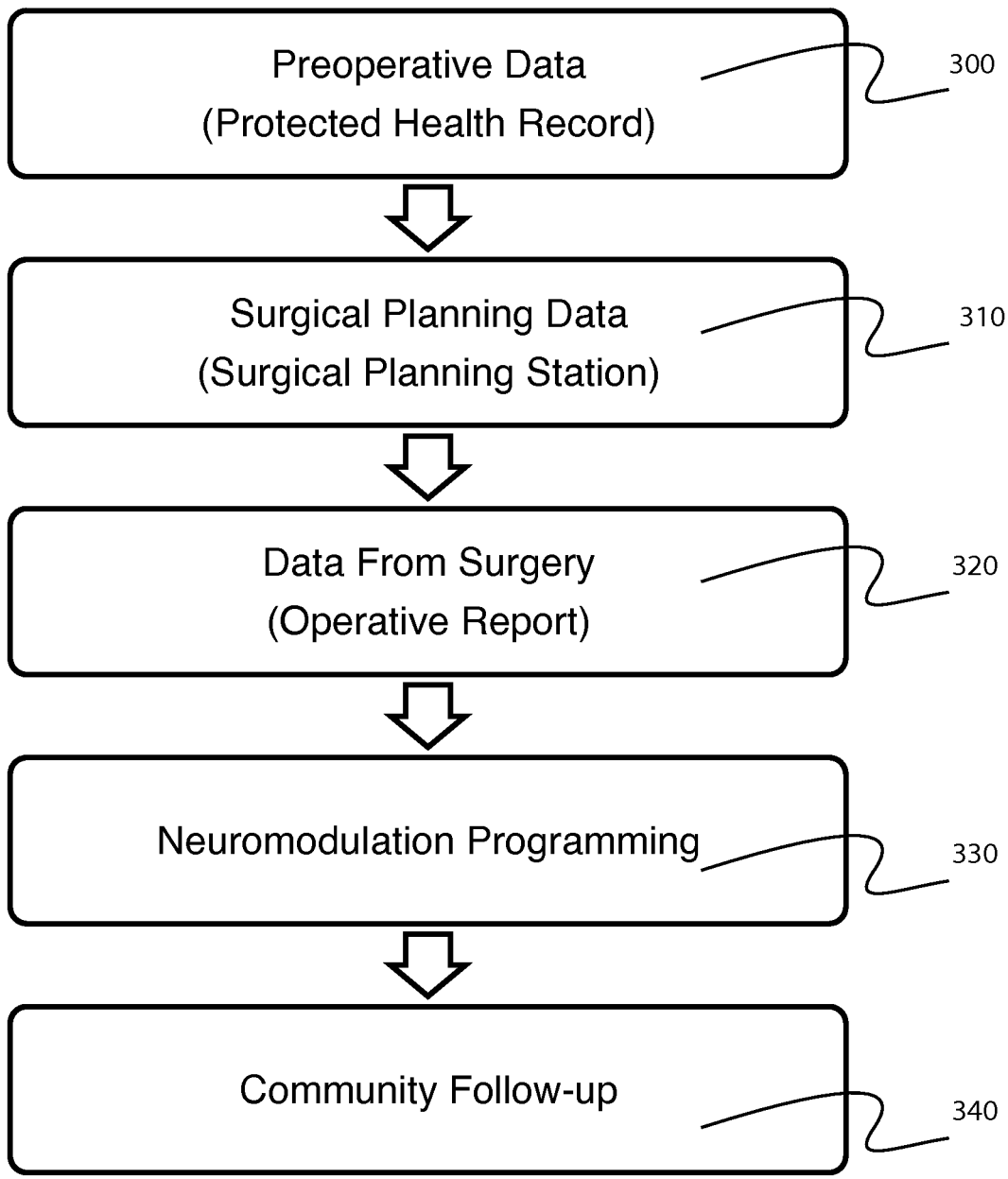
FIG. 3 is a PRIOR ART data flow diagram demonstrating data flow for neuromodulation from pre-authorization to surgical planning data to data from the surgery to neuromodulation programming to follow up within the community.
Figure 4:
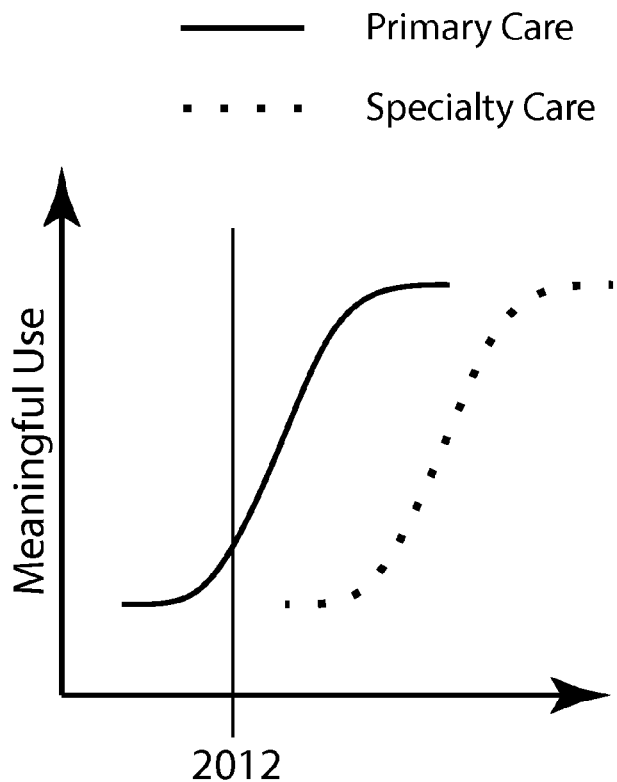
FIG. 4 is a suggested diagram depicting the rate of adoption of meaningful use of the electronic health record (EHR) depicting electronic health record technology adoption lagging that for specialty care.
Figure 6:
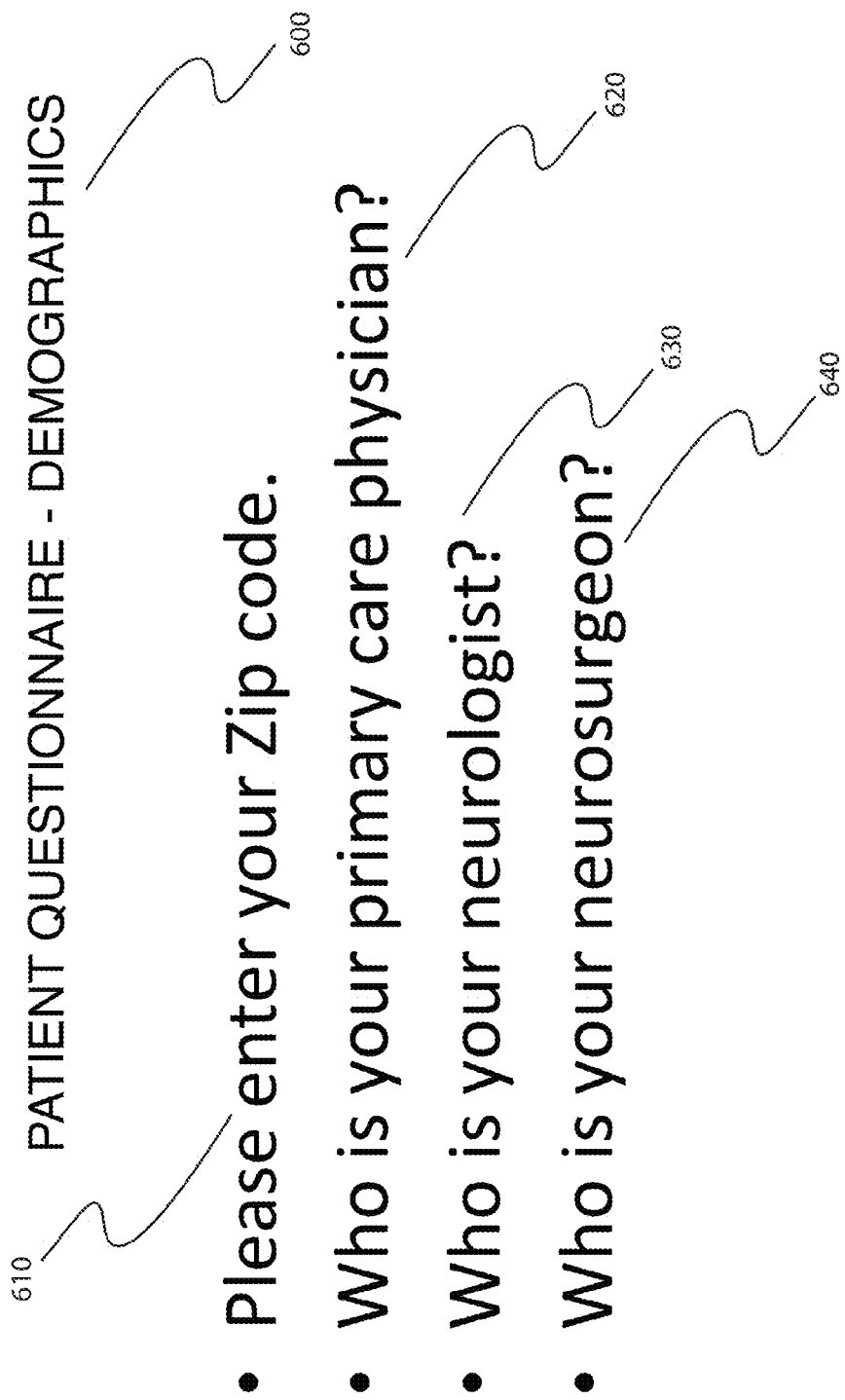
FIG. 6 is a PRIOR ART drawing of a typical Parkinson's Disease Questionnaire (PDQ) wherein FIG. 6 requests demographics data.

SOCIAL: Significant hurdles exist for the wide adoption of social media and connectivity within technology non-savvy population such as the elderly PD population. To circumvent this, a data advocate serves as a surrogate for adoption and interaction at regional group support meetings such as the (APDA). The data advocate provides ongoing feedback on the 1) data fields collected, 2) reports generated (such as FIG. 3) for participants and partners in community health, 3) the participant feedback for the ease of use, 4) the relative impact of in person, kiosk or paper interface with the registry versus independent access. A method, within the registry, is provided for displaying potential referrals given the disease burden of the individual with disease based upon responses from the cohort or a selected population. Individuals diagnosed with a disease are able to indicate an interest in participating in individual with disease referrals and being in contact with others of a similar representative data profile. A method of utilizing and determining the impact of social networking on how individuals diagnosed with a disease feel about their progress with with/out treatment is provided. The individual with disease or authorized representative of the individual with disease can utilize these methods using the Client Interface device, computer, computer system, or other device such as a tablet computer, a laptop computer, a desktop computer, or a smart phone or game console.

Community Support Group Data Portal:

A method of standardizing, simplifying, and objectifying clinical outcomes tracking, culminating in population health measurements of PD individuals diagnosed with a disease in the home and in the setting of support group-based periodic meetings is disclosed. The method includes determination of entry points for participants include the home environment as well as in the setting of community regional support meetings. Together with community partners (APDA), the interface for registrants can be tailored and a non-computerized modality can be provided for interacting with the registry through the setting of community outreach events and conjoint volunteers. Specific entry points for participants include the home environment as well as in the setting of community regional support meetings. For example, with the partnership of the APDA, the research coordinator could travel to attend regional APDA meetings throughout the year as well as monthly meetings within a city, county, region, or state.

The disclosed method includes developing a system for state, national, or global population health able to address diseases within the restorative neurosciences (such as multiple sclerosis, essential tremor, dystonia, normal pressure hydrocephalus, spinal and gait disorders) and beyond. Entry points for participants include the home environment as well as in the setting of community regional support meetings.

Workflow of the embodiment includes: a regional support group meeting; for example: A data advocate may travel and attend regional support group meetings. The support network provides ongoing feedback on: 1) Data fields collected, 2) Reports generated (for example, FIG. 3) for participants and partners in community health, 3) Participant feedback related to ease of use, and 4) relative impact of in person, kiosk or paper interface with the registry versus independent access. The method includes tailoring community partner registry interfaces as well as providing a non-computerized modality for interacting with the registry through the setting of community outreach events and conjoint volunteers.

Figure 8:
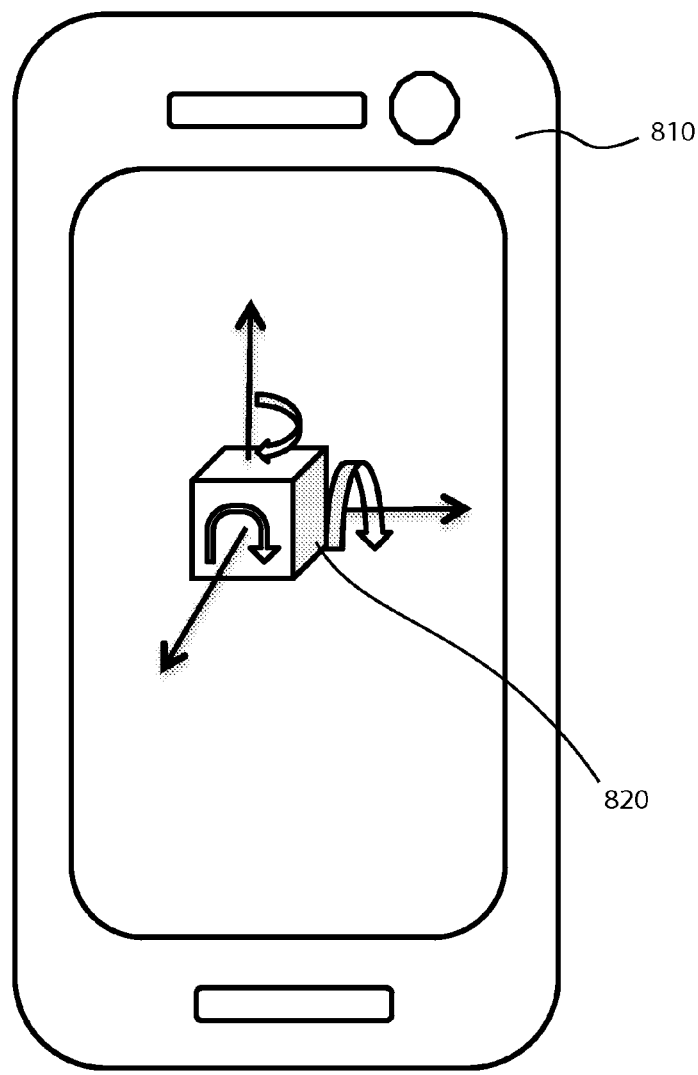
FIG. 8 depicts a wirelessly linked mobile health device with multiple on-board sensors such as an accelerometer, gyroscope, camera, microphone, speaker and position determination capability such as GPS or processed location data based upon wireless network access.

ASSESS: An aim of an embodiment is to enable youthful and progressed participants to visualize their disease state progress within their cohort in relative performance of a simple motor test, objectively obtained with respect to medication intake and surgical treatment. Early and late stage disease individuals diagnosed with a disease are identified, and through a questionnaire, a history of diagnoses and treatments, or other means individuals diagnosed with a disease are associated with a position on a timeline is presented utilizing relevant factors (e.g. for PD: 1) diagnosis of PD, 2) onset of levodopa use, 3) medication refractory status, 4) date of first consideration of surgery as a next step in treatment, 5) surgery, 6) falls, 7) meaningful work/leisure activity engagement, 8) independent living. A visualization of the disease burden is optionally provided using a display of a Client Interface Device or computer (FIG. 8). Methods of ensuring early and late stage disease individuals diagnosed with a disease have meaningful access and derive meaningful utility from the tools are implemented using, for example, designated or authorized individual with disease representatives, or, with appropriate privacy and security safeguards and permissions, reporting of test result using a Server or other computer or computer system.

Population Health and Comparative Effectiveness Research

The disclosed method influences individual with disease care with monitored quality metrics and provides a method of understanding the impact of emerging therapies on limiting human suffering within the disease (PD) population. The method of OMS based comparative effectiveness research (CER) aims to empower individuals diagnosed with a disease, providers and community partners (APDA/NPF) in identifying and reversing treatment disparities in PD healthcare delivery in a selected PD population.

The disclosed embodiments provide a method of expanding early pilot study data though individual with disease rapid participant recruitment to facilitate highly powered inquiries with broad application in local, regional, state, national, and global public health CER inquiries The method of providing reports aims to lowering the cost of understanding treatment differences and increase the velocity of validating new treatments for the clinic. By example, a research associate or individual with disease, or physician may identify a trend in diagnosis or measurement or treatment of disease. By example, should a physician propose a method of performing a fifteen-minute objective test to be performed using devices freely available within the individual with disease and provider community, allowing unprecedented ease of participation for longitudinal testing over time, such a proposal could be a target for rapid dissemination. By this example, the proposal could be posted within a research portal with advertisement of the proposal guided by the selection criteria of the investigator. Users could affirm or vote in favor of the project and to the extent the project could be performed outside the clinical environment, data could be aggregated quickly. By example, users could organize under a proposal that individuals diagnosed with a disease would perform a pronation/supination bradykinesia test on a daily basis for a period of time, such as six months, while various objective data were recorded. Health data such as medication intake, visits to providers, quality of life information, travel information, physician measured metrics could be aggregated to answer questions about treatment during the year. For example around the time of surgical intervention such as deep brain stimulation. The method facilitates early adoption of new therapy such as deep brain stimulation through the use of monitored quality metrics.

An aspect of the present invention is a method of social media monitoring and integration utilizing analysis of public data such as TWITTER® software. FACEBOOK® social network, and similar open and publicly reported social network events. (TWITTER is a registered trademark of Twitter Inc., and FACEBOOK is a registered trademark and brand name of Facebook, Inc.) For example, the reporting fields and aggregate data fields are searched with a search engine and other technologies as in the following example of cohort database permissive generation. In cooperation with such a data provider, for example Google Inc., a report is generated regarding the frequency and location of searches similar to an individual with disease's location or placement on the TIMELINE. Given a cohort location of, for example 250 miles from home, a distance an individual with disease may reasonably travel for regional care, location of search term density can be displayed. For example, if it could be known that a certain population of individuals diagnosed with a disease resided within a community with two treatment centers located 250 miles apart along an interstate distance, one could combine density of search data of those within the intervening lenticular shaped 250 mile driving distance are from both centers. One could then determine the frequency of twitter feed and Internet searches based upon location by IP address or GPS location during the search and process the relationship between cost, quality, and travel for the cohort. One could report based upon these aggregate data and transmit the results over mobile or other networks for reporting and assistance in presenting data surrounding the choices that individuals diagnosed with a disease with similar characteristics are making. One can combine the clustering of the individuals diagnosed with a disease in a population map with the clustering of providers and with a heat map of activity of search terms to demonstrate activity within a region. Additionally, active research or publications by physicians or others treating individuals diagnosed with a disease at the centers can be selectively added to the cohort database based upon impact factor and regency of the publication and NIH or other funding awarded as well as preclinical, clinical, or other research provided. An overall population treatment impact factor can be computationally determined. The algorithm can be tuned via neural network or other learning algorithm by the actual responses of the subset of individuals undergoing treatment by inquiries as to their relative weighting of cost, travel, and import of the factors involved in the algorithm. A suggestion item could be added and a calculation of the most frequently suggested addition could be added to determine when and if further inquiries should be added. For example: Treatment Impact Factor (provider) is derived from weight 1×(average publication impact factor)×average number of publications×average number of citations×[1/(current year−average publication year)]+weight 2×(NIH funding dollars average per year of practice)+weight 3×number of active, enrolling clinical trials+weight 4×number of preclinical trials active+weight 5×number of collaborators named on publications since beginning practice in this location+weight 6×number of known outreach speaking engagements outside the host institution in past 2 years+weight 7×(multiple other factors).

Factors measured from an institutional ranking perspective include: number of physicians treating a disease process, average wait time for clinic appointment, number of regional offerings unique to the institution, number of voids of service or offerings causing travel to the adjacent facilities. These are example factors to be placed in the learning algorithm similar to that for the individual provider.

Public Health Portal/Reporting:

Public health reports are provided based upon the permission matrix to enable determinations of numerators and denominators of the population with disease or undergoing therapy as well as density and provider/resource availability by zip code, an address, or information about the individual with disease, such as gender, age, ethnicity, membership in an association or other group, or disease status or progression. CER of medical and surgical interventions is possible by zip code.

An aspect of the disclosure provides a method of improving the health of the people in a selected population by quantifying results of health care intervention. To the extent treatment changes occur over time, an analogy can be drawn to continuous quality improvement. Individuals diagnosed with a disease in the community could benefit from avoiding randomization to a non-treatment arm under the models of evidence-based medicine employing randomized trials. Methods of developing and validating tools for measuring the improvement in the health of the target population may be expanded through the use of the community based registry system. For example, after deep brain stimulation surgery, someone may read a report of concerns regarding traveling in a hybrid electric vehicle or other vehicle with an electromagnet such as driving a ferryboat with electric motors driven by motors or turbines such as electric trains. Such an evaluation of automobile travel, by example, could occur by the method of an application for mobile health with connectivity such as Bluetooth, which wirelessly paired with the host automobile or otherwise determined the travel device. Aggregate GPS data and other data from a device such as a wristwatch device able to perform measurements in the background could determine through aggregate algorithms if a user of the registry system were driving the target automobile based upon wrist and arm motion or based upon visual input from devices such as Google GLASS® display and services or other similar device and determine position within the vehicle based upon arm movement and magnetometer date. Knowing the model number of the automobile and interfacing with the automobile manufacturer, one could obtain electrical field maps from the automobile testing and understand the relative location of the device within the automobile. Combined with surgical information regarding unilateral versus bilateral implantation of the cranial devices and implantable pulse generators in the case of DBS, one could determine the likelihood of an open "loop" allowing for an inductive energy transfer. Given that 1% of the population over 60 has Parkinson's disease and many drive a PRIUS® automobile (available from Toyota Motor Corporation with BLUETOOTH® telecommunications equipment available from BLUETOOTH SIG, Inc. pairing technology, and a subset of those have DBS neuromodulation where the device and stimulation information can be known from medical records, one could see by this example, how a community based approach allowing the blending of medical and non-medical data on behalf of the participant could yield a significant number of individuals diagnosed with a disease in the numerator and denominator of a question such as "does one reasonably feel safe in an electric car with DBS for PD?". The alternative in this example is that there is a single case report of such potential interference with the individuals diagnosed with a disease, device manufacturers, physicians, and automobile manufacturers with no clear way to easily answer a question about the possible effects of these interactions in the community despite a large cohort of potentially affected participants in a time when neuro-stimulation in the retiring population is rising concomitant with the use of electric motor-containing vehicles. By example linking to other sections in the current patent application, one could envision a report of the most actively participated or recruited to studies given a position in the TIMELINE. There is reasonable expectation that industry or investment such as "kickstarter" and other "croudfunding" modalities could be linked to this method. One could establish a baseline in those PD individuals diagnosed with a disease driving electric motor powered vehicles and then seek funding based upon preliminary data for the next phase of the study. Supposing such an inquiry led to a significant finding, further randomized trials could be planned resulting in a finding which may influence automobile or neuro-stimulator design. Additionally, an alert could be set if the client user device magnetometer 5265 detects magnetic fields associated with the electromotor above and beyond an average acquired within the cohort (FIG. 22). Such an App based approach could alternatively gather background magnetometer data aggregated by type of automobile and upload to the central server for further governmental and industry reporting.

In summary, the several embodiments propose methods of developing and validating tools for measuring the improvement in health of the target population, methods of rapid integration of global micro-research tools into the clinical and community settings, method of facilitating participant/individual with disease inquiries within the dataset, methods of collaboration with academic medical centers, method of collaborating with state and federal government, method of collaborating with PD community centers, method of developing objective measures (OMS) of the "health" of the disease cohort (e.g. regional PD population), method of developing a system for statewide population health to address diseases such as multiple sclerosis, essential tremor, dystonia, normal pressure hydrocephalus, spinal and gait disorders, method of Expanding pilot studies expected to have broad application in public health CER, lowering the cost of understanding treatment differences and increasing the velocity of validating new treatments for the clinic, method of creating public/private hybrid partnerships for CER, method of advancing this modality rapidly to the national scale through collaboration with the NPF QII database and the neurosurgical N2QOD database in accordance with the principles of the present invention.

Financial:

Method of supporting insurance approval of treatments: Method(s) of permission-based interfacing with either insurance carriers' data systems or hospital data systems permit selected extraction of information for insurance purposes, with individual with disease consent with appropriate security controls. The disclosed system, implemented by one or more Servers and accessed by Client Interface Devices or other computers or computer systems, supports insurance approval of treatments and also supports feedback or rebates which individuals diagnosed with a disease me subscribe to in order to bargain directly with insurers for their current or future care future care. An example of this would be an individual with disease who consents to monitoring for a period of six months in exchange for a reduction in premiums.

Academic:

Method of facilitating a clinical validation and translational comparative effectiveness research (CER) though a community registry environment: Clinical validation and translational research and CER are facilitated by a permission-based release of the data and a portal for pre-approved data aggregation and publication without the need for a new institutional board review of each subset of the inquiry. Specific individual with disease consent can be obtained to reach out to state and hospital databases on their behalf for the specific purpose of research. The interface can be implemented using the Client Interface Device and digital certificates or public/private keys, where a Server can act on the individual with disease's behalf and request and obtain data from another computer or computer system. Included in the embodiment is a method of allowing trial data or implementation of data specific requests to be widely distributed by the use of a single study number representing the encoded methods of research. Individuals diagnosed with a disease can participate from home using Client Interface Devices or other computers or devices to facilitate this research if needed. Specific entry points for participants include the home environment as well as in the setting of community regional support meetings. For example, with the partnership of the APDA, the research coordinator will travel to attend regional APDA or similar meetings throughout the year as well as monthly meetings within the individual with disease's region. The APDA or a similar group can provide ongoing feedback on the 1) data fields collected, 2) reports generated (FIG. 3) for participants and partners in community health, 3) the participant feedback for the ease of use, 4) the relative impact of in person, kiosk or paper interface with the registry versus independent access. Methods for feedback to the individuals diagnosed with a disease are allowed; including tracking of which research protocol the individuals diagnosed with a disease' data was contributed to in the end. Additional feedback is provided to allow a participant to know where they reside in the midst of an ongoing research program. These algorithms are then "published" internally for individuals diagnosed with a disease to select to ask questions of their location within a specific cohort.

The method and system provides individuals diagnosed with a disease an ability to visualize their progress within a selected cohort or population by providing and optionally comparing objective measurements of performance of a simple motor test, obtained with respect to medication intake and surgical treatment.

Figure 28:
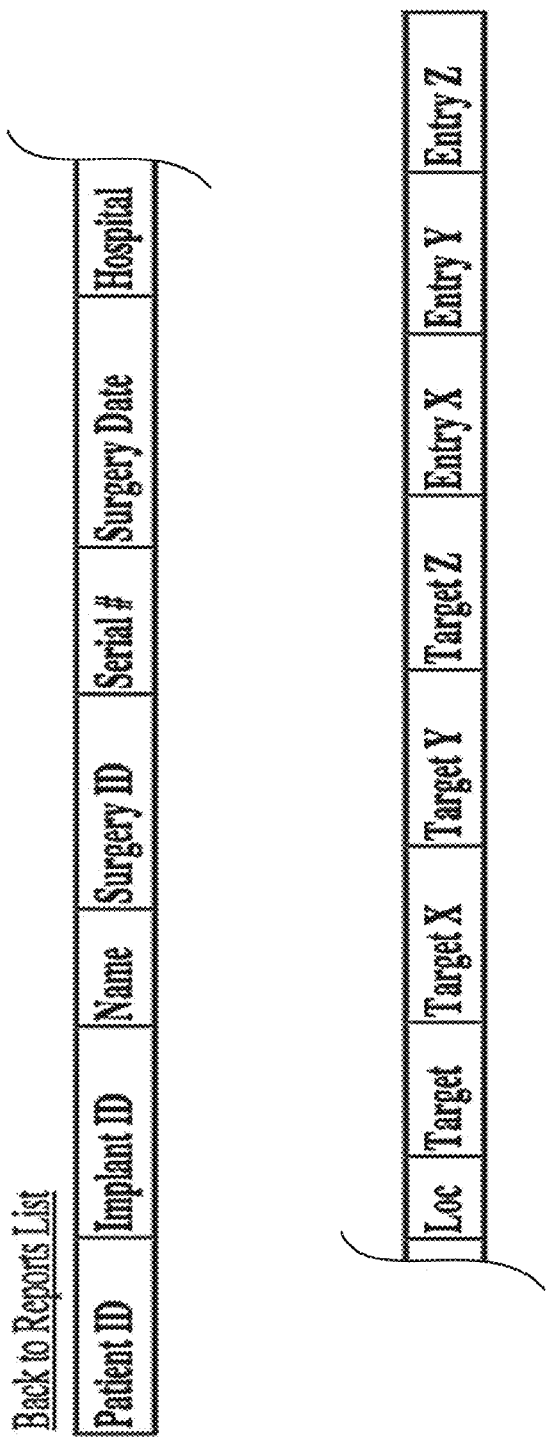
FIG. 28 depicts an Implant Trajectory Report detailing the Anatomic Target XYZ, and Entry XYZ in a specific reference frame (in this case AC/PC space). Relative location of the implant within the aggregate cohort is displayed and reported, facilitating the automated calculation of the target and implant direction vectors of the cohort.
Figure 34A:
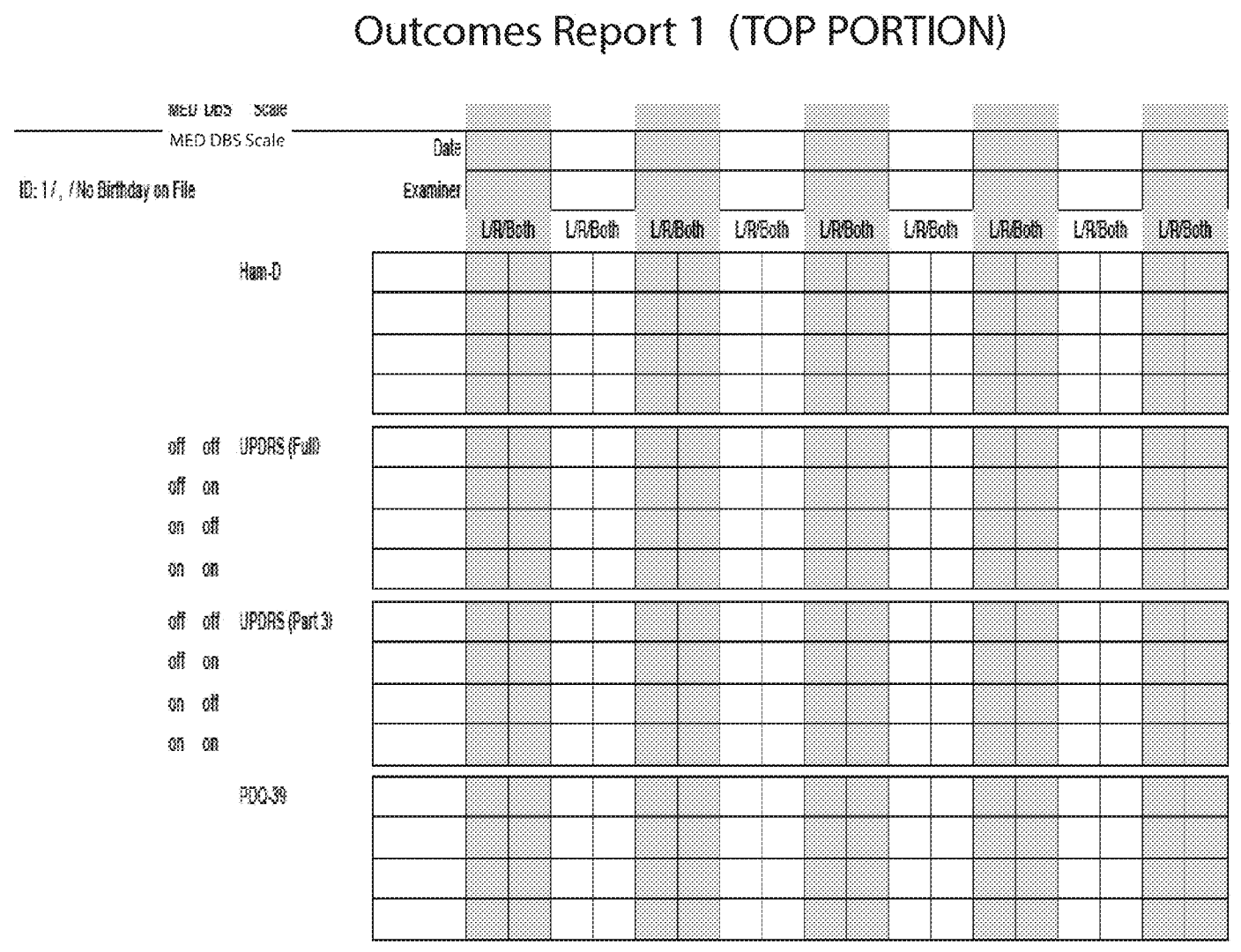
Figure 34B:
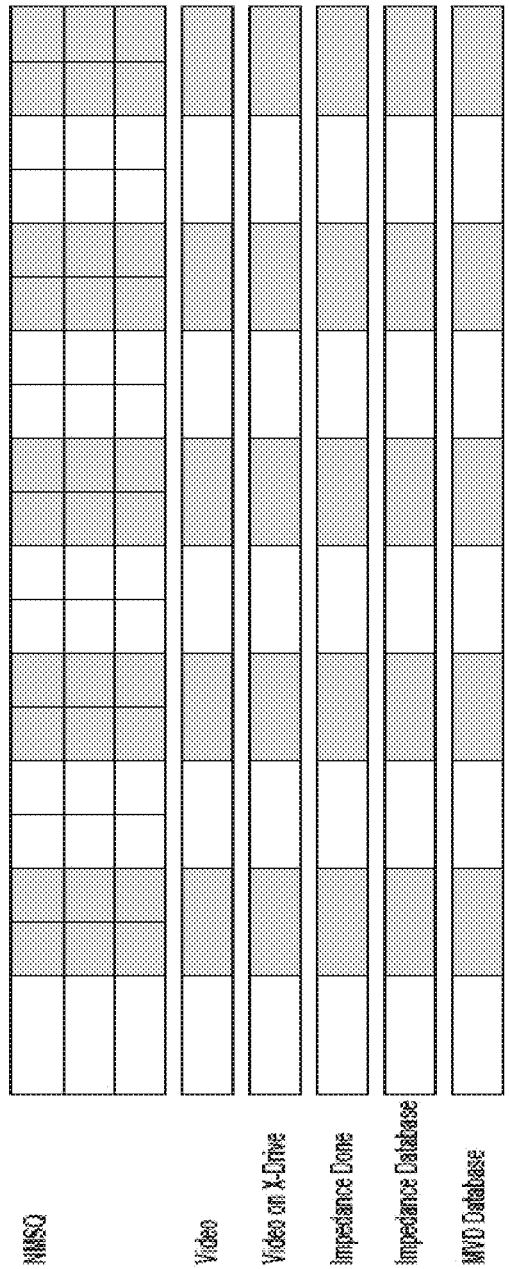

PROVIDER: Method of decreasing health care provider burden in assessments: An example of this method is the movement disorders outcomes report (FIG. 26) generated for the provider. A reports screen guides the user to the appropriate report. Reports are generated for age and gender breakdown of surgical implants (e.g. DBS, FIG. 27), anatomic target and entry points (e.g. DBS, FIG. 28), Consent Report (FIG. 29), Surgery Report (FIG. 30), Calculated Active X/Y/Z (FIG. 31), Reports—Left and Right with Distance from Ave Target (FIG. 32), Active Implant Report (FIG. 33), Outcomes Report 1 (FIG. 34A and FIG. 34B), All active implants with impedances (FIG. 35). A provider can access an INDIVIDUAL WITH DISEASE ENCOUNTER REPORT, INDIVIDUAL WITH DISEASE TO INDIVIDUAL WITH DISEASE DISCUSSION REFERRAL REPORT, and INDIVIDUAL WITH DISEASE TO COHORT ASSESSMENT REPORT. A physician may generate a PROVIDER VISIT SUMMARY.

DECISION SUPPORT: The disclosed method provides use metrics such as: 1) Time from diagnosis to significant milestones including in the case of PD segment 1(first medication administration until adding second medication: length of time in this segment, number of health care provider visits, number of visits to physical therapy or exercise modalities, average travel during this segment, medication use during this period), segment 2 (adding of second medication [often levodopa] until considered medically refractory: length of time in this segment, number of health care provider visits, number of visits to physical therapy or exercise modalities, average travel during this segment, medication use during this period), segment 3 (medication refractory until decision for restorative neurosurgery: length of time in this segment, number of health care provider visits, number of visits to physical therapy or exercise modalities, average travel during this segment, medication use during this period), segment 4 (perioperative: length of time in this segment, number of health care provider visits, number of visits to physical therapy or exercise modalities, average travel during this segment, medication use during this period, target selection, days in hospital, insurance provider, hospital visited, compilation, implant location (ac/pc xyz), activated at time of hospitalization (yes/no), initial active stimulation parameters including location, estimated volume of tissue activated at time of activation, impedance pairwise and monopolar of all contacts, rechargeable vs. primary cell technology, simultaneous bilateral vs. staged bilateral implantation vs. unilateral implantation with planned interval greater than 6 months between implantation, preoperative neuropsychometric testing including mini-mental status exam results, diary results including questionnaire data such as Parkinson's disease questionnaire 8 and 39, Hamilton depression score preoperatively, unified Parkinson disease rating scale total and motor (1987 Fahn) on and off medication preoperatively, objective measures preoperatively on and off medication including, timed up and go, bradykinesia assessment including finger tapping, pronation supination (gyroscope), berg balance test, and other metrics), segment 5 (post discharge until 3 months follow-up: length of time in this segment, number of health care provider visits, number of visits to physical therapy or exercise modalities, average travel during this segment, medication use during this period, target selection, days in hospital, insurance provider, hospital visited, compilation, implant location (ac/pc xyz) on follow-up scan if available, device battery status and voltage, active stimulation parameters including location, estimated volume of tissue activated at time of activation, estimation of energy delivered (to assess battery life), impedance pairwise and monopolar of all contacts, preoperative neuropsychometric testing including mini-mental status exam results, diary results including questionnaire data such as Parkinson's disease questionnaire 8 and 39, Hamilton depression score preoperatively, unified Parkinson disease rating scale total and motor (1987 Fahn) on and off medication preoperatively, objective measures preoperatively on and off medication including, timed up and go, bradykinesia assessment including finger tapping, pronation supination (gyroscope), berg balance test, and other metrics), segment 6 (3 months follow-up until 6 months: length of time in this segment, number of health care provider visits, number of visits to physical therapy or exercise modalities, average travel during this segment, medication use during this period, target selection, days in hospital, insurance provider, hospital visited, compilation, implant location (ac/pc xyz) on follow-up scan if available, device battery status and voltage, active stimulation parameters including location, estimated volume of tissue activated at time of activation, estimation of energy delivered (to assess battery life), impedance pairwise and monopolar of all contacts, preoperative neuropsychometric testing including mini-mental status exam results, diary results including questionnaire data such as Parkinson's disease questionnaire 8 and 39, Hamilton depression score preoperatively, unified Parkinson disease rating scale total and motor (1987 Fahn) on and off medication preoperatively, objective measures preoperatively on and off medication including, timed up and go, bradykinesia assessment including finger tapping, pronation supination (gyroscope), berg balance test, and other metrics), segment 7 (6 months until 1 year: length of time in this segment, number of health care provider visits, number of visits to physical therapy or exercise modalities, average travel during this segment, medication use during this period, target selection, days in hospital, insurance provider, hospital visited, compilation, implant location (ac/pc xyz) on follow-up scan if available, device battery status and voltage, active stimulation parameters including location, estimated volume of tissue activated at time of activation, estimation of energy delivered (to assess battery life), impedance pairwise and monopolar of all contacts, preoperative neuropsychometric testing including mini-mental status exam results, diary results including questionnaire data such as Parkinson's disease questionnaire 8 and 39, Hamilton depression score preoperatively, unified Parkinson disease rating scale total and motor (1987 Fahn) on and off medication preoperatively, objective measures preoperatively on and off medication including, timed up and go, bradykinesia assessment including finger tapping, pronation supination (gyroscope), berg balance test, and other metrics, stimulation induced side effects including speech, balance, cognitive changes including executive function changes), segment 8 and beyond (yearly intervals: length of time in this segment, number of health care provider visits, number of visits to physical therapy or exercise modalities, average travel during this segment, medication use during this period, target selection, days in hospital, insurance provider, hospital visited, compilation, implant location (ac/pc xyz) on follow-up scan if available, device battery status and voltage, active stimulation parameters including location, estimated volume of tissue activated at time of activation, estimation of energy delivered (to assess battery life), impedance pairwise and monopolar of all contacts, preoperative neuropsychometric testing including mini-mental status exam results, diary results including questionnaire data such as Parkinson's disease questionnaire 8 and 39, Hamilton depression score preoperatively, unified Parkinson disease rating scale total and motor (1987 Fahn) on and off medication preoperatively, objective measures preoperatively on and off medication including, timed up and go, bradykinesia assessment including finger tapping, pronation supination (gyroscope), berg balance test, and other metrics, estimated device battery life remaining, complications, stimulation induced side effects including speech, balance, cognitive changes including executive function changes). These metrics may be stored in one or more Servers, which may communicate with Client Interface Devices or other computers or computer systems or devices to implement upload, download, viewing, and access control features of the method such as authentication, granting and revocation of access privileges, non-repudiation, logging, and audit trail records.

A computerized system integrating data transmitted over wireless or wired or tethered communication systems to aggregate data from the clinic to treatment facilities, to the home and or community environments. The proposed connected and mobile embodiments facilitate cross referencing with internal and external databases including the Medicare database to establish cost for the each individual with disease, segment of care, category, and potential therapy. By example, while evaluating the six-month improvement of individuals diagnosed with a disease with deep brain stimulation or other intervention, medication use is a valid outcome measure. To the extent a rigorous and reliable medication history is not available, or in addition to aggregate data on mediation use, the payer could provide reimbursement data for medications. One could receive data from such an inquiry on a spectrum of coarse to granular data level such as the reimbursement of a medication for a individual with disease (boolean0 [coarse] to number of refills of a medication, doses, dates and times of refills to actual cost information. Length of stay inquiry as well as the neurostimulator implantations equipment and implantation dates are used to calculate average reimbursement based upon available payer data. Other quality of life metrics document impact on quality of life such as quality metrics supporting the expense of the surgery including return to work, quality improved life years, improvement in functional scales, improvement in objective measures, and improvement in social medial and other reports of happiness and quality of life. Metrics of comparative effectiveness are established based upon the above stated and other metrics and statistical methods of power analysis and other analysis are provided to establish scientific and other validity for treatment modalities. In the event of non-powered results, and establishment of recommended number of numerator or denominator additions are included to assist with recruitment In support of clinical trials and quality improvement metrics, estimates of time and cost are used to power a realistic number of individuals diagnosed with a disease and expense required to achieve certain follow-up goals. A drop-out rate is calculated at different points in therapy and in follow-up, and methods including telephone calls, reminder e-mails, and direct mailings are used both the attempt to assess the reasons for follow-up loss, make changes to ensure compliance and retention, and add feedback to the improvement of the system. The data advocate will review these results on a periodic basis for integration in quality and other initiatives.

Details of the Neurosurgical Database Embodiment:

Deep brain stimulation (DBS) is a form of neuromodulation used within the restorative neurosciences and has been widely used as a strong therapeutic measure for various movement disorders and psychiatric deficits, and the treatment of epilepsy. Notably, the location of DBS implant is crucial to the efficacy of the surgery. The full knowledge of implant leads relative to the brain anatomical structures is critical for surgery quality control and future improvement as well as for clinical outcomes of postoperative stimulator programming. The complexity of surgery-data production and management has been a major barrier for the surgeons to effectively improve the surgery quality and to communicate with the individuals diagnosed with a disease regarding the surgery quality. Systematic methods are needed to help the neurosurgeons and members of the treating neuromodulation team with the implant lead-location data input, analysis, and display. This disclosure presents a connected system to meet and integrate multiple DBS surgery-related data processing and analysis needs. This refined care management database and method is targeted at providing metrics to enable decision support allowing treatment quality improvement and thereby clinical practice outcome improvement.

This embodiment addresses workflow and data transfer hurdles impeding the analysis of implant efficacy at the level of the individual surgeon or institution, yet forms a data structure basis for multi-site access. The flowchart below is a brief summary of the surgery data acquisition, storage, analysis, and display. There have not been any commercial programs, automated methods, or any systematic procedures available for the surgeons to manage the surgery data. This system develops and integrates the following components to a plug-and-use system: web based data acquisition system, wireless access device or Client Interface Device with algorithm for encoding data input from neurostimulator device, secure database, data structure, web based data retrieval system or Server, web based 3D display system using a Client Interface Device, and statistical analysis system with presentation of results using a Client Interface Device. Further, the application features include a web based data acquisition system using a Client Interface Device, and wireless, web-enabled device entry using a, possibly second, Client Interface Device. In all cases, the Client Interface Device may be a special-purpose or customized device designed for the indicated purpose or a computer or computer system, including consumer-grade devices such as tablet computers, laptops, and smart phones running one or more stored programs to implement the stated purpose(s). A matrix of matrix concept will be used to order data for acquisition, display, and analysis. N dimensional registration will be used.

The following primary data input and storage format is implemented in the system:

Object Oriented Data Structure for Functional Neurosurgery for the Electronic Medical Record Deep brain stimulation (DBS) has been widely used as a strong therapeutic measure for various movement disorders and psychiatric deficits. Notably, the accuracy of DBS implant location is crucial to the efficacy of the surgery. The full knowledge of implant leads relative to the brain anatomical structures is critical for surgery quality control and future improvement as well as for clinical outcomes of postoperative stimulator programming. However, there have not been systematic methods to help the surgeons with the implant lead-location data input, analysis, and display.

Figure 37:
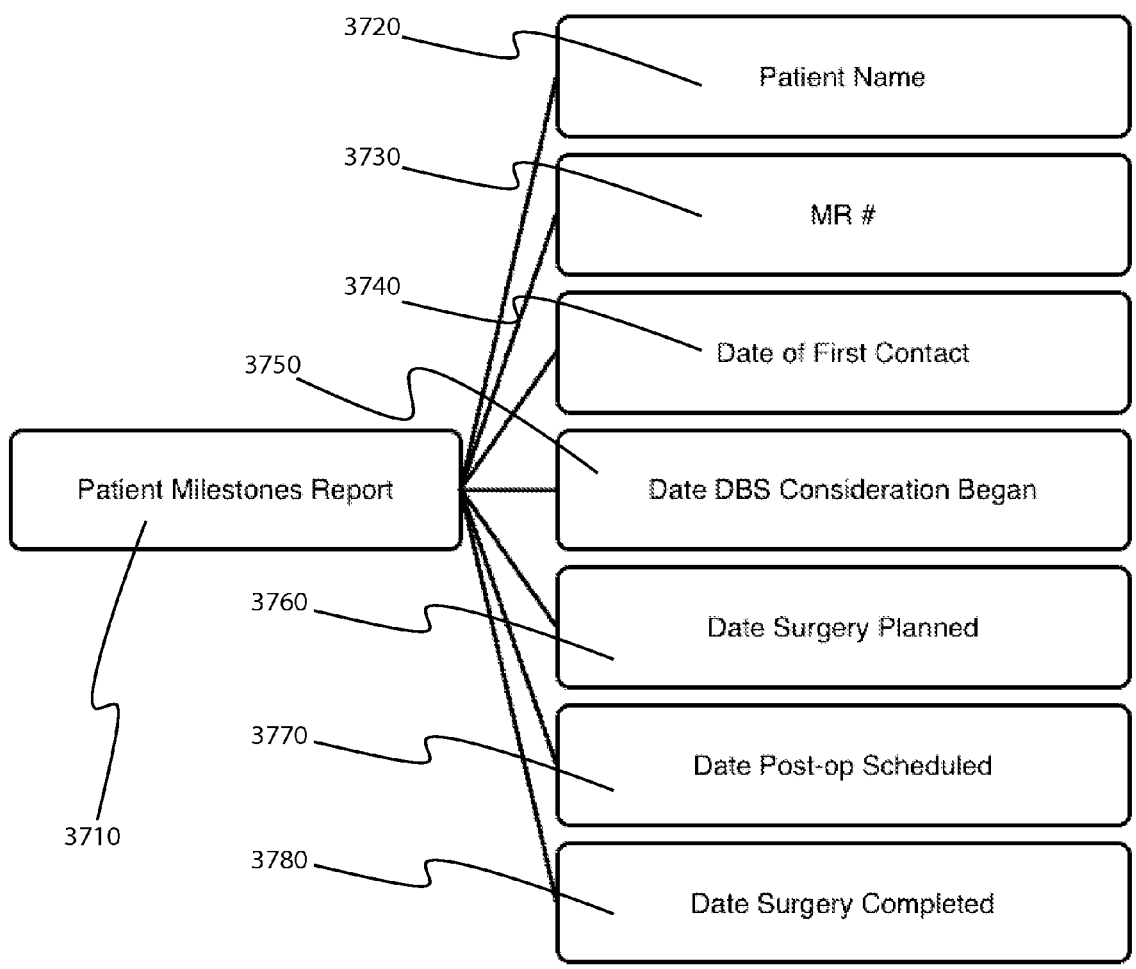
FIG. 37 outlines individual with disease milestones relevant to collaborators in operative neuromodulation and perioperative management generated from a cohort database.

Individual with Disease Tracking Module:

A surgical tracking module to allow the user to understand one component of the timeline. An input screen tracks factors important to surgical perioperative care (FIG. 36). A report of the individual with disease-tracking module (FIG. 37) allows the user to review the cohort with granularity and understand the metrics of flow of the cohort through the surgical procedure. Alternatively, the TREATMENT TIMELINE will visualize the cohort as individual dots or items where one can hover or click on the dot for further information. The travel along the surgical pathway of the cohort can be compared across sites for quality improvement and throughput considerations. An automated aggregate report automatically calculates the mean time from first contact or similar event to the next metric such as date of surgical consideration to the date surgery is planned to the date the surgery is completed. This algorithm takes into account all required steps within the protocol such as in the case of DBS surgery, preoperative cognitive and neuropsychometric evaluations, physical therapy evaluations, objective measures evaluations, and other similar metrics. Cross-institutional benchmarks can be used in insurance or government reporting to demonstrate efficiency of care delivered. When available, cost data associated with each step and with the aggregate treatment are reported and able to be compared across institutions.

Figure 38:
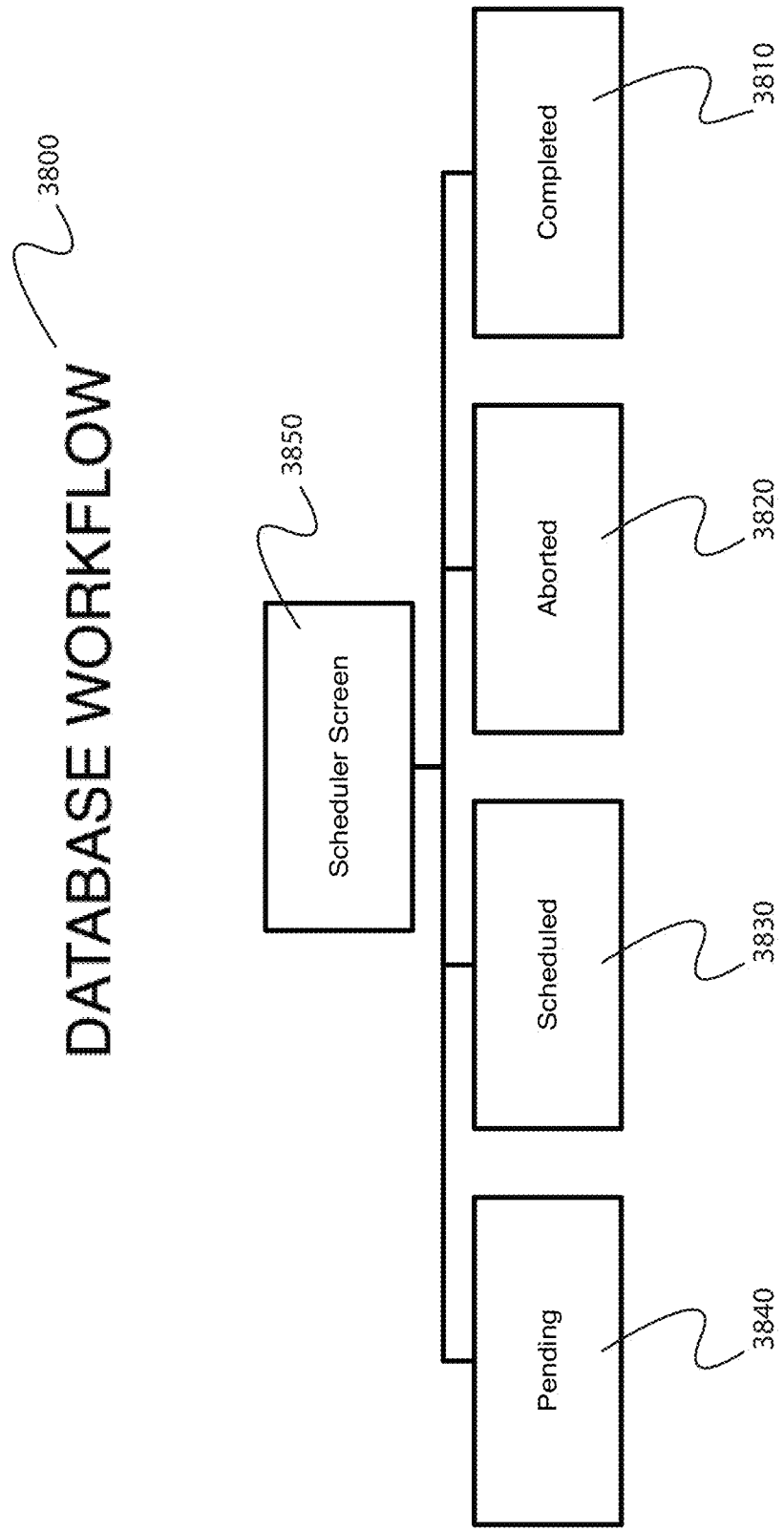
FIG. 38 is a diagram depicting the overall workflow from a scheduler screen allowing rapid visualization of pending, scheduled, incomplete, and completed.

Surgical Module:

The following primary data input and storage format is implemented in the system: (FIG. 38) allowing the tracking of individual individuals diagnosed with a disease from planning to scheduling to surgical completion outcome.

Figure 39A:
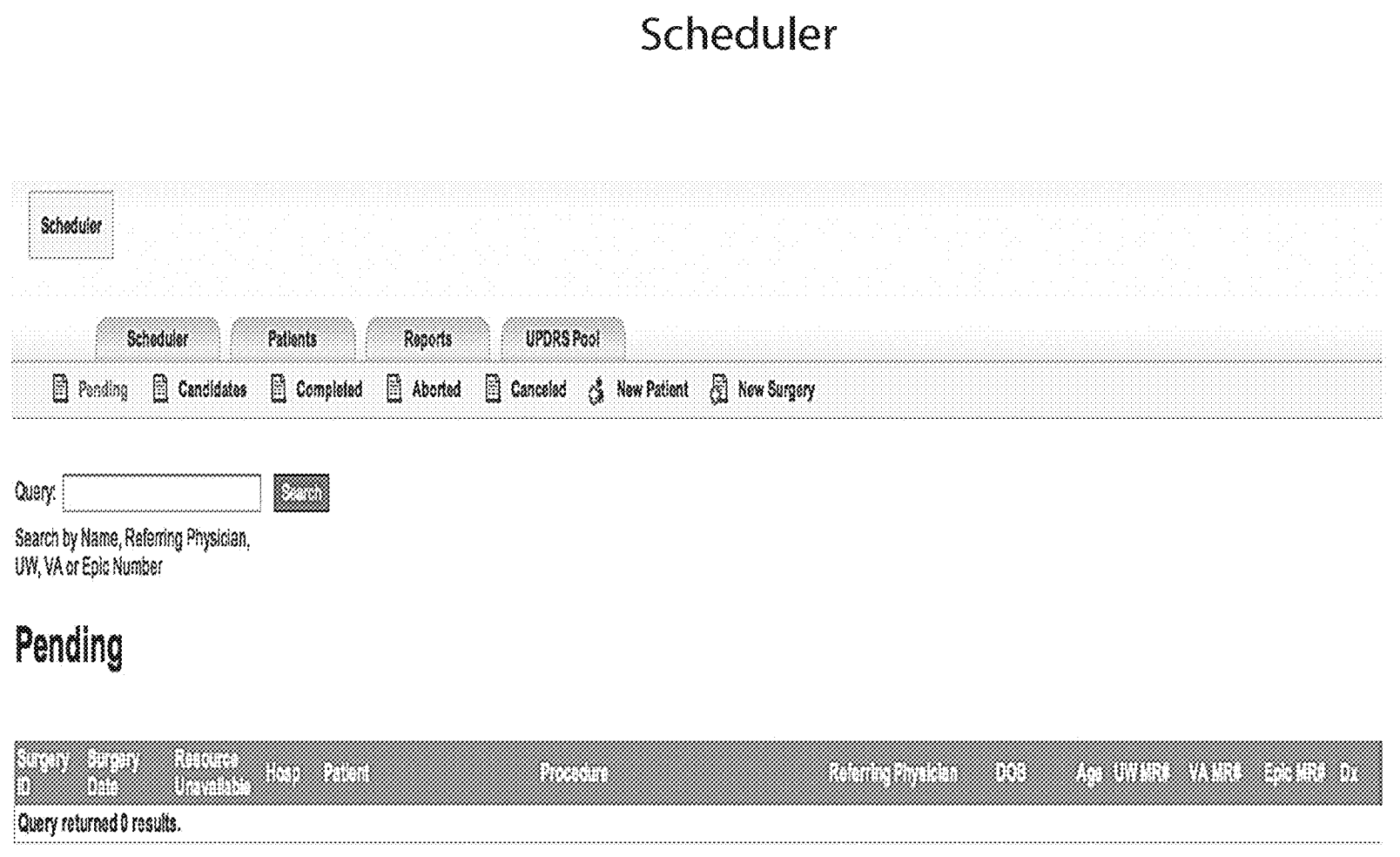
Figure 39B:
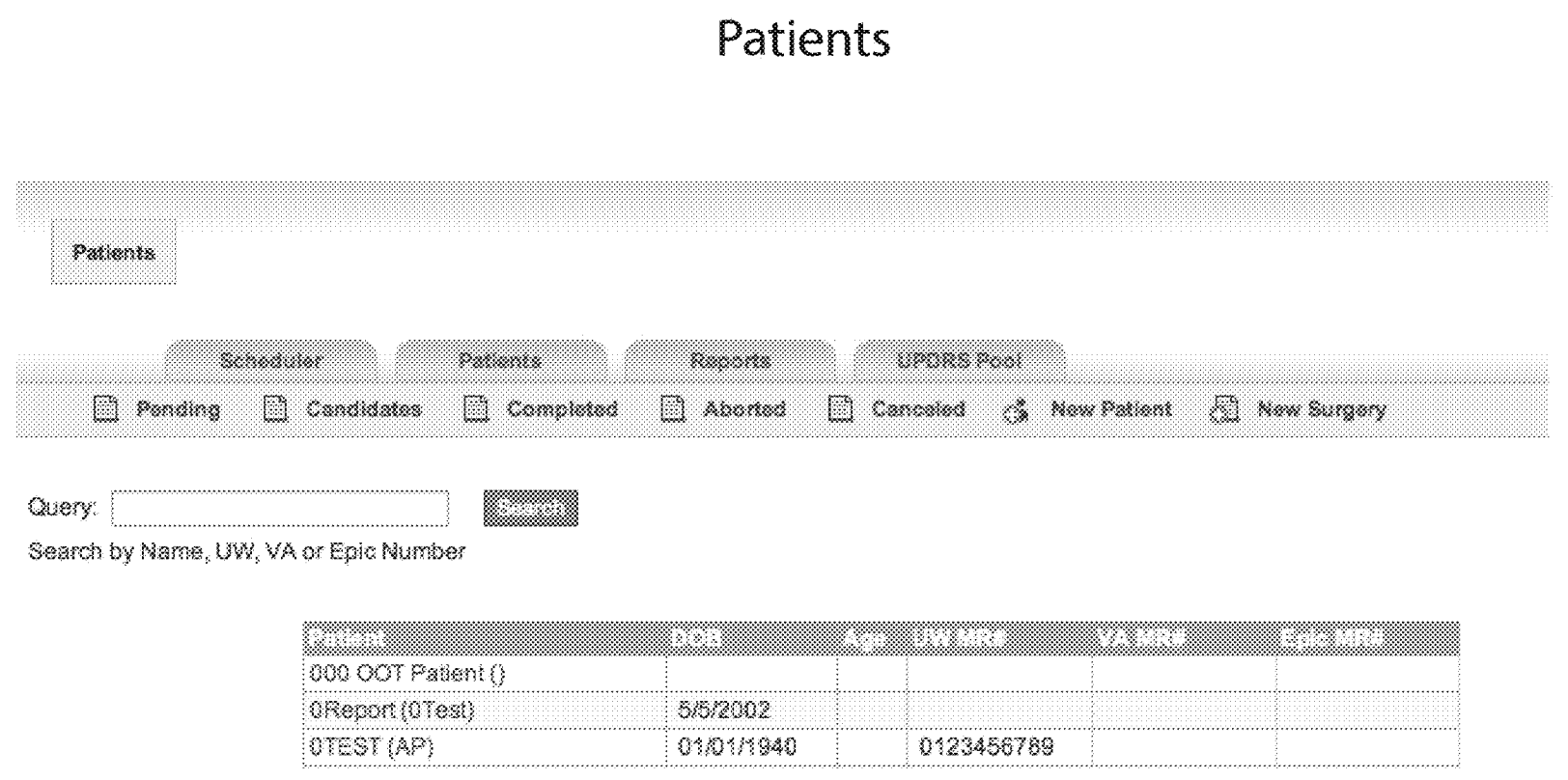
Figure 39C:
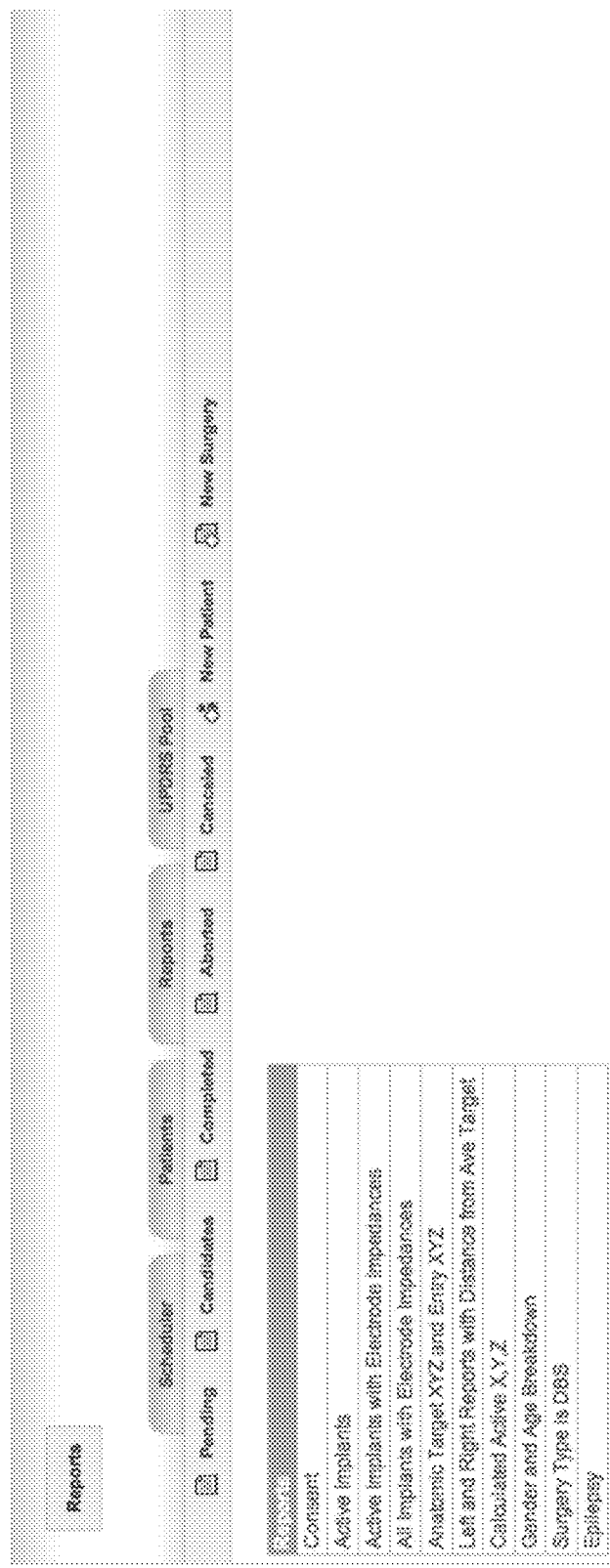
Figure 39D:
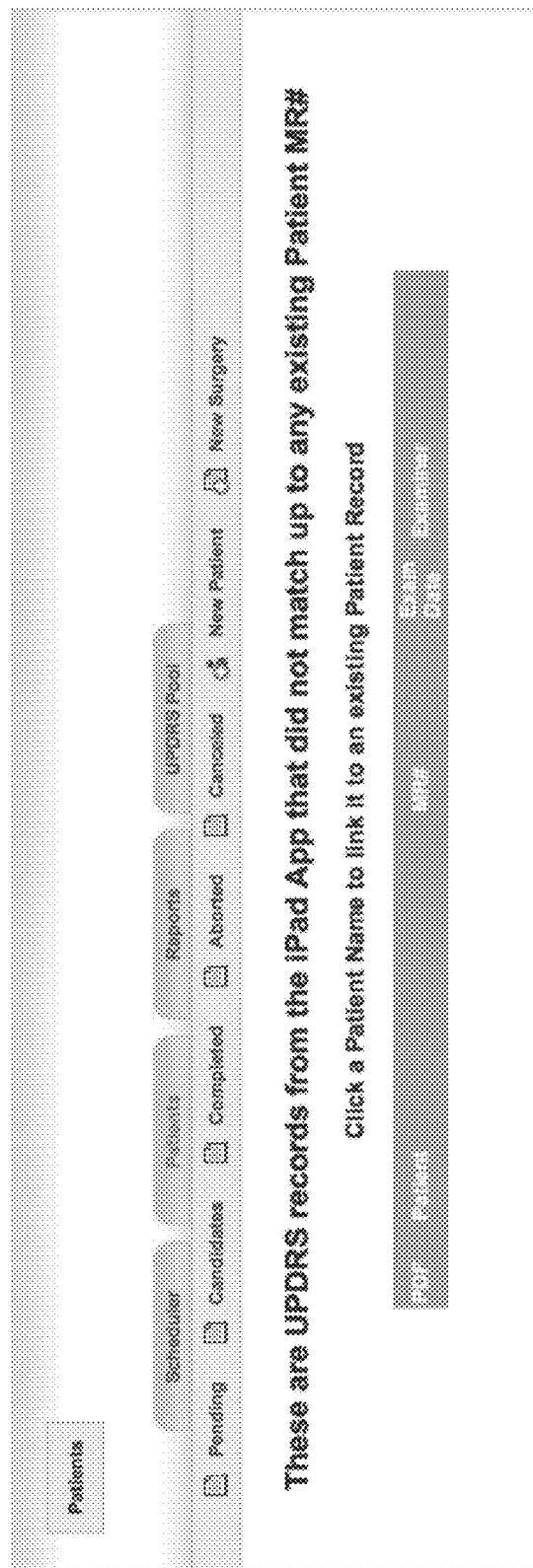

The Surgery Scheduler Screen (FIG. 39) allows all pending surgeries to be seen across the collaborative cohort. Providers from different specialties view and plan metrics for the upcoming surgery including: Surgery ID, Surgery Date, Availability of Selected Resources, Hospital, Individual with disease, Procedure, Referring Physician, DOB, Age, Record locator numbers, and Diagnosis.

Figure 41:
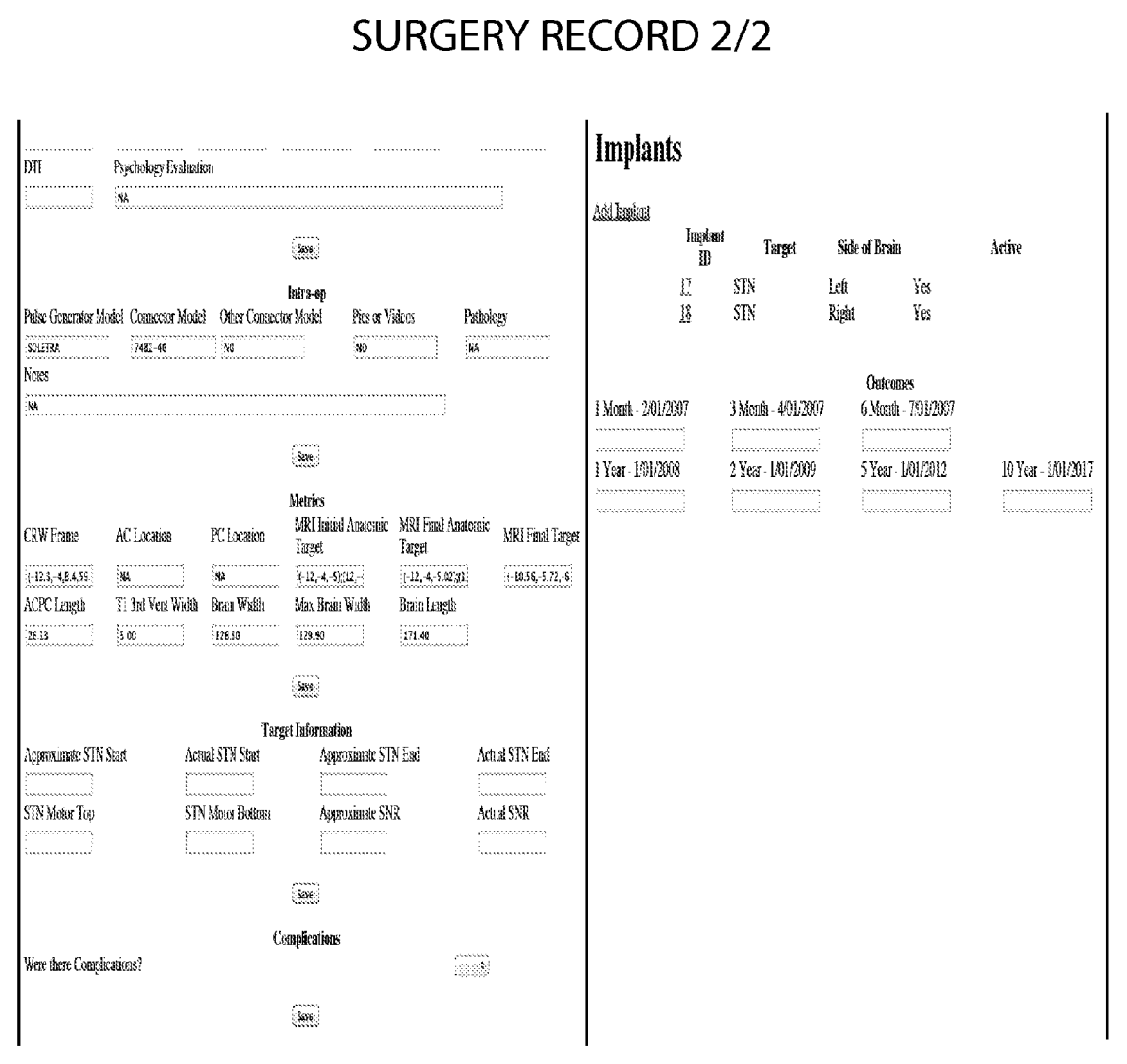
Figure 42:
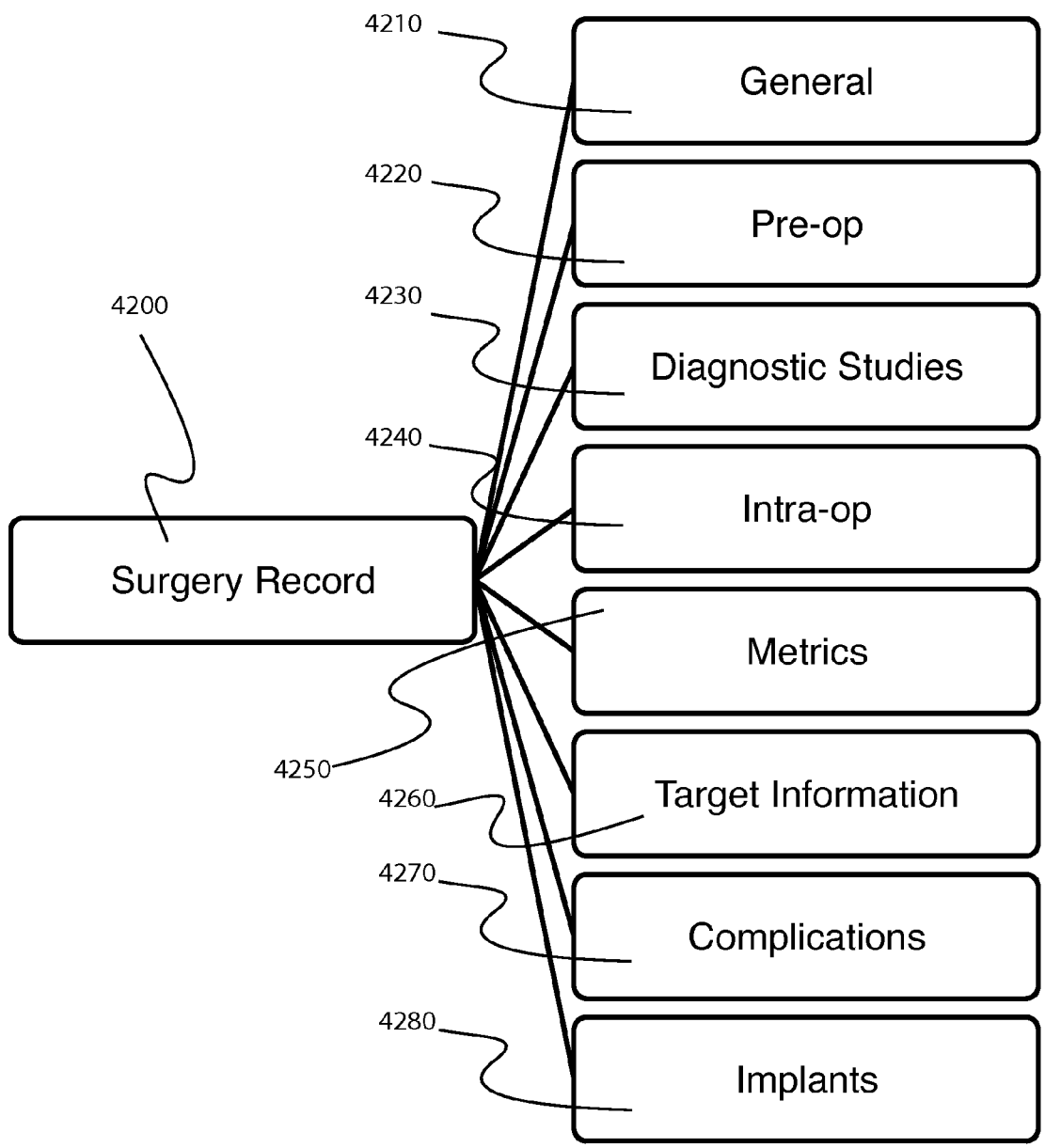
FIG. 42 is a diagram of the sections of a surgery record. This record shows further detail of the involved items in a representative surgery record (general, preop, diagnostic studies, intraop, metrics, charter information, complications and implants).

The Surgery Record interface appears as in (FIG. 40) and (FIG. 41) with a Surgery Record detail having the overall data structure organization described in (FIG. 42).

Figure 43:
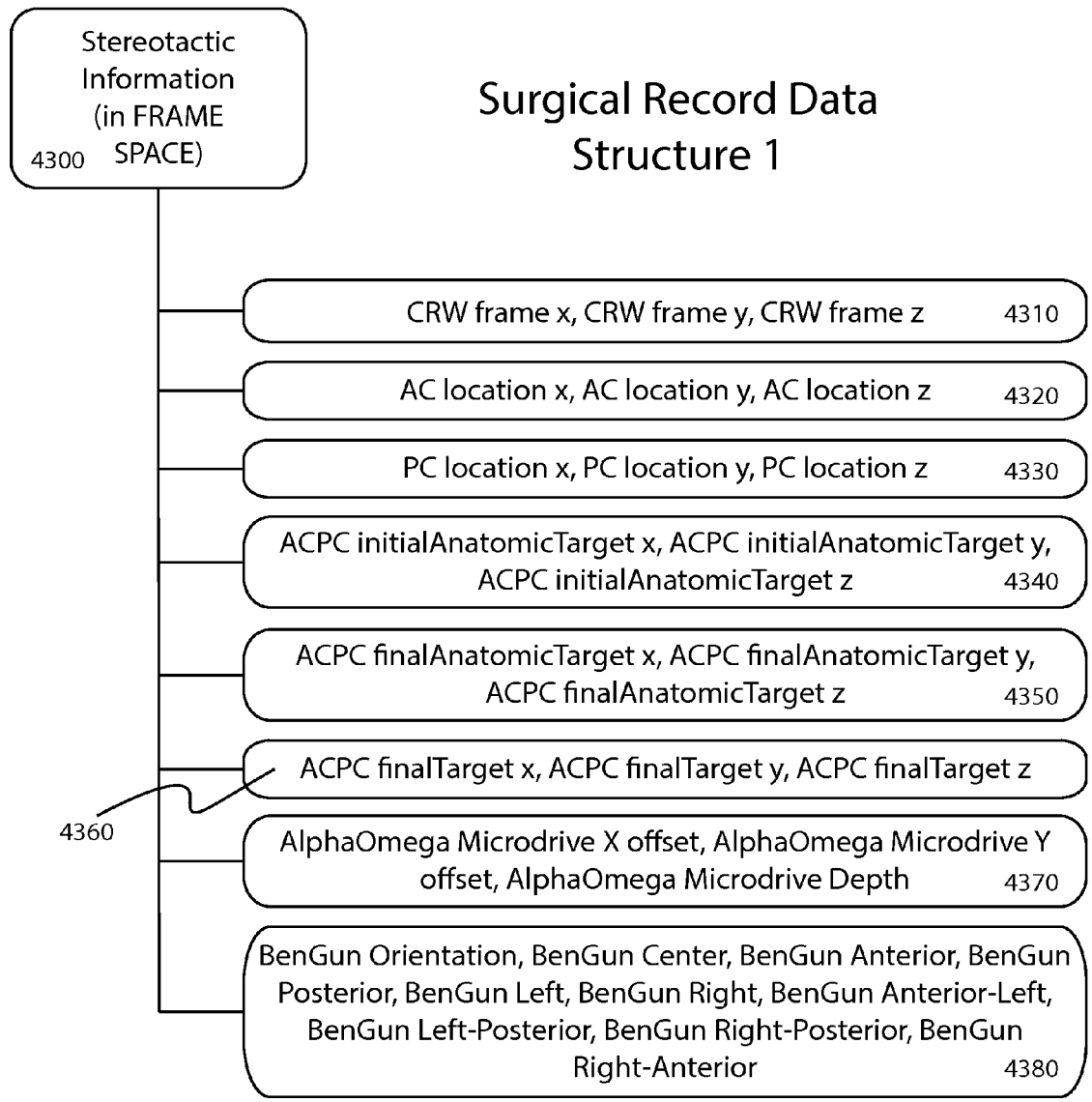
FIG. 43 is a diagram of the Surgical Record in detail (Surgical Record Data Structure 1) describing stereotactic information in a representative reference space (frame space) including in reference to internal brain landmarks (such as ACPC space) and in reference to micro-drive orientation and array information.
Figure 44:
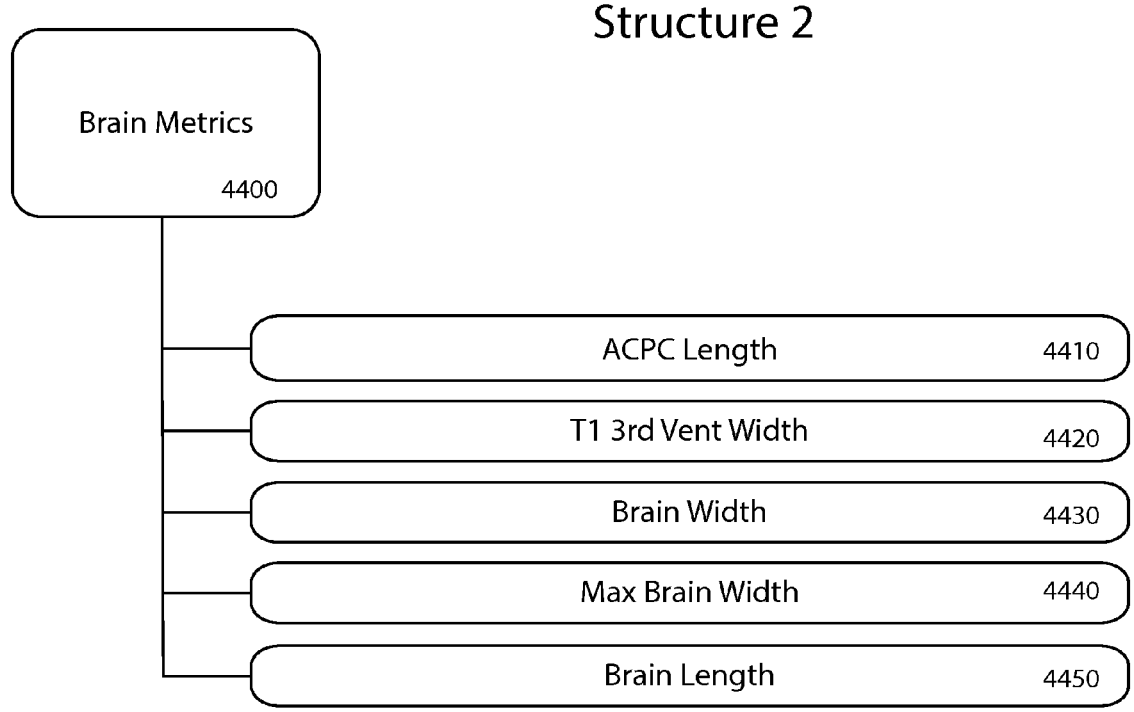
FIG. 44 is a second diagram of the Surgical Record in detail (Surgical Record Data Structure 2) describing target structure metrics for assigning to the cohort (such as brain third ventricular width, trajectory distance to ventricular wall, and distance to other internal landmarks).
Figure 45:
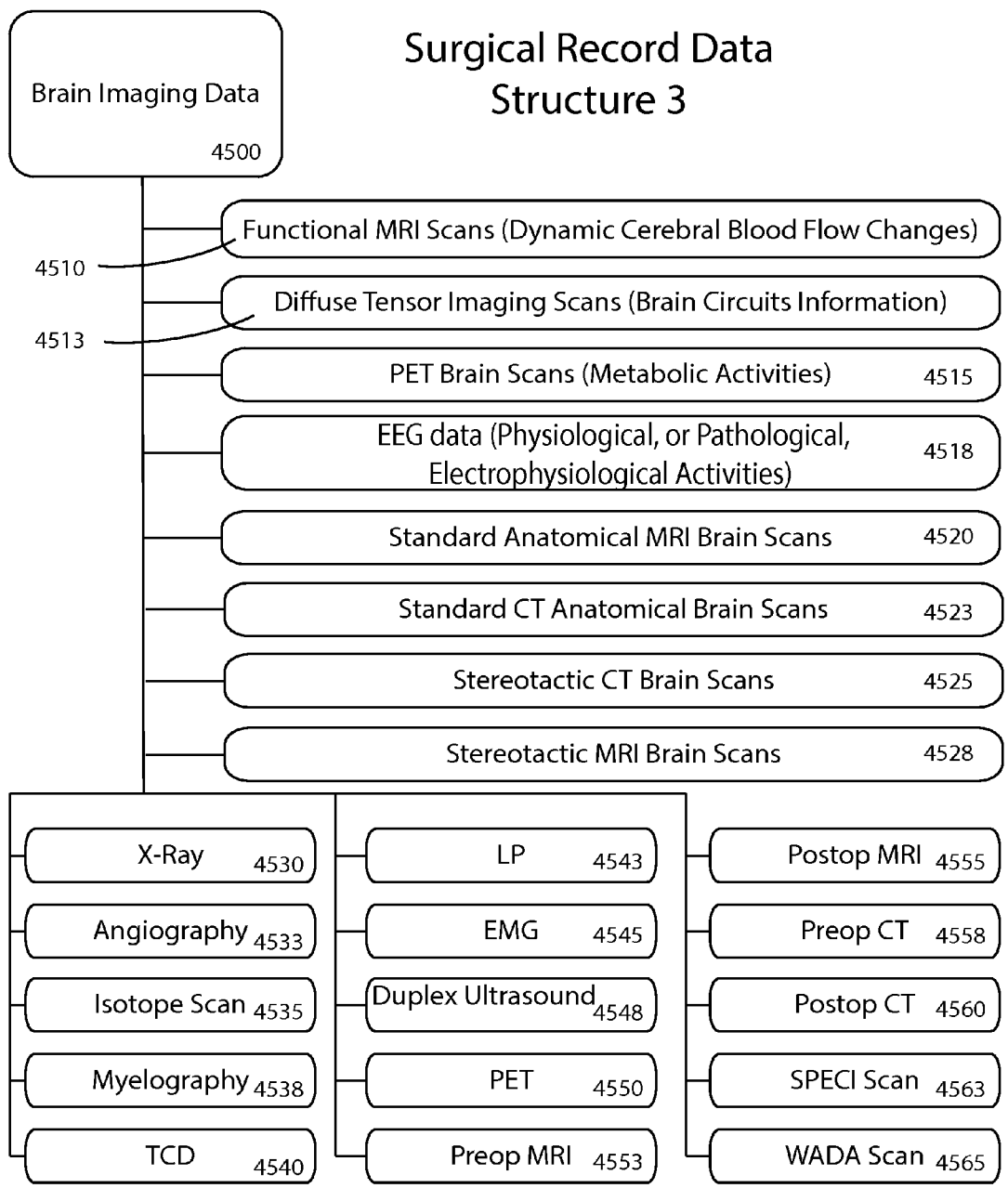
FIG. 45 is a third diagram of the Surgical Record in detail (Surgical Record Data Structure 3) describing data associated with a particular surgical procedure (functional MRI, MRI with diffusion tensor imaging, CT scans, EEG, standard anatomical MRI brain scan, standard CT, x-ray, angiography, myelography TCD duplex ultrasound, SPECT, WADA, MEG, TMS, PET).
Figure 46:
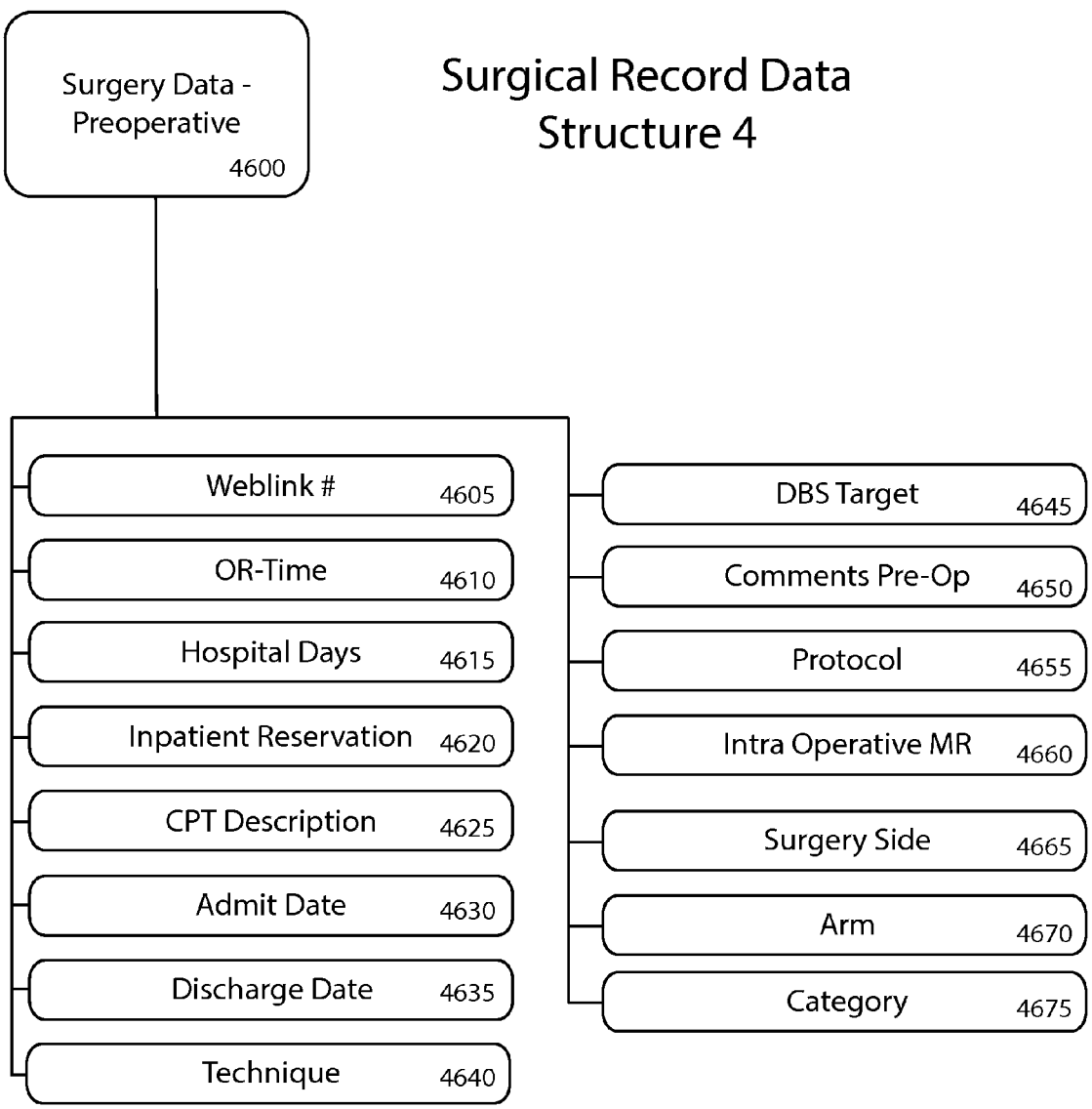
FIG. 46 is depicts Surgical Record Data Structure 4 outlining preoperative surgical data relevant to a surgery for neuromodulation.
Figure 47:
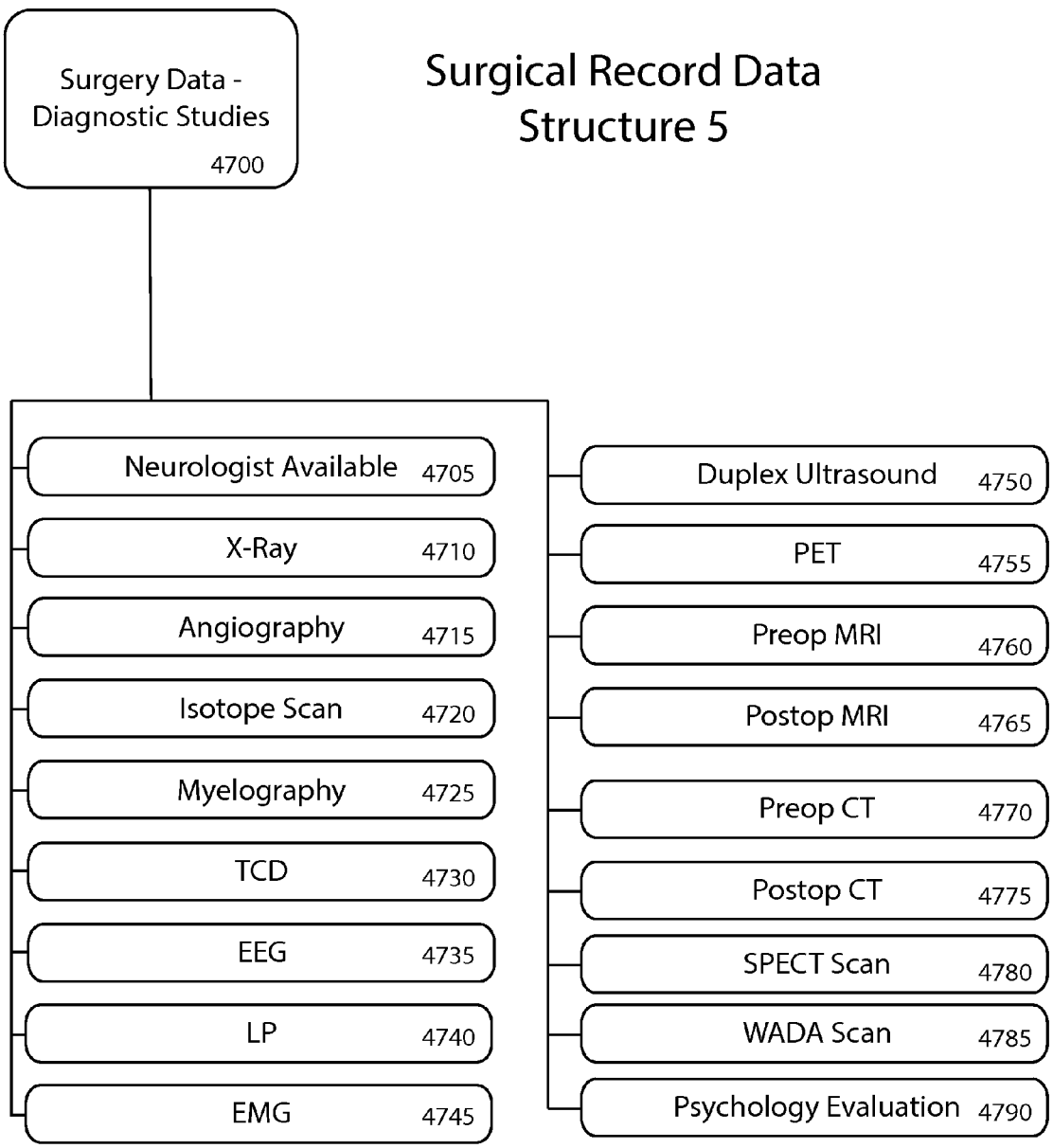
FIG. 47 depicts Surgical Record Data Structure 5 outlining surgery data for diagnostic studies and relevant guiding data for the surgery.
Figure 48:
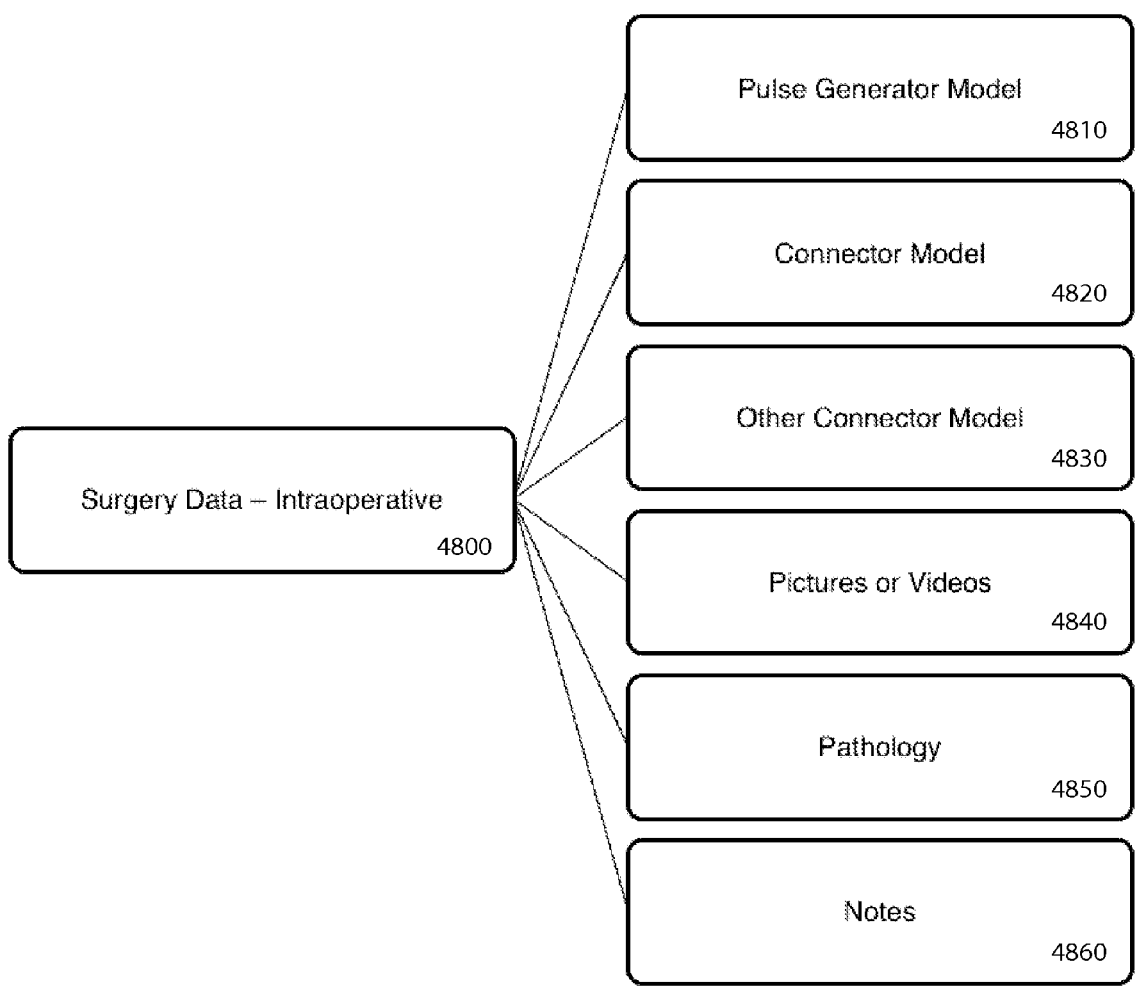
FIG. 48 depicts Surgery Record Data Structure 6—data—Intraoperative—outlining surgery and implant data associated with the extra-cranial portion of the implant.
Figure 51:
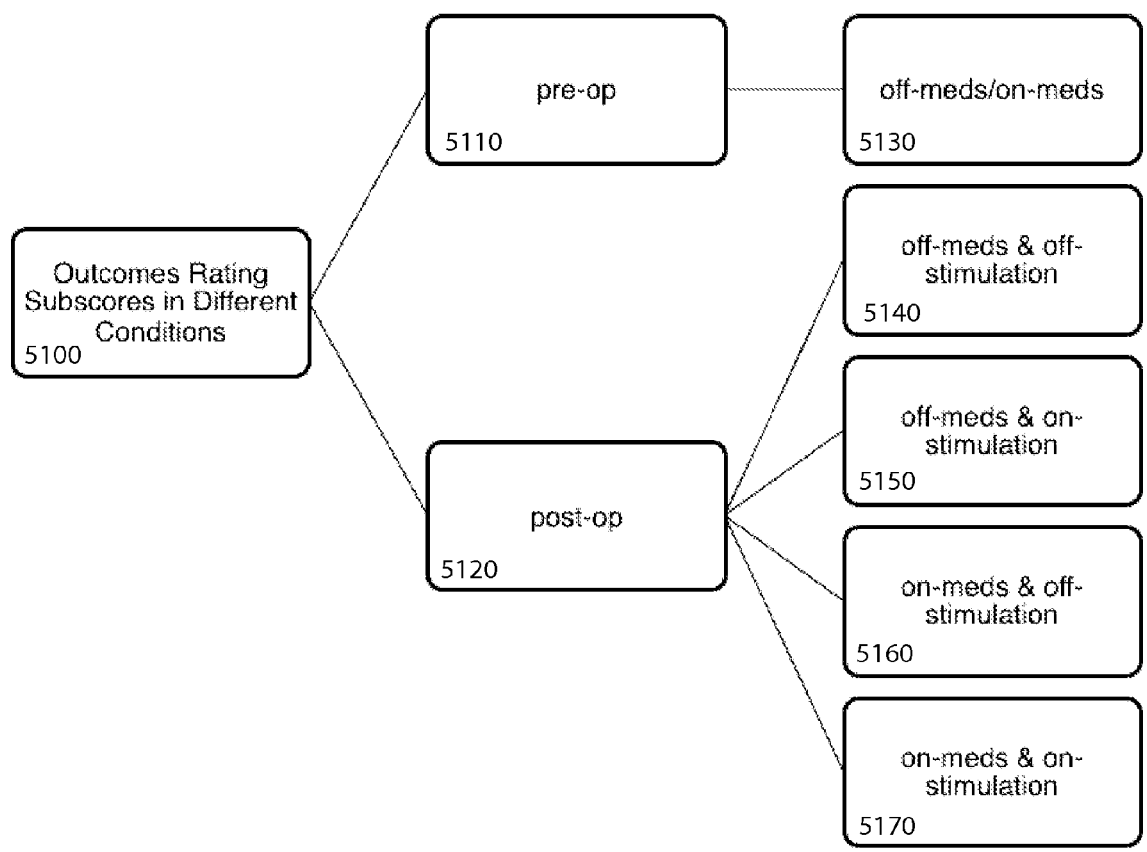
FIG. 51 provides details of Surgical Record Data Structure 9 containing outcomes of ratings description for pre- and post-op, on and off medication evaluations.
Figure 54:
FIG. 54 is a parasagittal image depicting the guidance by magnetic resonance imaging (MRI) of an insert into a specific brain location, quantified by calculations within MRI space according to an aspect of the present invention.
Figure 55:
FIG. 55 is a lateral "scout" image derived from a computed tomography (CT) scan of the head after implantation of cortical surface electrodes implanted for the purpose of epilepsy monitoring and seizure localization similar to a lateral radiograph of the electrode montage according to an aspect of the present invention. The cross-hairs depict a given electrode in the reference volume CT space.
Figure 56:
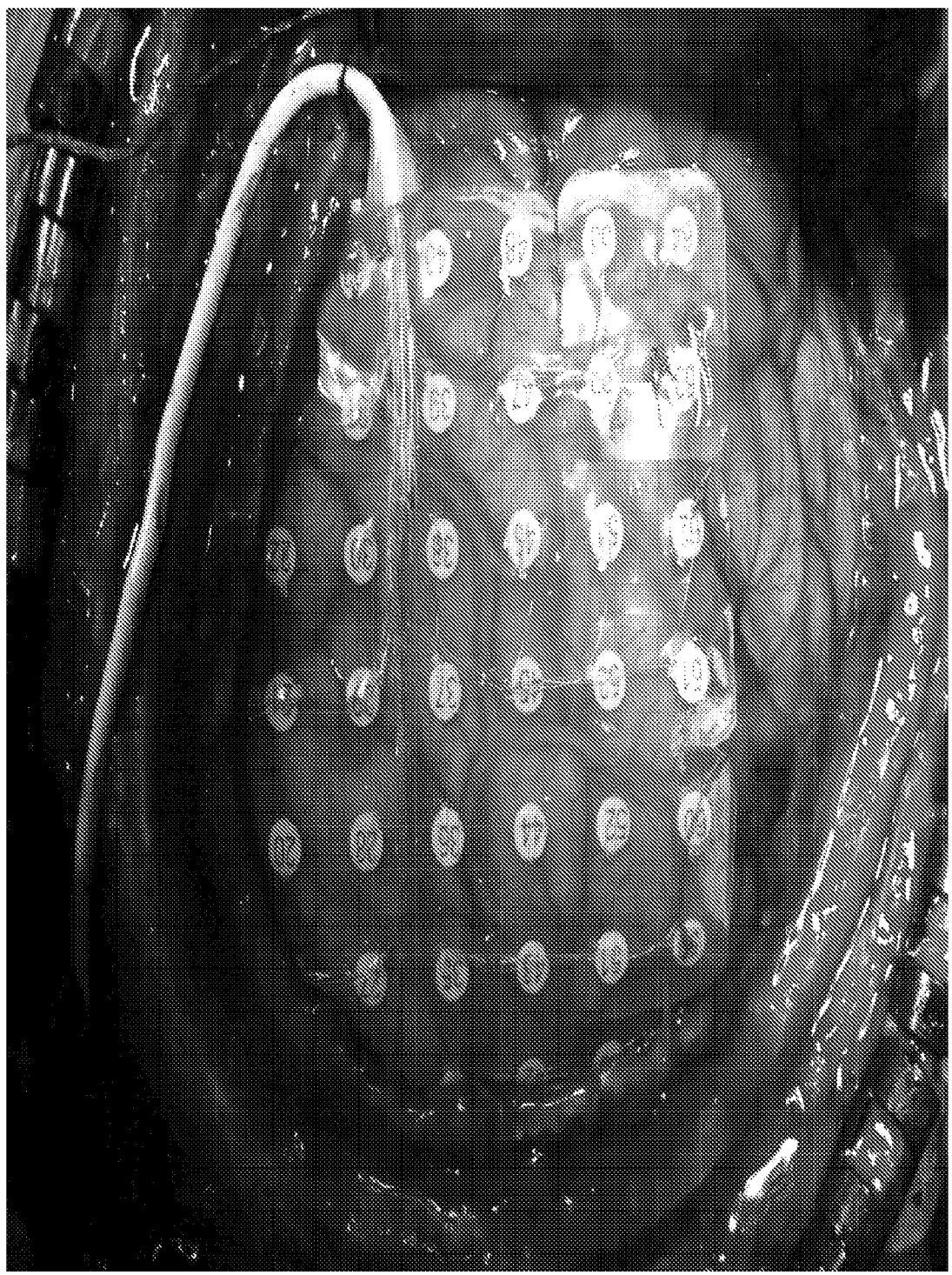
FIG. 56 is a surface image of an array of electrodes overlying the surface of the brain with visualization of underlying surface anatomy of the brain including cortical vasculature and sulcal/gyral patterns according to an aspect of the present invention.
Figure 57:
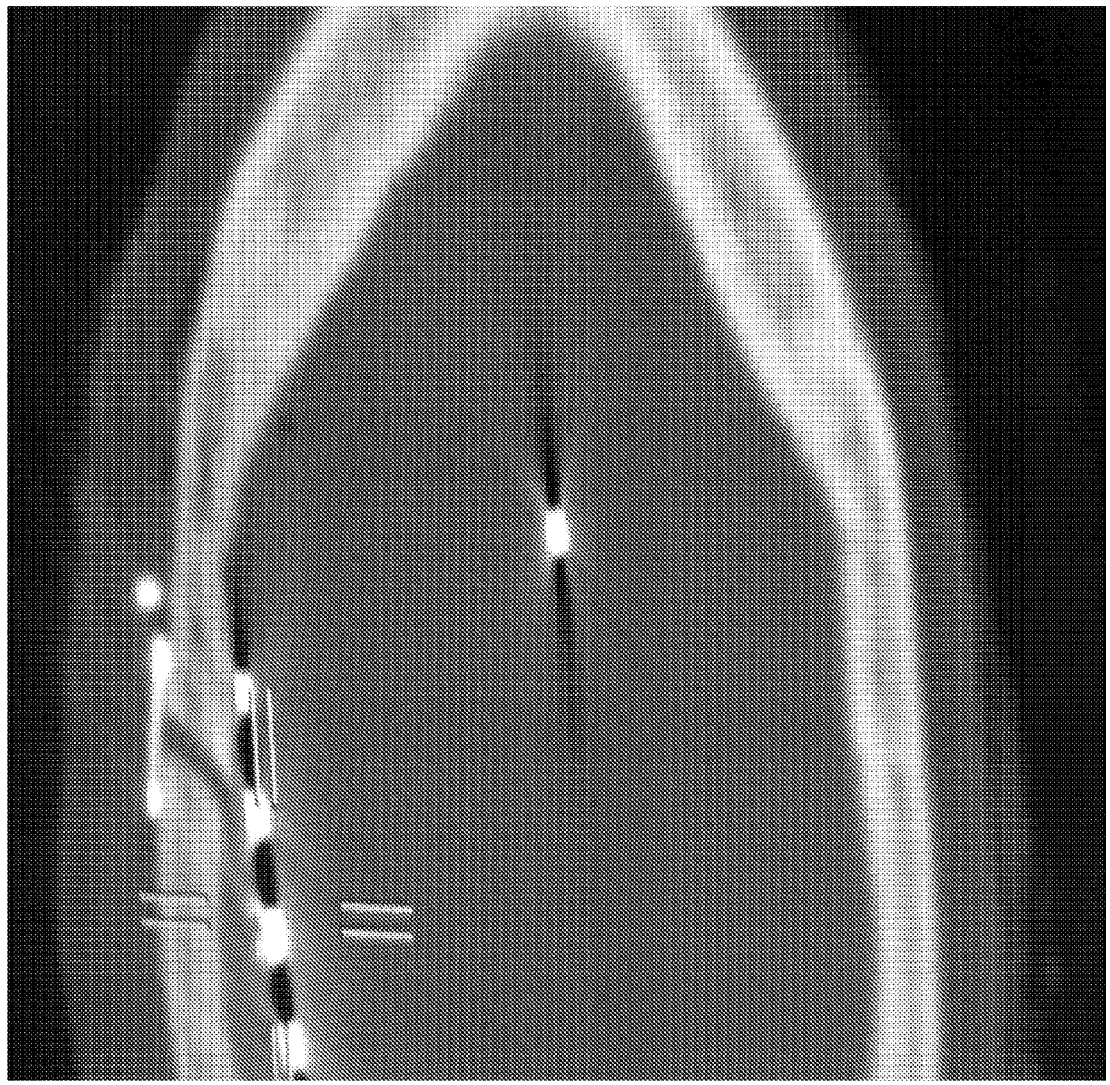
FIG. 57 is an axial image of the resulting computed tomography (CT) of an implanted cortical grid montage of surface electrodes allowing precise localization of the electrode contact in reconstructed 3D CT space according to an aspect of the present invention.
Figure 58:
FIG. 58 is an image depicting volume reconstruction from a computed tomography (CT) scan obtained after cortical grid montage implantation of surface electrodes according to an aspect of the present invention. Electrodes are segmented from the underlying cortical anatomy and a 3D reconstruction performed allowing both rapid visualization and identification of electrode locations within 3D CT space.
Figure 59:
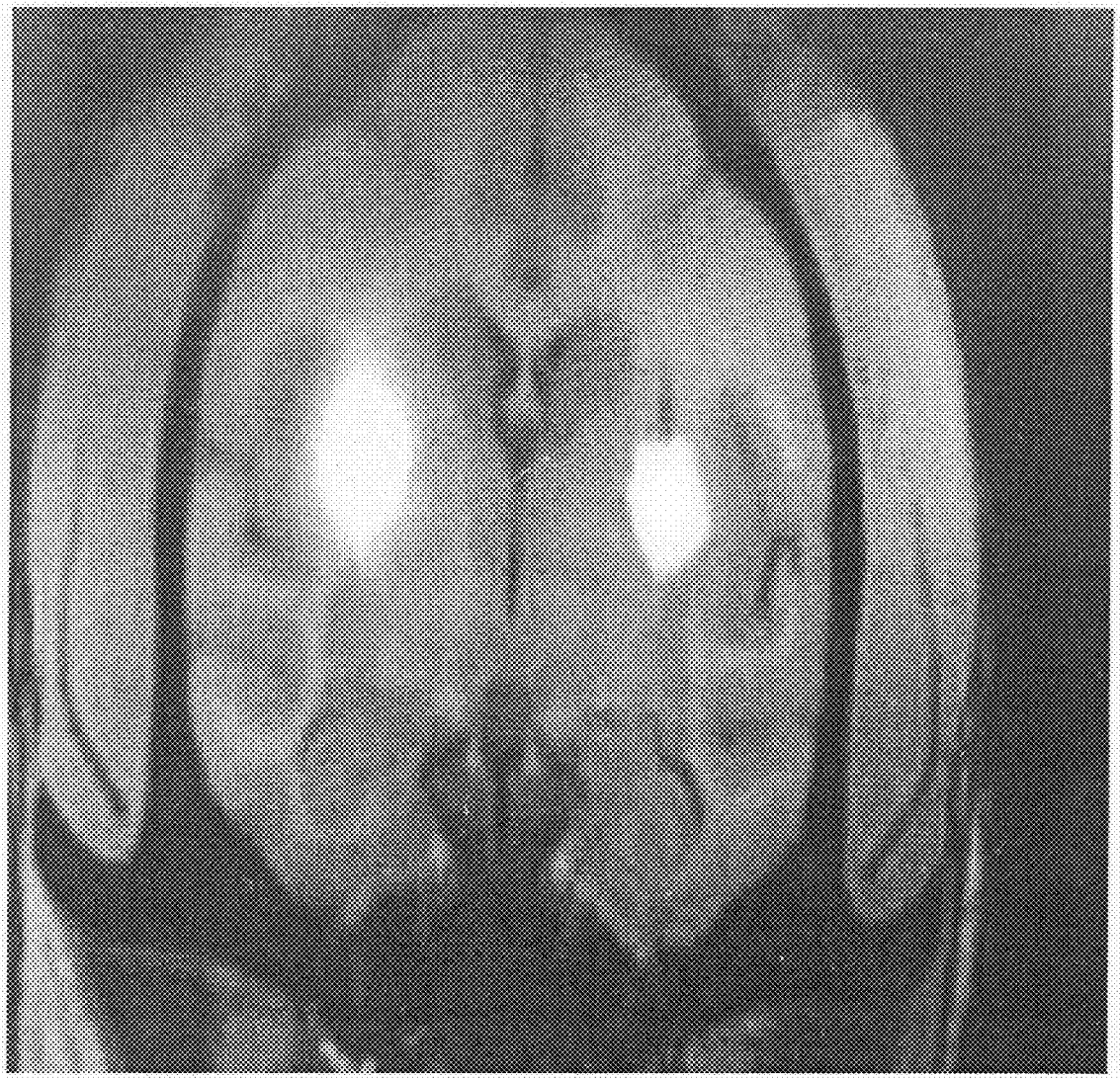
FIG. 59 is an image depicting bilateral infusions within the putamen with location of infusion catheter tip measured before contrast infusion and volume of infusion characterized and measured as previously described according to an aspect of the present invention.
Figure 60:
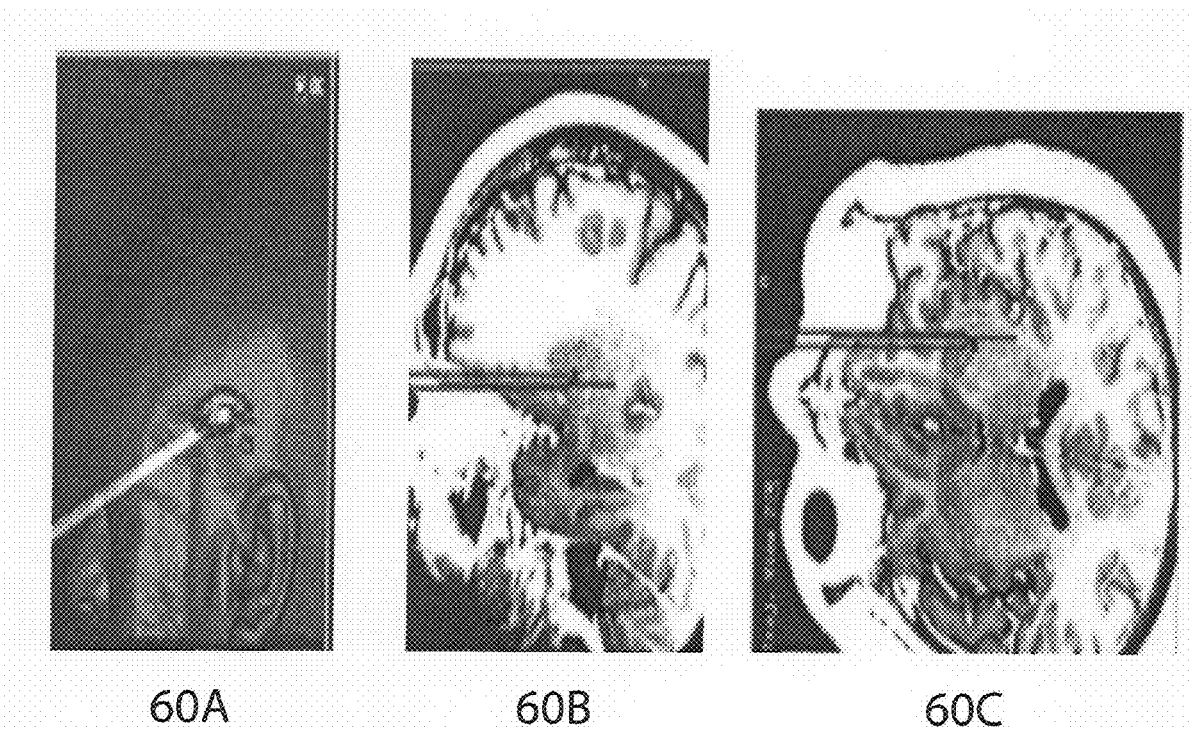
FIG. 60 comprises images depicting a frontal approach in three views.
Figure 61:
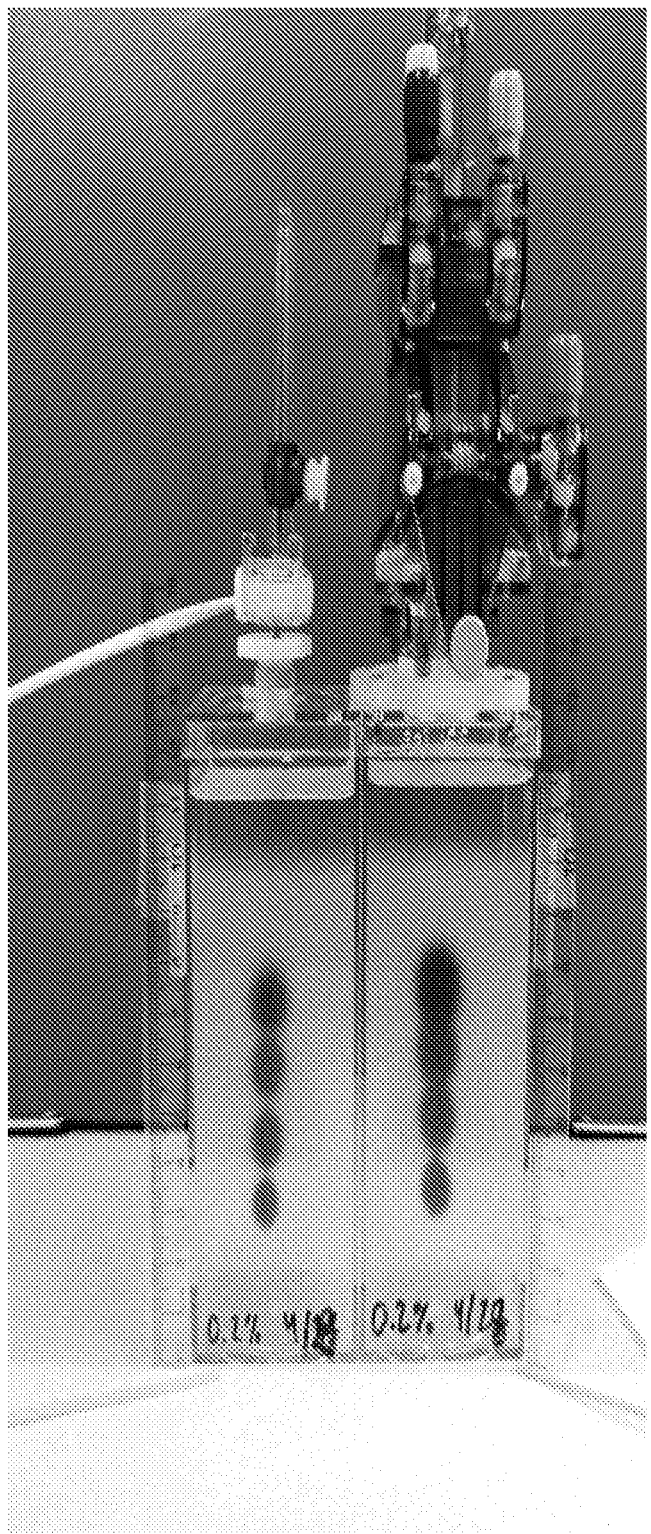
FIG. 61 is an image depicting multiple stacked infusions along a single trajectory in an agarose gel model of the brain according to an aspect of the present invention.
Figure 62A:
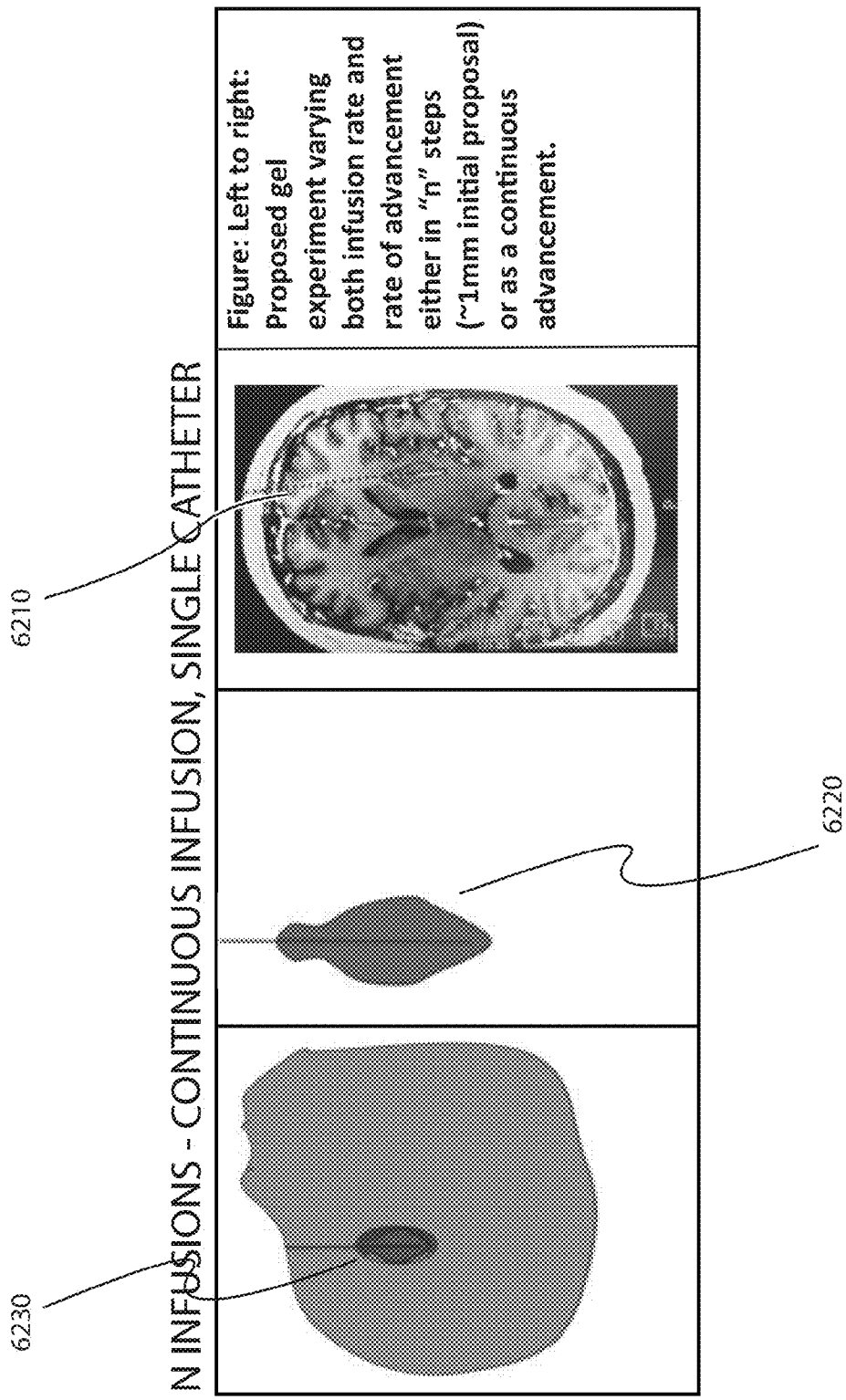
FIG. 62A is an image depicting a frontal approach to the putamen for multiple or shaped infusion payloads through a single approach to fill relatively large portions of the putamen according to an aspect of the present invention.
Figure 62B:
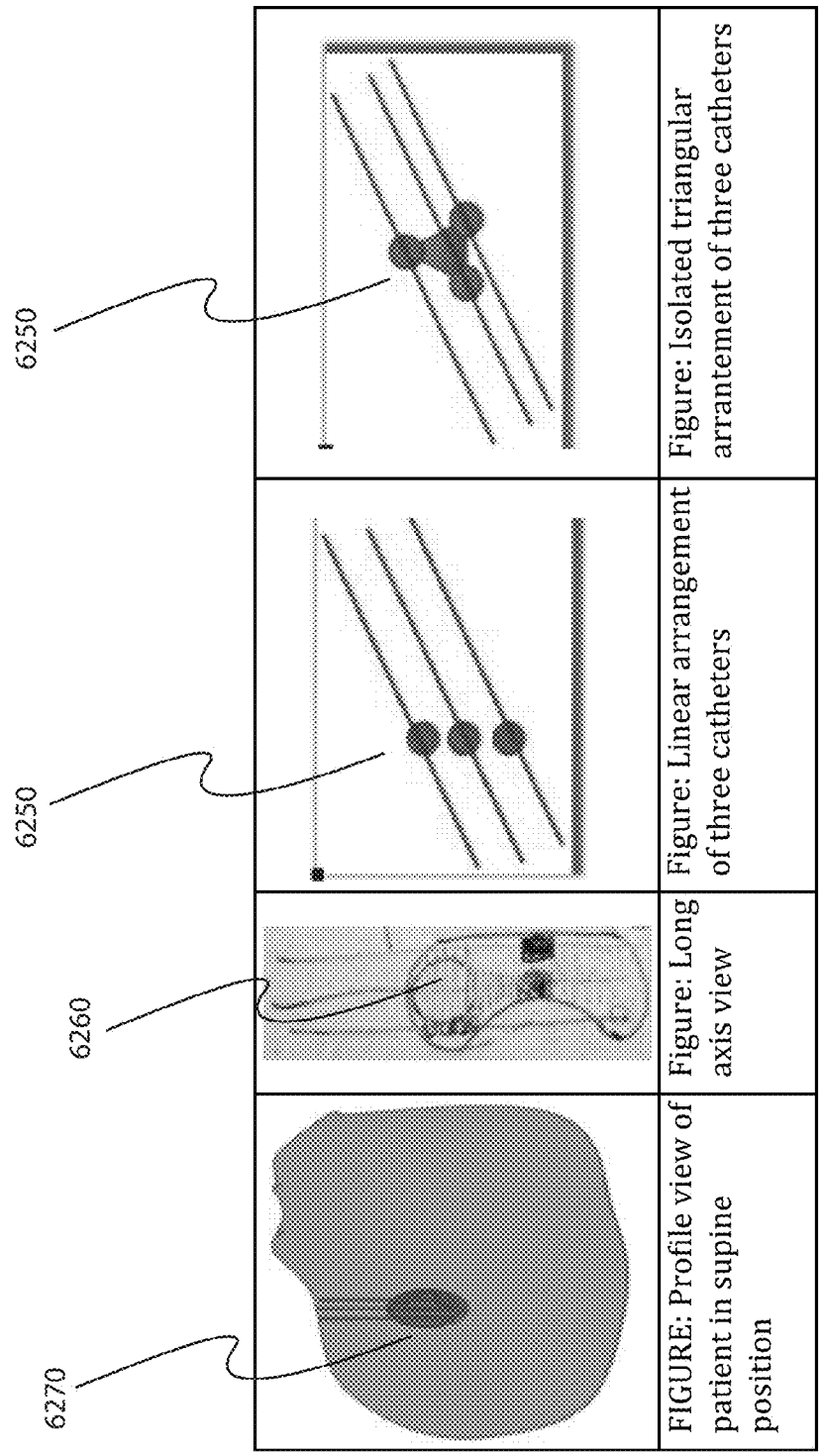
FIG. 62B and FIG. 62C are further images depicting a strategy of multiple infusion catheters creating a varied and tailored 3D parenchymal infusion according to an aspect of the present invention.
Figure 62C:
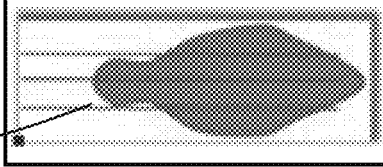

The Surgery Record example data structure is currently implemented as follows: Surgery Record Data Structure: {Stereotactic Information (FIG. 43), Brain Metrics (FIG. 44), Brain Imaging Data (FIG. 45), Surgery Data—Preoperative (FIG. 46), Surgery Data—Diagnostic Studies (FIG. 47), Surgery Data—Intraoperative (FIG. 48), Surgery Data—Complications (FIG. 49), Programming Information—Including active implants/contacts and outcome measures (FIG. 50), Outcomes Rating Subscores in Different Conditions (Examples of rating subscores, including but not limited to: PDQ 39, UPDRS III; (FIG. 51))}:

INTRAOPERATIVE TRAJECTORY LOGGING: Tracking of implant trajectories planned (FIG. 53), and actual (FIG. 52) including microelectrode recording is provided as follows: Given these objects: CRW Frame (Frame Space): Always: Frame space (x, y, z, ring, arc) [4 degrees of freedom]; a neuro-surgical drive, for example, an Alpha Omega LTD of Nazareth, Israel NeuroNav Drive™ microdrive (Perpendicular to Trajectory): XY offset+depth [3 degrees of freedom]; BenGun insert (Perpendicular to Trajectory, x=0, z=0 lines of microdrive and Ben-gun are parallel): Orientation+5 options. Intracranial trajectories may be used to deliver single or multiple payloads or implants or therapies along linear or curved or via ultrasonic or radiosurgery methods. Examples of delivered therapies with an equation describing the therapy or implant include, but are not limited to implantable electrodes via the frame based, MRI guided (FIG. 54), or other approach (DBS, cortical and surface electrodes (FIG. 55), (FIG. 56), (FIG. 57), (FIG. 58)), delivered therapy via infusion via the vertex approach (FIG. 59), transfrontal approach (FIG. 60) or other approaches involving the delivery of single or multiple (FIG. 61) or shaped (FIG. 62A-C) infusion payloads, used for gene therapy, protein delivery and other therapeutics, light beam therapy such as laser ablation, stereotactic radiosurgery delivering single or multiple doses of beam radiation or fractionated and tailored radiation as well as other delivered therapies which may be tracked and analyzed.

The Following Mathematical Calculations May be Built into the System for the Purpose of Data Transformation, Analysis, and Output:

ACPC xyz off pre-op MRI, Choose Initial Anatomic Target, CT Scan with Frame Fiducials, Fusion of MRI to CT Scan; Derivation of Initial Anatomic Target in Frame Space (x, y, z), Trajectory Planning in Frame Space (ring, arc), Intra-Operative Microelectrode Recording Passes (CRW frame x, y, z, ring, arc; micro-drive xy stage; Ben-gun orientation and 1 of 5 pre-determined Ben-gun slots), Derivation of Final Anatomic Target in Frame Space, Post-Operative MRI or CT Scanning (this scan has brain shift due to post-operative changes), Re-determine ACPC on Post-Operative Scan, Measure Post-Operative Electrode Location with TI (MRI parameters: GE 1.5 Tesla, TE, TR, Voxel size, spin, flip angle), Determine Errors, 3D Visualization of Microelectrode Recording Passes (Initial Anatomic Trajectory, Intra-Operative MER Trajectories, Final Anatomic Trajectory, Final Trajectory); Updated Current Active Contact(s) and Volume of Tissue Responding Calculations; Integration of MER Trajectories and DBS Implant Location into Individual with disease Specific Atlas with Segmented Nuclei; Population Atlas with Segmented Nuclei; Overlay of Volume of Tissue Response on Segmented Tissue Atlas and Population Atlas, Correlation of Electrode Location and VTR to Individual with disease Clinical Outcome, Statistical Modeling to Suggest Best Future Implant.

Use of this Target for Implantation without MER Under Real Time Imaging Such as the Interventional MRI Suite Correlation of electrode parameters and outcomes or physical measures. In the case of implanted devices such as deep brain stimulator implants, the parameters of stimulation are used to calculate a tissue activation volume map overlaid with relevant anatomical correlation in order to derive the stimulation related effect within the cohort of and the efficacy of the location and programming based effects. In the case of measures of physical changes such as drug delivery, a record of parameters associated with delivery are correlated with known local changes over time to generate a delivery map related to the therapy showing that delivery to a certain location appears more efficacious than to another. In the case of fluidic delivery along a linear trajectory, a specific technique associated with multiple collinear infusions has been reported as novel and related to outcome, namely the technique of delivering multiple trajectories with sequential advancements of the catheter versus retractions. As we have shown this technique in gel (SILLAY 2013) and animal models is more spherically round and delivered in accordance with desired infusion clouds, this is a specific example of a recorded volume of distribution over time. We describe this strategy as novel for the first time and believe the technique of infusion, also known as the infusion protocol or strategy warrants inclusion within the data structure. Additionally, any preoperative infusion planning and modeling in 3D warrants recording as well as the differences between the delivery plan and that which was delivered. Metrics for delivered substrate density can be recorded in a normalized or individual with disease specific atlas and referenced to internal landmarks and internal functional anatomical structures to correlate differences in delivery over a 3D space to individual with disease specific and cohort outcome over time.

The Report Data Structure is Summarized as Follows:

3D Plot of location of implant; 3D plot of active stimulation parameters; 3D Plot of location of active contacts; 3D Plot of location of DBS electrodes; 31) Plot of location of any forms of surface electrodes; Data summary (variance of implants).

Figure 63:
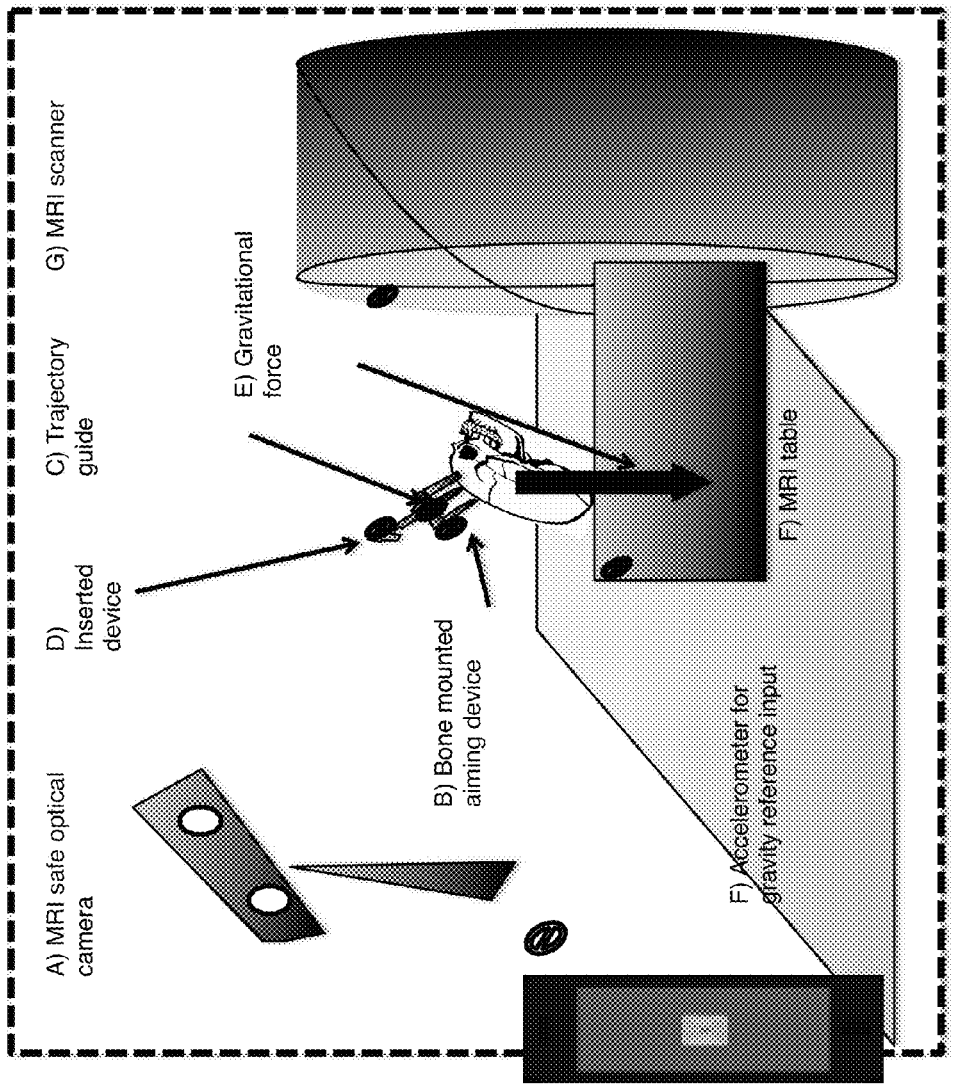
FIG. 63 is an image depicting the addition of a mobile-tracked: Gravitational Input for Image Guidance in the MRI Surgical Environment according to an aspect of the present invention.
Figure 64:
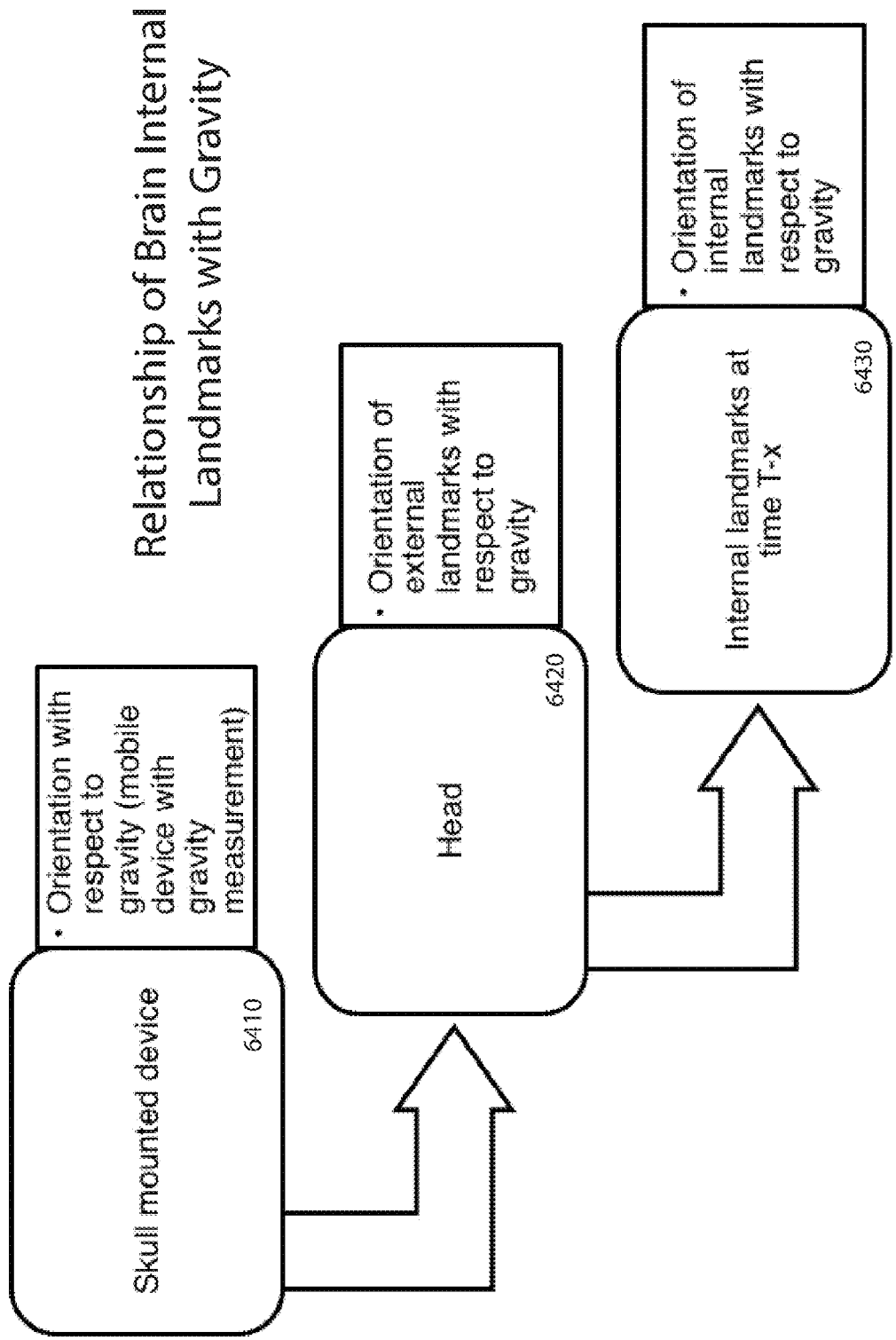
FIG. 64 is an image depicting a method for computing the gravitational direction vector with respect to internal and external landmarks in preparation for analysis such as with intracranial brain shift according to an aspect of the present invention.

Surgical Implant Analysis with Respect to Gravitational Effects:

DETERMINING AC/PC POSITION WITH RESPECT TO GRAVITY. Method of measuring the relative position of the subject's brain to gravity using a handheld device: Head position accounting for gravity: Head position is an important factor in the degree and direction of intracranial brain shift during stereotactic surgery. A Client Interface Device containing appropriate sensors, such as an Apple iPhone or iPad running the iOS operating system and a stored software program (app) with a stored Transform matrix from a surgical planning station can be utilized. The relative force of gravity on the brain can be derived from a reference scan with a known orientation to gravity (iMRI surgery, (FIG. 63)). Documenting brain position over time is possible with additional assistance of the gravity component of surgery during the implantation. Figure (FIG. 64) demonstrates the relationship of internal landmarks of the brain and head position relative to gravity.

Figure 65:
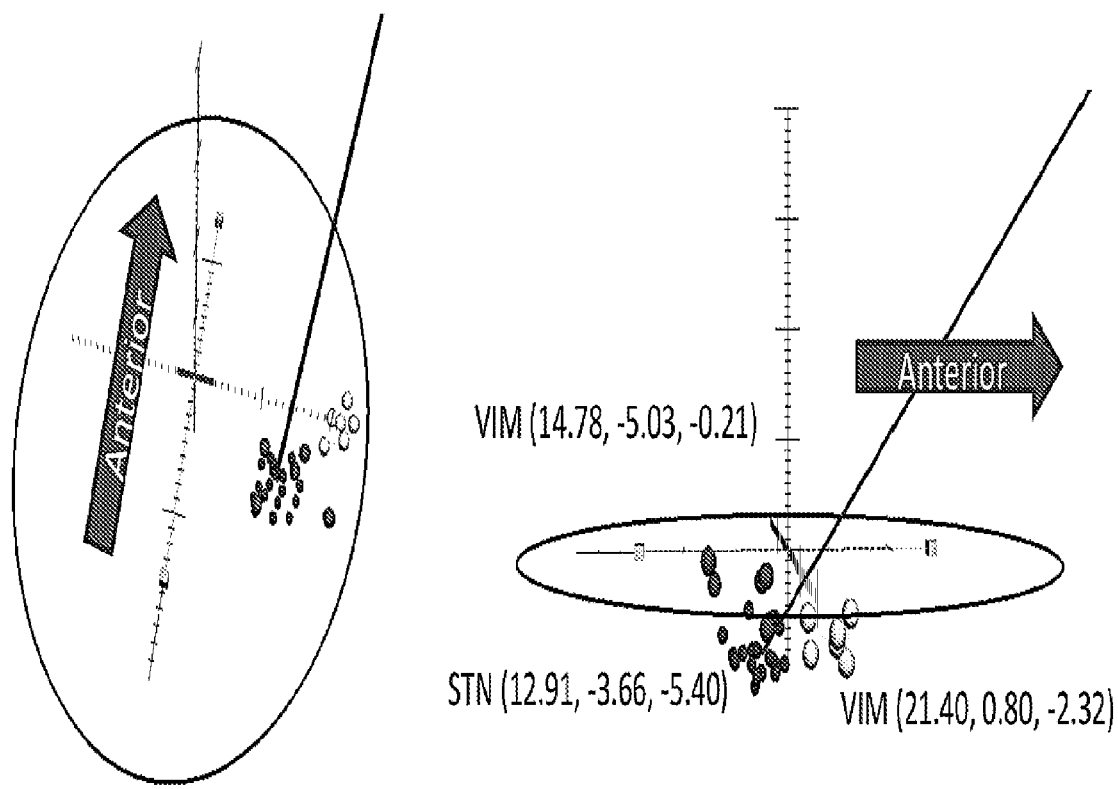
FIG. 65 depicts Implant Variance within the 3D framework of certain brain internal landmarks. This report lists numerically displays separately graphically the location and stimulation parameters of an active implant. In the case of protein, gene therapy or other therapy relevant metrics are substituted.
Figure 67:
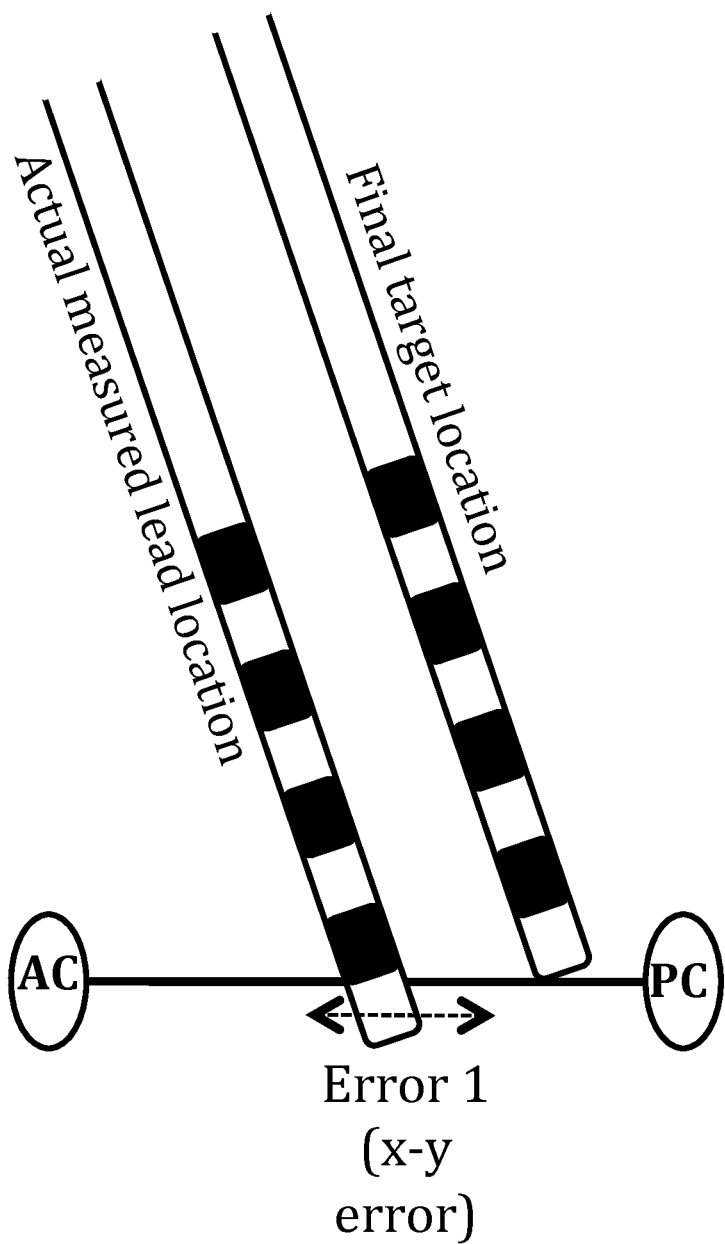
FIG. 67 depicts the mismatch between the calculated and measured location of a brain implant with respect to internal brain landmarks such as the space defined by the anterior commissure, posterior commissure, and a midline point near the cranial vertex according to an aspect of the present invention.
Figure 68:
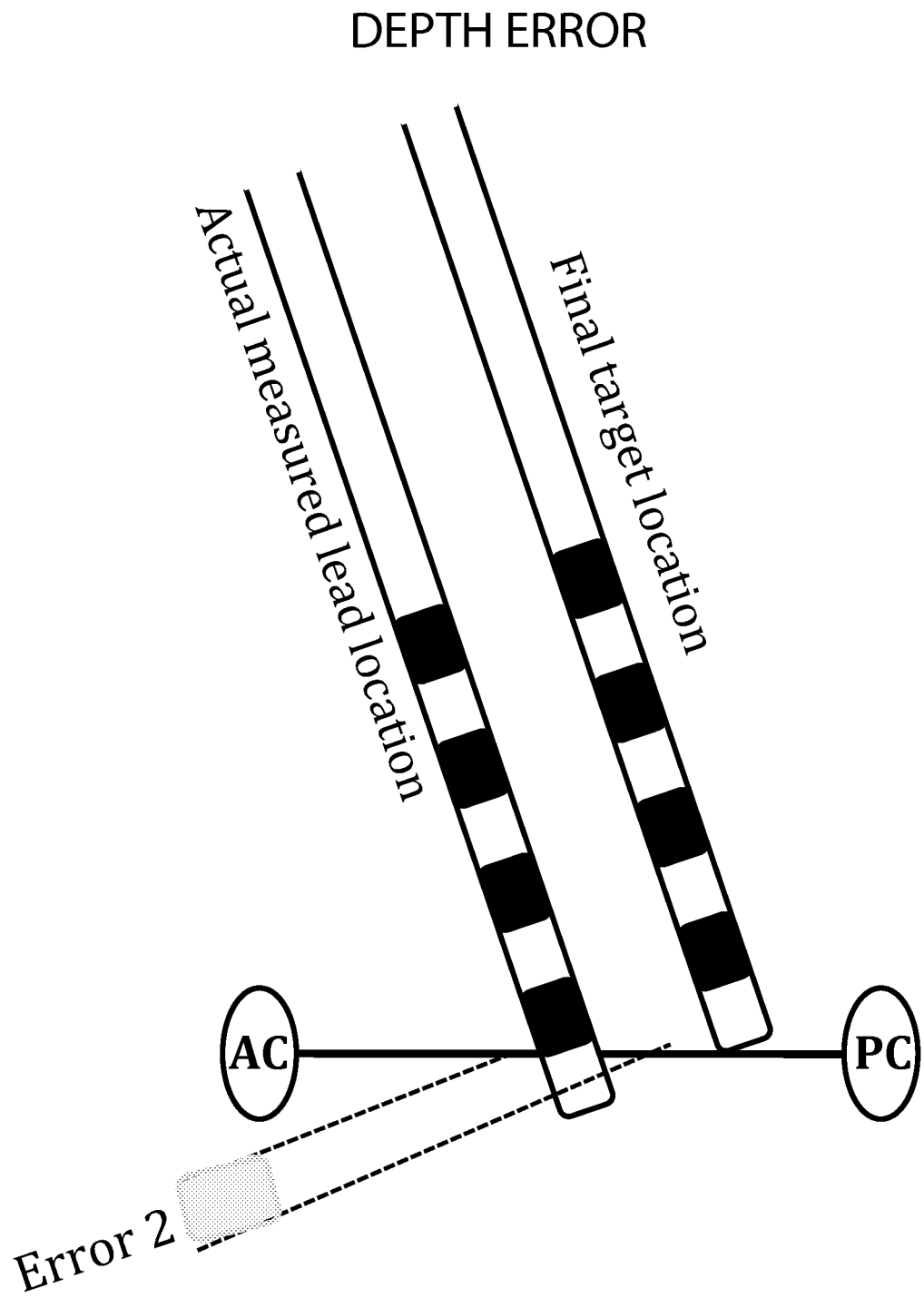
FIG. 68 is depicts the mismatch between the calculated and measured location of a brain implant with respect to brain implant landmarks such as the parallel distance (depth) of the intended implant trajectory.
Figure 69:
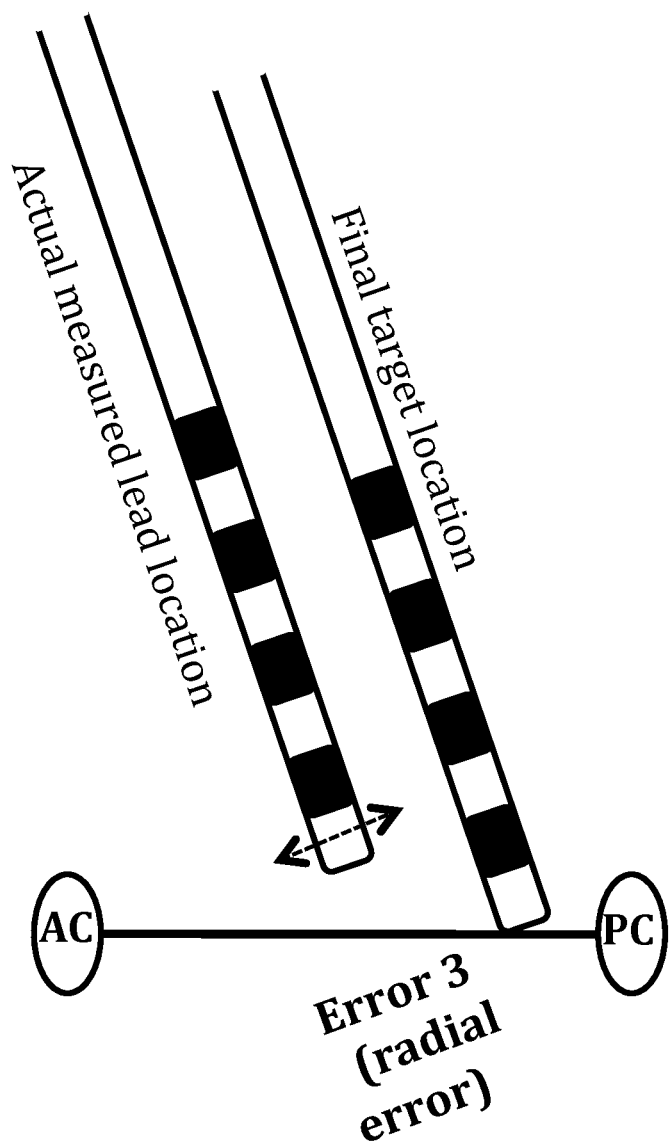
FIG. 69 depicts the mismatch between the calculated and measured location of a brain implant with respect to brain implant landmarks such as the radial or perpendicular distance (radial error) with respect to the intended implant trajectory according to an aspect of the present invention.
Figure 70:
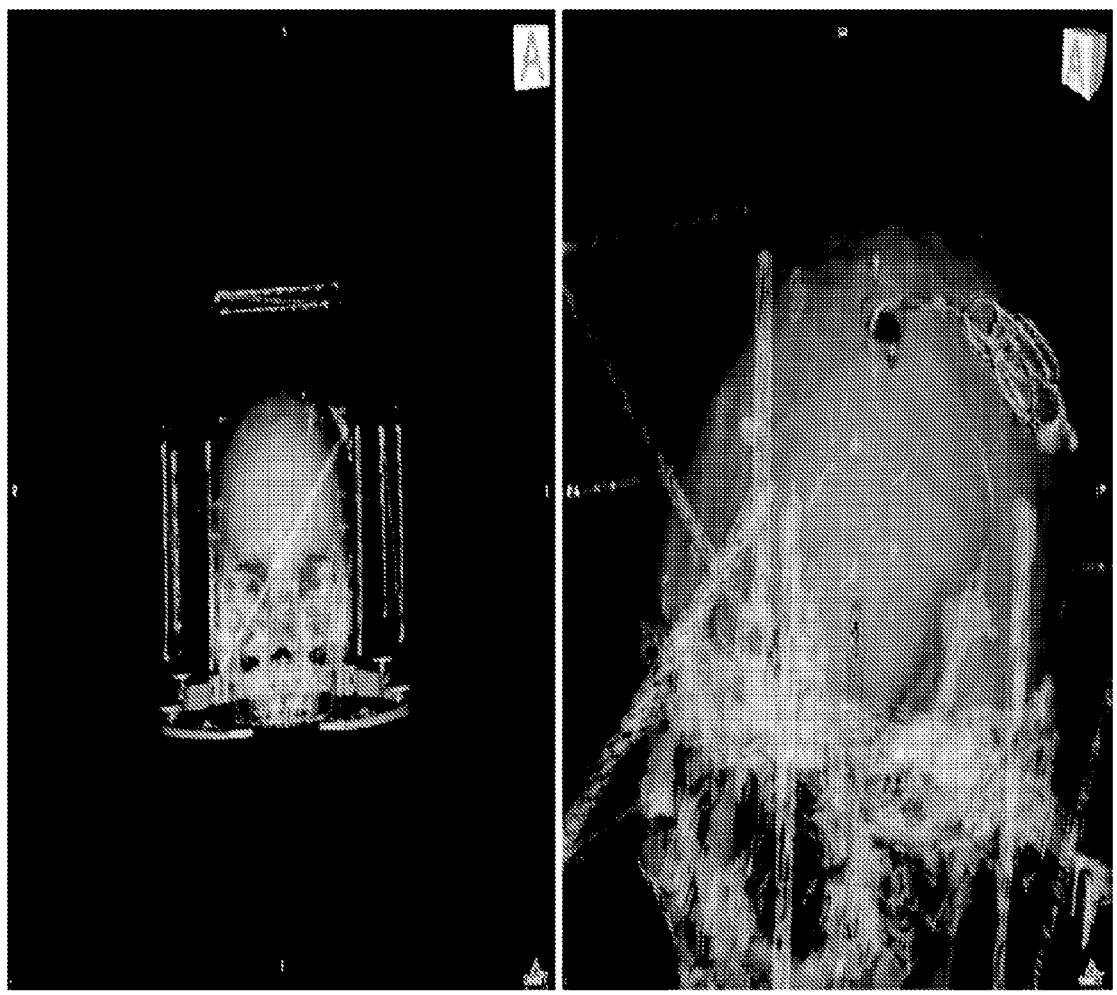
FIG. 70 is a volume reconstruction of the implanted electrodes from an acquired computed tomography image obtained at the time of second sided surgery following the first sided implantation according to an aspect of the present invention.

Accommodation for Intracranial Brain Shift:

Background and Technical aspects of the embodiment: Deep brain stimulation (DBS) has been widely used as a strong therapeutic measure for various movement disorders and psychiatric deficits. Its neural mechanisms still have remained uncertain. Notably, the accuracy of DBS implant location is crucial to the efficacy of the surgery and implant variance has been reported (FIG. 65). DBS lead location errors are closely related to postoperative clinical outcomes, surgery complication, and long-term individual with disease satisfaction. Error is introduced with the shifting brain during intracranial surgery. Regarding the implant accuracy, it has been commonly observed of the discrepancy between the presumed final anatomical target and the measured final target. These differences may represent aggregate errors including, but not limited to, (1) frame error, (2) intra-operative brain shift (FIG. 66), calculation errors of lead offset [in the plane of AC/PC internal landmarks (FIG. 67), with respect to the relative depth of the electrodes with respect to the intended trajectory depth (FIG. 68), and as radial error with respect to the intended trajectory (FIG. 69)] and (4) MRI distortion due to lead location artifact. How these individual factors, however, influence the lead location errors has been the subject of recent study in the literature, however further work is warranted. Notably, it has not been systematic methods for the precise evaluation of lead location errors. Error is commonly measured either as XY error (within the AC/PC plane, (FIG. 67), RADIAL error (FIG. 69), or DEPTH error (FIG. 68). Existing methods have not addressed several errors sources. We describe novel algorithms for the calculation of brain and implant movement with respect to internal and external landmarks (implant error). A high resolution CT scan acquired in two dimensions and added stack-wise to create a 3D volumetric scan or a de novo acquired 3D scan is obtained (alternatively, an MRI scan of the brain can be obtained) on of lead location errors. Illustration of brain implant with respect to landmarks associated with the stereotactic frame as well as bony landmarks of the individual with disease (FIG. 70) (adapted from Sillay, Kumbier, Ross et al. 2012, FIG. 5)). In particular, radial error is the one of the major factors affecting therapy as the electrode must be removed and re-inserted to correct for radial error, however stimulation programming changes are able to adjust stimulation within a multi-contact montage. In the absence of correct coverage of error sources, the existing scarce algorithms may not generate the accurate DBS lead location errors.

Method of determining the position of the brain at the time of implantation of a rigid device, which becomes flexible over time. Participants are able to upload a standard DICOM image set from a Client Interface Device or a computer or computer system over a web based acquisition system or alternatively instruct a Server or other computer system to transfer images to the registry. The representative images are noted as to the time with respect to the intracranial surgery as well as the expected implants. Manual or automatic segmentation of the brain electrodes is performed. The tip of the electrode and trajectory of the active electrode montage is calculated. The entirety of the electrode is segmented in order to determine the relative retraction of the electrode during the time of resolution of intracranial changes. The eigenvector of the implant with origin at the tip is calculated. The active stimulation parameters are applied to the eigenvector and electrode configuration to determine the location of stimulation (described separately). The brain shift calculated retraction of the electrode is added in a cranial direction along the eigenvector in the event intracranial pneumocephalus was noted on the scan. The degree of this change applied is described separately and related to the time since implantation of the device.

Figure 71:
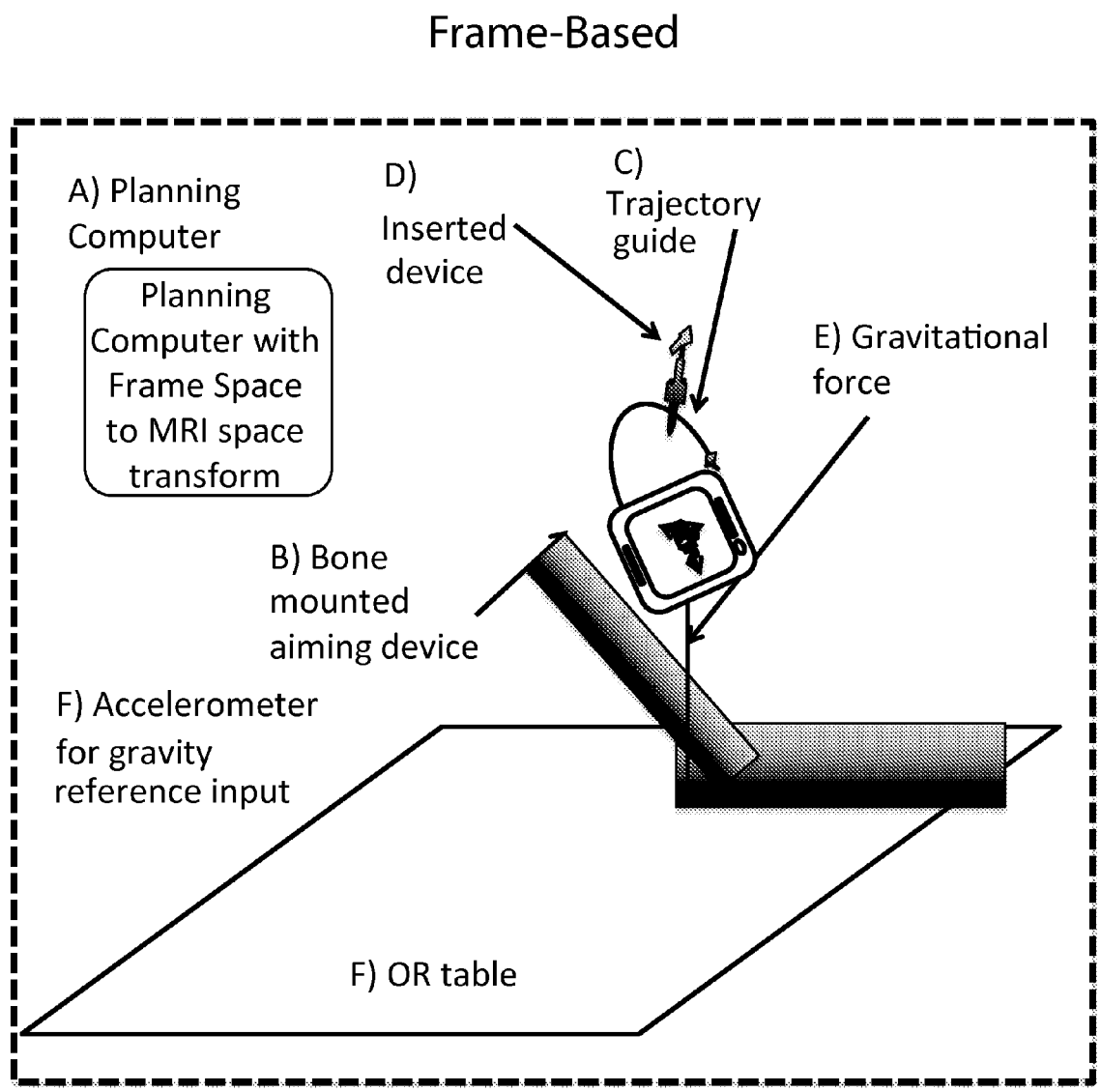
FIG. 71 depicts the gravitational force measurement with a wireless linked mobile medical device for the purpose of referencing the relative gravity component of a stereotactic frame according to an aspect of the present invention.
Figure 72:
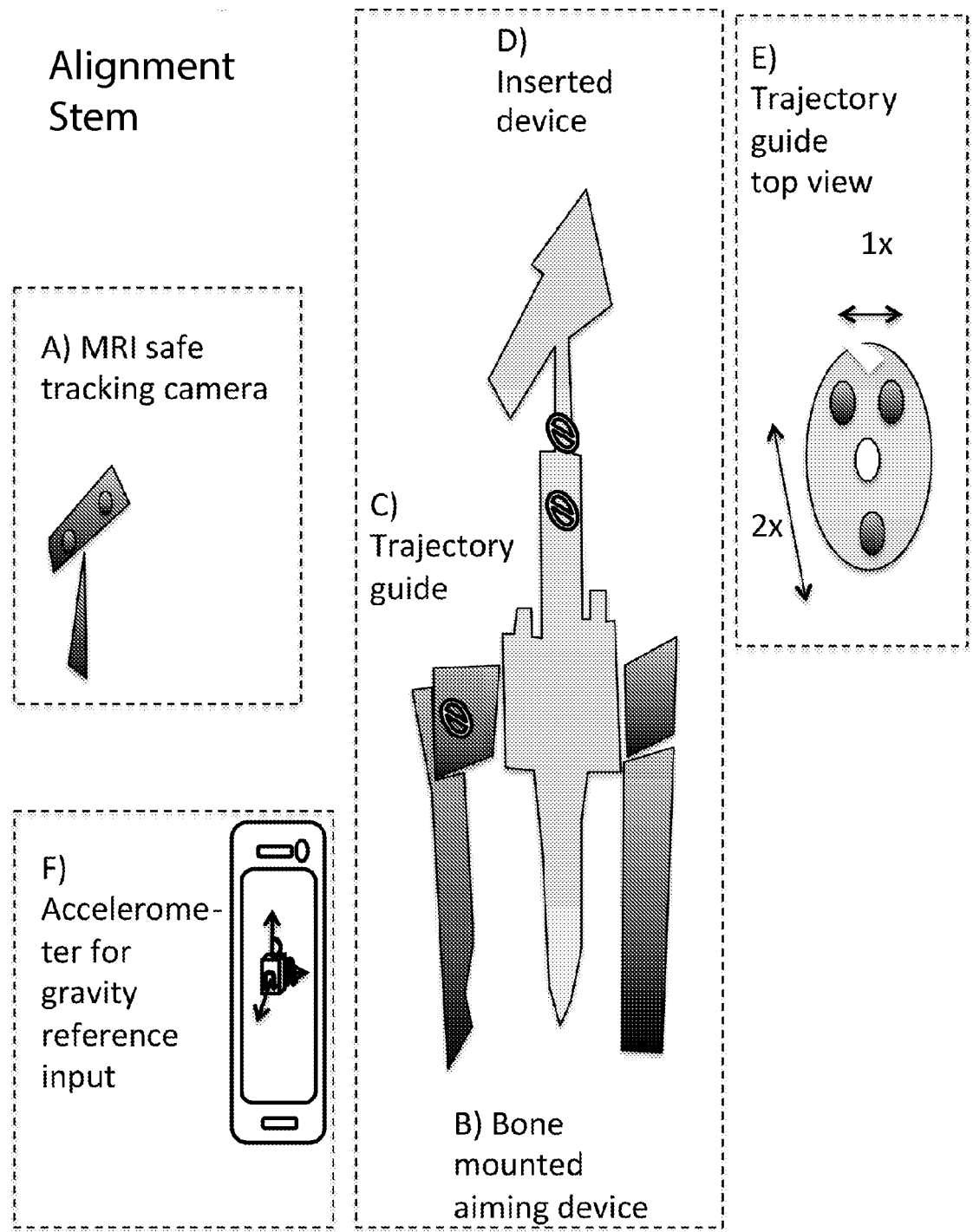
FIG. 72 depicts components and optical tracking devices with the mobile device able to provide gravitational input into the alignment stem position via tracking from the same optical camera comprising devices of A) an MRI safe tracking camera; B) a bone mounted aiming device; C) a trajectory guide; D) an inserted device; E) a trajectory guide top view and F) an accelerometer for a gravity reference input.
Figure 73:
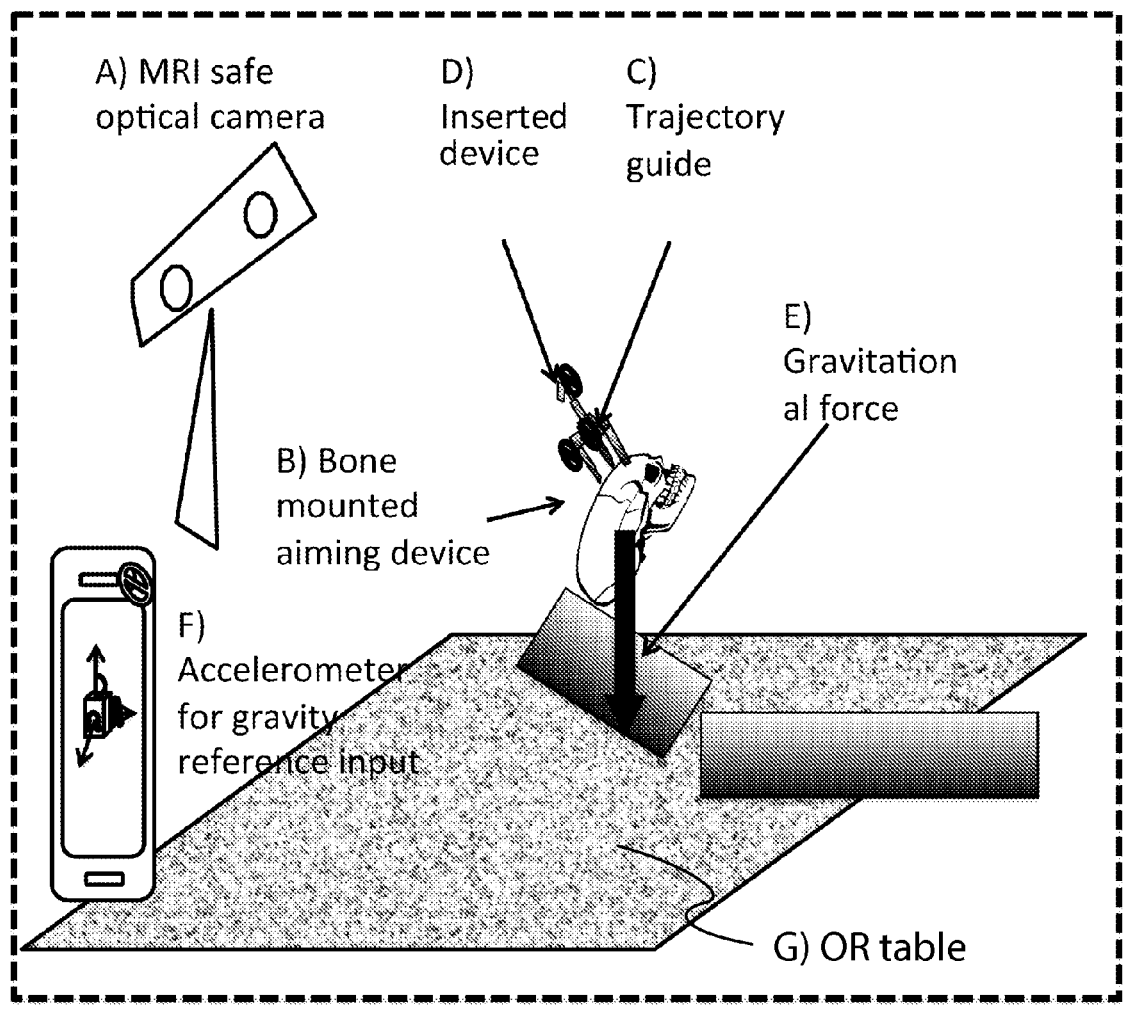
FIG. 73 depicts a first of two mini-frames showing a relatively recumbent position of a patent's skull vertex when undergoing a surgery requiring cranial opening and the devices A), B), C), D) and F) of FIG. 72 and further including E) gravitational force and G) the operating room (OR) table according to an aspect of the present invention.
Figure 74:
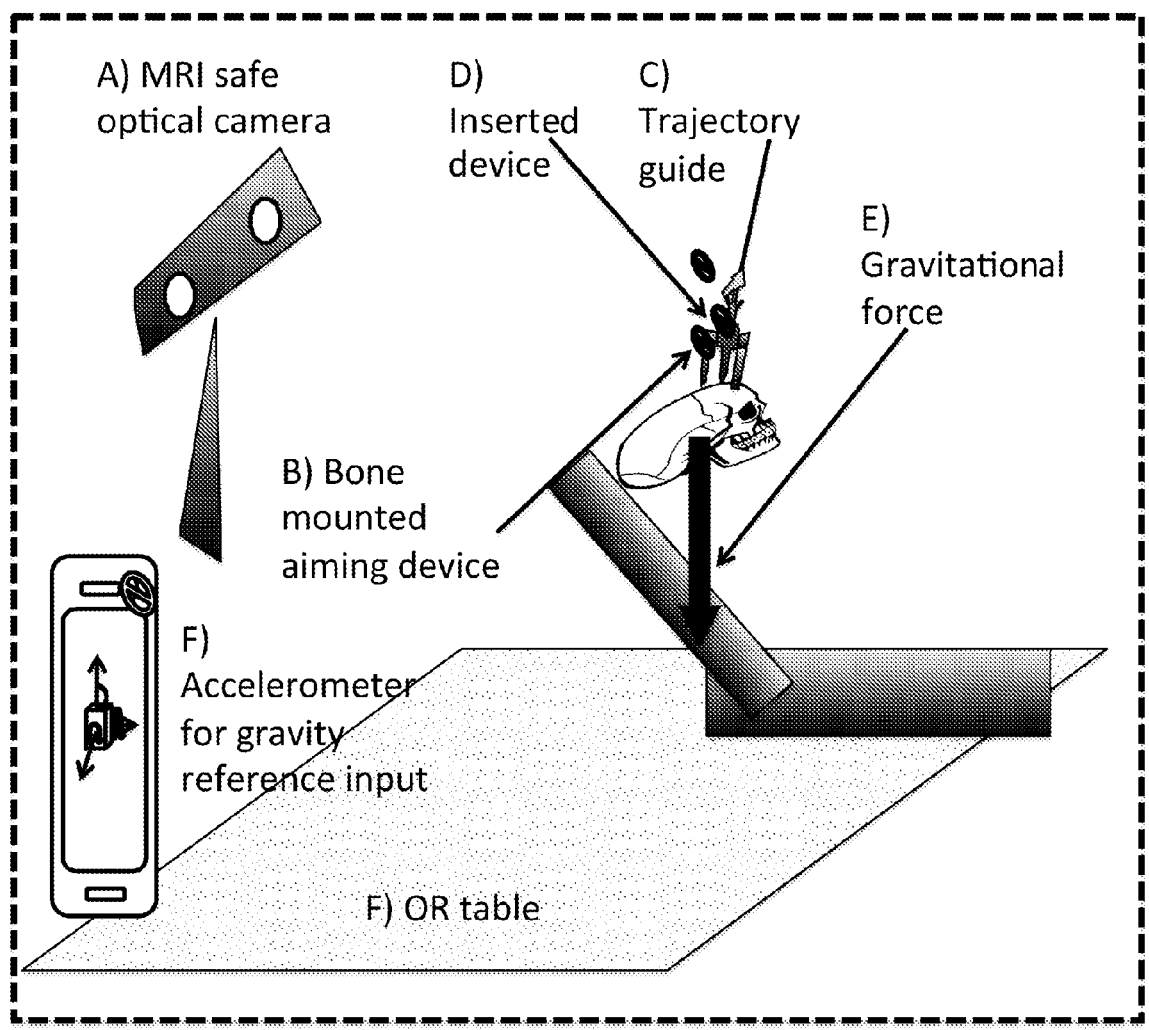
FIG. 74 depicts the second of two mini-frames showing a relatively upright position of a patient's skull vertex when undergoing a surgery requiring cranial opening and the devices A), B), C), D) of FIG. 72 and further including E) gravitational force and F) the operating room (OR) table according to an aspect of the present invention.
Figure 76D:

Method of accounting for motion of the brain within the skull and deviation of the brain implant with reference to internal and external landmarks: The anterior commissure, posterior commissure, and midline point at the cranial vertex are identified to establish the relationship of image space to AC/PC space. This is performed either with internal or external calculations. Calculations are performed to record the gravitational vector at the time of surgery when within an optical tracking environment, frame-based environment (FIG. 71) or other environment using a smart-phone or other gravitational sensor containing unit (FIG. 72). In the case of a more relative recumbent position (FIG. 73), versus a more upright position (FIG. 74) the risks of air embolism (a surgical risk) are increased, while the more recumbent position may be associated with more antero-posterior brain shift.

Ambulatory Care Clinical Model

Figure 77:
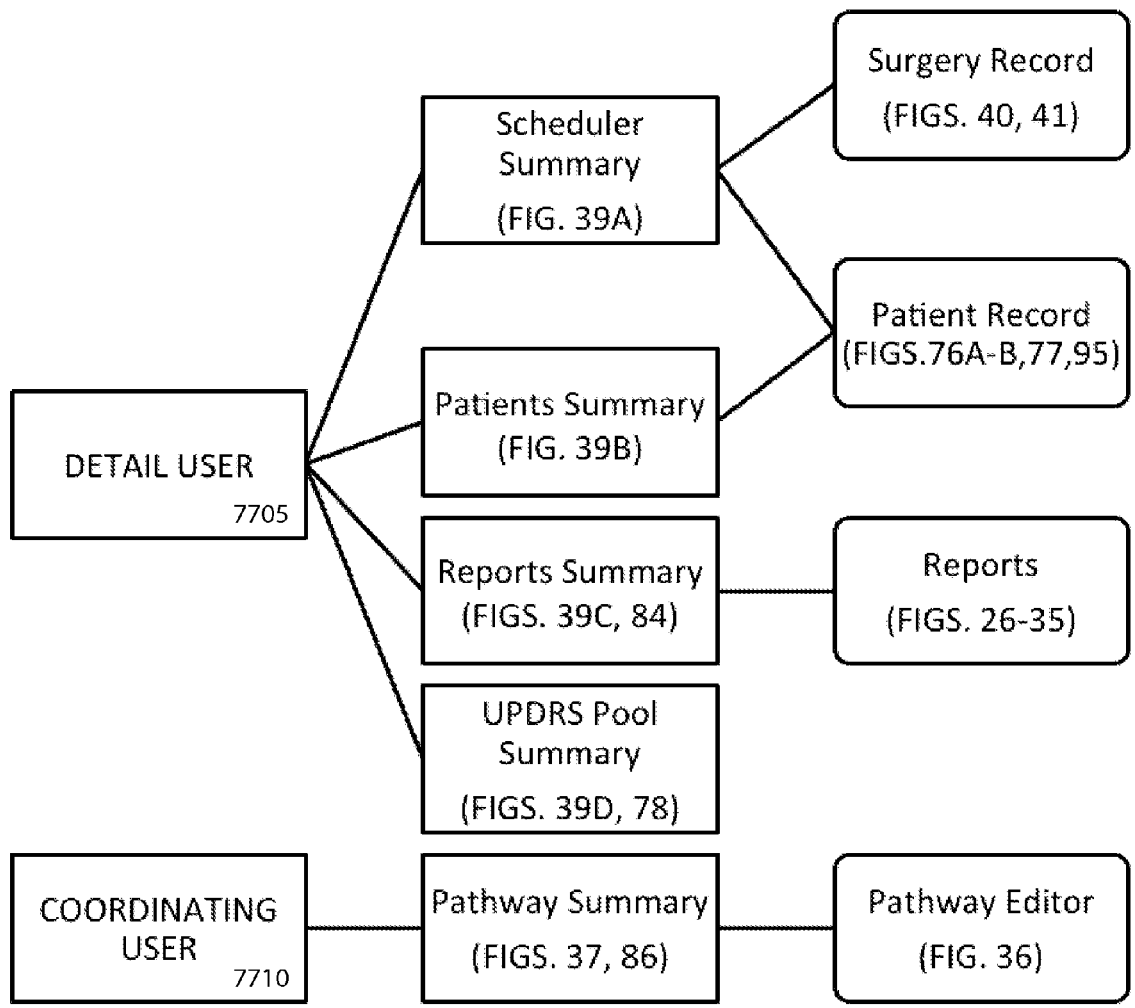
FIG. 77 is a diagram showing the navigation of a user within the representative database for the restorative neurosciences according to an aspect of the present invention.

The system provides aggregate clinical and device programming and outcomes measures as well as provision for subjective measures and objective measures of treatment to be included, and reported. When objective measurements are transferred, a checksum is provided and incoming data are pooled for review if there is any question regarding the information destination (FIG. 75). The summary screen provides the report summary (FIG. 76A-D) and (FIG. 77) for further navigation. The programming visit screen is selected (FIG. 78) and (FIG. 79). Alternatively, the surgical treatment summary is reviewed (FIG. 80; FIG. 81A-B).

Figure 82:
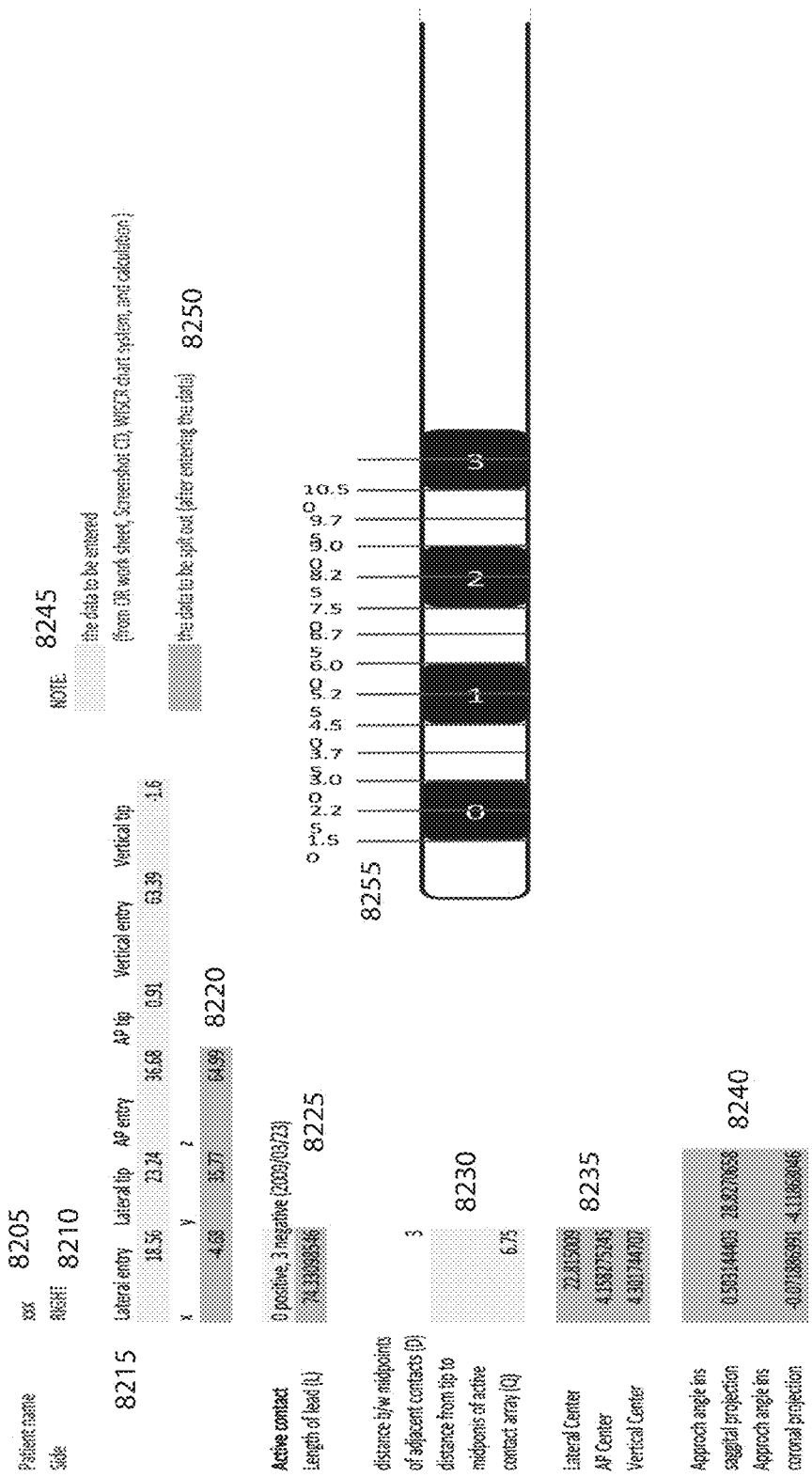
FIG. 82 is a representative screen capture from an active stimulation calculator for determining the offset of the origin and shape of volume of tissue stimulated given an implant location and active contacts for a quadrapolar array according to an aspect of the present invention.

Determining Location of Stimulation:

In order to prepare for stimulation versus location analysis and potential closed loop stimulation algorithms, the location of stimulation within a given coordinate system is determined. An implantable brain device may have multiple electrodes of a given confirmation and orientation (A Medtronic 3387 quadrapolar lead has a symmetric quadrapolar montage 1.5 mm in height, 1.5 mm in interspace, and 1.27 mm in diameter) with the ability of activation of one or many electrodes. To obtain the optimal clinical outcomes after DBS surgery, individuals diagnosed with a disease are required to undergo stimulation programming by the medical care providers by changing programming of one or more of the parameters within a possibility of may thousands of selections: (1) active contact(s) combinations, (2) monopolar contact versus bipolar contacts, (3) voltage, (4) frequency, and (5) pulse width. The centroid of active stimulation is determined from the lead tip given implant geometry and calculated (FIG. 82).

Stimulation Versus Lead Location Analysis

Figure 83:
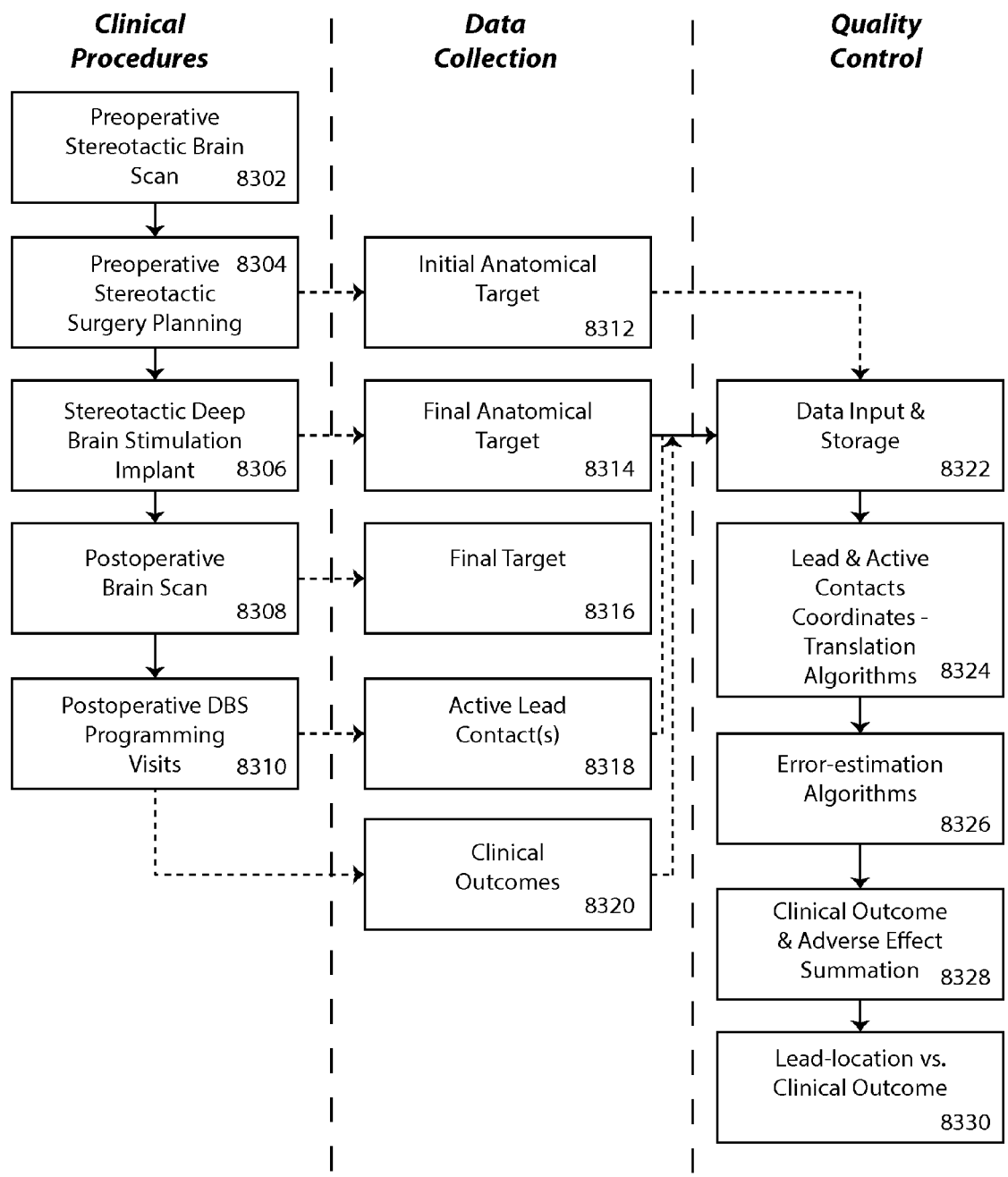
FIG. 83 is a representative workflow diagram for the processing of brain implant data for quality control and lead location versus clinical outcome analysis.

An accurate location of implants and active contact(s) is correlated with clinical outcomes (e.g., the Unified Parkinson's Disease Rating Scale scores, UPDRS) according to the following workflow (FIG. 83). We establish the correct algorithms for lead and active contact locations and build them into the program with the database for processing of data. These algorithms are used to calculate important quality control information, such as mean errors, standard deviations, overall individual with disease complications, and the correlation between locations and UPDRS scores. Other quality control information may be calculated or used.

Reports

Additional reports are provided to assist in the navigation of the modules. Report examples include (FIG. 84).

Figure 85:
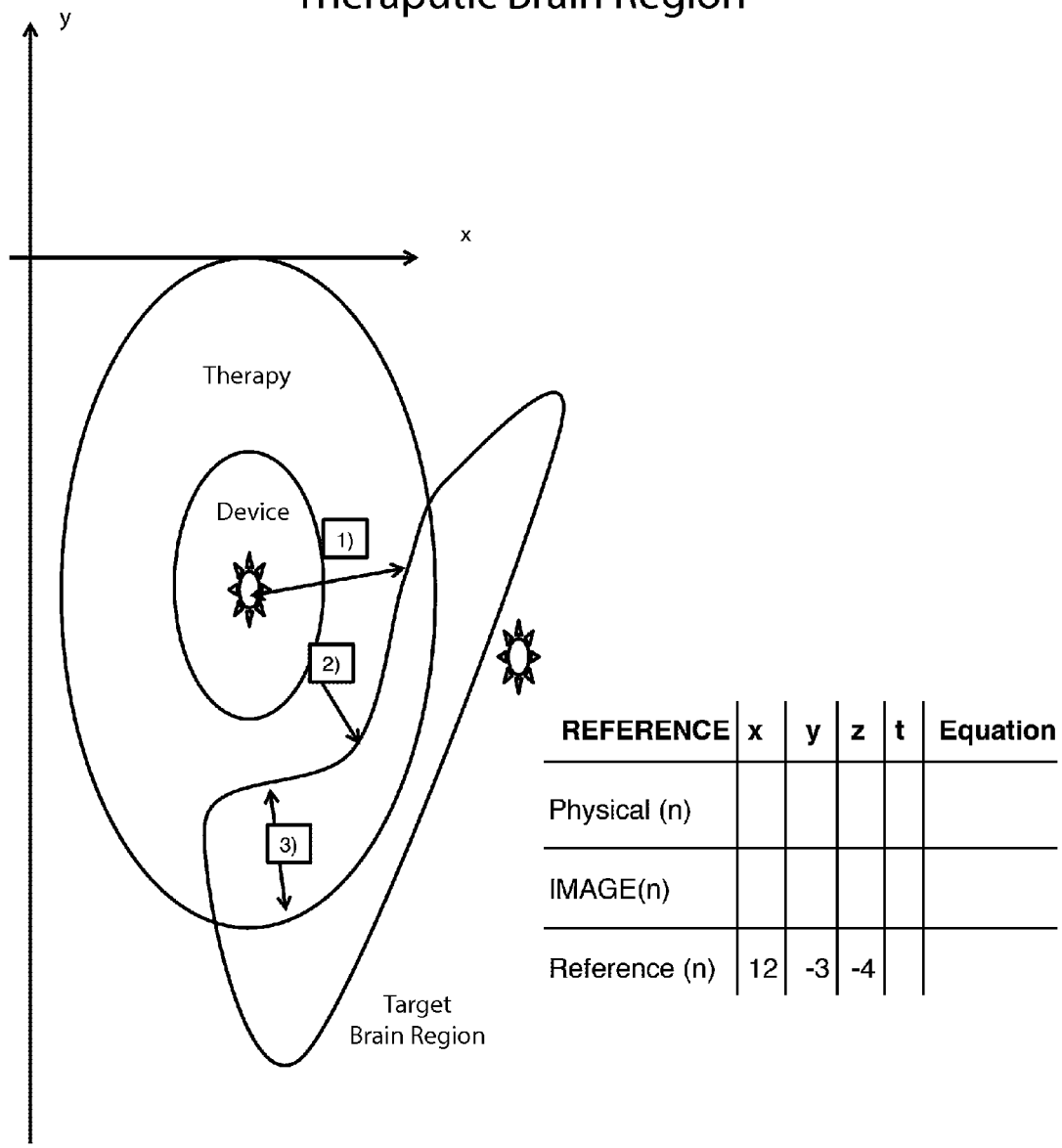
FIG. 85 is a representative visualization of the centroid of a trajectory, the outer limit of a device, a range of therapy delivered, and a surrounding representative area of interest for therapy delivery. This figure includes the location and direction vector describing these items at a given time of a number of identified points (3D reduced to 2-D and a single coordinate plane for the purposes of visualization).
Figure 86:
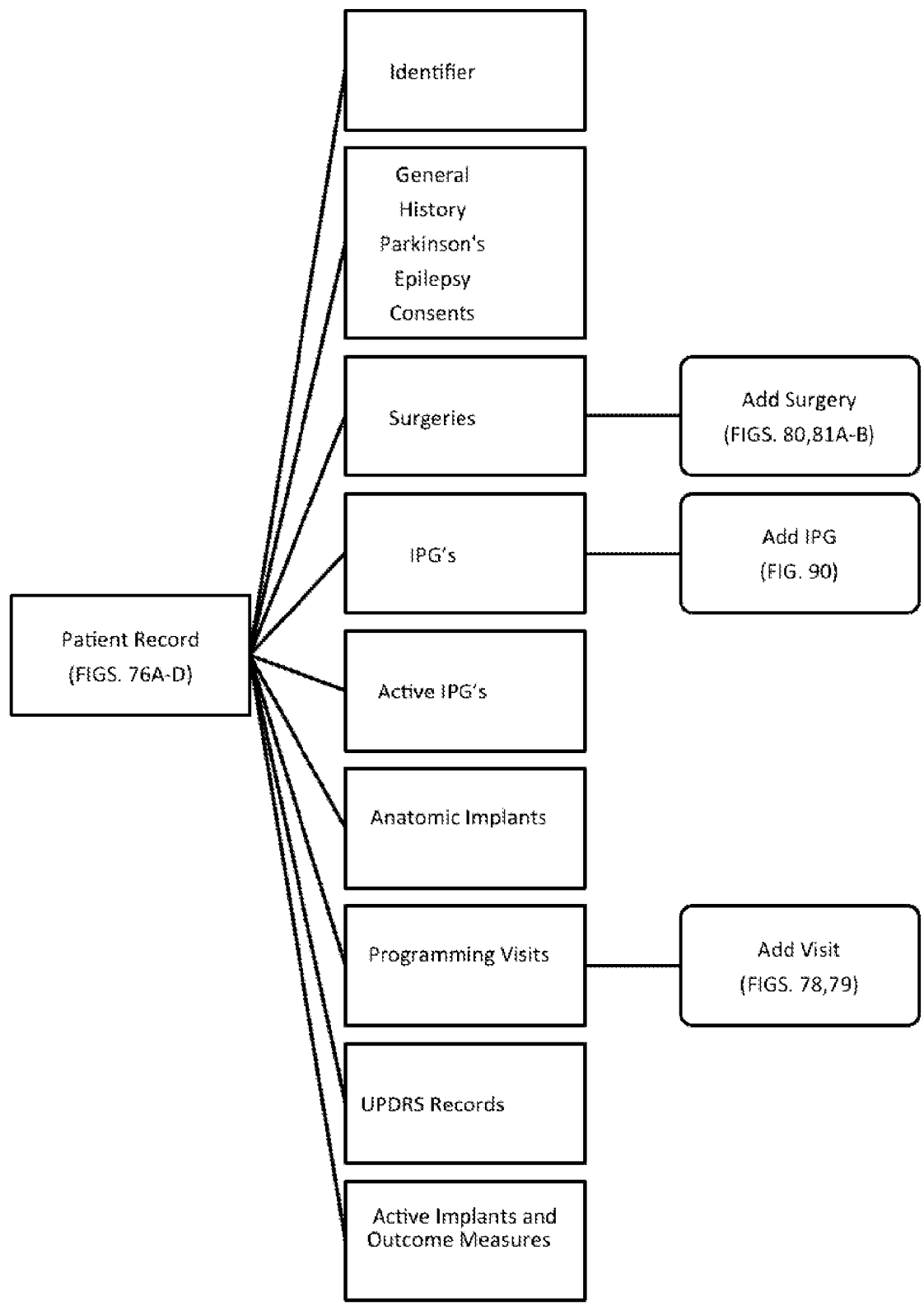
FIG. 86 is a figure diagramming the navigation of a user within a generated representative cohort database for the restorative neurosciences for the purposes of adding events and implant data.
Figure 91:
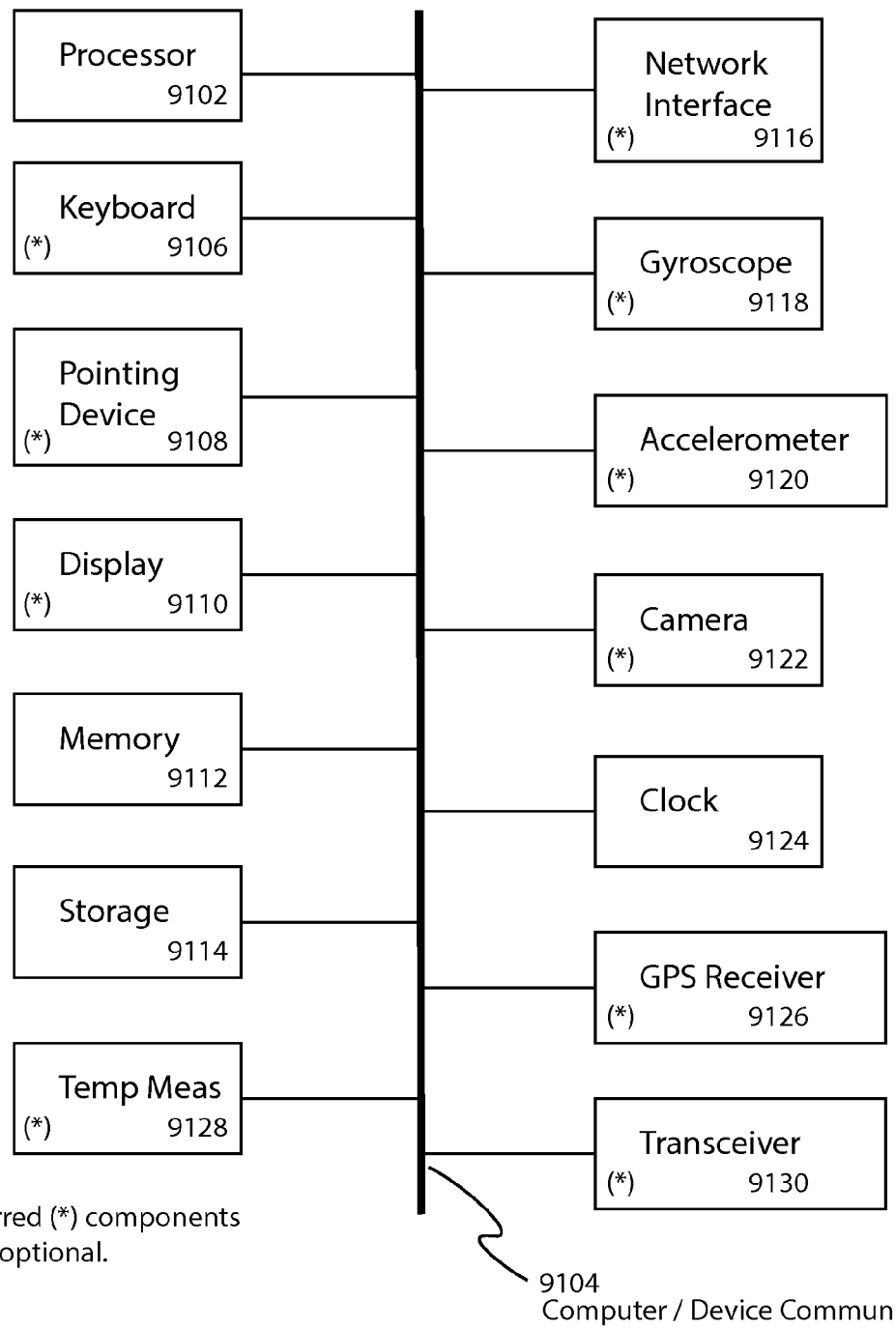
FIG. 91 is a diagram depicting the onboard devices envisioned within an ideal client device.
Figure 92:
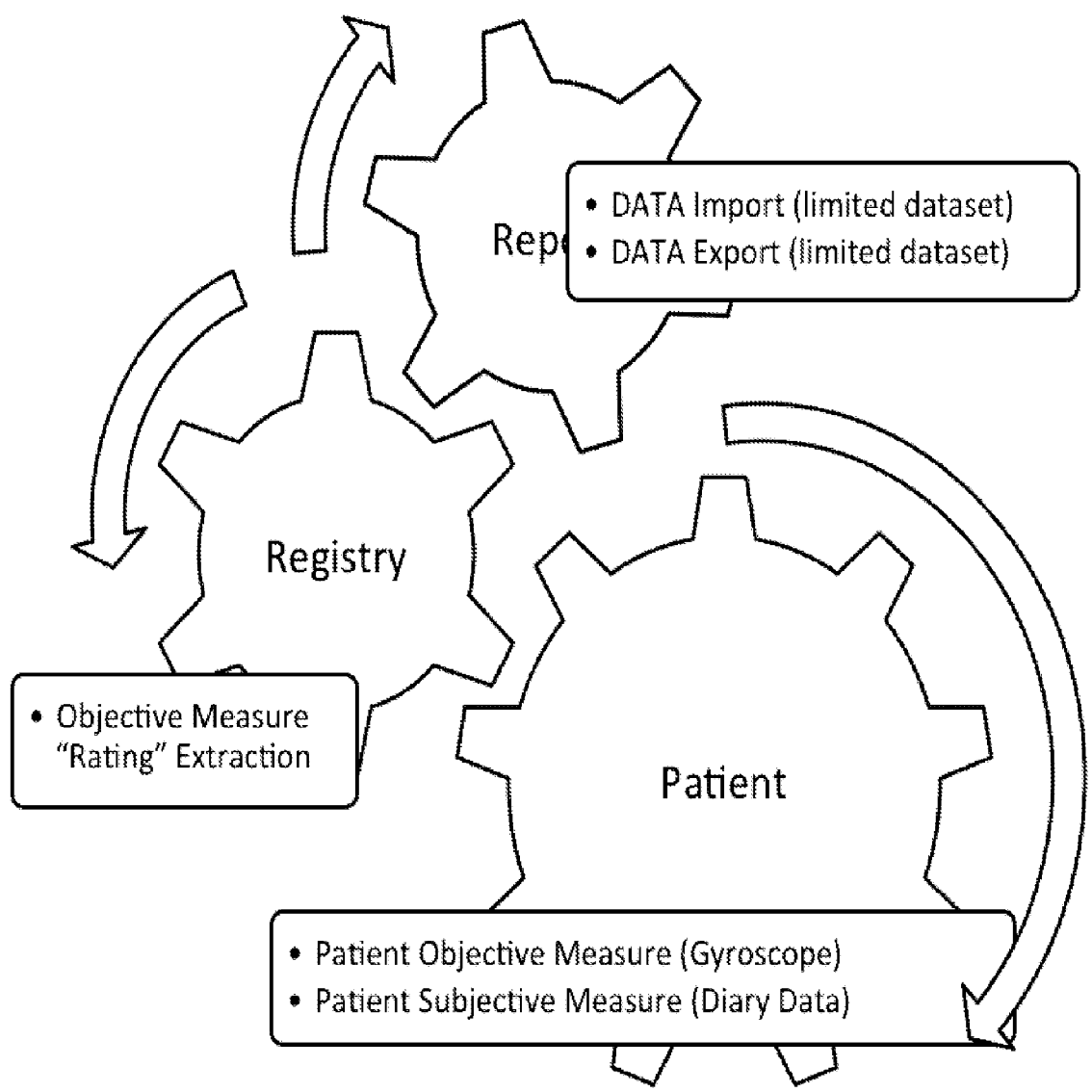
FIG. 92 depicts an individual with disease interacting with a data exchange server environment with automated objective measure extraction and with automated reporting.
Figure 93:
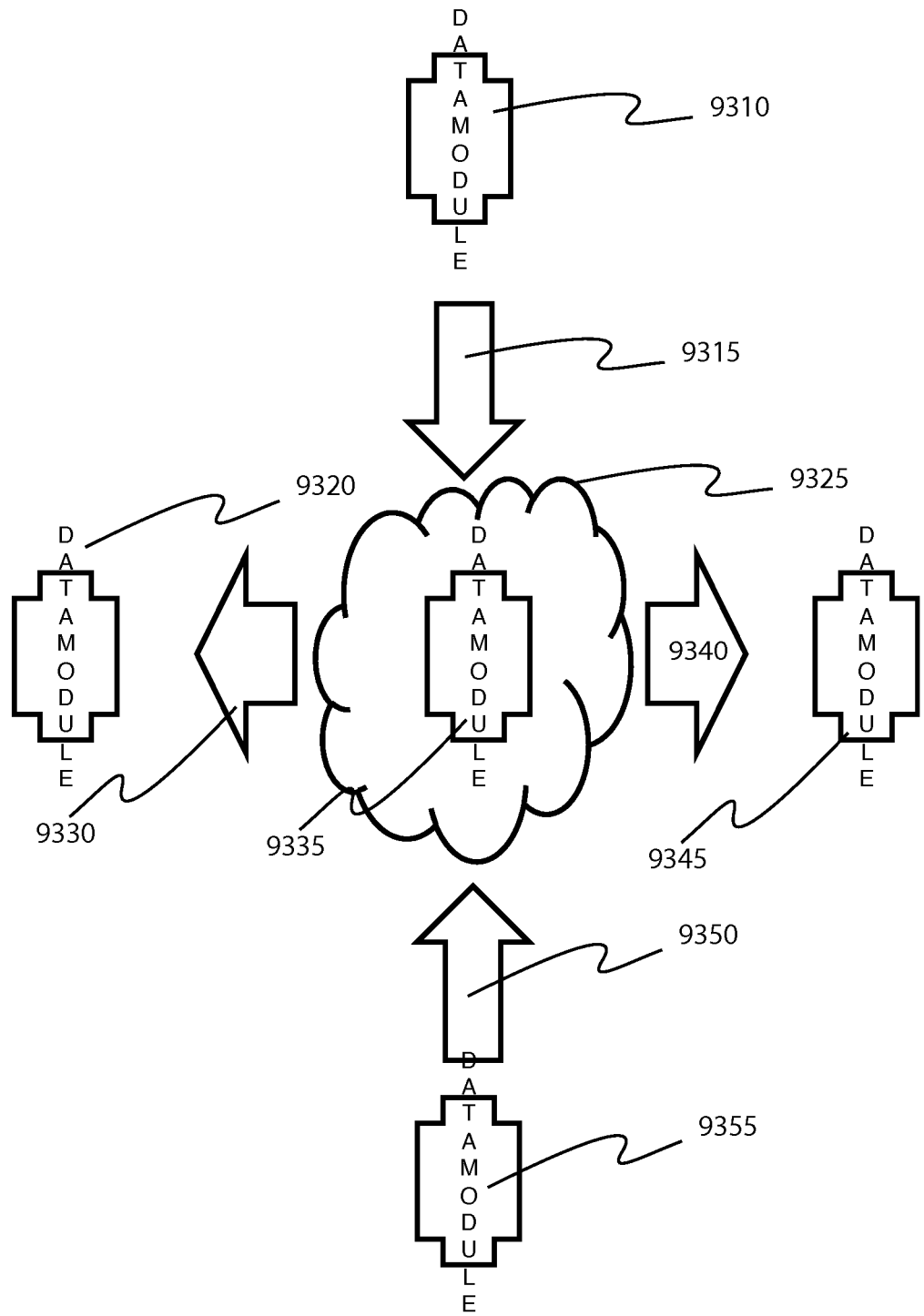
FIG. 93 is depicts the simultaneous acquisition and disbursement of data to be exchanged based upon permissions and to separate sources.
Figure 94:
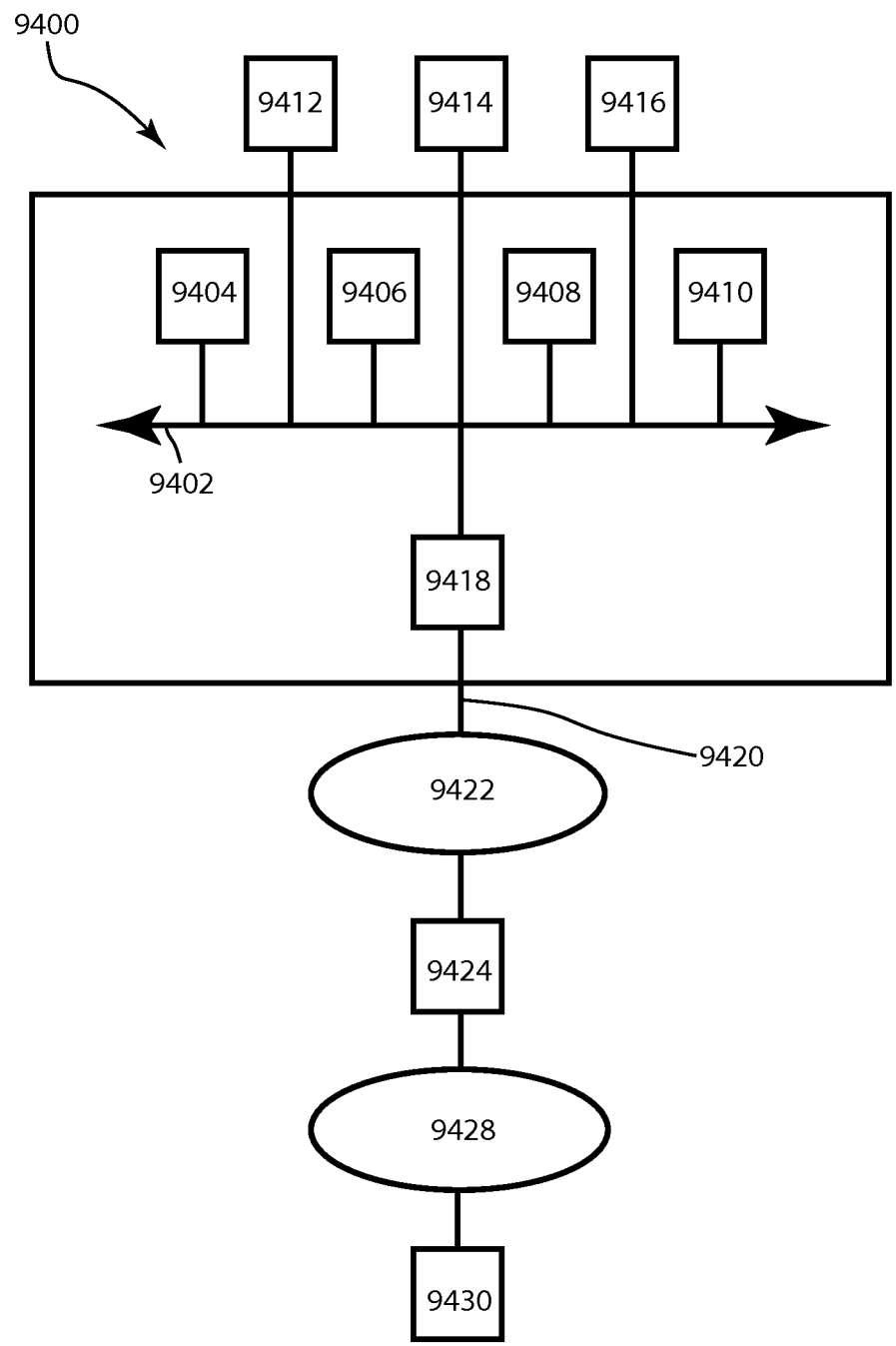
FIG. 94 depicts multiple communications along a data exchange bus according to an aspect of the present invention.
Figure 95:
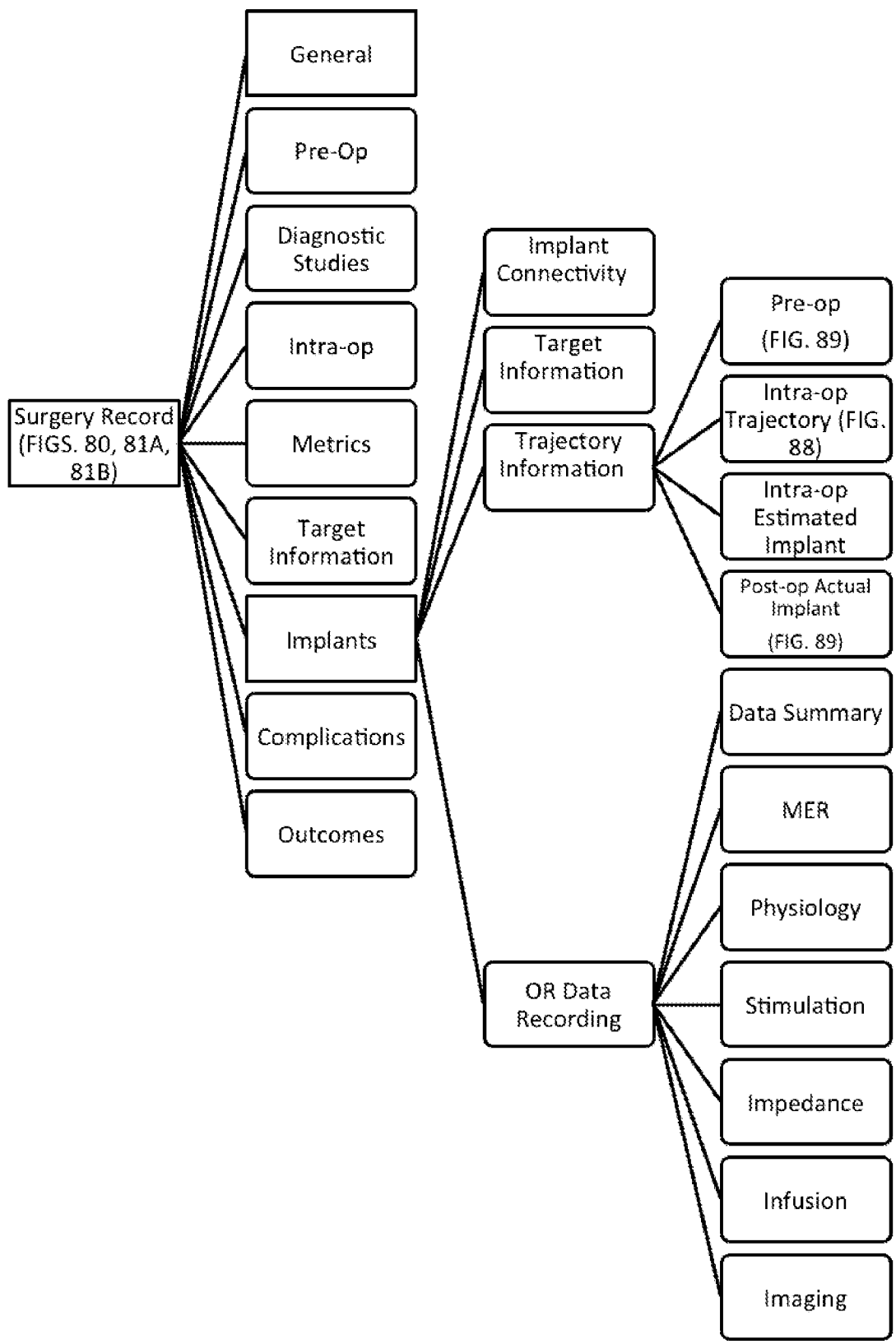
FIG. 95 depicts navigation steps within the implant section of the representative database for defining the location of implants or delivered therapy.
Figure 97:
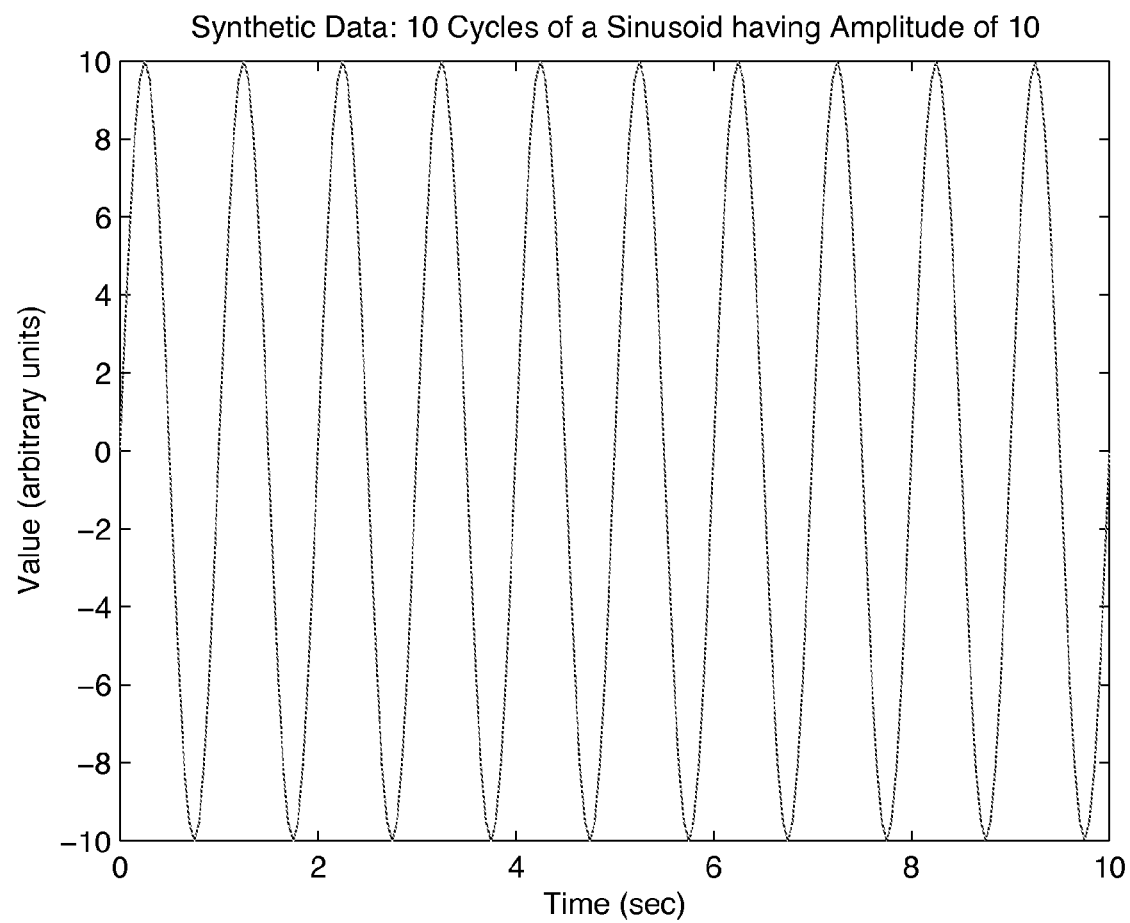
FIG. 97 depicts synthetic data with 10 cycles of a sinusoid having an amplitude of 10.
Figure 98:
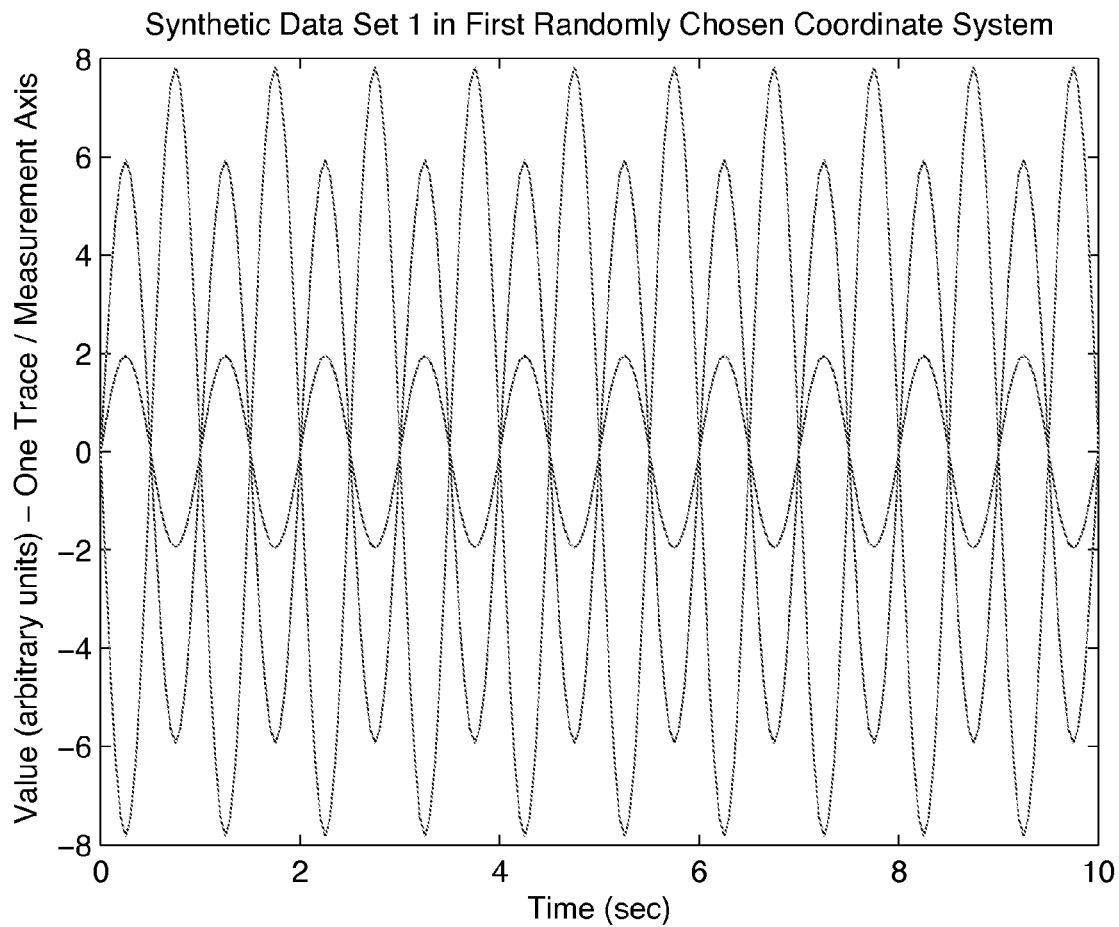
FIG. 98 depicts the Synthetic Data Set 1 in First Randomly Chosen Coordinate System according to an aspect of the present invention.
Figure 99:
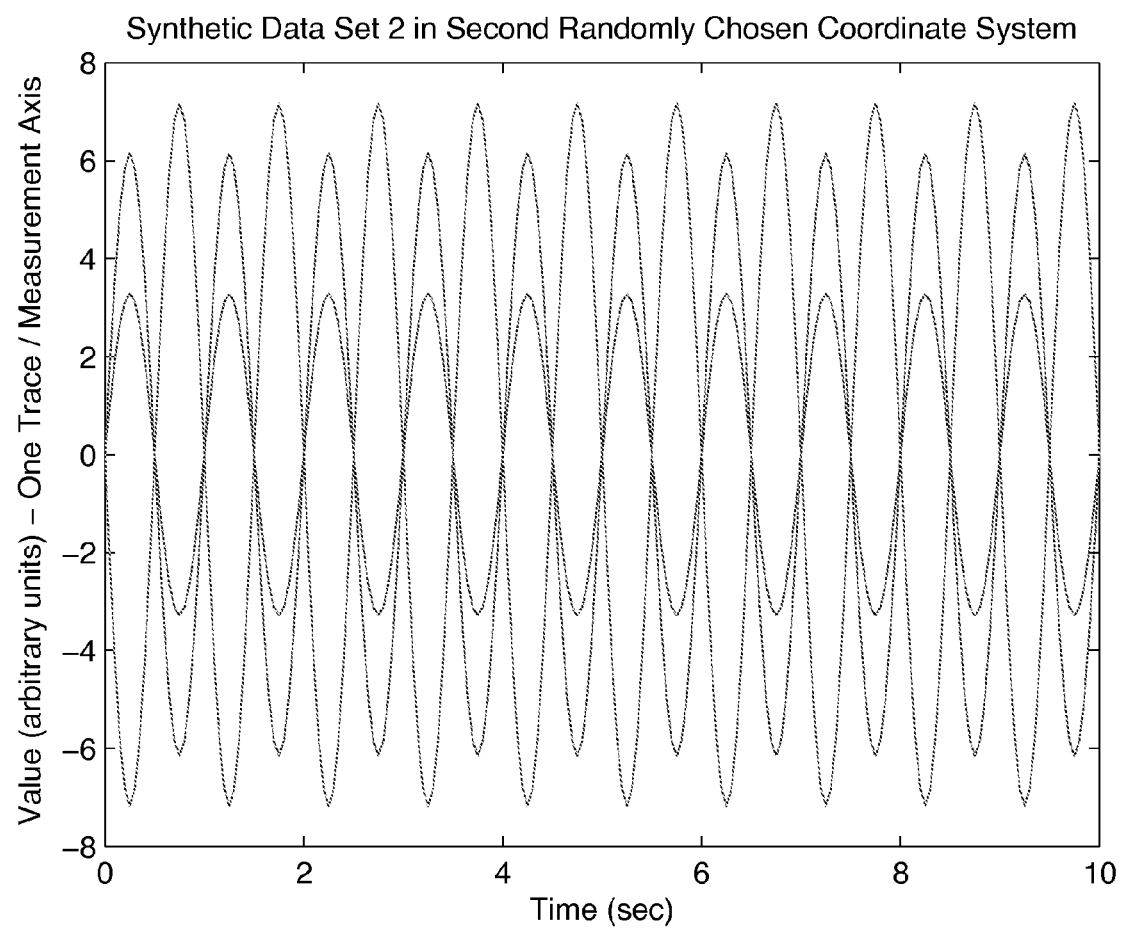
FIG. 99 depicts the Synthetic Data Set 2 in Second Randomly Chosen Coordinate System according to an aspect of the present invention.
Figure 100:
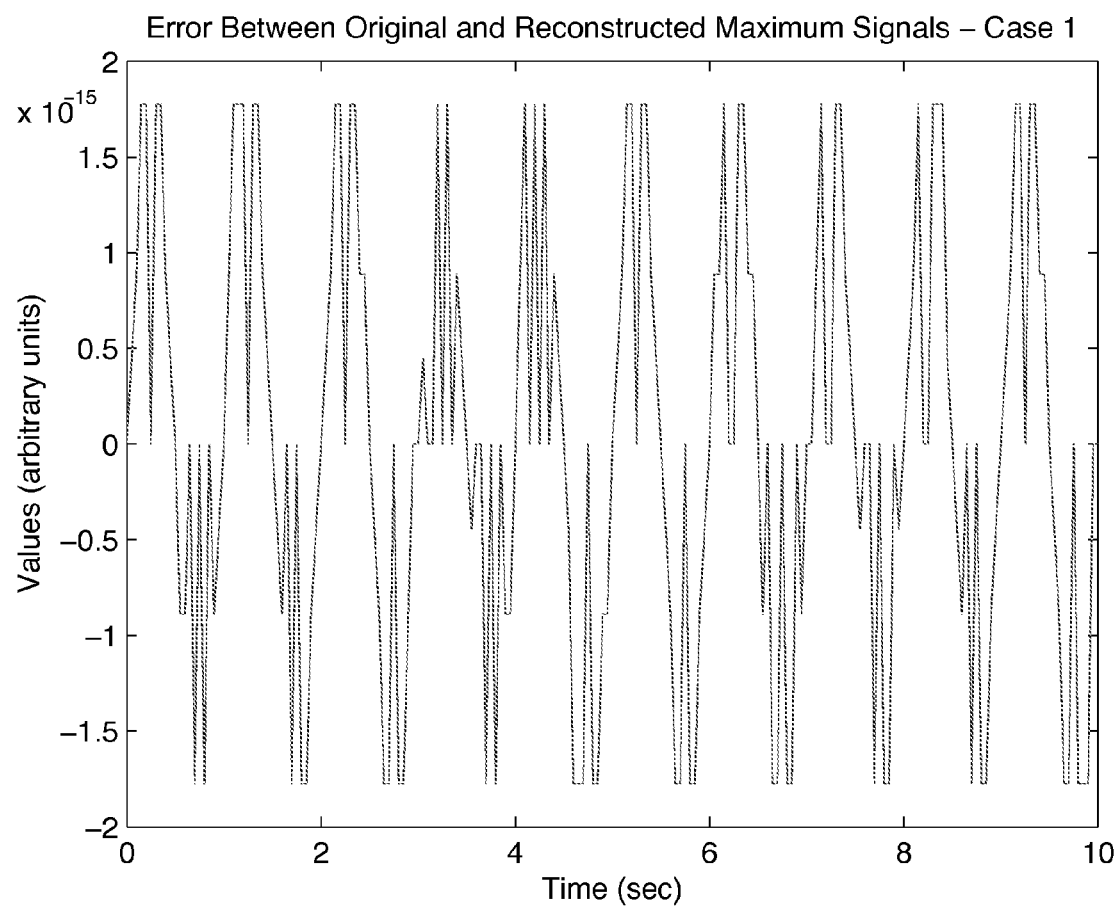
FIG. 100 depicts the Error Between Original and Reconstructed Maximum Signals—Case 1.
Figure 101:
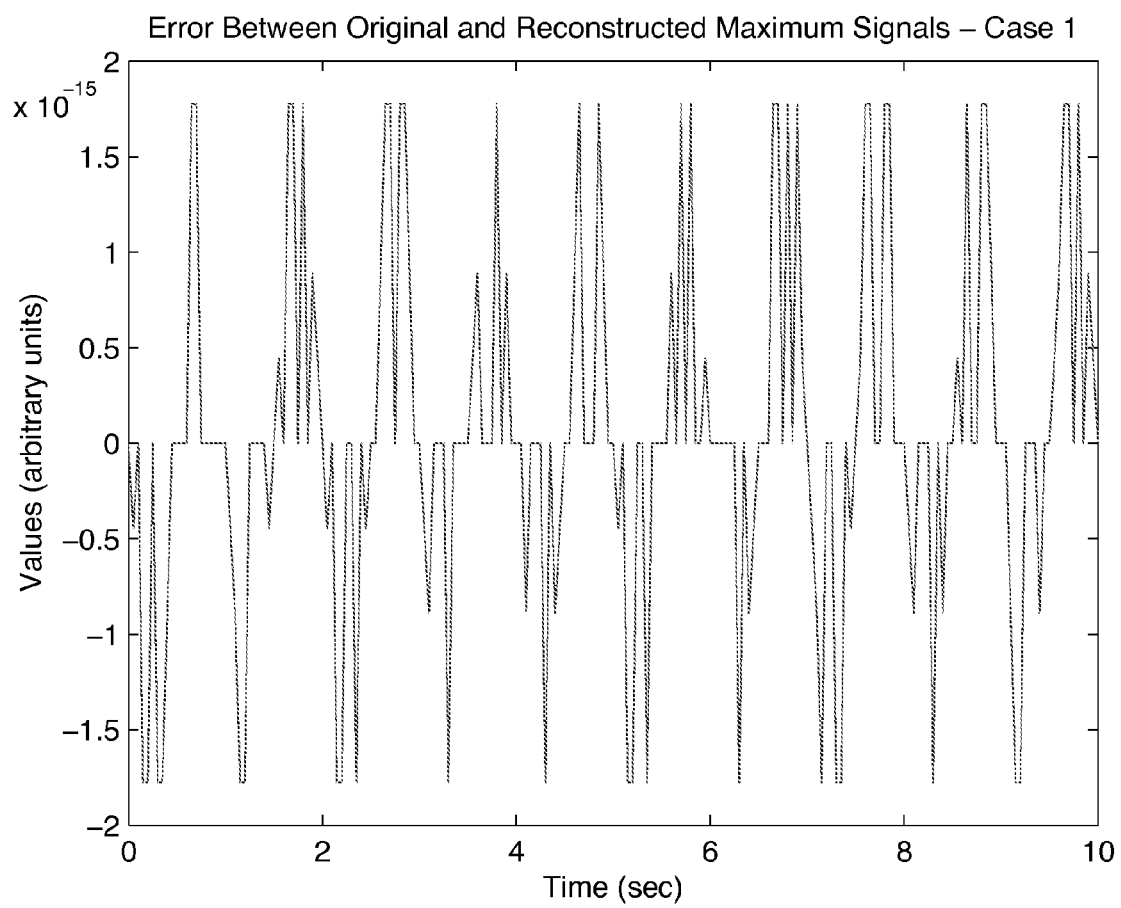
FIG. 101 depicts the Error Between Original and Reconstructed Maximum Signals—Case 1.

Other Examples of Implants to be Tracked and Therapy to be Monitored:

For the purposes of documentation of location of delivered therapy at a given point, consider Figure (FIG. 85). Also, shown in FIG. 86 is a data relationship between patient records on the left (FIGS. 76A-D) and additional surgery, visits and such on the right via a data identifier, general history, UPDRS scores, implants and such shown in the center. FIGS. 88A, 88B, and 88C are screen captures from a representative database for the capturing of perioperative trajectories and associated metrics. FIG. 89 is a representative screen capture depicting the post implantation location, errors, and notes associated with the procedure. FIG. 90 is a representative screen capture depicting the addition of a new neurostimulator pulse generator device and associated linkages to brain implants. FIG. 91 is a diagram depicting the onboard devices envisioned within an ideal client device. FIG. 92 depicts an individual with disease interacting with a data exchange server environment with automated objective measure extraction and with automated reporting. FIG. 93 depicts the simultaneous acquisition and disbursement of data to be exchanged based upon permissions and to separate sources. FIG. 94 depicts multiple communications along a data exchange bus according to an aspect of the present invention. FIG. 95 depicts navigation steps within the implant section of the representative database for defining the location of implants or delivered therapy. FIG. 96 is an example data exchange mapping matrix for users to allow de-identified reporting to be identified or identified data to be exchanged with healthcare providers. FIG. 97 depicts synthetic data with 10 cycles of a sinusoid having an amplitude of 10.

With rigid, semi-flexible, and flexible implants, variation of therapeutic device location may move over time with respect to external and internal anatomy. In the case of thin-film electrodes, location of actual implantation is recorded for the montage and contacts based upon automated or semi-automated interpretation of imaging studies or magnetometer or similar data. The location of the device at subsequent time periods is automatically replaced within the database calculations to ensure the most accurate systems location is used for therapy delivery calculations. For example, a 100×100 contact thin-film electrode array with a 250 micron spacing grid overlying a horizontally situated cortical sulcus may be deployed and found to be at the coronal suture of the skull in an anteroposterior location with zero degrees of rotation and 4 centimeters from the midline and then at the six month imaging timeframe, be found to have moved anterior by 5 mm. The reporting system will alert the practitioner of the abnormality and provide a correlation of the impedance mapping heat map of the grid before and after the suspected change as well as the longitudinal change over time. To the extent the impedance of the montage has stabilized over time and the relative impedance signal of the underlying sulcus is unchanged, an alert will advise the user that the device and brain are hypothesized to have migrated together. Should a trend in change of impedance mapping be shifted with the direction of the implant, an alert of the more likely fixation of the electrode to the external anatomy of skull, dura, and scar with underlying shift over the cortex will be given. The impedance map will be used to report in an automated way the likely programming alterations needed to deliver comparable stimulation to the affected areas. Similarly in the case of recording electrode data acquired through the montage, an alert will be given to show a likely spatial fidelity of the recordings or a recommended automated recalibration of the electrode signals to relevant cortical anatomy.

In the case of fluidic delivery, thermal, radiation, or other therapy delivered along a linear or curved intraparenchymal trajectory, external cortical trajectory, or via an endovascular or other fluid space delivery method, the target and entry points are defined based upon anatomical landmarks and the implant 3D structure is segmented to derive a resulting equation of the implant trajectory an resulting therapy with reference to the tip of the device or center of the target, or therapy. Metrics associated with these findings at the time of surgery and at later times are associated computationally to outcomes measures and an alert results for those statistically significantly outside of the cohort and trends between cohorts with differing techniques is calculated.

An example of this is in the delivery of multiple collinear fluidic infusions along a single trajectory. The novel reporting of a technique contrary to the historically performed technique has been reported, namely successive advancements of a catheter or delivery system to delivery multiple payloads of fluidic delivery versus the historic retraction technique. In the case of multiple deliveries of therapy, the multiple deliveries of therapy are captured and automatically segmented and added to the surgical plan in the case of image guided surgery, real-time impedance measurements or other metrics such as ultrasound or microelectrode recording or impedance spectroscopy are alternatively used to characterize the environment and progression of the implant or delivery system through the tissue. In the case of retraction versus further advancement, an alert is provided to indicate to the proceduralist that the best practice advancement technique is not being used.

Another example is in the case of multiple catheter delivery where a similar technique is used as above, however further mapping of impedance or imaging data is possible in association with imaging sequences, including imaging sequences obtained along the axis of or perpendicular to the axis of the delivery implant with MRI or other imaging modalities. An automated alert is provided if therapy is reaching a predefined infusion border, therapy concentration limit, outflow or loss pathway, or if an individual with disease outcome measure threshold is reaching a limit. An example of this would be to ensure the plan of n number of infusion clouds in a triangular or other arrangement were being delivered based upon the monitoring of MRI or ultrasound or another similar technique A further example of this technique is to deliver a shaped infusion with real-time monitoring and closed loop delivery similar to a 3d printer technology where along one or multiple trajectories infusion pumps in the case of fluidic delivery are independently controlled and hydraulic advancement mechanisms are independently controlled. The hydraulic advancement system or other method of advancing a rigid device such as mechanical push pull cabling, screw rotation along a base with a fixator or other method is used to advance the device. Recordings of impedance, impedance spectroscopy, MRI, CT, or other imaging modalities as well as catheter impedance, pressure, line infusion pressure, and optical properties of transmittance and other methods of determining tissue type, location, presence or absence of factors such as swelling, necrosis, or other damage as well as methods of measuring tissue concentrations of substances such as using voltage amperometry or other methods such as microdialysis or other means of determining tissue factors. The automated system will alter flow or delivery in the event of changes in an individual with disease outcome, vital signs, temperature, findings on imaging or by other means to detect a complication such as stroke or hemorrhage or other finding. The relative rate of advancement of the device(s) and the relative rate of infusion are altered to provide a shaped infusion result in an automated way based upon such factors as change in line pressure over time, maximum line pressure, external catheter measured pressure with single or multiple sensors, or with minimum and maximum insertion rate, change in volume delivered over time, volume of distribution versus infusion, change in volume of distribution versus infusion over time, distance from relative structures such as blood vessels, ventricular anatomy, white matter versus gray matter tracts, other infusion or other trajectories during the present or during previous infusions, body temperature, line infusate temperature, molecular weight or other characteristics of the infusate such as heparin sulfate binding or other factor which may portend a more favorable rapid infusion versus slower infusion for a longer period of time, infusion rate, change in infusion rate over time, presence of catheter port occlusion, status of catheter port occlusion mitigation strategy algorithm implantation.

Outcomes measures and real-time assessment are used to inform closed-loop or feedback controlled therapy such as the controlling of an infusion pump, delivering continuous levodopa or other medication therapy in the case of Parkinson disease. For example, the wristwatch or other similar device or devices mounted on one or more limbs or trunk or clothing device or shoes or hat or head or face or backpack like device or hip or belt mounted device will monitor for movement for detecting relevant events such as time of waking, and state of wakefulness, movement, medication intake via oral or other infusion, presence of medication-induced side effects such as levodopa induced dyskinesias, presence of paucity of medications such as resting tremor, and GPS or other movement metrics to determine activity level and type. Combined with known stimulation or other therapy metrics, and computation of recommended further adjustment or therapy will be made and an alert given to the user or to the relevant care provider. In the case of a fluid filled delivery pump, the pump will be instructed or instructions displayed for increasing or decreasing the level of delivered therapy. Should other testing be indicated, an alert will sound asking the user to perform a test or take a measurement. Examples of such tests include weight, blood pressure, reaction time or other physical coordination or balance test, bradykinesia assessment such as finger tapping, or pronation supination of the extremity, or to perform a cognitive test. These aggregate results of background and alerted testing are provided to the data warehouse for reporting to stakeholders as well as for further programming or informing alerts for programming devices. Another example of an alert testing is to ask the user to ensure the device is activated and to enter parameters measured with an individual with disease controller such as battery life, impedance measurements, neurostimulator settings, GPS location, activity level, diary data, cognitive data, medication use data, or other metric.

Alerts are additionally provided for the user to upload body weight, and height as well as age, gender, and sex.

Implants communicate via wired and wireless protocols powered by primary cell, and rechargeable technologies including through aggregation of background energy derived from ambient cellular and other electromagnetic transmissions. Neurostimulation can be shaped and altered via feedback mechanisms from the objective and subjective measures included within the aggregate system.

Alerts are additionally provided for the user to upload body weight, and height as well as age, gender, and sex.

Implants communicate via wired and wireless protocols powered by primary cell, and rechargeable technologies including through aggregation of background energy derived from ambient cellular and other electromagnetic transmissions. Neurostimulation can be shaped and altered via feedback mechanisms from the objective and subjective measures included within the aggregate system.

Content-based recognition (CBIR) is used for brain implant error measurement using the anterior and posterior commissures, midline point, brain width, third ventricular width, maximum brain length and parasagittal brain length and other measurements.

Figure 109:
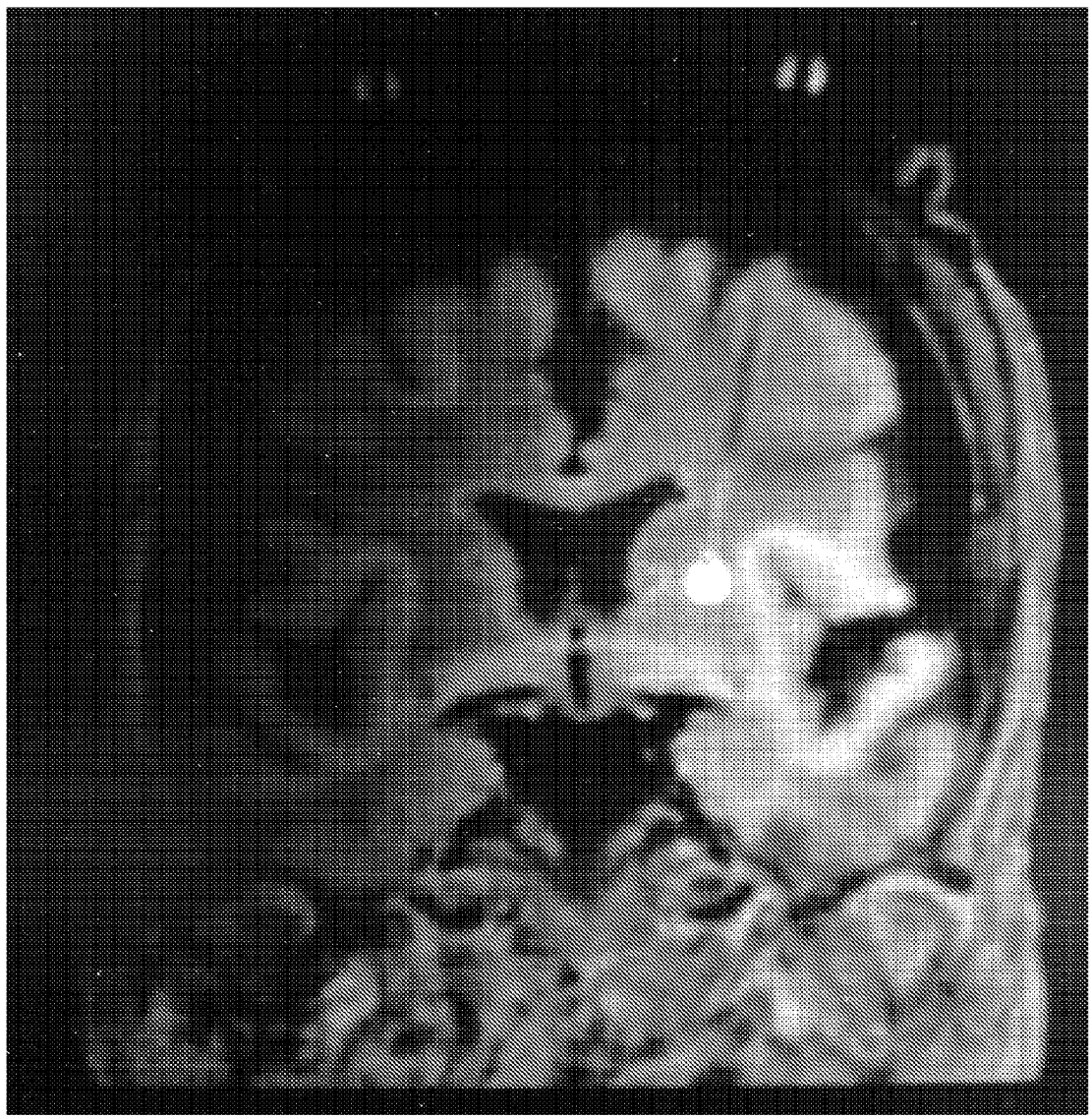
FIG. 109 is a figure demonstrating a coronal MRI image during the first of two collinear infusions of 0.017% bromophenol Blue/2 mM gadoteridol within a formalin fixed human brain using the MRI Interventions 14 gauge SmartFlow Catheter.
Figure 110:
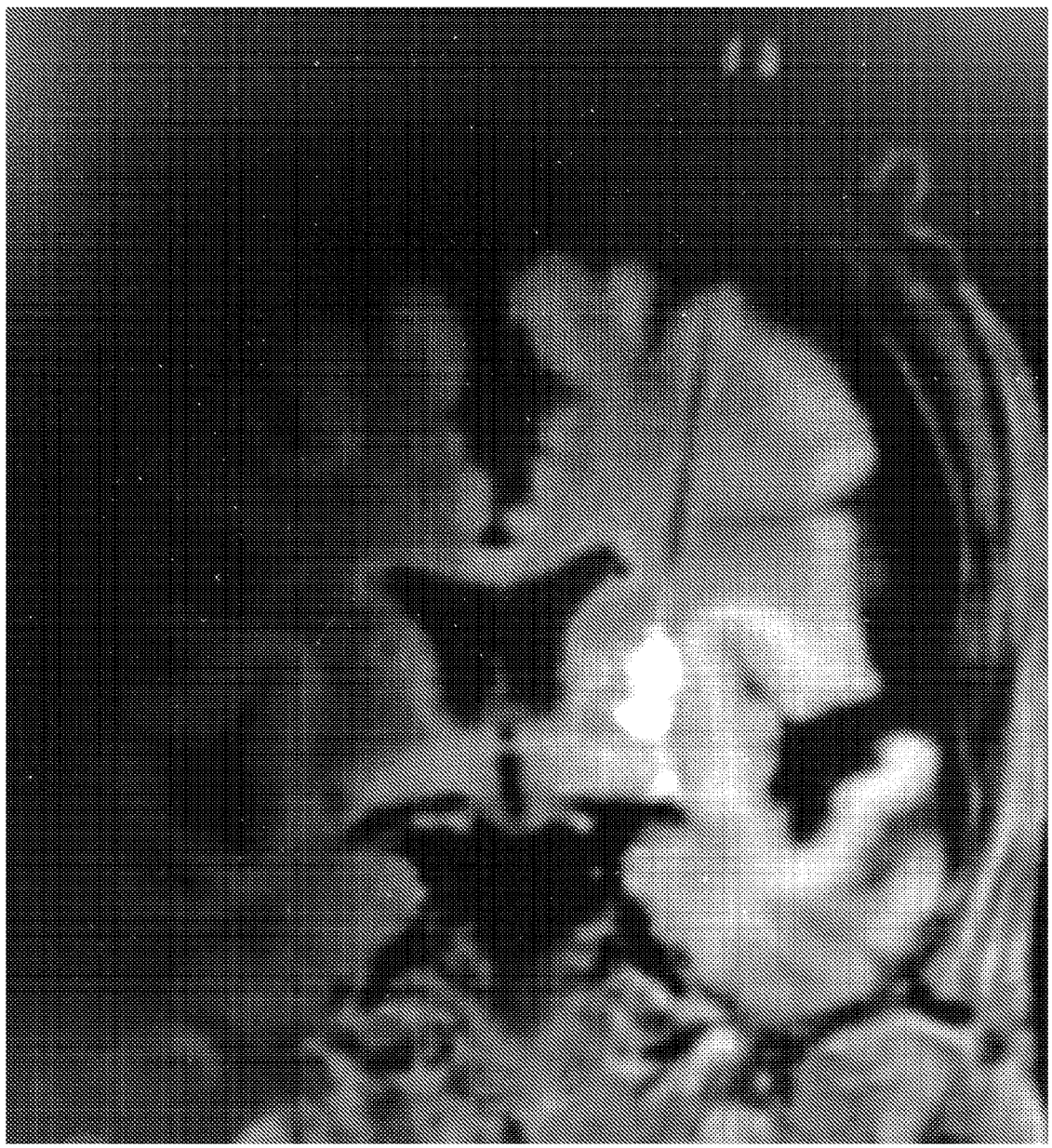
FIG. 110 is a figure demonstrating a coronal MRI image during the second of two collinear infusions of 0.017% bromophenol Blue/2 mM gadoteridol within a formalin fixed human brain using the MRI Interventions 14 gauge SmartFlow Catheter.
Figure 111:
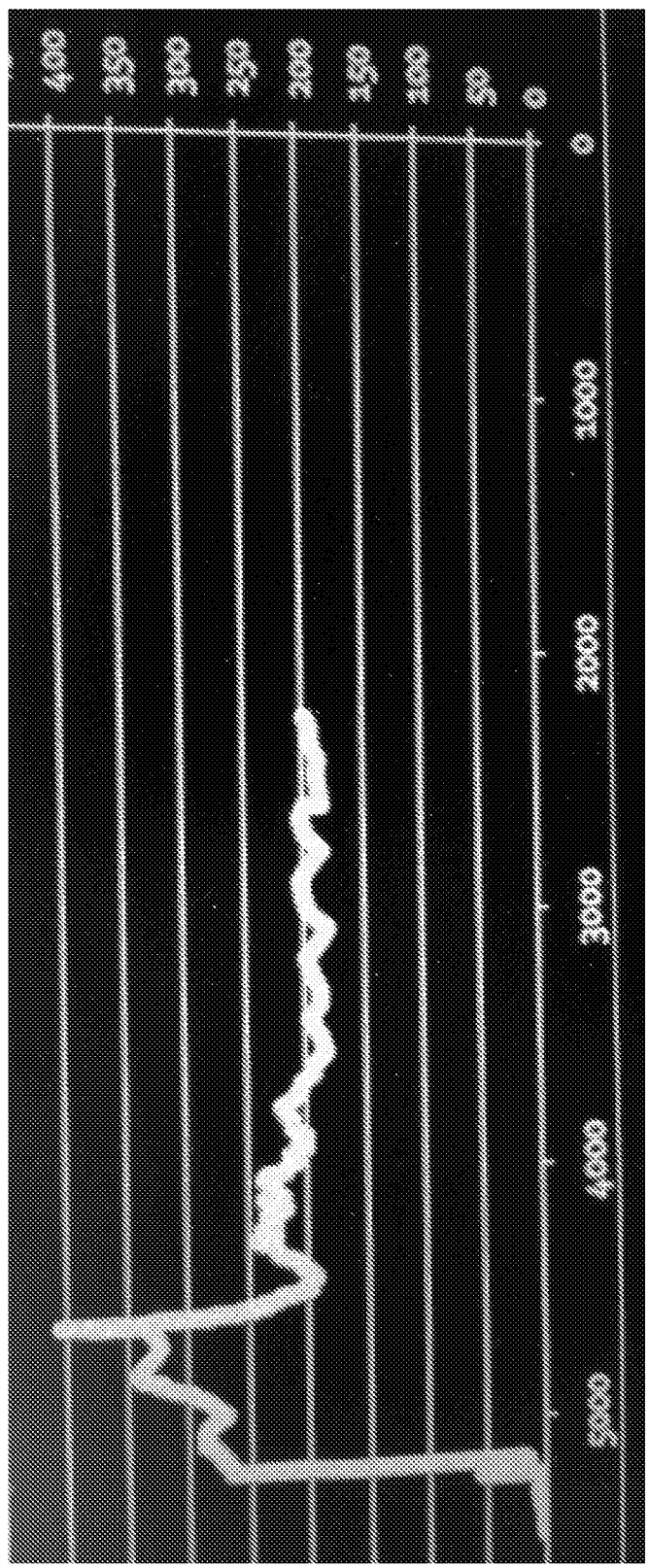
FIG. 111 is a figure of catheter line pressure during the infusion depicted in FIG. 109.

Multiple Collinear Infusion Clouds are possible to be created with advancement rather than retraction (FIGS. 109-111; Sillay, 2012 and 2013), however the technique of advancement rather than retraction has not been previously described (Sillay, 2013) and can be automated with a hydraulic or other computer controlled advancement system (Sillay WARF IDR 2011) and could be used to shape infusions with a single or with multiple array(s) of catheters (SILLAY WARF IDR 2012) in order to provide computerized feedback controlled 3D infusion shaping to a predetermined desired infusion shape). CBIR image processing combined with microelectrode recording as well as impedance tomography provide registration for this computerized registration algorithm and system.

The device represented by FIG. 8 may have short range, non-FCC controlled frequency transmission to implants and other local devices and also have long range frequencies (FCC approval) for communication with our medical database hierarchy. Time of day and date can be important so that periodic measurements may be collected into a cohort database during sleep and other typically unmonitored times of the day (except in a hospital setting where an individual with disease is woken every three hours to take temperature and BP) of body temperature, blood pressure and our device may monitor restless sleep syndrome (night tremors) and the like. Sensors may measure and the processor software determine asymmetric gait versus antalgic gait (see, for example, FIG. 106).

The individual with disease or the doctor may store/download to the local device (FIG. 8) what medication treatment protocol the individual with disease is personally using to be able to develop a true cohort database with other similarly situated individuals diagnosed with a disease.

All U.S. patents, published applications and articles referenced herein should be deemed incorporated by reference herein as to their entire contents. The claims which follow are merely exemplary of the many claims that may be made to aspects of the present invention. Indeed, there may be multiple inventions disclosed in the present discussion and will be claimed in continuation and divisional applications as deemed appropriate.

REFERENCES

Bibliography

Albers, T. W. (2011). *Development of an Objective Motor Score for Monitoring the Progression and Severity of Parkinson's Disease*. Master of Science in Electrical and Computer Engineering, Portland State University.

Boraud T., Tison F., Gross C. Quantification of motor slowness in Parkinson's disease: Correlations between the tapping test and single joint ballistic movement parameters (1997) *Parkinsonism and Related Disorders*, 3 (1), Elsevier, pp. 47-50.

Dunnewold, R. J. W., Jacobi, C. E., van Hilten, J. J. 1997. Quantitative assessment of bradykinesia in patients with Parkinson's Disease. *J of Neurosc Mthds*, Elsevier, 74: 107-112.

Dunnewold R J W, Hoff J I, Van Pelt C J, et al. Ambulatory quantitative assessment of body position, bradykinesia and hypokinesia in Parkinson's disease. J Clin Neurophysiol 1998; 15): 235-42

Fahn, S. R. L. E., R. L. Elton, and UPDRS Development Committee. "Unified Parkinson's disease rating scale." *Recent developments in Parkinson's disease* 2 (1987): 153-163.

Goetz, Christopher G., Glenn T. Stebbins, David Wolff, William DeLecuw, Helen Bronte-Stewart, Rodger Elble, Mark Hallett et al. "Testing objective measures of motor impairment in early Parkinson's disease: Feasibility study of an at-home testing device." *Movement Disorders* 24, no. 4 (2009): 551-556.

Hoehn M M, Yahr M M D. Parkinsonism: onset, progression and mortality. Neurology 1967; 17: pp. 427-42 (Ovid reprint 1998).

Hoff, J. I., Wagemans, E. A., van Hilten, B. J. 2001. Ambulatory Objective Assessment of Tremor in Parkinson's Disease. *Clinical Neuropharm.* 24(5): 280-283.

Mamorita, N., et al. 2009. Development of a system for measurement and analysis of tremor using a three-axis accelerometer. *Methods Inf Med.* 48: 589-594.

Larsen T A, LeWitt P A, Caine D B. "*Theoretical and practical issues in assessment of deficits and therapy in parkinsonism.*" In: Calne D B, Horowski R, MacDonald R J, Wuttke W, eds. Lisuride and other dopamine agonists. New York: Raven Press, 1983; 363-73.

Figuerias-Mendez et al., 2009. Deep Brain Stimulation: 12 year's experience and 150 patients treated with a follow-up of over a year. Revista de neurologia (10): pp. 511-516.

McGirt, Matthew J., et al. "The National Neurosurgery Quality and Outcomes Database (N2QOD): general overview and pilot-year project description." *Neurosurgical focus* 34.1 (2013): E6.

McNames, J. (2012), "APDM Wearable Inertial Monitors," APDM Inc., 5 pages

McNames, J. et al. "SYSTEM FOR DATA MANAGEMENT, ANALYSIS, AND COLLABORATION OF MOVEMENT DISORDER DATA." U.S. patent application Ser. No. 12/763,538, filed Apr. 20, 2010, (2010/0268551 published Oct. 21, 2010.)

Okun, Michael S., et al. "Piloting the NPF data-driven quality improvement initiative." *Parkinsonism & Related Disorders* 16 (2010): pp. 517-521.

Great Lakes Neurologic (video and accelerometer)

Cambridge Neurologics (a device with an accelerometer)

QMAT (Voice, accelerometer, pegboard, paddles).

Papavassiliou, E., et al, 2004. Thalamic deep brain stimulation for essential tremor: relation of lead location to outcome. Neurosurg 54: 1120-1130.

Papapctropoulos S, Jagid J R, Sengun C, Singer C, Gallo B V: Objective monitoring of tremor and bradykinesia during DBS surgery for Parkinson disease. Neurology 70: 1244-1249, 2008.

Patel, S., K. Lorincz, et al. (2009). "Monitoring motor fluctuations in patients with Parkinson's disease using wearable sensors." *IEEE transactions on information technology in biomedicine* 13(6): 864-873.

Rusk, H., J. Baran, et al. (2011). *Optimization of Tremor Assessment Using the Apple iPhone* 4, 15th International Congress of Parkinson's Disease and Movement Disorders, Toronto, Canada.

Salarian, A., H. Russmann, et al. (2007). "Quantification of tremor and bradykinesia in Parkinson's disease using a novel ambulatory monitoring system." *IEEE transactions on bio-medical engineering* 54(2): 313-322.

Taylor Tavares, A., Jefferis, G., Koop, M., Hill, B., Hastie, T., Heit, G., BronteStewart, H., 2005. Quantitative measurements of alternating finger tapping in Parkinson's disease correlate with UPDRS motor disability and reveal the improvement in fine motor control from medication and deep brain stimulation. Mov. Disord., Vol. 20, pp. 1286-1298.

van Hilten J J, van der Zwan A D, Zwinderman A H, Roos R A C. "*Rating impairment and disability in Parkinson's disease: evaluation of the Unified Parkinson's Disease Rating Scale.*" "Movement Disorders" 1994; 9:84-8.

Yokoe, M., et al. 2009. Opening Velocity, a novel parameter, for finger tapping test in patients with Parkinson's Disease. *Parkinsonism and Related Disorders.* 15: 440-444.

Yu. H., and Neimat, J. S., 2008. The treatment of movement disorders by deep brain stimulation. Neurotherap 5(1): 26-36.

Zhang et al., 2009. Long-term results of thalamic deep brain stimulation for essential tremor. J Neurosurg, 112, pp. 1271-1276.

Rusk H, Baran J, Kumbier L, Ninman N, Dent L, Sillay K. *Optimization of Tremor Assessment Using the iPOD*. 15th International Congress of Parkinson's Disease and Movement Disorders. Toronto, Canada, Jun. 5-9, 2011.

Stefansic, J., V. Morgan, K. Sillay, M. Gorelik, G. Humbert, and R. Thompson. "Integration of functional MRI into a commercial image-guided surgical system." In *Proceedings of the 11th Scientific Meeting and Exhibition of the International Society for Magnetic Resonance in Medicine, Toronto. Ontario, Canada*. 2003.

Smith, Joseph R., Karl Sillay, Peter Winkler, Don W. King, and David W. Loring. "Orbitofrontal epilepsy: electroclinical analysis of surgical cases and literature review." *Stereotactic and functional neurosurgery* 82, no. 1 (2004): 20-25.

Sillay, Karl A., Jason C. Chen, and Erwin B. Montgomery. "Long Term Measurement of Therapeutic Electrode Impedance in Deep Brain Stimulation." *Neuromodulation: Technology at the Neural Interface* 13, no. 3 (2010): pp. 195-200.

Sillay, Karl, Dominic Schomberg, Angelica Hinchman, Lauren Kumbier, Chris Ross, Ken Kubota, Ethan Brodsky, and Gurwattan Miranpuri. "Benchmarking the ERG valve tip and MRI Interventions Smart Flow neurocatheter convection-enhanced delivery system's performance in a gel model of the brain: employing infusion protocols proposed for gene therapy for Parkinson's disease." *Journal of Neural Engineering* 9, no. 2 (2012), IOP Publishing: pp. 1-13.

Sillay K, Rutecki P, Cicora K, Worrell G, Drazkowski D, Shih J, Sharan A. Morrell M, Williams J, Wingeier B. "Long-term measurement of impedance in chronically-implanted depth and subdural electrodes during responsive neurostimulation in humans," *Brain Stimulation*, 1-9, (Accepted for publication, Elsevier, 2013)

Sillay, Karl, Angelica Hinchman, Lauren Kumbier, Dominic Schomberg, Chris Ross, Ken Kubota, Martin Brady. Ethan Brodsky, Gurwattan Miranpuri, and Raghu Raghavan. "Strategies for the Delivery of Multiple Collinear infusion Clouds in Convection-Enhanced Delivery in the Treatment of Parkinson's Disease." *Stereotactic and Functional Neurosurgery* 91, no. 3 (2013): 153-161.

Brady, M. L., Raghavan, R., Alexander, A., Kubota, K., Sillay, K., & Emborg, M. E. (2013). Pathways of Infusate Loss during Convection-Enhanced Delivery into the Putamen Nucleus. *Stereotactic and functional neurosurgery*, 91(2), 69-78.

Sillay, K. A., L. M. Kumbier, C. Ross, M. Brady, A. Alexander, A. Gupta, N. Adluru, G. S. Miranpuri, and J. C. Williams. "Perioperative Brain Shift and Deep Brain Stimulating Electrode Deformation Analysis: Implications for rigid and non-rigid devices." *Annals of biomedical engineering*, V. 41, No. 2, pp. 293-304, (Sep. 26, 2012).

Sillay K. *Parkinson Disease Management App*. MacHealthcare.org/Apple Webinar. Summer, 2012 (weblink: http://www.machealthcare.org/articles/25/parkinson-s-disease-management-a)

What we claim is:

1. A method for use with a medical mobile communications device, the method for collecting objective medical data, processing the collected medical data and for comparing progress of an individual diagnosed with a neurological disease in relation to a cohort of similar selected individuals diagnosed with the neurological disease, the method for use with the medical mobile communications device comprising:

storing in a memory of the medical mobile communications device a clock time and date with reference to a location of the medical mobile communications device via a programmed computer processor of the medical mobile communications and periodically transmitting the stored clock time, location and date data associated with identity data of the individual diagnosed with the neurological disease via a communications interface connected to the programmed computer processor to a remote server having a medical health record database for storage in the medical health record database, the identity data of the individual diagnosed with the neurological disease being stored in the memory of the medical mobile communications device having been received by an input device and processed by the programmed computer processor of the medical mobile communications device;

storing in the memory associated with the computer processor of the medical mobile communications device objective medical data of the individual diagnosed with the disease, the objective medical data determined using one of a gyroscope and an accelerometer of the medical mobile communications device and processed for storage with the stored clock time, date, location and identity data by the programmed computer processor;

receiving via a communications interface of the medical mobile communications device aggregate objective medical data of the cohort of similar selected individuals diagnosed with the neurological disease according to gender, age and presence or absence of surgical implants comprising one of a deep brain stimulator and a drug delivery system adapted to be implanted in the cohort of similar selected individuals diagnosed with the neurological disease from the remote server having the medical health record database;

comparing by the programmed computer processor the objective medical data of the individual diagnosed with the neurological disease with the aggregate objective medical data of the cohort received via the medical mobile communications device;

repeating the storing of clock time and date, the storing of objective medical data of the individual diagnosed with the neurological disease in memory of the medical mobile communications device, the receiving of the aggregate objective medical data of the cohort from the remote server and the comparing of the objective medical data of the individual diagnosed with the neurological disease with the aggregate objective medical data of the cohort at a later clock time and date determined with reference to location; and displaying data on a display of the medical mobile communications device indicative of progress of the diagnosed neurological disease of the individual diagnosed with the neurological disease compared to the aggregate objective medical data of the cohort indicative of the progress of the diagnosed neurological disease of the cohort responsive to the repeated comparing of the respective objective medical data of the individual and the aggregate objective medical data of the cohort diagnosed with the neurological disease by the programmed computer processor;

the objective medical data of the individual and the aggregate objective medical data of the cohort diagnosed with the neurological disease comprising extremity movement data, the extremity movement data of the individual diagnosed with the neurological disease comprising at least one of angular acceleration and linear acceleration measurement values over time determined using the one of the gyroscope and the accelerometer of the medical mobile communications device for storage in the memory and processing by the programmed computer processor of the medical mobile communications device adapted to be stored in memory of the medical mobile communications device during pronation/supination movement of a human body extremity of the individual diagnosed with the neurological disease, the medical mobile communications device adapted to be coupled to the human body extremity of the individual diagnosed with the neurological disease.

2. The method for use with the medical mobile communications device of claim 1, the method further including detecting speech of the individual diagnosed with the neurological disease and recording associated speech data in the associated memory of the programmed computer processor of the medical mobile communications device.

3. The method for use with the medical mobile communications device of claim 1 adapted for use with a camera connected to the medical mobile communications device, the method further comprising using the camera to capture video image data of the individual diagnosed with the neurological disease performing human body extremity movement, and
deriving via the programmed computer processor of the medical mobile communications device the objective medical data responsive to receipt of the captured video image data from the camera.

4. The method for use with the medical mobile communications device of claim 1 further comprising determining the direction of gravity via a gravitational sensor of the medical mobile communications device and determining a coordinate frame of reference via the programmed computer processor of the medical mobile communications device, the programmed computer processor using the determined direction of gravity by the gravitational sensor to determine the coordinate frame of reference with respect to the earth.

5. The method for use with the medical mobile communications device of claim 1 further comprising receiving body temperature data of the individual diagnosed with the disease via a body temperature sensor coupled to the medical mobile communications device and, recording the received body temperature data in the associated memory of the medical mobile communications device for comparison with aggregate body temperature data of the cohort diagnosed with the neurological disease received via the communications interface from the remote medical record database.

6. The method for use with the medical mobile communications device of claim 1, the communications interface of the medical mobile communications device further communicating with a neuro-stimulator adapted to be implanted in a brain of the individual diagnosed with the neurological disease, the communications interface for communicating neuro-stimulator control data computed by the programmed computer processor of the medical mobile communications device to the neuro-stimulator for modifying the neuro-stimulator operation via feedback.

7. The method for use with the medical mobile communications device of claim 6, the neuro-stimulator adapted to be implanted in the brain of the individual diagnosed with the neurological disease comprising a remotely controllable deep brain stimulator adapted to be implanted in the brain of the individual diagnosed with the neurological disease.

8. The method for use with the medical mobile communications device of claim 1, the communications interface further communicating with a drug delivery system adapted to be implanted in the individual diagnosed with the neurological disease, the communications interface transferring drug delivery system control data computed by the programmed computer processor of the medical mobile communications device to the drug delivery system for automatically varying an amount of drug for delivery by the drug delivery system to the individual diagnosed with the neurological disease.

9. The method for use with the medical mobile communications device of claim 1, the communications interface cooperating with the display and programmed computer processor of the medical mobile communications device, the programmed computer processor executing software for calculating responsive to the received objective medical data of the individual diagnosed with the neurological disease and the display displaying, responsive to the calculating, a recommended medication dosage and identity of medication adapted to be administered to the individual diagnosed with the neurological disease.

10. The method for use with the medical mobile communications device of claim 1, the communications interface outputting to the display responsive to the programmed computer processor of the medical mobile communications device, the programmed computer processor executing software for calculating and the display displaying, responsive to the calculating, a recommended human body extremity movement program comprising forearm pronation/supination adapted for use by the individual with the diagnosed neurological disease, the at least one of collected pronation/supination angular acceleration and linear acceleration data of the individual diagnosed with the neurological disease for comparison by the programmed computer processor with aggregate forearm pronation/supination data of the cohort diagnosed with the neurological disease received from the remote medical record database and further outputting a rating of the individual diagnosed with the disease relative to the selected cohort.

11. The method for use with the medical mobile communications device of claim 1 further comprising receiving barometric pressure from a barometer coupled to the medical mobile communications device and receiving environmental temperature from a thermometer coupled to the medical mobile communications device at a location indicated by a global positioning system of the medical mobile communications device for storage in the associated memory of the programmed computer processor of the medical mobile communications device.

12. The method for use with the medical mobile communications device of claim 11 further comprising receiving and storing environmental humidity data and perspiration data of the individual diagnosed with the neurological disease, the environmental humidity and perspiration data output by a meter coupled to the medical mobile communications device.

13. The method for use with the medical mobile communications device of claim 1 for selection of the cohort of similar individuals diagnosed with the neurological disease, the medical mobile communications device adapted for receiving input data by the individual diagnosed with the neurological disease, the individual input data comprising age, gender, body weight, presence or absence of surgical implants comprising one of a deep brain stimulator and a drug delivery system and personal identification data of the individual diagnosed with the neurological disease for transmittal to the remote server via the communications interface.

14. The method for use with the medical mobile communications device of claim 1 wherein the neurological disease comprises Parkinson's disease.

15. The method for use with the medical mobile communications device of claim 1 wherein the neurological disease comprises one of Parkinson's disease, Alzheimer's disease, dementia, epilepsy, multiple sclerosis, essential tremor, dystonia, hydrocephalus, a spinal disorder, a gait disorder and stroke.

16. The method for use with the medical mobile communications device of claim 1, the medical mobile communications device adapted to be one of worn or implanted at a wrist location of a left or right arm extremity of a human body.

17. The method for use with the medical mobile communications device of claim 1 further comprising using a pressure transducer of the medical mobile communications device to measure pressure of a human body extremity.

18. The method for use with the medical mobile communications device of claim 1 further comprising sensing oxygen level via a pulse oximeter connected to the medical mobile communications device, the pulse oximeter further adapted to sense oxygen level of blood of the individual diagnosed with the neurological disease.

19. The method for use with the medical mobile communications device of claim 1 further comprising measuring pressure via a pressure transducer adapted to be connected to a human body extremity by one of clothing or a tether, the pressure transducer coupled to the programmed computer processor of the medical mobile communications device adapted to measure relative use of the human body extremity.

20. The method for use with the medical mobile communications device of claim 19 wherein the foot extremity comprises an ankle.

21. The method for use with the medical mobile communications device of claim 1 wherein the extremity movement data adapted to be input to the device determined using the one of the gyroscope and the accelerometer comprises one of forearm pronation and supination data, the extremity movement data comprising pronation/supination movements of the forearm according to a pronation protocol adapted for use by the individual diagnosed with the neurological disease and the method further comprising inputting the extremity movement data determined using the one of the gyroscope and the accelerometer to the programmed computer processor of the medical mobile communication device adapted for assessing bradykinesia of the individual diagnosed with the neurological disease.

22. The method for use with the medical mobile communications device of claim 1 further comprising determining global position data by a global position system connected to the programmed computer processor of the medical mobile communications device of a location of the medical mobile communications device when coupled to the human body extremity of the individual diagnosed with a neurological disease and determining by the programmed computer processor time zone data for transmitting a universal time and date determined by the device and transmitting the objective medical data of the individual for storage at the remote server.

23. The method for use with the medical mobile communications device of claim 1, further comprising receiving aggregate objective medical data of the cohort diagnosed with the neurological disease at the medical mobile communications device via the communications interface in response to sending a query by the communications interface to the remote server having the medical health record database.

24. A method for use with a medical mobile communications device adapted for obtaining medical measurement data from an individual diagnosed with a neurological disease, the method comprising:
processing the medical measurement data by a programmed computer processor of the medical mobile communications device,
computing objective measurement data by the programmed computer processor of the medical mobile communications device from the processed medical measurement data, and
transmitting the computed objective measurement data of the individual diagnosed with the neurological disease for storage in a remote medical health record database, the method for use with a medical mobile communications device further comprising:
determining and periodically storing in a memory of the programmed computer processor and transmitting by a communications interface of the medical mobile communications device for storage at the remote medical record database a universal time of day and date of receipt of the computed objective measurement data of the individual diagnosed with the neurological disease associated with location data of the medical mobile communications device;
communicating by the communications interface of the medical mobile communications device with the remote medical health record database for storing the computed objective measurement data, the objective measurement data obtainable from the medical measurement data input to the programmed computer processor from a sensor adapted for sensing extremity movement data from a pronation/supination protocol adapted to be performed by the individual diagnosed with the neurological disease for storage in memory of the medical mobile communications device and for communication to the remote medical health record database;
collecting the extremity movement data of the pronation/supination protocol from the sensor comprising one of a gyroscope and an accelerometer of the medical mobile communications device, the extremity movement data adapted to be obtained from the of angular and linear acceleration measurements calculated with respect to at least three axes of a distinguished coordinate system adapted for the pronation/supination protocol and universal time and date, the medical mobile communications device adapted to be coupled to a human body extremity of the individual diagnosed with the neurological disease;
receiving individual identity data input for storage in memory of the medical mobile communications device;
storing the one of collected angular and linear acceleration measurement data of the individual diagnosed with the neurological disease in memory of the medical mobile communications device with the stored individual identity data;
determining a direction of maximum motion of the extremity of the individual diagnosed with the neurological disease by the programmed computer processor of the medical mobile communications device adapted to be coupled to the extremity of the individual from at least a subset of the collected extremity movement data and using the determined direction to compute the objective measurement data; and
communicating the computed objective measurement data via the communications interface of the medical mobile communications device, said computed objective measurement data comprising an estimate of a variation present in the collected objective measurement data and the universal time of day and date, to the remote medical health record database, the programmed computer processor of the medical mobile communications device actuating a display of the medical mobile communications device adapted for displaying the computed objective measurement data of the individual diagnosed with the neurological disease responsive to the computing.

25. The method for use with the medical mobile communications device of claim 24, the one of angular and linear acceleration measurement data adapted to be collected responsive to forearm pronation/supination movements by the individual diagnosed with the neurological disease over time and according to the pronation/supination protocol.

26. The method for use with the medical mobile communications device of claim 24, the method further comprising determining the direction and value of maximum motion in the distinguished coordinate system adapted to be determined of the extremity during pronation/supination movements performed by the individual diagnosed with the neurological disease, the determining of direction and value performed by the programmed computer processor of the remote medical health record database responsive to the sensor.

27. A method for use with a medical mobile communications device adapted for use by an individual diagnosed with a neurological disease and having an associated, activatable deep brain stimulator adapted to be implanted in the individual diagnosed with the neurological disease, the medical mobile communications device comprising one of a gyroscope and an accelerometer, a communications interface, and a programmed computer processor of the medical mobile communications device, wherein the programmed computer processor executes software for:

computing a distinguished coordinate system, a distinguished coordinate of the distinguished coordinate system adapted to value a greatest motion of the individual diagnosed with the disease and using the distinguished coordinate system adapted to determine forearm extremity motion data comprising a value of one of maximum rate of angular acceleration, of degrees traveled per oscillation of a forearm extremity, peak angular velocity and of hesitation over time, data for computing the forearm extremity motion data adapted to be sensed by one of an accelerometer and a gyroscope for input to the programmed computer processor, the forearm extremity motion data adapted to be collected responsive to forearm extremity pronation/supination movements by the individual diagnosed with the neurological disease and stored in memory associated with the programmed computer processor;

the programmed computer processor calculating and the memory storing the forearm extremity motion data during pronation/supination and adapted for storing the forearm extremity motion data in accordance with the distinguished coordinate system, the forearm extremity motion data correlating with a clinical rating scale for the diagnosed neurological disease, the forearm extremity motion data responsive to deep brain stimulation activation and deactivation via the communications interface of the medical mobile communications device;

receiving, via the communications interface of the medical mobile communications device, aggregate forearm extremity motion data of a cohort of similar selected individuals diagnosed with the neurological disease according to gender, age and one of presence or absence of surgical implants comprising one of a deep brain stimulator and a drug delivery system relative to the individual diagnosed with the disease, the aggregate data calculated according to a clinical rating scale for the diagnosed disease;

calculating clinical rating score data of the individual diagnosed with the disease;

comparing the forearm extremity motion data of the individual diagnosed with the disease to the cohort according to the clinical rating scale for the diagnosed neurological disease; and displaying relative values of the forearm extremity motion data calculated according to the clinical rating scale for the diagnosed neurological disease for display by a display of the medical mobile communications device.

28. The method for use with the medical mobile communications device of claim 27 further comprising a magnetometer for detecting a magnetic field of an electromotor and an alerter of the medical mobile communications device, the alerter, responsive to a magnetic field above an average magnetic field acquired within the cohort, adapted to alert the individual diagnosed with the neurological disease of the magnetic field value above the average magnetic field acquired within the cohort.

29. The method for use with the medical mobile communications device of claim 27 further comprising an associated medical drug delivery system adapted to be implanted in the individual diagnosed with the neurological disease, the method further comprising the communications interface communicating drug delivery control data to the medical drug delivery system, the programmed computer processor calculating the drug delivery control data.

30. The method for use with the medical communications device of claim 27, the diagnosed neurological disease being Parkinson's disease and the clinical rating scale for the diagnosed neurological disease being a unified Parkinson's disease rating scale.

* * * * *